US009938514B2

(12) United States Patent
Ghanshani et al.

(10) Patent No.: US 9,938,514 B2
(45) Date of Patent: *Apr. 10, 2018

(54) METHODS OF INTRACELLULAR CONVERSION OF SINGLE-CHAIN PROTEINS INTO THEIR DI-CHAIN FORM

(71) Applicant: Allergan, Inc., Irvine, CA (US)

(72) Inventors: Sanjiv Ghanshani, Irvine, CA (US); Linh Q. Le, Tustin, CA (US); Yi Liu, Irvine, CA (US); Lance E. Steward, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,302

(22) Filed: May 16, 2016

(65) Prior Publication Data

US 2016/0319265 A1   Nov. 3, 2016

Related U.S. Application Data

(60) Division of application No. 14/038,328, filed on Sep. 26, 2013, now Pat. No. 9,340,813, which is a continuation of application No. 13/575,222, filed as application No. PCT/US2011/022272 on Jan. 24, 2011, now Pat. No. 8,546,108.

(51) Int. Cl.
| | |
|---|---|
| *C12P 21/04* | (2006.01) |
| *C12N 9/52* | (2006.01) |
| *C07K 14/33* | (2006.01) |
| *C12N 9/50* | (2006.01) |
| *C12N 15/70* | (2006.01) |
| *C12P 21/00* | (2006.01) |
| *C12P 21/06* | (2006.01) |

(52) U.S. Cl.
CPC .............. *C12N 9/52* (2013.01); *C07K 14/33* (2013.01); *C12N 9/506* (2013.01); *C12N 15/70* (2013.01); *C12P 21/00* (2013.01); *C12P 21/06* (2013.01); *C07K 2319/50* (2013.01); *C12N 2799/026* (2013.01)

(58) Field of Classification Search
CPC ...... C07K 14/00; C07K 14/195; C12N 9/506; C12N 15/67; C12P 21/00
USPC .......................... 435/41, 69.1, 71.1, 219, 221
See application file for complete search history.

(56) References Cited

U.S. PATENT DOCUMENTS

| | | | |
|---|---|---|---|
| 5,364,791 A | 11/1994 | Vegeto | |
| 5,464,758 A | 11/1995 | Gossen | |
| 5,514,578 A | 5/1996 | Hogness | |
| 5,665,566 A | 9/1997 | LaVallie | |
| 5,814,618 A | 9/1998 | Bujard | |
| 5,874,534 A | 2/1999 | Vegeto | |
| 5,935,934 A | 8/1999 | Vegeto | |
| 5,989,545 A | 11/1999 | Foster | |
| 6,245,531 B1 | 6/2001 | Hogness | |
| 6,461,617 B1 | 10/2002 | Shone | |
| 6,500,436 B2 | 12/2002 | Donovan | |
| 6,586,224 B1 | 7/2003 | Rubingh | |
| 6,632,440 B1 | 10/2003 | Quinn | |
| 6,746,859 B1 | 6/2004 | LaVallie | |
| 6,843,998 B1 | 1/2005 | Steward | |
| 6,903,187 B1 | 6/2005 | Steward | |
| 7,022,329 B2 | 4/2006 | Donovan | |
| 7,132,259 B1 | 11/2006 | Dolly | |
| 7,132,529 B2 | 11/2006 | Crooke | |
| 7,244,437 B2 | 7/2007 | Donovan | |
| 7,273,722 B2 | 9/2007 | Lin | |
| 7,393,925 B2 | 7/2008 | Steward | |
| 7,413,742 B2 | 8/2008 | Donovan | |
| 7,419,676 B2 | 9/2008 | Dolly | |
| 7,425,338 B2 | 9/2008 | Donovan | |
| 7,491,799 B2 | 2/2009 | Steward | |
| 7,514,088 B2 | 4/2009 | Steward | |
| 8,546,108 B2 * | 10/2013 | Ghanshani | ............ C07K 14/33 435/220 |
| 2003/0180289 A1 | 9/2003 | Foster | |
| 2004/0018589 A1 | 1/2004 | Zhong | |
| 2005/0023309 A1 | 2/2005 | Haugland | |
| 2008/0031931 A1 | 2/2008 | Gunn | |
| 2008/0032930 A1 | 2/2008 | Steward | |
| 2008/0032931 A1 | 2/2008 | Steward | |
| 2008/0057575 A1 | 3/2008 | Fernandez-Salas | |
| 2008/0138893 A1 | 6/2008 | Steward | |
| 2008/0161226 A1 | 7/2008 | Steward | |
| 2008/0187960 A1 | 8/2008 | Foster | |
| 2008/0213830 A1 | 9/2008 | Steward | |

(Continued)

FOREIGN PATENT DOCUMENTS

WO    2005-023309    3/2005

OTHER PUBLICATIONS

U.S. Appl. No. 11/776,075, filed Jul. 11, 2007, Lance E. Steward.
Ausubel, Frederick et al, Current Protocols in Molecular Biology, 2004, 16 Pages, John Wiley & Sons, Inc.
Benihoud, Karim et al, Adenovirus Vectors for Gene Delivery, Current Opinion in Biotechnology, 1999, 440-447, 10.
Biewenga, Jeike et al, Plasmid-Mediated Gene Transfer in Neurons Using the Bioloistics Technique, Journal of Neuroscience Methods, 1997, 67-75, 71.
Blesch, Armin, Lentiviral and MLV Based Retroviral Vectors for Ex Vivo and In Vivo Gene Transfer, Methods, 2004, 164-172, 33.
Bueler, Hansruedi, Adeno-Associated Viral Vectors for Gene Transfer and Gene Therapy, Biol. Chem., Jun. 1999, 613-622, 380.
Burton, Edward et al, Gene Delivery Using Herpes Simplex Virus Vectors, DNA and Cell Biology, 2002, 915-936, 21(12).
Cabrita, Lisa, Enhancing the Stability and Solubility of TEV Protease Using in Silico Design, Protein Science, Nov. 1, 2007, 2360-2367, 16 (11), Cold-Spring Harbor Laboratory Press.

(Continued)

*Primary Examiner* — Rodney P Swartz

(74) *Attorney, Agent, or Firm* — Brigitte C. Phan; Ted A. Chan

(57) ABSTRACT

The present specification discloses expression constructs comprising single-chain proteins comprising a di-chain loop region comprising an exogenous protease cleavage site and a protease that can cleave the exogenous protease cleavage site located within the di-chain loop, cell compositions comprising such expression construct, and intracellular methods of converting the single-chain protein into its di-chain form.

5 Claims, 3 Drawing Sheets

(56) References Cited

U.S. PATENT DOCUMENTS

| | | |
|---|---|---|
| 2008/0221012 A1 | 9/2008 | Steward |
| 2008/0241881 A1 | 10/2008 | Steward |
| 2009/0004224 A1 | 1/2009 | Steward |
| 2009/0005313 A1 | 1/2009 | Steward |
| 2009/0018081 A1 | 1/2009 | Steward |
| 2009/0035822 A1 | 2/2009 | Foster |
| 2009/0048431 A1 | 2/2009 | Steward |
| 2009/0069238 A1 | 3/2009 | Steward |
| 2009/0162341 A1 | 6/2009 | Foster |

OTHER PUBLICATIONS

Davis, J.M., Basic Cell Culture: A Practical Approach, 2002, 10 Pages, 2nd Edition, Oxford University Press.

Doyle, Alan et al, Cell & Tissue Culture: Laboratory Procedures, 1998, 18 Pages, John Wiley & Sons, Inc.

Ehrengruber, Markus, Alphaviral Gene Transfer in Neurobiology, Brain Research Bulletin, 2002, 13-22, 59(1).

Federico, Maurizio, From Lentiviruses to Lentivirus Vectors, Methods in Molecular Biology, 2003, 3-15, 229.

Fernandez, Joseph et al, Gene Expression Systems: Using Nature for the Art of Expression, 1999, 8 Pages, Academic Press.

Freshney, R. Lan, Culture of Animal Cells: A Manual of Basic Technique, 2000, 10 Pages, 4th Edition, Wiley-Liss.

Frolov, Ilya et al, Alphavirus-Based Expression Vectors: Strategies and Applications, Proc Nat Acad Sci, Oct. 1996, 11371-11377, 93.

Golzio, M. et al, In Vitro and In Vivo Electric Field-Mediated Permeabilization, Gene Transfer, and Expression, Methods, 2004, 126-135, 33.

Goosen, Mattheus et al, Insect Cell Culture Engineering, 1993, 4 Pages, Marcel Dekker, Inc.

Grandi, Paola et al, Targeting HSV Amplicon Vectors, Methods, 2004, 179-186, 33.

Gresch, Oliver et al, New Non-Viral Method for Gene Transfer Into Primary Cells, Methods, 2004, 151-163, 33.

Harrison, Maureen et al, General Techniques of Cell Culture, 1997, 3 Pages, Cambridge University Press.

Hermens, Wim et al, Transient Gene Transfer to Neurons and Glia: Analysis of Adenoviral Vector Performance in the CNA and PNS, Journal of Neuroscience Methods, 1997, 85-98, 71.

Higgins, S.J. et al, Protein Expression: A Practical Approach, 1999, 8 Pages, Oxford University Press.

Humeau, Yann et al, How Botulinum and Tetanus Neurotoxins Block Neurotransmitter Release, Biochimie, 2000, 427-446, 82.

Huser, Andreas et al, Baculovirus Vectors: Novel Mammalian Cell Gene-Delivery Vehicles and Their Applications, Am J Pharmacogonomics, 2003, 53-63, 3(1).

Jordan, Martin et al, Transfection of Adherent and Suspended Cells by Calcium Phosphate, Methods, 2004, 136-143, 33.

Kapust, Rachel et al, Controlled Intracellular Processing of Fusion Proteins by TEV Protease, Protein Expression and Purification, Mar. 13, 2000, 312-318, 19.

Kost, Thomas et al, Recombinant Baculoviruses as Mammalian Cell Gene-Delivery Vectors, Trends in Biotechnology, Apr. 2002, 173-180, 20(4).

Lai, Chooi May et al, Adenovirus and Adeno-Associated Virus Vectors, DNA and Cell Biology, 2002, 895-913, 21 (12).

Lalli, Giovanna, The Journey of Tetanus and Botulinum Neurotoxins in Neurons, Trends in Microbiology, Sep. 2003, 431-437, 11 (9), US.

Lipham, William, Cosmetic and Clinical Applications of Botulinum Toxin, 2004, 2 Pages, Slack Inc.

Lorenzano, C. et al, No Clinical or Neurophysiological Evidence of Botulinum Toxin Diffusion to Non-Injected Muscles in Patients With Hemifacial Spasm, Neurotoxicity Research, 2006, 141-144, 9(2,3).

Masters, John, Animal Cell Culture: A Practical Approach, 2000, 7 Pages, 3rd Edition, Oxford University Press.

Mizuguchi, Hiroyuki et al, Approaches for Generating Recombinant Adenovirus Vectors, Advanced Drug Delivery Reviews, 2001, 165-176, 52.

Naldini, Luigi et al, In Vivo Gene Delivery and Stable Transduction of Nondividing Cells by a lentiviral Vector, Science, Apr. 12, 1996, 263-267, 272.

O'Brien, John et al, Biolistic and Diolistic Transfection: Using the Gene Gun to Deliver DNA and Lipophilic Dyes into Mammalian Cells, Methods, 2004, 121-125, 33.

Poeschla, Eric, Non-Primate Lentiviral Vectors, Current Opinion in Molecular Therapeutics, 2003, 529-540, 5(5).

Recillas-Targa, Felix, Gene Transfer and Expression in Mammalian Cell Lines and Transgenic Animals, Methods in Molecular Biology, 2004, 417-433, 267.

Sambrook, Joseph et al, Introducing Cloned Genes Into Cultured Mammalian Cells, Molecular Cloning, 2001, 16.1-16.62. 3rd Edition.

Tonini, Tiziana et al, Transient Production of Retroviral- and Lentiviral-Based Vectors for the Trandsduction of Mammalian Cells, Methods in Molecular Biology, 2004, 141-148, 285.

Tuton, Kathryn et al, Botulinum and Tetanus Neurotoxins: Structure, Function and Therapeutic Utility, Trends in Biochemical Sciences, Nov. 2002, 552-558, 27(11).

Van Den Berg, Susanne, Improved Solubility of TEV Protease by Directed Evolution, J. Biotechnology, Feb. 10, 2006, 291-298, 121(3).

Vlak, J.M. et al, Insect Cell Cultures: Fundamental and Applied Aspects, 1996, 5 Pages, Kluwer Academic Publishers.

Wolkowicz, Roland et al, Lentiviral Vectors for the Delivery of DNA into Mammalian Cells, Methods in Molecular Biology, 2004, 391-411, 246.

Zhang, Chun et al, Polyethylenimine Strategies for Plasmid Delivery to Brain-Derived Cells, Methods, 2004, 144-150, 33.

Patent Cooperation Treaty, Notification of Transmittal of the International Search Report and the Written Opinion of the.International Searching Authority, or the Declaration, Form PCT/ISA/220, Int. App. No. PCT/US2011/022272, Jan. 24, 2011.

* cited by examiner

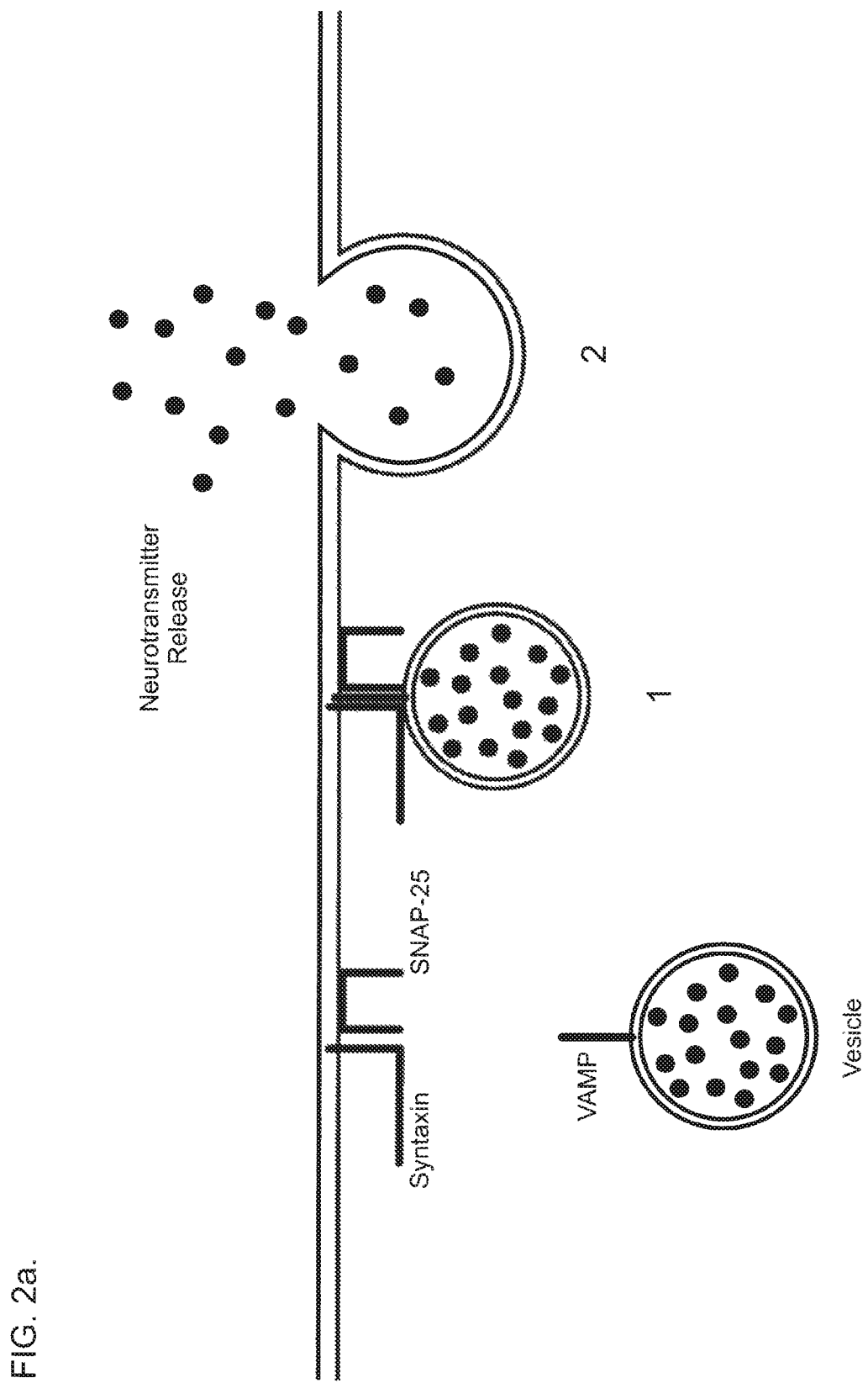

FIG. 2b.

SEQUENCE LISTING

<160> NUMBER OF SEQ ID NOS: 107

<210> SEQ ID NO 1
<211> LENGTH: 1296
<212> TYPE: PRT
<213> ORGANISM: Clostridium botulinum Serotype A

<400> SEQUENCE: 1

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
                 20                  25                  30

Val Lys Ala Phe Lys Ile His Asn Lys Ile Trp Val Ile Pro Glu Arg
             35                  40                  45

Asp Thr Phe Thr Asn Pro Glu Glu Gly Asp Leu Asn Pro Pro Pro Glu
 50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
```

```
                        245                 250                 255
Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
        340                 345                 350

Asn Phe Val Lys Phe Phe Lys Val Leu Asn Arg Lys Thr Tyr Leu Asn
    355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
        420                 425                 430

Gly Ile Ile Thr Ser Lys Thr Lys Ser Leu Asp Lys Gly Tyr Asn Lys
    435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
        500                 505                 510

Glu Asn Ile Ser Ile Glu Asn Leu Ser Ser Asp Ile Ile Gly Gln Leu
    515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
            565                 570                 575

Leu Asn Pro Ser Arg Val Tyr Thr Phe Phe Ser Ser Asp Tyr Val Lys
        580                 585                 590

Lys Val Asn Lys Ala Thr Glu Ala Ala Met Phe Leu Gly Trp Val Glu
    595                 600                 605

Gln Leu Val Tyr Asp Phe Thr Asp Glu Thr Ser Glu Val Ser Thr Thr
610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
            645                 650                 655

Ile Phe Ser Gly Ala Val Ile Leu Leu Glu Phe Ile Pro Glu Ile Ala
        660                 665                 670
```

```
Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085
```

-continued

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1291
<212> TYPE: PRT
<213> ORGANISM: Clostridium botulinum Serotype B

<400> SEQUENCE: 2

Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

```
Ile Gln Asn His Phe Ala Ser Arg Glu Gly Phe Gly Ile Met Gln
            180                 185                 190

Met Lys Phe Cys Pro Glu Tyr Val Ser Val Phe Asn Val Gln Glu
            195                 200                 205

Asn Lys Gly Ala Ser Ile Phe Asn Arg Arg Gly Tyr Phe Ser Asp Pro
            210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590
```

-continued

```
Trp Val Lys Gln Ile Val Asn Asp Phe Val Ile Glu Ala Asn Lys Ser
            595                 600                 605
Asn Thr Met Asp Lys Ile Ala Asp Ile Ser Leu Ile Val Pro Tyr Ile
        610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
            660                 665                 670
Asp Asn Lys Asn Lys Ile Lys Thr Ile Asp Asn Ala Leu Thr Lys
        675                 680                 685
Arg Asn Glu Lys Trp Ser Asp Met Tyr Gly Leu Ile Val Ala Gln Trp
690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
Arg Tyr Asn Ile Tyr Ser Glu Lys Glu Lys Ser Asn Ile Asn Ile Asp
            740                 745                 750
Phe Asn Asp Ile Asn Ser Lys Leu Asn Glu Gly Ile Asn Gln Ala Ile
        755                 760                 765
Asp Asn Ile Asn Asn Phe Ile Asn Gly Cys Ser Val Ser Tyr Leu Met
770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
Leu Ile Gly Ser Ala Glu Tyr Glu Lys Ser Lys Val Asn Lys Tyr Leu
            820                 825                 830
Lys Thr Ile Met Pro Phe Asp Leu Ser Ile Tyr Thr Asn Asp Thr Ile
        835                 840                 845
Leu Ile Glu Met Phe Asn Lys Tyr Asn Ser Glu Ile Leu Asn Asn Ile
850                 855                 860
Ile Leu Asn Leu Arg Tyr Lys Asp Asn Asn Leu Ile Asp Leu Ser Gly
865                 870                 875                 880
Tyr Gly Ala Lys Val Glu Val Tyr Asp Gly Val Glu Leu Asn Asp Lys
                885                 890                 895
Asn Gln Phe Lys Leu Thr Ser Ser Ala Asn Ser Lys Ile Arg Val Thr
            900                 905                 910
Gln Asn Gln Asn Ile Ile Phe Asn Ser Val Phe Leu Asp Phe Ser Val
        915                 920                 925
Ser Phe Trp Ile Arg Ile Pro Lys Tyr Lys Asn Asp Gly Ile Gln Asn
930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Arg Ile Ile Trp Thr Leu Ile
                965                 970                 975
Asp Ile Asn Gly Lys Thr Lys Ser Val Phe Phe Glu Tyr Asn Ile Arg
            980                 985                 990
Glu Asp Ile Ser Glu Tyr Ile Asn Arg Trp Phe Phe Val Thr Ile Thr
        995                 1000                1005
Asn Asn Leu Asn Asn Ala Lys Ile Tyr Ile Asn Gly Lys Leu Glu Ser
```

```
                1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
                1060                1065                1070

Glu Arg Tyr Lys Ile Gln Ser Tyr Ser Glu Tyr Leu Lys Asp Phe Trp
                1075                1080                1085

Gly Asn Pro Leu Met Tyr Asn Lys Glu Tyr Tyr Met Phe Asn Ala Gly
                1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
                1155                1160                1165

Leu Asp Phe Phe Asn Leu Asn Gln Glu Trp Arg Val Tyr Thr Tyr Lys
                1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
                1220                1225                1230

Asp Glu Ile Gly Leu Ile Gly Ile His Arg Phe Tyr Glu Ser Gly Ile
                1235                1240                1245

Val Phe Glu Glu Tyr Lys Asp Tyr Phe Cys Ile Ser Lys Trp Tyr Leu
                1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290

<210> SEQ ID NO 3
<211> LENGTH: 1291
<212> TYPE: PRT
<213> ORGANISM: Clostridium botulinum Serotype C1

<400> SEQUENCE: 3

Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
                 20                  25                  30

Pro Glu Lys Ala Phe Arg Ile Thr Gly Asn Ile Trp Val Ile Pro Asp
             35                  40                  45

Arg Phe Ser Arg Asn Ser Asn Pro Asn Leu Asn Lys Pro Pro Arg Val
         50                  55                  60

Thr Ser Pro Lys Ser Gly Tyr Tyr Asp Pro Asn Tyr Leu Ser Thr Asp
 65                  70                  75                  80

Ser Asp Lys Asp Pro Phe Leu Lys Glu Ile Ile Lys Leu Phe Lys Arg
                 85                  90                  95
```

-continued

```
Ile Asn Ser Arg Glu Ile Gly Glu Glu Leu Ile Tyr Arg Leu Ser Thr
            100                 105                 110

Asp Ile Pro Phe Pro Gly Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                    165                 170                 175

Asn Asn Thr Phe Ala Ala Gln Glu Gly Phe Gly Ala Leu Ser Ile Ile
                180                 185                 190

Ser Ile Ser Pro Arg Phe Met Leu Thr Tyr Ser Asn Ala Thr Asn Asp
            195                 200                 205

Val Gly Glu Gly Arg Phe Ser Lys Ser Glu Phe Cys Met Asp Pro Ile
        210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                    245                 250                 255

Phe Tyr Ser Gln Tyr Asn Val Lys Leu Glu Tyr Ala Glu Ile Tyr Ala
                260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
        290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                    325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                    405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
        450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                    485                 490                 495

Val Asp Gln Val Ile Leu Ser Lys Asn Thr Ser Glu His Gly Gln Leu
                500                 505                 510

Asp Leu Leu Tyr Pro Ser Ile Asp Ser Glu Ser Glu Ile Leu Pro Gly
```

-continued

```
            515                 520                 525
Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                    565                 570                 575

Lys Val Tyr Thr Tyr Phe Pro Thr Leu Ala Asn Lys Val Asn Ala Gly
                    580                 585                 590

Val Gln Gly Gly Leu Phe Leu Met Trp Ala Asn Asp Val Val Glu Asp
                595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                    645                 650                 655

Thr Ile Leu Leu Glu Ala Phe Pro Glu Phe Thr Ile Pro Ala Leu Gly
                    660                 665                 670

Ala Phe Val Ile Tyr Ser Lys Val Gln Glu Arg Asn Glu Ile Ile Lys
                675                 680                 685

Thr Ile Asp Asn Cys Leu Glu Gln Arg Ile Lys Arg Trp Lys Asp Ser
690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                    725                 730                 735

Ala Ile Lys Ala Lys Ile Asp Leu Glu Tyr Lys Lys Tyr Ser Gly Ser
                    740                 745                 750

Asp Lys Glu Asn Ile Lys Ser Gln Val Glu Asn Leu Lys Asn Ser Leu
                755                 760                 765

Asp Val Lys Ile Ser Glu Ala Met Asn Asn Ile Asn Lys Phe Ile Arg
                770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                    805                 810                 815

Leu Ile Asp Ser His Asn Ile Ile Leu Val Gly Glu Val Asp Lys Leu
                    820                 825                 830

Lys Ala Lys Val Asn Asn Ser Phe Gln Asn Thr Ile Pro Phe Asn Ile
                835                 840                 845

Phe Ser Tyr Thr Asn Asn Ser Leu Leu Lys Asp Ile Ile Asn Glu Tyr
                850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                    885                 890                 895

Gly Asp Val Gln Leu Asn Pro Ile Phe Pro Phe Asp Phe Lys Leu Gly
                    900                 905                 910

Ser Ser Gly Glu Asp Arg Gly Lys Val Ile Val Thr Gln Asn Glu Asn
                915                 920                 925

Ile Val Tyr Asn Ser Met Tyr Glu Ser Phe Ser Ile Ser Phe Trp Ile
                930                 935                 940
```

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
            965                 970                 975

Leu Val Phe Thr Leu Lys Gln Asn Glu Asp Ser Glu Gln Ser Ile Asn
        980                 985                 990

Phe Ser Tyr Asp Ile Ser Asn Asn Ala Pro Gly Tyr Asn Lys Trp Phe
    995                 1000                1005

Phe Val Thr Val Thr Asn Asn Met Met Gly Asn Met Lys Ile Tyr Ile
    1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
                1045                1050                1055

Gly Leu Ile Thr Ser Asp Ser Asp Asn Ile Asn Met Trp Ile Arg Asp
                1060                1065                1070

Phe Tyr Ile Phe Ala Lys Glu Leu Asp Gly Lys Asp Ile Asn Ile Leu
            1075                1080                1085

Phe Asn Ser Leu Gln Tyr Thr Asn Val Val Lys Asp Tyr Trp Gly Asn
    1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135

Arg Asn Asn Asn Asp Phe Asn Glu Gly Tyr Lys Ile Ile Ile Lys Arg
                1140                1145                1150

Ile Arg Gly Asn Thr Asn Asp Thr Arg Val Arg Gly Gly Asp Ile Leu
            1155                1160                1165

Tyr Phe Asp Met Thr Ile Asn Asn Lys Ala Tyr Asn Leu Phe Met Lys
    1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Tyr Ala Ser Gln Ile Phe
                1220                1225                1230

Lys Ser Asn Phe Asn Gly Glu Asn Ile Ser Gly Ile Cys Ser Ile Gly
            1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290

<210> SEQ ID NO 4
<211> LENGTH: 1276
<212> TYPE: PRT
<213> ORGANISM: Clostridium botulinum Serotype D

<400> SEQUENCE: 4

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr

```
                    20                  25                  30
Pro Val Lys Ala Phe Met Ile Thr Gln Asn Ile Trp Val Ile Pro Glu
            35                  40                  45
Arg Phe Ser Ser Asp Thr Asn Pro Ser Leu Ser Lys Pro Pro Arg Pro
        50                  55                  60
Thr Ser Lys Tyr Gln Ser Tyr Tyr Asp Pro Ser Tyr Leu Ser Thr Asp
65                  70                  75                  80
Glu Gln Lys Asp Thr Phe Leu Lys Gly Ile Ile Lys Leu Phe Lys Arg
                85                  90                  95
Ile Asn Glu Arg Asp Ile Gly Lys Lys Leu Ile Asn Tyr Leu Val Val
            100                 105                 110
Gly Ser Pro Phe Met Gly Asp Ser Ser Thr Pro Glu Asp Thr Phe Asp
        115                 120                 125
Phe Thr Arg His Thr Thr Asn Ile Ala Val Glu Lys Phe Glu Asn Gly
        130                 135                 140
Ser Trp Lys Val Thr Asn Ile Ile Thr Pro Ser Val Leu Ile Phe Gly
145                 150                 155                 160
Pro Leu Pro Asn Ile Leu Asp Tyr Thr Ala Ser Leu Thr Leu Gln Gly
                165                 170                 175
Gln Gln Ser Asn Pro Ser Phe Glu Gly Phe Gly Thr Leu Ser Ile Leu
            180                 185                 190
Lys Val Ala Pro Glu Phe Leu Leu Thr Phe Ser Asp Val Thr Ser Asn
        195                 200                 205
Gln Ser Ser Ala Val Leu Gly Lys Ser Ile Phe Cys Met Asp Pro Val
        210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
Phe Phe Ser Gln Asp Gly Pro Asn Val Gln Phe Glu Glu Leu Tyr Thr
            260                 265                 270
Phe Gly Gly Leu Asp Val Glu Ile Ile Pro Gln Ile Glu Arg Ser Gln
        275                 280                 285
Leu Arg Glu Lys Ala Leu Gly His Tyr Lys Asp Ile Ala Lys Arg Leu
        290                 295                 300
Asn Asn Ile Asn Lys Thr Ile Pro Ser Ser Trp Ile Ser Asn Ile Asp
305                 310                 315                 320
Lys Tyr Lys Lys Ile Phe Ser Glu Lys Tyr Asn Phe Asp Lys Asp Asn
                325                 330                 335
Thr Gly Asn Phe Val Val Asn Ile Asp Lys Phe Asn Ser Leu Tyr Ser
            340                 345                 350
Asp Leu Thr Asn Val Met Ser Glu Val Val Tyr Ser Ser Gln Tyr Asn
        355                 360                 365
Val Lys Asn Arg Thr His Tyr Phe Ser Arg His Tyr Leu Pro Val Phe
        370                 375                 380
Ala Asn Ile Leu Asp Asp Asn Ile Tyr Thr Ile Arg Asp Gly Phe Asn
385                 390                 395                 400
Leu Thr Asn Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
            420                 425                 430
Phe Thr Lys Val Cys Leu Arg Leu Thr Lys Asn Ser Arg Asp Asp Ser
        435                 440                 445
```

```
Thr Cys Ile Lys Val Lys Asn Arg Leu Pro Tyr Val Ala Asp Lys
    450             455             460

Asp Ser Ile Ser Gln Glu Ile Phe Glu Asn Lys Ile Ile Thr Asp Glu
465             470             475             480

Thr Asn Val Gln Asn Tyr Ser Asp Lys Phe Ser Leu Asp Glu Ser Ile
                485             490             495

Leu Asp Gly Gln Val Pro Ile Asn Pro Glu Ile Val Asp Pro Leu Leu
            500             505             510

Pro Asn Val Asn Met Glu Pro Leu Asn Leu Pro Gly Glu Glu Ile Val
        515             520             525

Phe Tyr Asp Asp Ile Thr Lys Tyr Val Asp Tyr Leu Asn Ser Tyr Tyr
    530             535             540

Tyr Leu Glu Ser Gln Lys Leu Ser Asn Asn Val Glu Asn Ile Thr Leu
545             550             555             560

Thr Thr Ser Val Glu Glu Ala Leu Gly Tyr Ser Asn Lys Ile Tyr Thr
                565             570             575

Phe Leu Pro Ser Leu Ala Glu Lys Val Asn Lys Gly Val Gln Ala Gly
            580             585             590

Leu Phe Leu Asn Trp Ala Asn Glu Val Val Glu Asp Phe Thr Thr Asn
        595             600             605

Ile Met Lys Lys Asp Thr Leu Asp Lys Ile Ser Asp Val Ser Val Ile
    610             615             620

Ile Pro Tyr Ile Gly Pro Ala Leu Asn Ile Gly Asn Ser Ala Leu Arg
625             630             635             640

Gly Asn Phe Asn Gln Ala Phe Ala Thr Ala Gly Val Ala Phe Leu Leu
                645             650             655

Glu Gly Phe Pro Glu Phe Thr Ile Pro Ala Leu Gly Val Phe Thr Phe
            660             665             670

Tyr Ser Ser Ile Gln Glu Arg Glu Lys Ile Ile Lys Thr Ile Glu Asn
        675             680             685

Cys Leu Glu Gln Arg Val Lys Arg Trp Lys Asp Ser Tyr Gln Trp Met
    690             695             700

Val Ser Asn Trp Leu Ser Arg Ile Thr Thr Gln Phe Asn His Ile Asn
705             710             715             720

Tyr Gln Met Tyr Asp Ser Leu Ser Tyr Gln Ala Asp Ala Ile Lys Ala
                725             730             735

Lys Ile Asp Leu Glu Tyr Lys Lys Tyr Ser Gly Ser Asp Lys Glu Asn
            740             745             750

Ile Lys Ser Gln Val Glu Asn Leu Lys Asn Ser Leu Asp Val Lys Ile
        755             760             765

Ser Glu Ala Met Asn Asn Ile Asn Lys Phe Ile Arg Glu Cys Ser Val
    770             775             780

Thr Tyr Leu Phe Lys Asn Met Leu Pro Lys Val Ile Asp Glu Leu Asn
785             790             795             800

Lys Phe Asp Leu Arg Thr Lys Thr Glu Leu Ile Asn Leu Ile Asp Ser
                805             810             815

His Asn Ile Ile Leu Val Gly Glu Val Asp Arg Leu Lys Ala Lys Val
            820             825             830

Asn Glu Ser Phe Glu Asn Thr Met Pro Phe Asn Ile Phe Ser Tyr Thr
        835             840             845

Asn Asn Ser Leu Leu Lys Asp Ile Ile Asn Glu Tyr Phe Asn Ser Ile
    850             855             860
```

```
Asn Asp Ser Lys Ile Leu Ser Leu Gln Asn Lys Asn Ala Leu Val
865                 870                 875                 880

Asp Thr Ser Gly Tyr Asn Ala Glu Val Arg Val Gly Asp Asn Val Gln
            885                 890                 895

Leu Asn Thr Ile Tyr Thr Asn Asp Phe Lys Leu Ser Ser Ser Gly Asp
        900                 905                 910

Lys Ile Ile Val Asn Leu Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
            965                 970                 975

Asp Val Asn Arg Lys Tyr Lys Ser Leu Ile Phe Asp Tyr Ser Glu Ser
        980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu Lys
1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
            1045                1050                1055

Ile Arg Asp Phe Asn Ile Phe Ser Lys Glu Leu Ser Asn Glu Asp Ile
        1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
    1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
            1125                1130                1135

Ile Lys Ser Val Ser Asp Lys Asn Pro Tyr Ser Arg Ile Leu Asn Gly
        1140                1145                1150

Asp Asn Ile Ile Leu His Met Leu Tyr Asn Ser Arg Lys Tyr Met Ile
        1155                1160                1165

Ile Arg Asp Thr Asp Thr Ile Tyr Ala Thr Gln Gly Gly Glu Cys Ser
    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
            1205                1210                1215

Cys Ser Gln Ile Phe Ser Ser Phe Arg Glu Asn Thr Met Leu Leu Ala
        1220                1225                1230

Asp Ile Tyr Lys Pro Trp Arg Phe Ser Phe Lys Asn Ala Tyr Thr Pro
        1235                1240                1245

Val Ala Val Thr Asn Tyr Glu Thr Lys Leu Leu Ser Thr Ser Ser Phe
    1250                1255                1260

Trp Lys Phe Ile Ser Arg Asp Pro Gly Trp Val Glu
1265                1270                1275
```

```
<210> SEQ ID NO 5
<211> LENGTH: 1252
<212> TYPE: PRT
<213> ORGANISM: Clostridium botulinum Serotype E

<400> SEQUENCE: 5
```

| | | | | | | | | | | | | | | | |
|---|---|---|---|---|---|---|---|---|---|---|---|---|---|---|---|
| Met | Pro | Lys | Ile | Asn | Ser | Phe | Asn | Tyr | Asn | Asp | Pro | Val | Asn | Asp | Arg |
| 1 | | | | 5 | | | | | 10 | | | | | 15 | |
| Thr | Ile | Leu | Tyr | Ile | Lys | Pro | Gly | Gly | Cys | Gln | Glu | Phe | Tyr | Lys | Ser |
| | | | 20 | | | | | 25 | | | | | 30 | | |
| Phe | Asn | Ile | Met | Lys | Asn | Ile | Trp | Ile | Ile | Pro | Glu | Arg | Asn | Val | Ile |
| | | 35 | | | | | 40 | | | | | 45 | | | |
| Gly | Thr | Thr | Pro | Gln | Asp | Phe | His | Pro | Pro | Thr | Ser | Leu | Lys | Asn | Gly |
| 50 | | | | | 55 | | | | | 60 | | | | | |
| Asp | Ser | Ser | Tyr | Tyr | Asp | Pro | Asn | Tyr | Leu | Gln | Ser | Asp | Glu | Glu | Lys |
| 65 | | | | 70 | | | | | 75 | | | | | 80 | |
| Asp | Arg | Phe | Leu | Lys | Ile | Val | Thr | Lys | Ile | Phe | Asn | Arg | Ile | Asn | Asn |
| | | | 85 | | | | | 90 | | | | | 95 | | |
| Asn | Leu | Ser | Gly | Gly | Ile | Leu | Leu | Glu | Glu | Leu | Ser | Lys | Ala | Asn | Pro |
| | | | 100 | | | | | 105 | | | | | 110 | | |
| Tyr | Leu | Gly | Asn | Asp | Asn | Thr | Pro | Asp | Asn | Gln | Phe | His | Ile | Gly | Asp |
| | | 115 | | | | | 120 | | | | | 125 | | | |
| Ala | Ser | Ala | Val | Glu | Ile | Lys | Phe | Ser | Asn | Gly | Ser | Gln | Asp | Ile | Leu |
| 130 | | | | | 135 | | | | | 140 | | | | | |
| Leu | Pro | Asn | Val | Ile | Ile | Met | Gly | Ala | Glu | Pro | Asp | Leu | Phe | Glu | Thr |
| 145 | | | | 150 | | | | | 155 | | | | | 160 | |
| Asn | Ser | Ser | Asn | Ile | Ser | Leu | Arg | Asn | Asn | Tyr | Met | Pro | Ser | Asn | His |
| | | | | 165 | | | | | 170 | | | | | 175 | |
| Gly | Phe | Gly | Ser | Ile | Ala | Ile | Val | Thr | Phe | Ser | Pro | Glu | Tyr | Ser | Phe |
| | | | 180 | | | | | 185 | | | | | 190 | | |
| Arg | Phe | Asn | Asp | Asn | Ser | Met | Asn | Glu | Phe | Ile | Gln | Asp | Pro | Ala | Leu |
| | | | 195 | | | | | 200 | | | | | 205 | | |
| Thr | Leu | Met | His | Glu | Leu | Ile | His | Ser | Leu | His | Gly | Leu | Tyr | Gly | Ala |
| 210 | | | | | 215 | | | | | 220 | | | | | |
| Lys | Gly | Ile | Thr | Thr | Lys | Tyr | Thr | Ile | Thr | Gln | Lys | Gln | Asn | Pro | Leu |
| 225 | | | | | 230 | | | | | 235 | | | | | 240 |
| Ile | Thr | Asn | Ile | Arg | Gly | Thr | Asn | Ile | Glu | Glu | Phe | Leu | Thr | Phe | Gly |
| | | | | 245 | | | | | 250 | | | | | 255 | |
| Gly | Thr | Asp | Leu | Asn | Ile | Ile | Thr | Ser | Ala | Gln | Ser | Asn | Asp | Ile | Tyr |
| | | | 260 | | | | | 265 | | | | | 270 | | |
| Thr | Asn | Leu | Leu | Ala | Asp | Tyr | Lys | Lys | Ile | Ala | Ser | Lys | Leu | Ser | Lys |
| | | | 275 | | | | | 280 | | | | | 285 | | |
| Val | Gln | Val | Ser | Asn | Pro | Leu | Leu | Asn | Pro | Tyr | Lys | Asp | Val | Phe | Glu |
| 290 | | | | | 295 | | | | | 300 | | | | | |
| Ala | Lys | Tyr | Gly | Leu | Asp | Lys | Asp | Ala | Ser | Gly | Ile | Tyr | Ser | Val | Asn |
| 305 | | | | | 310 | | | | | 315 | | | | | 320 |
| Ile | Asn | Lys | Phe | Asn | Asp | Ile | Phe | Lys | Lys | Leu | Tyr | Ser | Phe | Thr | Glu |
| | | | | 325 | | | | | 330 | | | | | 335 | |
| Phe | Asp | Leu | Ala | Thr | Lys | Phe | Gln | Val | Lys | Cys | Arg | Gln | Thr | Tyr | Ile |
| | | | 340 | | | | | 345 | | | | | 350 | | |
| Gly | Gln | Tyr | Lys | Tyr | Phe | Lys | Leu | Ser | Asn | Leu | Leu | Asn | Asp | Ser | Ile |
| | | | 355 | | | | | 360 | | | | | 365 | | |
| Tyr | Asn | Ile | Ser | Glu | Gly | Tyr | Asn | Ile | Asn | Asn | Leu | Lys | Val | Asn | Phe |
| | | | 370 | | | | | 375 | | | | | 380 | | |

```
Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
            405                 410                 415

Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
            450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
```

```
              805                 810                 815
Asp Thr Leu Asn Asn Ser Ile Pro Phe Lys Leu Ser Ser Tyr Thr Asp
                820                 825                 830
Asp Lys Ile Leu Ile Ser Tyr Phe Asn Lys Phe Phe Lys Arg Ile Lys
                835                 840                 845
Ser Ser Ser Val Leu Asn Met Arg Tyr Lys Asn Asp Lys Tyr Val Asp
    850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
                915                 920                 925
Lys Ile Val Asn Val Asn Asn Glu Tyr Thr Ile Ile Asn Cys Met Arg
                930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
                965                 970                 975
Tyr Gly Asn Ala Asn Gly Ile Ser Asp Tyr Ile Asn Lys Trp Ile Phe
                980                 985                 990
Val Thr Ile Thr Asn Asp Arg Leu Gly Asp Ser Lys Leu Tyr Ile Asn
                995                 1000                1005
Gly Asn Leu Ile Asp Gln Lys Ser Ile Leu Asn Leu Gly Asn Ile His
    1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                1045                1050                1055
Thr Glu Ile Gln Thr Leu Tyr Ser Asn Glu Pro Asn Thr Asn Ile Leu
                1060                1065                1070
Lys Asp Phe Trp Gly Asn Tyr Leu Leu Tyr Asp Lys Glu Tyr Tyr Leu
                1075                1080                1085
Leu Asn Val Leu Lys Pro Asn Asn Phe Ile Asp Arg Arg Lys Asp Ser
                1090                1095                1100
Thr Leu Ser Ile Asn Asn Ile Arg Ser Thr Ile Leu Leu Ala Asn Arg
1105                1110                1115                1120
Leu Tyr Ser Gly Ile Lys Val Lys Ile Gln Arg Val Asn Asn Ser Ser
                1125                1130                1135
Thr Asn Asp Asn Leu Val Arg Lys Asn Asp Gln Val Tyr Ile Asn Phe
                1140                1145                1150
Val Ala Ser Lys Thr His Leu Phe Pro Leu Tyr Ala Asp Thr Ala Thr
                1155                1160                1165
Thr Asn Lys Glu Lys Thr Ile Lys Ile Ser Ser Ser Gly Asn Arg Phe
                1170                1175                1180
Asn Gln Val Val Val Met Asn Ser Val Gly Asn Asn Cys Thr Met Asn
1185                1190                1195                1200
Phe Lys Asn Asn Asn Gly Asn Asn Ile Gly Leu Leu Gly Phe Lys Ala
                1205                1210                1215
Asp Thr Val Val Ala Ser Thr Trp Tyr Tyr Thr His Met Arg Asp His
                1220                1225                1230
```

```
Thr Asn Ser Asn Gly Cys Phe Trp Asn Phe Ile Ser Glu Glu His Gly
        1235                1240                1245

Trp Gln Glu Lys
    1250

<210> SEQ ID NO 6
<211> LENGTH: 1274
<212> TYPE: PRT
<213> ORGANISM: Clostridium botulinum Serotype F

<400> SEQUENCE: 6

Met Pro Val Ala Ile Asn Ser Phe Asn Tyr Asn Asp Pro Val Asn Asp
  1               5                  10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
            35                  40                  45

Arg Asn Thr Ile Gly Thr Asn Pro Ser Asp Phe Asp Pro Pro Ala Ser
        50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
```

```
              340                 345                 350
Glu Ser Asp Leu Ala Asn Lys Phe Lys Val Lys Cys Arg Asn Thr Tyr
            355                 360                 365
Phe Ile Lys Tyr Glu Phe Leu Lys Val Pro Asn Leu Leu Asp Asp Asp
            370                 375             380
Ile Tyr Thr Val Ser Glu Gly Phe Asn Ile Gly Asn Leu Ala Val Asn
385                 390                 395                 400
Asn Arg Gly Gln Ser Ile Lys Leu Asn Pro Lys Ile Ile Asp Ser Ile
                405                 410                 415
Pro Asp Lys Gly Leu Val Glu Lys Ile Val Lys Phe Cys Lys Ser Val
            420                 425                 430
Ile Pro Arg Lys Gly Thr Lys Ala Pro Pro Arg Leu Cys Ile Arg Val
        435                 440                 445
Asn Asn Ser Glu Leu Phe Phe Val Ala Ser Gly Ser Ser Tyr Asn Glu
        450                 455                 460
Asn Asp Ile Asn Thr Pro Lys Glu Ile Asp Asp Thr Thr Asn Leu Asn
465                 470                 475                 480
Asn Asn Tyr Arg Asn Asn Leu Asp Glu Val Ile Leu Asp Tyr Asn Ser
                485                 490                 495
Gln Thr Ile Pro Gln Ile Ser Asn Arg Thr Leu Asn Thr Leu Val Gln
                500                 505                 510
Asp Asn Ser Tyr Val Pro Arg Tyr Asp Ser Asn Gly Thr Ser Glu Ile
            515                 520                 525
Glu Glu Tyr Asp Val Val Asp Phe Asn Val Phe Phe Tyr Leu His Ala
            530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Asp Ile Phe Phe Ser Ser Glu
                565                 570                 575
Phe Ile Asp Thr Ile Asn Lys Pro Val Asn Ala Ala Leu Phe Ile Asp
            580                 585                 590
Trp Ile Ser Lys Val Ile Arg Asp Phe Thr Thr Glu Ala Thr Gln Lys
        595                 600                 605
Ser Thr Val Asp Lys Ile Ala Asp Ile Ser Leu Ile Val Pro Tyr Val
        610                 615                 620
Gly Leu Ala Leu Asn Ile Ile Ile Glu Ala Glu Lys Gly Asn Phe Glu
625                 630                 635                 640
Glu Ala Phe Glu Leu Leu Gly Val Gly Ile Leu Leu Glu Phe Val Pro
                645                 650                 655
Glu Leu Thr Ile Pro Val Ile Leu Val Phe Thr Ile Lys Ser Tyr Ile
                660                 665                 670
Asp Ser Tyr Glu Asn Lys Asn Lys Ala Ile Lys Ala Ile Asn Asn Ser
            675                 680                 685
Leu Ile Glu Arg Glu Ala Lys Trp Lys Glu Ile Tyr Ser Trp Ile Val
        690                 695                 700
Ser Asn Trp Leu Thr Arg Ile Asn Thr Gln Phe Asn Lys Arg Lys Glu
705                 710                 715                 720
Gln Met Tyr Gln Ala Leu Gln Asn Gln Val Asp Ala Ile Lys Thr Ala
                725                 730                 735
Ile Glu Tyr Lys Tyr Asn Asn Tyr Thr Ser Asp Glu Lys Asn Arg Leu
                740                 745                 750
Glu Ser Glu Tyr Asn Ile Asn Asn Ile Glu Glu Glu Leu Asn Lys Lys
            755                 760                 765
```

```
Val Ser Leu Ala Met Lys Asn Ile Glu Arg Phe Met Thr Glu Ser Ser
        770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
        835                 840                 845

Thr Asn Asp Lys Ile Leu Ile Ile Tyr Phe Asn Arg Leu Tyr Lys Lys
        850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
                900                 905                 910

Leu Ser Glu Val Asn Ile Ala Gln Asn Asn Asp Ile Ile Tyr Asn Ser
        915                 920                 925

Arg Tyr Gln Asn Phe Ser Ile Ser Phe Trp Val Arg Ile Pro Lys His
        930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                965                 970                 975

Cys Glu Ile Ile Trp Thr Leu Gln Asp Thr Ser Gly Asn Lys Glu Asn
                980                 985                 990

Leu Ile Phe Arg Tyr Glu Glu Leu Asn Arg Ile Ser Asn Tyr Ile Asn
        995                 1000                1005

Lys Trp Ile Phe Val Thr Ile Thr Asn Asn Arg Leu Gly Asn Ser Arg
        1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                1045                1050                1055

Asp Asp Glu Thr Tyr Val Gly Ile Arg Tyr Phe Lys Val Phe Asn Thr
                1060                1065                1070

Glu Leu Asp Lys Thr Glu Ile Glu Thr Leu Tyr Ser Asn Glu Pro Asp
                1075                1080                1085

Pro Ser Ile Leu Lys Asn Tyr Trp Gly Asn Tyr Leu Leu Tyr Asn Lys
        1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                1125                1130                1135

Ser Val Phe Leu Asn Tyr Lys Leu Tyr Glu Gly Val Glu Val Ile Ile
                1140                1145                1150

Arg Lys Asn Gly Pro Ile Asp Ile Ser Asn Thr Asp Asn Phe Val Arg
                1155                1160                1165

Lys Asn Asp Leu Ala Tyr Ile Asn Val Val Asp Arg Gly Val Glu Tyr
                1170                1175                1180
```

```
Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
            1205                1210                1215

Gly Asn Asn Cys Thr Met Asn Phe Gln Asn Asn Asn Gly Ser Asn Ile
        1220                1225                1230

Gly Leu Leu Gly Phe His Ser Asn Asn Leu Val Ala Ser Ser Trp Tyr
            1235                1240                1245

Tyr Asn Asn Ile Arg Arg Asn Thr Ser Ser Asn Gly Cys Phe Trp Ser
            1250                1255                1260

Ser Ile Ser Lys Glu Asn Gly Trp Lys Glu
1265                1270
```

<210> SEQ ID NO 7
<211> LENGTH: 1297
<212> TYPE: PRT
<213> ORGANISM: Clostridium botulinum Serotype G

<400> SEQUENCE: 7

```
Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
            275                 280                 285
```

```
Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
                340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
        370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
            435                 440                 445

Gln Cys Ile Ile Val Asn Asn Glu Asp Leu Phe Phe Ile Ala Asn Lys
        450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
            515                 520                 525

Gln Ser Ala Leu Lys Lys Ile Phe Val Asp Gly Asp Ser Leu Phe Glu
        530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Phe Thr Ser
            595                 600                 605

Glu Ser Thr Gln Lys Ser Thr Ile Asp Lys Val Ser Asp Val Ser Ile
610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
            660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
            690                 695                 700
```

-continued

```
Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
            725                 730                 735

Lys Ile Ile Glu Asp Gln Tyr Asn Arg Tyr Ser Glu Glu Asp Lys Met
            740                 745                 750

Asn Ile Asn Ile Asp Phe Asn Asp Ile Asp Phe Lys Leu Asn Gln Ser
            755                 760                 765

Ile Asn Leu Ala Ile Asn Asn Ile Asp Asp Phe Ile Asn Gln Cys Ser
770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
            805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
            885                 890                 895

Ile Phe Asn Asp Ile Gly Asn Gly Gln Phe Lys Leu Asn Asn Ser Glu
            900                 905                 910

Asn Ser Asn Ile Thr Ala His Gln Ser Lys Phe Val Val Tyr Asp Ser
            915                 920                 925

Met Phe Asp Asn Phe Ser Ile Asn Phe Trp Val Arg Thr Pro Lys Tyr
            930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
            965                 970                 975

Arg Ile Ile Trp Thr Leu Ile Asp Val Asn Ala Lys Ser Lys Ser Ile
            980                 985                 990

Phe Phe Glu Tyr Ser Ile Lys Asp Asn Ile Ser Asp Tyr Ile Asn Lys
            995                1000                1005

Trp Phe Ser Ile Thr Ile Thr Asn Asp Arg Leu Gly Asn Ala Asn Ile
           1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
           1045                1050                1055

Asp Thr Thr Lys Phe Val Trp Ile Lys Asp Phe Asn Ile Phe Gly Arg
           1060                1065                1070

Glu Leu Asn Ala Thr Glu Val Ser Ser Leu Tyr Trp Ile Gln Ser Ser
           1075                1080                1085

Thr Asn Thr Leu Lys Asp Phe Trp Gly Asn Pro Leu Arg Tyr Asp Thr
           1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
```

```
                        1125              1130              1135

Asn Ala Ala Ile Asn Tyr Gln Asn Leu Tyr Leu Gly Leu Arg Phe Ile
                1140              1145              1150

Ile Lys Lys Ala Ser Asn Ser Arg Asn Ile Asn Asn Asp Asn Ile Val
                1155              1160              1165

Arg Glu Gly Asp Tyr Ile Tyr Leu Asn Ile Asp Asn Ile Ser Asp Glu
                1170              1175              1180

Ser Tyr Arg Val Tyr Val Leu Val Asn Ser Lys Glu Ile Gln Thr Gln
1185              1190              1195              1200

Leu Phe Leu Ala Pro Ile Asn Asp Asp Pro Thr Phe Tyr Asp Val Leu
                1205              1210              1215

Gln Ile Lys Lys Tyr Tyr Glu Lys Thr Thr Tyr Asn Cys Gln Ile Leu
                1220              1225              1230

Cys Glu Lys Asp Thr Lys Thr Phe Gly Leu Phe Gly Ile Gly Lys Phe
                1235              1240              1245

Val Lys Asp Tyr Gly Tyr Val Trp Asp Thr Tyr Asp Asn Tyr Phe Cys
                1250              1255              1260

Ile Ser Gln Trp Tyr Leu Arg Arg Ile Ser Glu Asn Ile Asn Lys Leu
1265              1270              1275              1280

Arg Leu Gly Cys Asn Trp Gln Phe Ile Pro Val Asp Glu Gly Trp Thr
                1285              1290              1295

Glu

<210> SEQ ID NO 8
<211> LENGTH: 1315
<212> TYPE: PRT
<213> ORGANISM: Clostridium tetani

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190

Ile Met Gln Met Ala Phe Cys Pro Glu Tyr Val Pro Thr Phe Asp Asn
```

-continued

```
            195                 200                 205
Val Ile Glu Asn Ile Thr Ser Leu Thr Ile Gly Lys Ser Lys Tyr Phe
210                 215                 220

Gln Asp Pro Ala Leu Leu Met His Glu Leu Ile His Val Leu His
225                 230                 235                 240

Gly Leu Tyr Gly Met Gln Val Ser Ser His Glu Ile Ile Pro Ser Lys
                    245                 250                 255

Gln Glu Ile Tyr Met Gln His Thr Tyr Pro Ile Ser Ala Glu Glu Leu
                260                 265                 270

Phe Thr Phe Gly Gly Gln Asp Ala Asn Leu Ile Ser Ile Asp Ile Lys
                    275                 280                 285

Asn Asp Leu Tyr Glu Lys Thr Leu Asn Asp Tyr Lys Ala Ile Ala Asn
                290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
                    325                 330                 335

Asn Gly Gln Tyr Ile Val Asn Glu Asp Lys Phe Gln Ile Leu Tyr Asn
                340                 345                 350

Ser Ile Met Tyr Gly Phe Thr Glu Ile Glu Leu Gly Lys Lys Phe Asn
                355                 360                 365

Ile Lys Thr Arg Leu Ser Tyr Phe Ser Met Asn His Asp Pro Val Lys
370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                    405                 410                 415

Arg Val Asn Thr Asn Ala Phe Arg Asn Val Asp Gly Ser Gly Leu Val
                420                 425                 430

Ser Lys Leu Ile Gly Leu Cys Lys Lys Ile Ile Pro Pro Thr Asn Ile
                435                 440                 445

Arg Glu Asn Leu Tyr Asn Arg Thr Ala Ser Leu Thr Asp Leu Gly Gly
450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
                    485                 490                 495

Asn Thr Lys Asn Lys Pro Leu Asn Phe Asn Tyr Ser Leu Asp Lys Ile
                500                 505                 510

Ile Val Asp Tyr Asn Leu Gln Ser Lys Ile Thr Leu Pro Asn Asp Arg
                515                 520                 525

Thr Thr Pro Val Thr Lys Gly Ile Pro Tyr Ala Pro Glu Tyr Lys Ser
                530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                    565                 570                 575

Thr Met Thr Asn Ser Val Asp Asp Ala Leu Ile Asn Ser Thr Lys Ile
                580                 585                 590

Tyr Ser Tyr Phe Pro Ser Val Ile Ser Lys Val Asn Gln Gly Ala Gln
                595                 600                 605

Gly Ile Leu Phe Leu Gln Trp Val Arg Asp Ile Ile Asp Asp Phe Thr
                610                 615                 620
```

```
Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
            645                 650                 655

Tyr Glu Gly Asn Phe Ile Gly Ala Leu Glu Thr Thr Gly Val Val Leu
        660                 665                 670

Leu Leu Glu Tyr Ile Pro Glu Ile Thr Leu Pro Val Ile Ala Ala Leu
        675                 680                 685

Ser Ile Ala Glu Ser Ser Thr Gln Lys Glu Lys Ile Ile Lys Thr Ile
690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
                725                 730                 735

Arg Ser Tyr Gln Met Tyr Arg Ser Leu Glu Tyr Gln Val Asp Ala Ile
            740                 745                 750

Lys Lys Ile Ile Asp Tyr Glu Tyr Lys Ile Tyr Ser Gly Pro Asp Lys
        755                 760                 765

Glu Gln Ile Ala Asp Glu Ile Asn Asn Leu Lys Asn Lys Leu Glu Glu
    770                 775                 780

Lys Ala Asn Lys Ala Met Ile Asn Ile Asn Ile Phe Met Arg Glu Ser
785                 790                 795                 800

Ser Arg Ser Phe Leu Val Asn Gln Met Ile Asn Glu Ala Lys Lys Gln
                805                 810                 815

Leu Leu Glu Phe Asp Thr Gln Ser Lys Asn Ile Leu Met Gln Tyr Ile
            820                 825                 830

Lys Ala Asn Ser Lys Phe Ile Gly Ile Thr Glu Leu Lys Lys Leu Glu
        835                 840                 845

Ser Lys Ile Asn Lys Val Phe Ser Thr Pro Ile Pro Phe Ser Tyr Ser
850                 855                 860

Lys Asn Leu Asp Cys Trp Val Asp Asn Glu Glu Asp Ile Asp Val Ile
865                 870                 875                 880

Leu Lys Lys Ser Thr Ile Leu Asn Leu Asp Ile Asn Asn Asp Ile Ile
                885                 890                 895

Ser Asp Ile Ser Gly Phe Asn Ser Ser Val Ile Thr Tyr Pro Asp Ala
            900                 905                 910

Gln Leu Val Pro Gly Ile Asn Gly Lys Ala Ile His Leu Val Asn Asn
        915                 920                 925

Glu Ser Ser Glu Val Ile Val His Lys Ala Met Asp Ile Glu Tyr Asn
    930                 935                 940

Asp Met Phe Asn Asn Phe Thr Val Ser Phe Trp Leu Arg Val Pro Lys
945                 950                 955                 960

Val Ser Ala Ser His Leu Glu Gln Tyr Gly Thr Asn Glu Tyr Ser Ile
                965                 970                 975

Ile Ser Ser Met Lys Lys His Ser Leu Ser Ile Gly Ser Gly Trp Ser
            980                 985                 990

Val Ser Leu Lys Gly Asn Asn Leu Ile Trp Thr Leu Lys Asp Ser Ala
        995                 1000                1005

Gly Glu Val Arg Gln Ile Thr Phe Arg Asp Leu Pro Asp Lys Phe Asn
    1010                1015                1020

Ala Tyr Leu Ala Asn Lys Trp Val Phe Ile Thr Ile Thr Asn Asp Arg
1025                1030                1035                1040
```

```
Leu Ser Ser Ala Asn Leu Tyr Ile Asn Gly Val Met Gly Ser Ala
                1045                1050                1055

Glu Ile Thr Gly Leu Gly Ala Ile Arg Glu Asp Asn Asn Ile Thr Leu
    1060                1065                1070

Lys Leu Asp Arg Cys Asn Asn Asn Gln Tyr Val Ser Ile Asp Lys
        1075                1080                1085

Phe Arg Ile Phe Cys Lys Ala Leu Asn Pro Lys Glu Ile Glu Lys Leu
    1090                1095                1100

Tyr Thr Ser Tyr Leu Ser Ile Thr Phe Leu Arg Asp Phe Trp Gly Asn
1105                1110                1115                1120

Pro Leu Arg Tyr Asp Thr Glu Tyr Tyr Leu Ile Pro Val Ala Ser Ser
                1125                1130                1135

Ser Lys Asp Val Gln Leu Lys Asn Ile Thr Asp Tyr Met Tyr Leu Thr
                1140                1145                1150

Asn Ala Pro Ser Tyr Thr Asn Gly Lys Leu Asn Ile Tyr Tyr Arg Arg
                1155                1160                1165

Leu Tyr Asn Gly Leu Lys Phe Ile Ile Lys Arg Tyr Thr Pro Asn Asn
        1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
                1205                1210                1215

Ala Phe Asn Asn Leu Asp Arg Ile Leu Arg Val Gly Tyr Asn Ala Pro
                1220                1225                1230

Gly Ile Pro Leu Tyr Lys Lys Met Glu Ala Val Lys Leu Arg Asp Leu
                1235                1240                1245

Lys Thr Tyr Ser Val Gln Leu Lys Leu Tyr Asp Asp Lys Asn Ala Ser
        1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
                1285                1290                1295

Lys Ile Leu Gly Cys Asp Trp Tyr Phe Val Pro Thr Asp Glu Gly Trp
                1300                1305                1310

Thr Asn Asp
        1315

<210> SEQ ID NO 9
<211> LENGTH: 1268
<212> TYPE: PRT
<213> ORGANISM: Clostridium baratii

<400> SEQUENCE: 9

Met Pro Val Asn Ile Asn Asn Phe Asn Tyr Asn Asp Pro Ile Asn Asn
  1               5                  10                  15

Thr Thr Ile Leu Tyr Met Lys Met Pro Tyr Tyr Glu Asp Ser Asn Lys
             20                  25                  30

Tyr Tyr Lys Ala Phe Glu Ile Met Asp Asn Val Trp Ile Ile Pro Glu
         35                  40                  45

Arg Asn Ile Ile Gly Lys Lys Pro Ser Asp Phe Tyr Pro Pro Ile Ser
     50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                 85                  90                  95
```

```
Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
            260                 265                 270

Ser Thr Asn Gln Lys Ile Tyr Val Ile Leu Leu Ser Asn Tyr Thr Ala
        275                 280                 285

Ile Ala Ser Arg Leu Ser Gln Val Asn Arg Asn Asn Ser Ala Leu Asn
    290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Arg
        355                 360                 365

Leu Leu Asp Leu Leu Asp Asp Asn Ile Tyr Ser Ile Ser Glu Gly Phe
    370                 375                 380

Asn Ile Gly Ser Leu Arg Val Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
            420                 425                 430

Ser Leu Cys Ile Lys Val Asn Asn Arg Asp Leu Phe Phe Val Ala Ser
        435                 440                 445

Glu Ser Ser Tyr Asn Glu Asn Gly Ile Asn Ser Pro Lys Glu Ile Asp
    450                 455                 460

Asp Thr Thr Ile Thr Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
            500                 505                 510
```

```
Asn Gly Thr Ser Glu Ile Lys Glu Tyr Thr Val Asp Lys Leu Asn Val
            515                 520                 525

Phe Phe Tyr Leu Tyr Ala Gln Lys Ala Pro Glu Gly Glu Ser Ala Ile
530                 535                 540

Ser Leu Thr Ser Ser Val Asn Thr Ala Leu Leu Asp Ala Ser Lys Val
545                 550                 555                 560

Tyr Thr Phe Phe Ser Ser Asp Phe Ile Asn Thr Val Asn Lys Pro Val
                565                 570                 575

Gln Ala Ala Leu Phe Ile Ser Trp Ile Gln Val Ile Asn Asp Phe
                580                 585                 590

Thr Thr Glu Ala Thr Gln Lys Ser Thr Ile Asp Lys Ile Ala Asp Ile
                595                 600                 605

Ser Leu Ile Val Pro Tyr Val Gly Leu Ala Leu Asn Ile Gly Asn Glu
610                 615                 620

Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
                645                 650                 655

Phe Thr Ile Lys Ser Phe Ile Asn Ser Asp Asp Ser Lys Asn Lys Ile
                660                 665                 670

Ile Lys Ala Ile Asn Asn Ala Leu Arg Glu Arg Glu Leu Lys Trp Lys
                675                 680                 685

Glu Val Tyr Ser Trp Ile Val Ser Asn Trp Leu Thr Arg Ile Asn Thr
                690                 695                 700

Gln Phe Asn Lys Arg Lys Glu Gln Met Tyr Gln Ala Leu Gln Asn Gln
705                 710                 715                 720

Val Asp Gly Ile Lys Lys Ile Glu Tyr Lys Tyr Asn Asn Tyr Thr
                725                 730                 735

Leu Asp Glu Lys Asn Arg Leu Arg Ala Glu Tyr Asn Ile Tyr Ser Ile
                740                 745                 750

Lys Glu Glu Leu Asn Lys Lys Val Ser Leu Ala Met Gln Asn Ile Asp
                755                 760                 765

Arg Phe Leu Thr Glu Ser Ser Ile Ser Tyr Leu Met Lys Leu Ile Asn
770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Pro Glu Leu Asn Asn Leu Val Ser Asn Thr Leu Asn Asn Ser
                820                 825                 830

Ile Pro Phe Glu Leu Ser Glu Tyr Thr Asn Asp Lys Ile Leu Ile His
                835                 840                 845

Ile Leu Ile Arg Phe Tyr Lys Arg Ile Ile Asp Ser Ser Ile Leu Asn
850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
                900                 905                 910

Asn Asn Thr Ile Ile Tyr Asn Ser Arg Tyr Gln Asn Phe Ser Val Ser
                915                 920                 925

Phe Trp Val Arg Ile Pro Lys Tyr Asn Asn Leu Lys Asn Leu Asn Asn
```

```
                930             935             940
Glu Tyr Thr Ile Ile Asn Cys Met Arg Asn Asn Ser Gly Trp Lys
945             950             955             960

Ile Ser Leu Asn Tyr Asn Asn Ile Ile Trp Thr Leu Gln Asp Thr
                965             970             975

Gly Asn Asn Gln Lys Leu Val Phe Asn Tyr Thr Gln Met Ile Asp Ile
            980             985             990

Ser Asp Tyr Ile Asn Lys Trp Thr Phe Val Thr Ile Thr Asn Asn Arg
        995             1000            1005

Leu Gly His Ser Lys Leu Tyr Ile Asn Gly Asn Leu Thr Asp Gln Lys
    1010            1015            1020

Ser Ile Leu Asn Leu Gly Asn Ile His Val Asp Asp Asn Ile Leu Phe
1025            1030            1035            1040

Lys Ile Val Gly Cys Asn Asp Thr Arg Tyr Val Gly Ile Arg Tyr Phe
            1045            1050            1055

Lys Ile Phe Asn Met Glu Leu Asp Lys Thr Glu Ile Glu Thr Leu Tyr
            1060            1065            1070

His Ser Glu Pro Asp Ser Thr Ile Leu Lys Asp Phe Trp Gly Asn Tyr
        1075            1080            1085

Leu Leu Tyr Asn Lys Lys Tyr Tyr Leu Leu Asn Leu Leu Lys Pro Asn
    1090            1095            1100

Met Ser Val Thr Lys Asn Ser Asp Ile Leu Asn Ile Asn Arg Gln Arg
1105            1110            1115            1120

Gly Ile Tyr Ser Lys Thr Asn Ile Phe Ser Asn Ala Arg Leu Tyr Thr
            1125            1130            1135

Gly Val Glu Val Ile Ile Arg Lys Val Gly Ser Thr Asp Thr Ser Asn
            1140            1145            1150

Thr Asp Asn Phe Val Arg Lys Asn Asp Thr Val Tyr Ile Asn Val Val
        1155            1160            1165

Asp Gly Asn Ser Glu Tyr Gln Leu Tyr Ala Asp Val Ser Thr Ser Ala
    1170            1175            1180

Val Glu Lys Thr Ile Lys Leu Arg Arg Ile Ser Asn Ser Asn Tyr Asn
1185            1190            1195            1200

Ser Asn Gln Met Ile Ile Met Asp Ser Ile Gly Asp Asn Cys Thr Met
            1205            1210            1215

Asn Phe Lys Thr Asn Asn Gly Asn Asp Ile Gly Leu Leu Gly Phe His
            1220            1225            1230

Leu Asn Asn Leu Val Ala Ser Ser Trp Tyr Tyr Lys Asn Ile Arg Asn
        1235            1240            1245

Asn Thr Arg Asn Asn Gly Cys Phe Trp Ser Phe Ile Ser Lys Glu His
    1250            1255            1260

Gly Trp Gln Glu
1265

<210> SEQ ID NO 10
<211> LENGTH: 1251
<212> TYPE: PRT
<213> ORGANISM: Clostridium butyricum

<400> SEQUENCE: 10

Met Pro Thr Ile Asn Ser Phe Asn Tyr Asn Asp Pro Val Asn Asn Arg
1               5               10              15

Thr Ile Leu Tyr Ile Lys Pro Gly Gly Cys Gln Gln Phe Tyr Lys Ser
            20              25              30
```

```
Phe Asn Ile Met Lys Asn Ile Trp Ile Ile Pro Glu Arg Asn Val Ile
         35                  40                  45
Gly Thr Ile Pro Gln Asp Phe Leu Pro Pro Thr Ser Leu Lys Asn Gly
 50                  55                  60
Asp Ser Ser Tyr Tyr Asp Pro Asn Tyr Leu Gln Ser Asp Gln Glu Lys
 65                  70                  75                  80
Asp Lys Phe Leu Lys Ile Val Thr Lys Ile Phe Asn Arg Ile Asn Asp
                 85                  90                  95
Asn Leu Ser Gly Arg Ile Leu Leu Glu Glu Leu Ser Lys Ala Asn Pro
                100                 105                 110
Tyr Leu Gly Asn Asp Asn Thr Pro Asp Gly Asp Phe Ile Ile Asn Asp
                115                 120                 125
Ala Ser Ala Val Pro Ile Gln Phe Ser Asn Gly Ser Gln Ser Ile Leu
130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
                180                 185                 190
Arg Phe Lys Asp Asn Ser Met Asn Glu Phe Ile Gln Asp Pro Ala Leu
            195                 200                 205
Thr Leu Met His Glu Leu Ile His Ser Leu His Gly Leu Tyr Gly Ala
            210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
                260                 265                 270
Thr Asn Leu Leu Ala Asp Tyr Lys Lys Ile Ala Ser Lys Leu Ser Lys
            275                 280                 285
Val Gln Val Ser Asn Pro Leu Leu Asn Pro Tyr Lys Asp Val Phe Glu
            290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Asn Asn Leu Lys Val Asn Phe
            370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
            435                 440                 445
Asn Thr Pro Lys Glu Ile Asp Asp Thr Val Thr Ser Asn Asn Asn Tyr
```

```
            450                 455                 460
Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Gly Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Leu Lys Ala Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880
```

```
Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Tyr Asp Asn Lys Tyr
            900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
            930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
            995                 1000                1005

Gly Asn Leu Ile Asp Lys Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
            1045                1050                1055

Thr Glu Ile Gln Thr Leu Tyr Asn Asn Glu Pro Asn Ala Asn Ile Leu
            1060                1065                1070

Lys Asp Phe Trp Gly Asn Tyr Leu Leu Tyr Asp Lys Glu Tyr Tyr Leu
            1075                1080                1085

Leu Asn Val Leu Lys Pro Asn Asn Phe Ile Asn Arg Arg Thr Asp Ser
            1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
            1125                1130                1135

Thr Asn Asp Asn Leu Val Arg Lys Asn Asp Gln Val Tyr Ile Asn Phe
            1140                1145                1150

Val Ala Ser Lys Thr His Leu Leu Pro Leu Tyr Ala Asp Thr Ala Thr
            1155                1160                1165

Thr Asn Lys Glu Lys Thr Ile Lys Ile Ser Ser Ser Gly Asn Arg Phe
            1170                1175                1180

Asn Gln Val Val Val Met Asn Ser Val Gly Asn Cys Thr Met Asn Phe
1185                1190                1195                1200

Lys Asn Asn Asn Gly Asn Asn Ile Gly Leu Leu Gly Phe Lys Ala Asp
            1205                1210                1215

Thr Val Val Ala Ser Thr Trp Tyr Tyr Thr His Met Arg Asp Asn Thr
            1220                1225                1230

Asn Ser Asn Gly Phe Phe Trp Asn Phe Ile Ser Glu Glu His Gly Trp
            1235                1240                1245

Gln Glu Lys
    1250

<210> SEQ ID NO 11
<211> LENGTH: 1035
<212> TYPE: PRT
<213> ORGANISM: Bos taurus
```

<400> SEQUENCE: 11

```
Met Gly Ser Lys Arg Ser Val Pro Ser Arg His Arg Ser Leu Thr Thr
 1               5                  10                  15
Tyr Glu Val Met Phe Ala Val Leu Phe Val Ile Leu Val Ala Leu Cys
             20                  25                  30
Ala Gly Leu Ile Ala Val Ser Trp Leu Ser Ile Gln Gly Ser Val Lys
         35                  40                  45
Asp Ala Ala Phe Gly Lys Ser His Glu Ala Arg Gly Thr Leu Lys Ile
     50                  55                  60
Ile Ser Gly Ala Thr Tyr Asn Pro His Leu Gln Asp Lys Leu Ser Val
 65                  70                  75                  80
Asp Phe Lys Val Leu Ala Phe Asp Ile Gln Gln Met Ile Asp Asp Ile
                 85                  90                  95
Phe Gln Ser Ser Asn Leu Lys Asn Glu Tyr Lys Asn Ser Arg Val Leu
            100                 105                 110
Gln Phe Glu Asn Gly Ser Ile Ile Val Ile Phe Asp Leu Leu Phe Asp
        115                 120                 125
Gln Trp Val Ser Asp Lys Asn Val Lys Glu Glu Leu Ile Gln Gly Ile
    130                 135                 140
Glu Ala Asn Lys Ser Ser Gln Leu Val Thr Phe His Ile Asp Leu Asn
145                 150                 155                 160
Ser Ile Asp Ile Thr Ala Ser Leu Glu Asn Phe Ser Thr Ile Ser Pro
                165                 170                 175
Ala Thr Thr Ser Glu Lys Leu Thr Thr Ser Ile Pro Leu Ala Thr Pro
            180                 185                 190
Gly Asn Val Ser Ile Glu Cys Pro Pro Asp Ser Arg Leu Cys Ala Asp
        195                 200                 205
Ala Leu Lys Cys Ile Ala Ile Asp Leu Phe Cys Asp Gly Glu Leu Asn
    210                 215                 220
Cys Pro Asp Gly Ser Asp Glu Asp Asn Lys Thr Cys Ala Thr Ala Cys
225                 230                 235                 240
Asp Gly Arg Phe Leu Leu Thr Gly Ser Ser Gly Ser Phe Glu Ala Leu
                245                 250                 255
His Tyr Pro Lys Pro Ser Asn Asn Thr Ser Ala Val Cys Arg Trp Ile
            260                 265                 270
Ile Arg Val Asn Gln Gly Leu Ser Ile Gln Leu Asn Phe Asp Tyr Phe
        275                 280                 285
Asn Thr Tyr Tyr Ala Asp Val Leu Asn Ile Tyr Glu Gly Met Gly Ser
    290                 295                 300
Ser Lys Ile Leu Arg Ala Ser Leu Trp Ser Asn Asn Pro Gly Ile Ile
305                 310                 315                 320
Arg Ile Phe Ser Asn Gln Val Thr Ala Thr Phe Leu Ile Gln Ser Asp
                325                 330                 335
Glu Ser Asp Tyr Ile Gly Phe Lys Val Thr Tyr Thr Ala Phe Asn Ser
            340                 345                 350
Lys Glu Leu Asn Asn Tyr Glu Lys Ile Asn Cys Asn Phe Glu Asp Gly
        355                 360                 365
Phe Cys Phe Trp Ile Gln Asp Leu Asn Asp Asn Glu Trp Glu Arg
    370                 375                 380
Thr Gln Gly Ser Thr Phe Pro Pro Ser Thr Gly Pro Thr Phe Asp His
385                 390                 395                 400
Thr Phe Gly Asn Glu Ser Gly Phe Tyr Ile Ser Thr Pro Thr Gly Pro
                405                 410                 415
```

```
Gly Gly Arg Arg Glu Arg Val Gly Leu Leu Thr Leu Pro Leu Asp Pro
            420                 425                 430

Thr Pro Glu Gln Ala Cys Leu Ser Phe Trp Tyr Tyr Met Tyr Gly Glu
            435                 440                 445

Asn Val Tyr Lys Leu Ser Ile Asn Ile Ser Ser Asp Gln Asn Met Glu
450                 455                 460

Lys Thr Ile Phe Gln Lys Glu Gly Asn Tyr Gly Gln Asn Trp Asn Tyr
465                 470                 475                 480

Gly Gln Val Thr Leu Asn Glu Thr Val Glu Phe Lys Val Ser Phe Tyr
                485                 490                 495

Gly Phe Lys Asn Gln Ile Leu Ser Asp Ile Ala Leu Asp Asp Ile Ser
            500                 505                 510

Leu Thr Tyr Gly Ile Cys Asn Val Ser Val Tyr Pro Glu Pro Thr Leu
            515                 520                 525

Val Pro Thr Pro Pro Glu Leu Pro Thr Asp Cys Gly Gly Pro His
    530                 535                 540

Asp Leu Trp Glu Pro Asn Thr Thr Phe Thr Ser Ile Asn Phe Pro Asn
545                 550                 555                 560

Ser Tyr Pro Asn Gln Ala Phe Cys Ile Trp Asn Leu Asn Ala Gln Lys
                565                 570                 575

Gly Lys Asn Ile Gln Leu His Phe Gln Glu Phe Asp Leu Glu Asn Ile
            580                 585                 590

Ala Asp Val Val Glu Ile Arg Asp Gly Glu Gly Asp Ser Leu Phe
            595                 600                 605

Leu Ala Val Tyr Thr Gly Pro Gly Pro Val Asn Asp Val Phe Ser Thr
            610                 615                 620

Thr Asn Arg Met Thr Val Leu Phe Ile Thr Asp Asn Met Leu Ala Lys
625                 630                 635                 640

Gln Gly Phe Lys Ala Asn Phe Thr Thr Gly Tyr Gly Leu Gly Ile Pro
                645                 650                 655

Glu Pro Cys Lys Glu Asp Asn Phe Gln Cys Lys Asp Gly Glu Cys Ile
            660                 665                 670

Pro Leu Val Asn Leu Cys Asp Gly Phe Pro His Cys Lys Asp Gly Ser
            675                 680                 685

Asp Glu Ala His Cys Val Arg Leu Phe Asn Gly Thr Thr Asp Ser Ser
690                 695                 700

Gly Leu Val Gln Phe Arg Ile Gln Ser Ile Trp His Val Ala Cys Ala
705                 710                 715                 720

Glu Asn Trp Thr Thr Gln Ile Ser Asp Asp Val Cys Gln Leu Leu Gly
                725                 730                 735

Leu Gly Thr Gly Asn Ser Ser Val Pro Thr Phe Ser Thr Gly Gly Gly
            740                 745                 750

Pro Tyr Val Asn Leu Asn Thr Ala Pro Asn Gly Ser Leu Ile Leu Thr
            755                 760                 765

Pro Ser Gln Gln Cys Leu Glu Asp Ser Leu Ile Leu Leu Gln Cys Asn
            770                 775                 780

Tyr Lys Ser Cys Gly Lys Lys Leu Val Thr Gln Glu Val Ser Pro Lys
785                 790                 795                 800

Ile Val Gly Gly Ser Asp Ser Arg Glu Gly Ala Trp Pro Trp Val Val
                805                 810                 815

Ala Leu Tyr Phe Asp Asp Gln Gln Val Cys Gly Ala Ser Leu Val Ser
            820                 825                 830
```

Arg Asp Trp Leu Val Ser Ala Ala His Cys Val Tyr Gly Arg Asn Met
            835                 840                 845

Glu Pro Ser Lys Trp Lys Ala Val Leu Gly Leu His Met Ala Ser Asn
850                 855                 860

Leu Thr Ser Pro Gln Ile Glu Thr Arg Leu Ile Asp Gln Ile Val Ile
865                 870                 875                 880

Asn Pro His Tyr Asn Lys Arg Lys Asn Asn Asp Ile Ala Met Met
                885                 890                 895

His Leu Glu Met Lys Val Asn Tyr Thr Asp Tyr Ile Gln Pro Ile Cys
            900                 905                 910

Leu Pro Glu Glu Asn Gln Val Phe Pro Pro Gly Arg Ile Cys Ser Ile
            915                 920                 925

Ala Gly Trp Gly Ala Leu Ile Tyr Gln Gly Ser Thr Ala Asp Val Leu
930                 935                 940

Gln Glu Ala Asp Val Pro Leu Leu Ser Asn Glu Lys Cys Gln Gln Gln
945                 950                 955                 960

Met Pro Glu Tyr Asn Ile Thr Glu Asn Met Val Cys Ala Gly Tyr Glu
                965                 970                 975

Ala Gly Gly Val Asp Ser Cys Gln Gly Asp Ser Gly Gly Pro Leu Met
            980                 985                 990

Cys Gln Glu Asn Asn Arg Trp Leu Leu Ala Gly Val Thr Ser Phe Gly
995                 1000                1005

Tyr Gln Cys Ala Leu Pro Asn Arg Pro Gly Val Tyr Ala Arg Val Pro
        1010                1015                1020

Arg Phe Thr Glu Trp Ile Gln Ser Phe Leu His
1025                1030                1035

<210> SEQ ID NO 12
<211> LENGTH: 183
<212> TYPE: PRT
<213> ORGANISM: Human rhinovirus C

<400> SEQUENCE: 12

Gly Pro Glu His Glu Phe Leu Asn Ala Leu Ile Arg Arg Asn Cys His
1               5                   10                  15

Ile Ile Thr Thr Asp Lys Gly Glu Phe Asn Leu Leu Gly Ile Tyr Ser
            20                  25                  30

Asn Cys Ala Val Val Pro Thr His Ala Glu Pro Gly Asp Val Val Asp
        35                  40                  45

Ile Asp Gly Arg Leu Val Arg Val Leu Lys Gln Gln Val Leu Thr Asp
    50                  55                  60

Met Asn Asp Val Asp Thr Glu Val Thr Val Leu Trp Leu Asp Gln Asn
65                  70                  75                  80

Glu Lys Phe Arg Asp Ile Arg Arg Phe Ile Pro Glu His Gln Gln Asp
                85                  90                  95

Trp His Asn Ile His Leu Ala Thr Asn Val Thr Lys Phe Pro Met Leu
            100                 105                 110

Asn Val Glu Val Gly His Thr Val Pro Tyr Gly Glu Ile Asn Leu Ser
        115                 120                 125

Gly Asn Ala Thr Cys Arg Leu Tyr Lys Tyr Asp Tyr Pro Thr Gln Pro
    130                 135                 140

Gly Gln Cys Gly Ala Val Leu Ala Asn Thr Gly Asn Ile Ile Gly Ile
145                 150                 155                 160

His Val Gly Gly Asn Gly Arg Val Gly Tyr Ala Ala Ala Leu Leu Arg
                165                 170                 175

Lys Tyr Phe Ala Glu Glu Gln
            180

<210> SEQ ID NO 13
<211> LENGTH: 183
<212> TYPE: PRT
<213> ORGANISM: Human enterovirus 71

<400> SEQUENCE: 13

Gly Pro Ser Leu Asp Phe Ala Leu Ser Leu Leu Arg Arg Asn Val Arg
  1               5                  10                  15

Gln Val Gln Thr Asp Gln Gly His Phe Thr Met Leu Gly Val Arg Asp
             20                  25                  30

Arg Leu Ala Val Leu Pro Arg His Ser Gln Pro Gly Lys Thr Ile Trp
         35                  40                  45

Ile Glu His Lys Leu Val Asn Val Leu Asp Ala Val Glu Leu Val Asp
     50                  55                  60

Glu Gln Gly Val Asn Leu Glu Leu Thr Leu Ile Thr Leu Asp Thr Asn
 65                  70                  75                  80

Glu Lys Phe Arg Asp Ile Thr Lys Phe Ile Pro Glu Asn Ile Ser Thr
                 85                  90                  95

Ala Ser Asp Ala Thr Leu Val Ile Asn Thr Glu His Met Pro Ser Met
            100                 105                 110

Phe Val Pro Val Gly Asp Val Gln Tyr Gly Phe Leu Asn Leu Ser
        115                 120                 125

Gly Lys Pro Thr His Arg Thr Met Met Tyr Asn Phe Pro Thr Lys Ala
145                 150                 155                 160

Gly Gln Cys Gly Gly Val Val Thr Ser Val Gly Lys Val Ile Gly Ile
145                 150                 155                 160

His Ile Gly Gly Asn Gly Arg Gln Gly Phe Cys Ala Gly Leu Lys Arg
                165                 170                 175

Ser Tyr Phe Ala Ser Glu Gln
            180

<210> SEQ ID NO 14
<211> LENGTH: 3054
<212> TYPE: PRT
<213> ORGANISM: Potyvirus

<400> SEQUENCE: 14

Met Ala Leu Ile Phe Gly Thr Val Asn Ala Asn Ile Leu Lys Glu Val
  1               5                  10                  15

Phe Gly Gly Ala Arg Met Ala Cys Val Thr Ser Ala His Met Ala Gly
             20                  25                  30

Ala Asn Gly Ser Ile Leu Lys Lys Ala Glu Thr Ser Arg Ala Ile
         35                  40                  45

Met His Lys Pro Val Ile Phe Gly Glu Asp Tyr Ile Thr Glu Ala Asp
     50                  55                  60

Leu Pro Tyr Thr Pro Leu His Leu Glu Val Asp Ala Glu Met Glu Arg
 65                  70                  75                  80

Met Tyr Tyr Leu Gly Arg Arg Ala Leu Thr His Gly Lys Arg Arg Lys
                 85                  90                  95

Val Ser Val Asn Asn Lys Arg Asn Arg Arg Lys Val Ala Lys Thr
            100                 105                 110

Tyr Val Gly Arg Asp Ser Ile Val Glu Lys Ile Val Val Pro His Thr
        115                 120                 125

```
Glu Arg Lys Val Asp Thr Thr Ala Ala Val Glu Asp Ile Cys Asn Glu
            130                 135                 140

Ala Thr Thr Gln Leu Val His Asn Ser Met Pro Lys Arg Lys Lys Gln
145                 150                 155                 160

Lys Asn Phe Leu Pro Ala Thr Ser Leu Ser Asn Val Tyr Ala Gln Thr
                165                 170                 175

Trp Ser Ile Val Arg Lys Arg His Met Gln Val Glu Ile Ile Ser Lys
            180                 185                 190

Lys Ser Val Arg Ala Arg Val Lys Arg Phe Glu Gly Ser Val Gln Leu
        195                 200                 205

Phe Ala Ser Val Arg His Met Tyr Gly Glu Arg Lys Val Asp Leu
210                 215                 220

Arg Ile Asp Asn Trp Gln Gln Glu Thr Leu Leu Asp Leu Ala Lys Arg
225                 230                 235                 240

Phe Lys Asn Glu Arg Val Asp Gln Ser Lys Leu Thr Phe Gly Ser Ser
                245                 250                 255

Gly Leu Val Leu Arg Gln Gly Ser Tyr Gly Pro Ala His Trp Tyr Arg
            260                 265                 270

His Gly Met Phe Ile Val Arg Gly Arg Ser Asp Gly Met Leu Val Asp
        275                 280                 285

Ala Arg Ala Lys Val Thr Phe Ala Val Cys His Ser Met Thr His Tyr
290                 295                 300

Ser Asp Lys Ser Ile Ser Glu Ala Phe Phe Ile Pro Tyr Ser Lys Lys
305                 310                 315                 320

Phe Leu Glu Leu Arg Pro Asp Gly Ile Ser His Glu Cys Thr Arg Gly
                325                 330                 335

Val Ser Val Glu Arg Cys Gly Val Ala Ala Ile Leu Thr Gln Ala
            340                 345                 350

Leu Ser Pro Cys Gly Lys Ile Thr Cys Lys Arg Cys Met Val Glu Thr
        355                 360                 365

Pro Asp Ile Val Glu Gly Glu Ser Gly Glu Ser Val Thr Asn Gln Gly
370                 375                 380

Lys Leu Leu Ala Met Leu Lys Glu Gln Tyr Pro Asp Phe Pro Met Ala
385                 390                 395                 400

Glu Lys Leu Leu Thr Arg Phe Leu Gln Gln Lys Ser Leu Val Asn Thr
                405                 410                 415

Asn Leu Thr Ala Cys Val Ser Val Lys Gln Leu Ile Gly Asp Arg Lys
            420                 425                 430

Gln Ala Pro Phe Thr His Val Leu Ala Val Ser Glu Ile Leu Phe Lys
        435                 440                 445

Gly Asn Lys Leu Thr Gly Ala Asp Leu Glu Glu Ala Ser Thr His Met
450                 455                 460

Leu Glu Ile Ala Arg Phe Leu Asn Asn Arg Thr Glu Asn Met Arg Ile
465                 470                 475                 480

Gly His Leu Gly Ser Phe Arg Asn Lys Ile Ser Ser Lys Ala His Val
                485                 490                 495

Asn Asn Ala Leu Met Cys Asp Asn Gln Leu Asp Gln Asn Gly Asn Phe
            500                 505                 510

Ile Trp Gly Leu Arg Gly Ala His Ala Lys Arg Phe Leu Lys Gly Phe
        515                 520                 525

Phe Thr Glu Ile Asp Pro Asn Glu Gly Tyr Asp Lys Tyr Val Ile Arg
530                 535                 540
```

Lys His Ile Arg Gly Ser Arg Lys Leu Ala Ile Gly Asn Leu Ile Met
545                     550                 555                 560

Ser Thr Asp Phe Gln Thr Leu Arg Gln Gln Ile Gln Gly Glu Thr Ile
                565                 570                 575

Glu Arg Lys Glu Ile Gly Asn His Cys Ile Ser Met Arg Asn Gly Asn
            580                 585                 590

Tyr Val Tyr Pro Cys Cys Val Thr Leu Glu Asp Gly Lys Ala Gln
            595                 600                 605

Tyr Ser Asp Leu Lys His Pro Thr Lys Arg His Leu Val Ile Gly Asn
        610                 615                 620

Ser Gly Asp Ser Lys Tyr Leu Asp Leu Pro Val Leu Asn Glu Glu Lys
625                 630                 635                 640

Met Tyr Ile Ala Asn Glu Gly Tyr Cys Tyr Met Asn Ile Phe Phe Ala
                645                 650                 655

Leu Leu Val Asn Val Lys Glu Glu Asp Ala Lys Asp Phe Thr Lys Phe
                660                 665                 670

Ile Arg Asp Thr Ile Val Pro Lys Leu Gly Ala Trp Pro Thr Met Gln
            675                 680                 685

Asp Val Ala Thr Ala Cys Tyr Leu Leu Ser Ile Leu Tyr Pro Asp Val
            690                 695                 700

Leu Arg Ala Glu Leu Pro Arg Ile Leu Val Asp His Asp Asn Lys Thr
705                 710                 715                 720

Met His Val Leu Asp Ser Tyr Gly Ser Arg Thr Thr Gly Tyr His Met
                725                 730                 735

Leu Lys Met Asn Thr Thr Ser Gln Leu Ile Glu Phe Val His Ser Gly
                740                 745                 750

Leu Glu Ser Glu Met Lys Thr Tyr Asn Val Gly Gly Met Asn Arg Asp
                755                 760                 765

Val Val Thr Gln Gly Ala Ile Glu Met Leu Ile Lys Ser Ile Tyr Lys
            770                 775                 780

Pro His Leu Met Lys Gln Leu Leu Glu Glu Pro Tyr Ile Ile Val
785                 790                 795                 800

Leu Ala Ile Val Ser Pro Ser Ile Leu Ile Ala Met Tyr Asn Ser Gly
                805                 810                 815

Thr Phe Glu Gln Ala Leu Gln Met Trp Leu Pro Asn Thr Met Arg Leu
                820                 825                 830

Ala Asn Leu Ala Ala Ile Leu Ser Ala Leu Ala Gln Lys Leu Thr Leu
                835                 840                 845

Ala Asp Leu Phe Gln Gln Arg Asn Leu Ile Asn Glu Tyr Ala Gln
850                 855                 860

Val Ile Leu Asp Asn Leu Ile Asp Gly Val Arg Val Asn His Ser Leu
865                 870                 875                 880

Ser Leu Ala Met Glu Ile Val Thr Ile Lys Leu Ala Thr Gln Glu Met
                885                 890                 895

Asp Met Ala Leu Arg Glu Gly Tyr Ala Val Thr Ser Glu Lys Val
                900                 905                 910

His Glu Met Leu Glu Lys Asn Tyr Val Lys Ala Leu Lys Asp Ala Trp
                915                 920                 925

Asp Glu Leu Thr Trp Leu Glu Lys Phe Ser Ala Ile Arg His Ser Arg
                930                 935                 940

Lys Leu Leu Lys Phe Gly Arg Lys Pro Leu Ile Met Lys Asn Thr Val
945                 950                 955                 960

Asp Cys Gly Gly His Ile Asp Leu Ser Val Lys Ser Leu Phe Lys Phe

```
                965                 970                 975
His Leu Glu Leu Leu Lys Gly Thr Ile Ser Arg Ala Val Asn Gly Gly
            980                 985                 990

Ala Arg Lys Val Arg Val Ala Lys Asn Ala Met Thr Lys Gly Val Phe
            995                 1000                1005

Leu Lys Ile Tyr Ser Met Leu Pro Asp Val Tyr Lys Phe Ile Thr Val
    1010                1015                1020

Ser Ser Val Leu Ser Leu Leu Leu Thr Phe Leu Phe Gln Ile Asp Cys
1025                1030                1035                1040

Met Ile Arg Ala His Arg Glu Ala Lys Val Ala Ala Gln Leu Gln Lys
            1045                1050                1055

Glu Ser Glu Trp Asp Asn Ile Ile Asn Arg Thr Phe Gln Tyr Ser Lys
            1060                1065                1070

Leu Glu Asn Pro Ile Gly Tyr Arg Ser Thr Ala Glu Glu Arg Leu Gln
            1075                1080                1085

Ser Glu His Pro Glu Ala Phe Glu Tyr Lys Phe Cys Ile Gly Lys
            1090                1095                1100

Glu Asp Leu Val Glu Gln Ala Lys Gln Pro Glu Ile Ala Tyr Phe Glu
1105                1110                1115                1120

Lys Ile Ile Ala Phe Ile Thr Leu Val Leu Met Ala Phe Asp Ala Glu
            1125                1130                1135

Arg Ser Asp Gly Val Phe Lys Ile Leu Asn Lys Phe Lys Gly Ile Leu
            1140                1145                1150

Ser Ser Thr Glu Arg Glu Ile Ile Tyr Thr Gln Ser Leu Asp Asp Tyr
            1155                1160                1165

Val Thr Thr Phe Asp Asp Asn Met Thr Ile Asn Leu Glu Leu Asn Met
            1170                1175                1180

Asp Glu Leu His Lys Thr Ser Leu Pro Gly Val Thr Phe Lys Gln Trp
1185                1190                1195                1200

Trp Asn Asn Gln Ile Ser Arg Gly Asn Val Lys Pro His Tyr Arg Thr
            1205                1210                1215

Glu Gly His Phe Met Glu Phe Thr Arg Asp Thr Ala Ala Ser Val Ala
            1220                1225                1230

Ser Glu Ile Ser His Ser Pro Ala Arg Asp Phe Leu Val Arg Gly Ala
            1235                1240                1245

Val Gly Ser Gly Lys Ser Thr Gly Leu Pro Tyr His Leu Ser Lys Arg
            1250                1255                1260

Gly Arg Val Leu Met Leu Glu Pro Thr Arg Pro Leu Thr Asp Asn Met
1265                1270                1275                1280

His Lys Gln Leu Arg Ser Glu Pro Phe Asn Cys Phe Pro Thr Leu Arg
            1285                1290                1295

Met Arg Gly Lys Ser Thr Phe Gly Ser Ser Pro Ile Thr Val Met Thr
            1300                1305                1310

Ser Gly Phe Ala Leu His His Phe Ala Arg Asn Ile Ala Glu Val Lys
            1315                1320                1325

Thr Tyr Asp Phe Val Ile Ile Asp Glu Cys His Val Asn Asp Ala Ser
            1330                1335                1340

Ala Ile Ala Phe Arg Asn Leu Leu Phe Glu His Glu Phe Glu Gly Lys
1345                1350                1355                1360

Val Leu Lys Val Ser Ala Thr Pro Pro Gly Arg Glu Val Glu Phe Thr
            1365                1370                1375

Thr Gln Phe Pro Val Lys Leu Lys Ile Glu Glu Ala Leu Ser Phe Gln
            1380                1385                1390
```

```
Glu Phe Val Ser Leu Gln Gly Thr Gly Ala Asn Ala Asp Val Ile Ser
            1395                1400                1405

Cys Gly Asp Asn Ile Leu Val Tyr Val Ala Ser Tyr Asn Asp Val Asp
            1410                1415                1420

Ser Leu Gly Lys Leu Leu Val Gln Lys Gly Tyr Lys Val Ser Lys Ile
1425                1430                1435                1440

Asp Gly Arg Thr Met Lys Ser Gly Gly Thr Glu Ile Ile Thr Glu Gly
            1445                1450                1455

Thr Ser Val Lys Lys His Phe Ile Val Ala Thr Asn Ile Ile Glu Asn
            1460                1465                1470

Gly Val Thr Ile Asp Ile Asp Val Val Asp Phe Gly Thr Lys Val
            1475                1480                1485

Val Pro Val Leu Asp Val Asp Asn Arg Ala Val Gln Tyr Asn Lys Thr
            1490                1495                1500

Val Val Ser Tyr Gly Glu Arg Ile Gln Lys Leu Gly Arg Val Gly Arg
1505                1510                1515                1520

His Lys Glu Gly Val Ala Leu Arg Ile Gly Gln Thr Asn Lys Thr Leu
            1525                1530                1535

Val Glu Ile Pro Glu Met Val Ala Thr Glu Ala Ala Phe Leu Cys Phe
            1540                1545                1550

Met Tyr Asn Leu Pro Val Thr Thr Gln Ser Val Ser Thr Thr Leu Leu
            1555                1560                1565

Glu Asn Ala Thr Leu Leu Gln Ala Arg Thr Met Ala Gln Phe Glu Leu
            1570                1575                1580

Ser Tyr Phe Tyr Thr Ile Asn Phe Val Arg Phe Asp Gly Ser Met His
1585                1590                1595                1600

Pro Val Ile His Asp Lys Leu Lys Arg Phe Lys Leu His Thr Cys Glu
            1605                1610                1615

Thr Phe Leu Asn Lys Leu Ala Ile Pro Asn Lys Gly Leu Ser Ser Trp
            1620                1625                1630

Leu Thr Ser Gly Glu Tyr Lys Arg Leu Gly Tyr Ile Ala Glu Asp Ala
            1635                1640                1645

Gly Ile Arg Ile Pro Phe Val Cys Lys Glu Ile Pro Asp Ser Leu His
            1650                1655                1660

Glu Glu Ile Trp His Ile Val Ala His Lys Gly Asp Ser Gly Ile
1665                1670                1675                1680

Gly Arg Leu Thr Ser Val Gln Ala Ala Lys Val Val Tyr Thr Leu Gln
            1685                1690                1695

Thr Asp Val His Ser Ile Ala Arg Thr Leu Ala Cys Ile Asn Arg Arg
            1700                1705                1710

Ile Ala Asp Glu Gln Met Lys Gln Ser His Phe Glu Ala Ala Thr Gly
            1715                1720                1725

Arg Ala Phe Ser Phe Thr Asn Tyr Ser Ile Gln Ser Ile Phe Asp Thr
            1730                1735                1740

Leu Lys Ala Asn Tyr Ala Thr Lys His Thr Lys Glu Asn Ile Ala Val
1745                1750                1755                1760

Leu Gln Gln Ala Lys Asp Gln Leu Leu Glu Phe Ser Asn Leu Ala Lys
            1765                1770                1775

Asp Gln Asp Val Thr Gly Ile Ile Gln Asp Phe Asn His Leu Glu Thr
            1780                1785                1790

Ile Tyr Leu Gln Ser Asp Ser Glu Val Ala Lys His Leu Lys Leu Lys
            1795                1800                1805
```

-continued

Ser His Trp Asn Lys Ser Gln Ile Thr Arg Asp Ile Ile Ala Leu
    1810                1815                1820

Ser Val Leu Ile Gly Gly Gly Trp Met Leu Ala Thr Tyr Phe Lys Asp
1825                1830                1835                1840

Lys Phe Asn Glu Pro Val Tyr Phe Gln Gly Lys Lys Asn Gln Lys His
                1845                1850                1855

Lys Leu Lys Met Arg Glu Ala Arg Gly Ala Arg Gly Gln Tyr Glu Val
            1860                1865                1870

Ala Ala Glu Pro Glu Ala Leu Glu His Tyr Phe Gly Ser Ala Tyr Asn
        1875                1880                1885

Asn Lys Gly Lys Arg Lys Gly Thr Thr Arg Gly Met Gly Ala Lys Ser
    1890                1895                1900

Arg Lys Phe Ile Asn Met Tyr Gly Phe Asp Pro Thr Asp Phe Ser Tyr
1905                1910                1915                1920

Ile Arg Phe Val Asp Pro Leu Thr Gly His Thr Ile Asp Glu Ser Thr
                1925                1930                1935

Asn Ala Pro Ile Asp Leu Val Gln His Glu Phe Gly Lys Val Arg Thr
            1940                1945                1950

Arg Met Leu Ile Asp Asp Glu Ile Glu Pro Gln Ser Leu Ser Thr His
        1955                1960                1965

Thr Thr Ile His Ala Tyr Leu Val Asn Ser Gly Thr Lys Lys Val Leu
    1970                1975                1980

Lys Val Asp Leu Thr Pro His Ser Ser Leu Arg Ala Ser Glu Lys Ser
1985                1990                1995                2000

Thr Ala Ile Met Gly Phe Pro Glu Arg Glu Asn Glu Leu Arg Gln Thr
                2005                2010                2015

Gly Met Ala Val Pro Val Ala Tyr Asp Gln Leu Pro Pro Lys Asn Glu
            2020                2025                2030

Asp Leu Thr Phe Glu Gly Glu Ser Leu Phe Lys Gly Pro Arg Asp Tyr
        2035                2040                2045

Asn Pro Ile Ser Ser Thr Ile Cys His Leu Thr Asn Glu Ser Asp Gly
    2050                2055                2060

His Thr Thr Ser Leu Tyr Gly Ile Gly Phe Gly Pro Phe Ile Ile Thr
2065                2070                2075                2080

Asn Lys His Leu Phe Arg Arg Asn Asn Gly Thr Leu Leu Val Gln Ser
                2085                2090                2095

Leu His Gly Val Phe Lys Val Lys Asn Thr Thr Thr Leu Gln Gln His
            2100                2105                2110

Leu Ile Asp Gly Arg Asp Met Ile Ile Ile Arg Met Pro Lys Asp Phe
        2115                2120                2125

Pro Pro Phe Pro Gln Lys Leu Lys Phe Arg Glu Pro Gln Arg Glu Glu
    2130                2135                2140

Arg Ile Cys Leu Val Thr Thr Asn Phe Gln Thr Lys Ser Met Ser Ser
2145                2150                2155                2160

Met Val Ser Asp Thr Ser Cys Thr Phe Pro Ser Ser Asp Gly Ile Phe
                2165                2170                2175

Trp Lys His Trp Ile Gln Thr Lys Asp Gly Gln Cys Gly Ser Pro Leu
            2180                2185                2190

Val Ser Thr Arg Asp Gly Phe Ile Val Gly Ile His Ser Ala Ser Asn
        2195                2200                2205

Phe Thr Asn Thr Asn Asn Tyr Phe Thr Ser Val Pro Lys Asn Phe Met
    2210                2215                2220

Glu Leu Leu Thr Asn Gln Glu Ala Gln Gln Trp Val Ser Gly Trp Arg

```
                2225                2230                2235                2240
Leu Asn Ala Asp Ser Val Leu Trp Gly Gly His Lys Val Phe Met Ser
                    2245                2250                2255
Lys Pro Glu Glu Pro Phe Gln Pro Val Lys Glu Ala Thr Gln Leu Met
                    2260                2265                2270
Asn Glu Leu Val Tyr Ser Gln Gly Glu Lys Arg Lys Trp Val Val Glu
                    2275                2280                2285
Ala Leu Ser Gly Asn Leu Arg Pro Val Ala Glu Cys Pro Ser Gln Leu
                    2290                2295                2300
Val Thr Lys His Val Val Lys Gly Lys Cys Pro Leu Phe Glu Leu Tyr
2305                2310                2315                2320
Leu Gln Leu Asn Pro Glu Lys Glu Ala Tyr Phe Lys Pro Met Met Gly
                    2325                2330                2335
Ala Tyr Lys Pro Ser Arg Leu Asn Arg Glu Ala Phe Leu Lys Asp Ile
                    2340                2345                2350
Leu Lys Tyr Ala Ser Glu Ile Glu Ile Gly Asn Val Asp Cys Asp Leu
                    2355                2360                2365
Leu Glu Leu Ala Ile Ser Met Leu Val Thr Lys Leu Lys Ala Leu Gly
                    2370                2375                2380
Phe Pro Thr Val Asn Tyr Ile Thr Asp Pro Glu Glu Ile Phe Ser Ala
2385                2390                2395                2400
Leu Asn Met Lys Ala Ala Met Gly Ala Leu Tyr Lys Gly Lys Lys Lys
                    2405                2410                2415
Glu Ala Leu Ser Glu Leu Thr Leu Asp Glu Gln Glu Ala Met Leu Lys
                    2420                2425                2430
Ala Ser Cys Leu Arg Leu Tyr Thr Gly Lys Leu Gly Ile Trp Asn Gly
                    2435                2440                2445
Ser Leu Lys Ala Glu Leu Arg Pro Ile Glu Lys Val Glu Asn Asn Lys
                    2450                2455                2460
Thr Arg Thr Phe Thr Ala Ala Pro Ile Asp Thr Leu Leu Ala Gly Lys
2465                2470                2475                2480
Val Cys Val Asp Asp Phe Asn Asn Gln Phe Tyr Asp Leu Asn Ile Lys
                    2485                2490                2495
Ala Pro Trp Thr Val Gly Met Thr Lys Phe Tyr Gln Gly Trp Asn Glu
                    2500                2505                2510
Leu Met Glu Ala Leu Pro Ser Gly Trp Val Tyr Cys Asp Ala Asp Gly
                    2515                2520                2525
Ser Gln Phe Asp Ser Ser Leu Thr Pro Phe Leu Ile Asn Ala Val Leu
                    2530                2535                2540
Lys Val Arg Leu Ala Phe Met Glu Glu Trp Asp Ile Gly Glu Gln Met
2545                2550                2555                2560
Leu Arg Asn Leu Tyr Thr Glu Ile Val Tyr Thr Pro Ile Leu Thr Pro
                    2565                2570                2575
Asp Gly Thr Ile Ile Lys Lys His Lys Gly Asn Asn Ser Gly Gln Pro
                    2580                2585                2590
Ser Thr Val Val Asp Asn Thr Leu Met Val Ile Ile Ala Met Leu Tyr
                    2595                2600                2605
Thr Cys Glu Lys Cys Gly Ile Asn Lys Glu Glu Ile Val Tyr Tyr Val
                    2610                2615                2620
Asn Gly Asp Asp Leu Leu Ile Ala Ile His Pro Asp Lys Ala Glu Arg
2625                2630                2635                2640
Leu Ser Arg Phe Lys Glu Ser Phe Gly Glu Leu Gly Leu Lys Tyr Glu
                    2645                2650                2655
```

-continued

```
Phe Asp Cys Thr Thr Arg Asp Lys Thr Gln Leu Trp Phe Met Ser His
            2660                2665                2670

Arg Ala Leu Glu Arg Asp Gly Met Tyr Ile Pro Lys Leu Glu Glu Glu
        2675                2680                2685

Arg Ile Val Ser Ile Leu Glu Trp Asp Arg Ser Lys Glu Pro Ser His
    2690                2695                2700

Arg Leu Glu Ala Ile Cys Ala Ser Met Ile Glu Ala Trp Gly Tyr Asp
2705                2710                2715                2720

Lys Leu Val Glu Glu Ile Arg Asn Phe Tyr Ala Trp Val Leu Glu Gln
            2725                2730                2735

Ala Pro Tyr Ser Gln Leu Ala Glu Glu Gly Lys Ala Pro Tyr Leu Ala
        2740                2745                2750

Glu Thr Ala Leu Lys Phe Leu Tyr Thr Ser Gln His Gly Thr Asn Ser
    2755                2760                2765

Glu Ile Glu Glu Tyr Leu Lys Val Leu Tyr Asp Tyr Asp Ile Pro Thr
2770                2775                2780

Thr Glu Asn Leu Tyr Phe Gln Ser Gly Thr Val Asp Ala Gly Ala Asp
2785                2790                2795                2800

Ala Gly Lys Lys Lys Asp Gln Lys Asp Lys Val Ala Glu Gln Ala
        2805                2810                2815

Ser Lys Asp Arg Asp Val Asn Ala Gly Thr Ser Gly Thr Phe Ser Val
    2820                2825                2830

Pro Arg Ile Asn Ala Met Ala Thr Lys Leu Gln Tyr Pro Arg Met Arg
        2835                2840                2845

Gly Glu Val Val Asn Leu Asn His Leu Leu Gly Tyr Lys Pro Gln
    2850                2855                2860

Gln Ile Asp Leu Ser Asn Ala Arg Ala Thr His Glu Gln Phe Ala Ala
2865                2870                2875                2880

Trp His Gln Ala Val Met Thr Ala Tyr Gly Val Asn Glu Glu Gln Met
            2885                2890                2895

Lys Ile Leu Leu Asn Gly Phe Met Val Trp Cys Ile Glu Asn Gly Thr
        2900                2905                2910

Ser Pro Asn Leu Asn Gly Thr Trp Val Met Met Asp Gly Glu Asp Gln
    2915                2920                2925

Val Ser Tyr Pro Leu Lys Pro Met Val Glu Asn Ala Gln Pro Thr Leu
        2930                2935                2940

Arg Gln Ile Met Thr His Phe Ser Asp Leu Ala Glu Ala Tyr Ile Glu
2945                2950                2955                2960

Met Arg Asn Arg Glu Arg Pro Tyr Met Pro Arg Tyr Gly Leu Gln Arg
            2965                2970                2975

Asn Ile Thr Asp Met Ser Leu Ser Arg Tyr Ala Phe Asp Phe Tyr Glu
        2980                2985                2990

Leu Thr Ser Lys Thr Pro Val Arg Ala Arg Glu Ala His Met Gln Met
    2995                3000                3005

Lys Ala Ala Ala Val Arg Asn Ser Gly Thr Arg Leu Phe Gly Leu Asp
        3010                3015                3020

Gly Asn Val Gly Thr Ala Glu Glu Asp Thr Glu Arg His Thr Ala His
3025                3030                3035                3040

Asp Val Asn Arg Asn Met His Thr Leu Leu Gly Val Arg Gln
            3045                3050

<210> SEQ ID NO 15
<211> LENGTH: 242
```

```
<212> TYPE: PRT
<213> ORGANISM: Potyvirus

<400> SEQUENCE: 15

Gly Glu Ser Leu Phe Lys Gly Pro Arg Asp Tyr Asn Pro Ile Ser Ser
1               5                   10                  15

Thr Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Ser Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 16
<211> LENGTH: 242
<212> TYPE: PRT
<213> ORGANISM: Potyvirus
<220> FEATURE:
<221> NAME/KEY: VARIANT
<222> LOCATION: 216
<223> OTHER INFORMATION: S219N

<400> SEQUENCE: 16

Gly Glu Ser Leu Phe Lys Gly Pro Arg Asp T

```
Asp Met Ile Ile Ile Arg Met Pro Lys Asp Phe Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asn Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 17
<211> LENGTH: 242
<212> TYPE: PRT
<213> ORGANISM: Potyvirus
<220> FEATURE:
<221> NAME/KEY: VARIANT
<222> LOCATION: 56
<223> OTHER INFORMATION: L56V
<220> FEATURE:
<221> NAME/KEY: VARIANT
<222> LOCATION: 135
<223> OTHER INFORMATION: S135G
<220> FEATURE:
<221> NAME/KEY: VARIANT
<222> LOCATION: 219
<223> OTHER INFORMATION: S219N

<400> SEQUENCE: 17

Gly Glu Ser Leu Phe Lys Gly Pro Arg Asp Tyr Asn Pro Ile Ser Ser
 1               5                  10                  15

Thr Ile Cys His Leu Thr Asn Glu Ser Asp Gly His Thr Thr Ser Leu
             20                  25                  30

Tyr Gly Ile Gly Phe Gly Pro Phe Ile Ile Thr Asn Lys His Leu Phe
         35                  40                  45

Arg Arg Asn Asn Gly Thr Leu Val Val Gln Ser Leu His Gly Val Phe
 50                  55                  60

Lys Val Lys Asn Thr Thr Thr Leu Gln Gln His Leu Ile Asp Gly Arg
 65                  70                  75                  80

Asp Met Ile Ile Ile Arg Met Pro Lys Asp Phe Pro Phe Pro Gln
                 85                  90                  95

Lys Leu Lys Phe Arg Glu Pro Gln Arg Glu Glu Arg Ile Cys Leu Val
             100                 105                 110

Thr Thr Asn Phe Gln Thr Lys Ser Met Ser Ser Met Val Ser Asp Thr
         115                 120                 125

Ser Cys Thr Phe Pro Ser Gly Asp Gly Ile Phe Trp Lys His Trp Ile
     130                 135                 140
```

```
Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asn Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 18
<211> LENGTH: 242
<212> TYPE: PRT
<213> ORGANISM: Potyvirus
<220> FEATURE:
<221> NAME/KEY: VARIANT
<222> LOCATION: 17
<223> OTHER INFORMATION: T17V
<220> FEATURE:
<221> NAME/KEY: VARIANT
<222> LOCATION: 68
<223> OTHER INFORMATION: N68D
<220> FEATURE:
<221> NAME/KEY: VARIANT
<222> LOCATION: 77
<223> OTHER INFORMATION: I77V
<220> FEATURE:
<221> NAME/KEY: VARIANT
<222> LOCATION: 219
<223> OTHER INFORMATION: S219N

<400> SEQUENCE: 18

Gly Glu Ser Leu Phe Lys Gly Pro Arg Asp Tyr Asn Pro Ile Ser Ser
1               5                   10                  15

Ser Ile Cys His Leu Thr Asn Glu Ser Asp Gly His Thr Thr Ser Leu
            20                  25                  30

Tyr Gly Ile Gly Phe Gly Pro Phe Ile Ile Thr Asn Lys His Leu Phe
        35                  40                  45

Arg Arg Asn Asn Gly Thr Leu Leu Val Gln Ser Leu His Gly Val Phe
    50                  55                  60

Lys Val Lys Asp Thr Thr Thr Leu Gln Gln His Leu Val Asp Gly Arg
65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
    130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190
```

```
Gln Glu Ala Gln Gln Trp Val Ser Gly Trp Arg Leu Asn Ala Asp Ser
            195                 200                 205

Val Leu Trp Gly Gly His Lys Val Phe Met Asn Lys Pro Glu Glu Pro
210                 215                 220

Phe Gln Pro Val Lys Glu Ala Thr Gln Leu Met Asn Glu Leu Val Tyr
225                 230                 235                 240

Ser Gln

<210> SEQ ID NO 19
<211> LENGTH: 242
<212> TYPE: PRT
<213> ORGANISM: Potyvirus
<220> FEATURE:
<221> NAME/KEY: VARIANT
<222> LOCATION: 44
<223> OTHER INFORMATION: N44V
<220> FEATURE:
<221> NAME/KEY: VARIANT
<222> LOCATION: 56
<223> OTHER INFORMATION: L56V
<220> FEATURE:
<221> NAME/KEY: VARIANT
<222> LOCATION: 135
<223> OTHER INFORMATION: S135G
<220> FEATURE:
<221> NAME/KEY: VARIANT
<222> LOCATION: 219
<223> OTHER INFORMATION: S219N

<400> SEQUENCE: 19

Gly Glu Ser Leu Phe Lys Gly Pro Arg Asp Tyr Asn Pro Ile Ser Ser
 1               5                  10                  15

Thr Ile Cys His Leu Thr Asn Glu Ser Asp Gly His Thr Thr Ser Leu
             20                  25                  30

Tyr Gly Ile Gly Phe Gly Pro Phe Ile Ile Thr Val Lys His Leu Phe
         35                  40                  45

Arg Arg Asn Asn Gly Thr Leu Val Val Gln Ser Leu His Gly Val Phe
     50                  55                  60

Lys Val Lys Asn Thr Thr Thr Leu Gln Gln His Leu Ile Asp Gly Arg
65                  70                  75                  80

Asp Met Ile Ile Ile Arg Met Pro Lys Asp Phe Pro Pro Phe Pro Gln
                 85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Gly Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asn Lys Pro Glu Glu Pro
210                 215                 220

Phe Gln Pro Val Lys Glu Ala Thr Gln Leu Met Asn Glu Leu Val Tyr
```

-continued

```
            225                 230                 235                 240

Ser Gln

<210> SEQ ID NO 20
<211> LENGTH: 242
<212> TYPE: PRT
<213> ORGANISM: Potyvirus
<220> FEATURE:
<221> NAME/KEY: VARIANT
<222> LOCATION: 56
<223> OTHER INFORMATION: L56V
<220> FEATURE:
<221> NAME/KEY: VARIANT
<222> LOCATION: 68
<223> OTHER INFORMATION: N68D
<220> FEATURE:
<221> NAME/KEY: VARIANT
<222> LOCATION: 135
<223> OTHER INFORMATION: S135G
<220> FEATURE:
<221> NAME/KEY: VARIANT
<222> LOCATION: 219
<223> OTHER INFORMATION: S219N

<400> SEQUENCE: 20

Gly Glu Ser Leu Phe Lys Gly Pro Arg Asp Tyr Asn Pro Ile Ser Ser
  1               5                  10                  15

Thr Ile Cys His Leu Thr Asn Glu Ser Asp Gly His Thr Thr Ser Leu
             20                  25                  30

Tyr Gly Ile Gly Phe Gly Pro Phe Ile Ile Thr Asn Lys His Leu Phe
         35                  40                  45

Arg Arg Asn Asn Gly Thr Leu Val Val Gln Ser Leu His Gly Val Phe
 50                  55                  60

Lys Val Lys Asp Thr Thr Thr Leu Gln Gln His Leu Ile Asp Gly Arg
 65                  70                  75                  80

Asp Met Ile Ile Ile Arg Met Pro Lys Asp Phe Pro Pro Phe Pro Gln
                 85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Gly Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asn Lys Pro Glu Glu Pro
    210                 215                 220

Phe Gln Pro Val Lys Glu Ala Thr Gln Leu Met Asn Glu Leu Val Tyr
225                 230                 235                 240

Ser Gln

<210> SEQ ID NO 21
<211> LENGTH: 242
<212> TYPE: PRT
```

```
<213> ORGANISM: Potyvirus
<220> FEATURE:
<221> NAME/KEY: VARIANT
<222> LOCATION: 17
<223> OTHER INFORMATION: T17S
<220> FEATURE:
<221> NAME/KEY: VARIANT
<222> LOCATION: 56
<223> OTHER INFORMATION: L56V
<220> FEATURE:
<221> NAME/KEY: VARIANT
<222> LOCATION: 68
<223> OTHER INFORMATION: N68D
<220> FEATURE:
<221> NAME/KEY: VARIANT
<222> LOCATION: 77
<223> OTHER INFORMATION: I77V
<220> FEATURE:
<221> NAME/KEY: VARIANT
<222> LOCATION: 219
<223> OTHER INFORMATION: S219N

<400> SEQUENCE: 21

Gly Glu Ser Leu Phe Lys Gly Pro Arg Asp Tyr Asn Pro Ile Ser Ser
  1               5                  10                  15

Ser Ile Cys His Leu Thr Asn Glu Ser Asp Gly His Thr Thr Ser Leu
             20                  25                  30

Tyr Gly Ile Gly Phe Gly Pro Phe Ile Ile Thr Asn Lys His Leu Phe
         35                  40                  45

Arg Arg Asn Asn Gly Thr Leu Val Val Gln Ser Leu His Gly Val Phe
     50                  55                  60

Lys Val Lys Asp Thr Thr Thr Leu Gln Gln His Leu Val Asp Gly Arg
 65                  70                  75                  80

Asp Met Ile Ile Ile Arg Met Pro Lys Asp Phe Pro Pro Phe Pro Gln
                 85                  90                  95

Lys Leu Lys Phe Arg Glu Pro Gln Arg Glu Arg Ile Cys Leu Val
            100                 105                 110

Thr Thr Asn Phe Gln Thr Lys Ser Met Ser Ser Met Val Ser Asp Thr
        115                 120                 125

Ser Cys Thr Phe Pro Ser Ser Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asn Lys Pro Glu Glu Pro
210                 215                 220

Phe Gln Pro Val Lys Glu Ala Thr Gln Leu Met Asn Glu Leu Val Tyr
225                 230                 235                 240

Ser Gln

<210> SEQ ID NO 22
<211> LENGTH: 242
<212> TYPE: PRT
<213> ORGANISM: Potyvirus
<220> FEATURE:
<221> NAME/KEY: VARIANT
<222> LOCATION: 17
```

<223> OTHER INFORMATION: T17S
<220> FEATURE:
<221> NAME/KEY: VARIANT
<222> LOCATION: 68
<223> OTHER INFORMATION: N68D
<220> FEATURE:
<221> NAME/KEY: VARIANT
<222> LOCATION: 77
<223> OTHER INFORMATION: I77V
<220> FEATURE:
<221> NAME/KEY: VARIANT
<222> LOCATION: 135
<223> OTHER INFORMATION: S135G
<220> FEATURE:
<221> NAME/KEY: VARIANT
<222> LOCATION: 219
<223> OTHER INFORMATION: S219N

<400> SEQUENCE: 22

```
Gly Glu Ser Leu Phe Lys Gly Pro Arg Asp Tyr Asn Pro Ile Ser Ser
  1               5                  10                  15

Ser Ile Cys His Leu Thr Asn Glu Ser Asp Gly His Thr Thr Ser Leu
             20                  25                  30

Tyr Gly Ile Gly Phe Gly Pro Phe Ile Ile Thr Asn Lys His Leu Phe
         35                  40                  45

Arg Arg Asn Asn Gly Thr Leu Leu Val Gln Ser Leu His Gly Val Phe
 50                  55                  60

Lys Val Lys Asp Thr Thr Thr Leu Gln Gln His Leu Val Asp Gly Arg
 65                  70                  75                  80

Asp Met Ile Ile Ile Arg Met Pro Lys Asp Phe Pro Pro Phe Pro Gln
                 85                  90                  95

Lys Leu Lys Phe Arg Glu Pro Gln Arg Glu Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Gly Asp Gly Ile Phe Trp Lys His Trp Ile
        130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
        195                 200                 205

Val Leu Trp Gly Gly His Lys Val Phe Met Asn Lys Pro Glu Glu Pro
210                 215                 220

Phe Gln Pro Val Lys Glu Ala Thr Gln Leu Met Asn Glu Leu Val Tyr
225                 230                 235                 240

Ser Gln
```

<210> SEQ ID NO 23
<211> LENGTH: 242
<212> TYPE: PRT
<213> ORGANISM: Potyvirus
<220> FEATURE:
<221> NAME/KEY: VARIANT
<222> LOCATION: 17
<223> OTHER INFORMATION: T17S
<220> FEATURE:
<221> NAME/KEY: VARIANT
<222> LOCATION: 44

```
<223> OTHER INFORMATION: N44V
<220> FEATURE:
<221> NAME/KEY: VARIANT
<222> LOCATION: 56
<223> OTHER INFORMATION: L56V
<220> FEATURE:
<221> NAME/KEY: VARIANT
<222> LOCATION: 68
<223> OTHER INFORMATION: N68D
<220> FEATURE:
<221> NAME/KEY: VARIANT
<222> LOCATION: 77
<223> OTHER INFORMATION: I77V
<220> FEATURE:
<221> NAME/KEY: VARIANT
<222> LOCATION: 135
<223> OTHER INFORMATION: S135G
<220> FEATURE:
<221> NAME/KEY: VARIANT
<222> LOCATION: (219)...(219)
<223> OTHER INFORMATION: S219N

<400> SEQUENCE: 23
```

Gly Glu Ser Leu Phe Lys Gly Pro Arg Asp Tyr Asn Pro Ile Ser Ser
 1               5                  10                  15

Ser Ile Cys His Leu Thr Asn Glu Ser Asp Gly His Thr Thr Ser Leu
            20                  25                  30

Tyr Gly Ile Gly Phe Gly Pro Phe Ile Ile Thr Val Lys His Leu Phe
        35                  40                  45

Arg Arg Asn Asn Gly Thr Leu Val Val Gln Ser Leu His Gly Val Phe
 50                  55                  60

Lys Val Lys Asp Thr Thr Thr Leu Gln Gln His Leu Val Asp Gly Arg
 65                  70                  75                  80

Asp Met Ile Ile Ile Arg Met Pro Lys Asp Phe Pro Pro Phe Pro Gln
                85                  90                  95

Lys Leu Lys Phe Arg Glu Pro Gln Arg Glu Arg Ile Cys Leu Val
            100                 105                 110

Thr Thr Asn Phe Gln Thr Lys Ser Met Ser Ser Met Val Ser Asp Thr
            115                 120                 125

Ser Cys Thr Phe Pro Ser Gly Asp Gly Ile Phe Trp Lys His Trp Ile
130                 135                 140

Gln Thr Lys Asp Gly Gln Cys Gly Ser Pro Leu Val Ser Thr Arg Asp
145                 150                 155                 160

Gly Phe Ile Val Gly Ile His Ser Ala Ser Asn Phe Thr Asn Thr Asn
                165                 170                 175

Asn Tyr Phe Thr Ser Val Pro Lys Asn Phe Met Glu Leu Leu Thr Asn
            180                 185                 190

Gln Glu Ala Gln Gln Trp Val Ser Gly Trp Arg Leu Asn Ala Asp Ser
            195                 200                 205

Val Leu Trp Gly Gly His Lys Val Phe Met Asn Lys Pro Glu Glu Pro
210                 215                 220

Phe Gln Pro Val Lys Glu Ala Thr Gln Leu Met Asn Glu Leu Val Tyr
225                 230                 235                 240

Ser Gln

```
<210> SEQ ID NO 24
<211> LENGTH: 3023
<212> TYPE: PRT
<213> ORGANISM: Potyvirus

<400>

-continued

```
Met Ala Ala Thr Met Ile Phe Gly Ser Phe Thr His Asp Leu Leu Gly
1               5                   10                  15

Lys Ala Met Ser Thr Ile His Ser Ala Val Thr Ala Glu Lys Asp Ile
            20                  25                  30

Phe Ser Ser Ile Lys Glu Arg Leu Glu Arg Lys Arg His Gly Lys Ile
        35                  40                  45

Cys Arg Met Lys Asn Gly Ser Ile Tyr Ile Lys Ala Ala Ser Ser Thr
    50                  55                  60

Lys Val Glu Lys Ile Asn Ala Ala Lys Lys Leu Ala Asp Asp Lys
65                  70                  75                  80

Ala Ala Phe Leu Lys Ala Gln Pro Thr Ile Val Asp Lys Ile Ile Val
                85                  90                  95

Asn Glu Lys Ile Gln Val Val Glu Ala Glu Val His Lys Arg Glu
                100                 105                 110

Asp Val Gln Thr Val Phe Phe Lys Lys Thr Lys Lys Arg Ala Pro Lys
            115                 120                 125

Leu Arg Ala Thr Cys Ser Ser Gly Leu Asp Asn Leu Tyr Asn Ala
            130                 135                 140

Val Ala Asn Ile Ala Lys Ala Ser Ser Leu Arg Val Glu Val Ile His
145                 150                 155                 160

Lys Lys Arg Val Cys Gly Glu Phe Lys Gln Thr Arg Phe Gly Arg Ala
                165                 170                 175

Leu Phe Ile Asp Val Ala His Ala Lys Gly His Arg Arg Ile Asp
            180                 185                 190

Cys Arg Met His Arg Arg Glu Gln Arg Thr Met His Met Phe Met Arg
    195                 200                 205

Lys Thr Thr Lys Thr Glu Val Arg Ser Lys His Leu Arg Lys Gly Asp
210                 215                 220

Ser Gly Ile Val Leu Leu Thr Gln Lys Ile Lys Gly His Leu Ser Gly
225                 230                 235                 240

Val Arg Asp Glu Phe Phe Ile Val Arg Gly Thr Cys Asp Ser Leu
                245                 250                 255

Leu Glu Ala Arg Ala Arg Phe Ser Gln Ser Ile Thr Leu Arg Ala Thr
            260                 265                 270

His Phe Ser Thr Gly Asp Ile Phe Trp Lys Gly Phe Asn Ala Ser Phe
            275                 280                 285

Gln Glu Gln Lys Ala Ile Gly Leu Asp His Thr Cys Thr Ser Asp Leu
            290                 295                 300

Pro Val Glu Ala Cys Gly His Val Ala Ala Leu Met Cys Gln Ser Leu
305                 310                 315                 320

Phe Pro Cys Gly Lys Ile Thr Cys Lys Arg Cys Ile Ala Asn Leu Ser
                325                 330                 335

Asn Leu Asp Phe Asp Thr Phe Ser Glu Leu Gln Gly Asp Arg Ala Met
            340                 345                 350

Arg Ile Leu Asp Val Met Arg Ala Arg Phe Pro Ser Thr His Thr
            355                 360                 365

Ile Arg Phe Leu His Asp Leu Phe Thr Gln Arg Val Thr Asn Pro
370                 375                 380

Asn Thr Ala Ala Phe Arg Glu Ile Leu Arg Leu Ile Gly Asp Arg Asn
385                 390                 395                 400

Glu Ala Pro Phe Ala His Val Asn Arg Leu Asn Glu Ile Leu Leu Leu
                405                 410                 415

Gly Ser Lys Ala Asn Pro Asp Ser Leu Ala Lys Ala Ser Asp Ser Leu
```

```
                420                 425                  430
Leu Glu Leu Ala Arg Tyr Leu Asn Asn Arg Thr Glu Asn Ile Arg Asn
            435                 440                 445
Gly Ser Leu Lys His Phe Arg Asn Lys Ile Ser Ser Lys Ala His Ser
            450                 455             460
Asn Leu Ala Leu Ser Cys Asp Asn Gln Leu Asp Gln Asn Gly Asn Phe
465                 470                 475                 480
Leu Trp Gly Leu Ala Gly Ile Ala Ala Lys Arg Phe Leu Asn Asn Tyr
                485                 490                 495
Phe Glu Thr Ile Asp Pro Glu Gln Gly Tyr Asp Lys Tyr Val Ile Arg
                500                 505             510
Lys Asn Pro Asn Gly Glu Arg Lys Leu Ala Ile Gly Asn Phe Ile Ile
            515                 520             525
Ser Thr Asn Leu Glu Lys Leu Arg Asp Gln Leu Glu Gly Glu Ser Ile
            530                 535             540
Ala Arg Val Gly Ile Thr Glu Glu Cys Val Ser Arg Lys Asp Gly Asn
545                 550                 555                 560
Tyr Arg Tyr Pro Cys Cys Cys Val Thr Leu Glu Asp Gly Ser Pro Met
                565                 570                 575
Tyr Ser Glu Leu Lys Met Pro Thr Lys Asn His Leu Val Ile Gly Asn
            580                 585                 590
Ser Gly Asp Pro Lys Tyr Leu Asp Leu Pro Gly Glu Ile Ser Asn Leu
            595                 600                 605
Met Tyr Ile Ala Lys Glu Gly Tyr Cys Tyr Ile Asn Ile Phe Leu Ala
            610                 615                 620
Met Leu Val Asn Val Asp Glu Ala Asn Ala Lys Asp Phe Thr Lys Arg
625                 630                 635                 640
Val Arg Asp Glu Ser Val Gln Lys Leu Gly Lys Trp Pro Ser Leu Ile
                645                 650                 655
Asp Val Ala Thr Glu Cys Ala Leu Leu Ser Thr Tyr Tyr Pro Ala Ala
                660                 665                 670
Ala Ser Ala Glu Leu Pro Arg Leu Leu Val Asp His Ala Gln Lys Thr
            675                 680                 685
Ile His Val Val Asp Ser Tyr Gly Ser Leu Asn Thr Gly Tyr His Ile
            690                 695             700
Leu Lys Ala Asn Thr Val Ser Gln Leu Glu Lys Phe Ala Ser Asn Thr
705                 710                 715                 720
Leu Glu Ser Pro Met Ala Gln Tyr Lys Val Gly Gly Leu Val Tyr Ser
                725                 730                 735
Glu Asn Asn Asp Ala Ser Ala Val Lys Ala Leu Thr Gln Ala Ile Phe
                740                 745                 750
Arg Pro Asp Val Leu Ser Glu Leu Ile Glu Lys Glu Pro Tyr Leu Met
            755                 760                 765
Val Phe Ala Leu Val Ser Pro Gly Ile Leu Met Ala Met Ser Asn Ser
            770                 775             780
Gly Ala Leu Glu Phe Gly Ile Ser Lys Trp Ile Ser Ser Asp His Ser
785                 790                 795                 800
Leu Val Arg Met Ala Ser Ile Leu Lys Thr Leu Ala Ser Lys Val Ser
                805                 810                 815
Val Ala Asp Thr Leu Ala Leu Gln Lys His Ile Met Arg Gln Asn Ala
                820                 825                 830
Asn Phe Leu Cys Gly Glu Leu Ile Asn Gly Phe Gln Lys Lys Lys Ser
            835                 840                 845
```

```
Tyr Thr His Ala Thr Arg Phe Leu Leu Met Ile Ser Glu Glu Asn Glu
850                 855                 860

Met Asp Asp Pro Val Leu Asn Ala Gly Tyr Arg Val Leu Glu Ala Ser
865                 870                 875                 880

Ser His Glu Ile Met Glu Lys Thr Tyr Leu Ala Leu Leu Glu Thr Ser
                885                 890                 895

Trp Ser Asp Leu Ser Leu Tyr Gly Lys Phe Lys Ser Ile Trp Phe Thr
                900                 905                 910

Arg Lys His Phe Gly Arg Tyr Lys Ala Glu Leu Phe Pro Lys Glu Gln
            915                 920                 925

Thr Asp Leu Gln Gly Arg Tyr Ser Asn Ser Leu Arg Phe His Tyr Gln
        930                 935                 940

Ser Thr Leu Lys Arg Leu Arg Asn Lys Gly Ser Leu Cys Arg Glu Arg
945                 950                 955                 960

Phe Leu Glu Ser Ile Ser Ser Ala Arg Arg Thr Thr Cys Ala Val
                965                 970                 975

Phe Ser Leu Leu His Lys Ala Phe Pro Asp Val Leu Lys Phe Ile Asn
            980                 985                 990

Thr Leu Val Ile Val Ser Leu Ser Met Gln Ile Tyr Tyr Met Leu Val
        995                 1000                1005

Ala Ile Ile His Glu His Arg Ala Ala Lys Ile Lys Ser Ala Gln Leu
    1010                1015                1020

Glu Glu Arg Val Leu Glu Asp Lys Thr Met Leu Leu Tyr Asp Asp Phe
1025                1030                1035                1040

Lys Ala Lys Leu Pro Glu Gly Ser Phe Glu Phe Leu Glu Tyr Thr
                1045                1050                1055

Arg Gln Arg Asp Lys Glu Val Tyr Glu Tyr Leu Met Met Glu Thr Thr
        1060                1065                1070

Glu Ile Val Glu Phe Gln Ala Lys Asn Thr Gly Gln Ala Ser Leu Glu
            1075                1080                1085

Arg Ile Ile Ala Phe Val Ser Leu Thr Leu Met Leu Phe Asp Asn Glu
        1090                1095                1100

Arg Ser Asp Cys Val Tyr Lys Ile Leu Thr Lys Phe Lys Gly Ile Leu
1105                1110                1115                1120

Gly Ser Val Glu Asn Asn Val Arg Phe Gln Ser Leu Asp Thr Ile Val
            1125                1130                1135

Pro Thr Gln Glu Glu Lys Asn Met Val Ile Asp Phe Glu Leu Asp Ser
            1140                1145                1150

Asp Thr Ala His Thr Pro Gln Met Gln Glu Gln Thr Phe Ser Asp Trp
        1155                1160                1165

Trp Ser Asn Gln Ile Ala Asn Asn Arg Val Val Pro His Tyr Arg Thr
        1170                1175                1180

Glu Gly Tyr Phe Met Gln Phe Thr Arg Asn Thr Ala Ser Ala Val Ser
1185                1190                1195                1200

His Gln Ile Ala His Asn Glu His Lys Asp Ile Ile Leu Met Gly Ala
            1205                1210                1215

Val Gly Ser Gly Lys Ser Thr Gly Leu Pro Thr Asn Leu Cys Lys Phe
        1220                1225                1230

Gly Gly Val Leu Leu Leu Glu Pro Thr Arg Pro Leu Ala Glu Asn Val
        1235                1240                1245

Thr Lys Gln Met Arg Gly Ser Pro Phe Phe Ala Ser Pro Thr Leu Arg
1250                1255                1260
```

```
Met Arg Asn Leu Ser Thr Phe Gly Ser Ser Pro Ile Thr Val Met Thr
1265                1270                1275                1280

Thr Gly Phe Ala Leu His Phe Ala Asn Asn Val Lys Glu Phe Asp
            1285                1290                1295

Arg Tyr Gln Phe Ile Ile Phe Asp Glu Phe His Val Leu Asp Ser Asn
                1300                1305                1310

Ala Ile Ala Phe Arg Asn Leu Cys His Glu Tyr Ser Tyr Asn Gly Lys
        1315                1320                1325

Ile Ile Lys Val Ser Ala Thr Pro Pro Gly Arg Glu Cys Asp Leu Thr
    1330                1335                1340

Thr Gln Tyr Pro Val Glu Leu Leu Ile Glu Glu Gln Leu Ser Leu Arg
1345                1350                1355                1360

Asp Phe Val Asp Ala Gln Gly Thr Asp Ala His Ala Asp Val Val Lys
            1365                1370                1375

Lys Gly Asp Asn Ile Leu Val Tyr Val Ala Ser Tyr Asn Glu Val Asp
                1380                1385                1390

Gln Leu Ser Lys Met Leu Asn Glu Arg Gly Phe Leu Val Thr Lys Val
        1395                1400                1405

Asp Gly Arg Thr Met Lys Leu Gly Gly Val Glu Ile Ile Thr Lys Gly
    1410                1415                1420

Ser Ser Ile Lys Lys His Phe Ile Val Ala Thr Asn Ile Ile Glu Asn
1425                1430                1435                1440

Gly Val Thr Leu Asp Val Asp Val Val Val Asp Phe Gly Leu Lys Val
            1445                1450                1455

Val Pro Asn Leu Asp Ser Asp Asn Arg Leu Val Ser Tyr Cys Lys Ile
                1460                1465                1470

Pro Ile Ser Leu Gly Glu Arg Ile Gln Arg Phe Gly Arg Val Gly Arg
        1475                1480                1485

Asn Lys Pro Gly Val Ala Leu Arg Ile Gly Glu Thr Ile Lys Gly Leu
    1490                1495                1500

Val Glu Ile Pro Ser Met Ile Ala Thr Glu Ala Ala Phe Leu Cys Phe
1505                1510                1515                1520

Val Tyr Gly Leu Pro Val Thr Thr Gln Asn Val Ser Thr Ser Ile Leu
            1525                1530                1535

Ser Gln Val Ser Val Arg Gln Ala Arg Val Met Cys Gln Phe Glu Leu
        1540                1545                1550

Pro Ile Phe Tyr Thr Ala His Leu Val Arg Tyr Asp Gly Ala Met His
    1555                1560                1565

Pro Ala Ile His Asn Ala Leu Lys Arg Phe Lys Leu Arg Asp Ser Glu
    1570                1575                1580

Ile Asn Leu Asn Thr Leu Ala Ile Pro Thr Ser Ser Ser Lys Thr Trp
1585                1590                1595                1600

Tyr Thr Gly Lys Cys Tyr Lys Gln Leu Val Gly Arg Leu Asp Ile Pro
            1605                1610                1615

Asp Glu Ile Lys Ile Pro Phe Tyr Thr Lys Glu Val Pro Glu Lys Val
                1620                1625                1630

Pro Glu Gln Ile Trp Asp Val Met Val Lys Phe Ser Ser Asp Ala Gly
        1635                1640                1645

Phe Gly Arg Met Thr Ser Ala Ala Ala Cys Lys Val Ala Tyr Thr Leu
    1650                1655                1660

Gln Thr Asp Ile His Ser Ile Gln Arg Thr Val Gln Ile Ile Asp Arg
1665                1670                1675                1680

Leu Leu Glu Asn Glu Met Lys Lys Arg Asn His Phe Asn Leu Val Val
```

-continued

```
                1685                1690                1695

Asn Gln Ser Cys Ser Ser His Phe Met Ser Leu Ser Ser Ile Met Ala
        1700                1705                1710

Ser Leu Arg Ala His Tyr Ala Lys Asn His Thr Gly Gln Asn Ile Glu
        1715                1720                1725

Ile Leu Gln Lys Ala Lys Ala Gln Leu Leu Glu Phe Ser Asn Leu Ala
        1730                1735                1740

Ile Asp Pro Ser Thr Thr Glu Ala Leu Arg Asp Phe Gly Tyr Leu Glu
1745                1750                1755                1760

Ala Val Arg Phe Gln Ser Glu Ser Glu Met Ala Arg Gly Leu Lys Leu
        1765                1770                1775

Ser Gly His Trp Lys Trp Ser Leu Ile Ser Arg Asp Leu Ile Val Val
        1780                1785                1790

Ser Gly Val Gly Ile Gly Leu Gly Cys Met Leu Trp Gln Phe Lys
        1795                1800                1805

Glu Lys Met His Glu Pro Val Lys Phe Gln Gly Lys Ser Arg Arg Arg
        1810                1815                1820

Leu Gln Phe Arg Lys Ala Arg Asp Asp Lys Met Gly Tyr Ile Met His
1825                1830                1835                1840

Gly Glu Gly Asp Thr Ile Glu His Phe Phe Gly Ala Ala Tyr Thr Lys
        1845                1850                1855

Lys Gly Lys Ser Lys Gly Lys Thr His Gly Ala Gly Thr Lys Ala His
        1860                1865                1870

Lys Phe Val Asn Met Tyr Gly Val Ser Pro Asp Glu Tyr Ser Tyr Val
        1875                1880                1885

Arg Tyr Leu Asp Pro Val Thr Gly Ala Thr Leu Asp Glu Ser Pro Met
        1890                1895                1900

Thr Asp Leu Asn Ile Val Gln Glu His Phe Gly Glu Ile Arg Arg Glu
1905                1910                1915                1920

Ala Ile Leu Ala Asp Ala Met Ser Pro Gln Gln Arg Asn Lys Gly Ile
        1925                1930                1935

Gln Ala Tyr Phe Val Arg Asn Ser Thr Met Pro Ile Leu Lys Val Asp
        1940                1945                1950

Leu Thr Pro His Ile Pro Leu Lys Val Cys Glu Ser Asn Asn Ile Ala
        1955                1960                1965

Gly Phe Pro Glu Arg Glu Gly Glu Leu Arg Arg Thr Gly Pro Thr Glu
        1970                1975                1980

Thr Leu Pro Phe Asp Ala Leu Pro Pro Glu Lys Gln Glu Val Ala Phe
1985                1990                1995                2000

Glu Ser Lys Ala Leu Leu Lys Gly Val Arg Asp Phe Asn Pro Ile Ser
        2005                2010                2015

Ala Cys Val Trp Leu Leu Glu Asn Ser Ser Asp Gly His Ser Glu Arg
        2020                2025                2030

Leu Phe Gly Ile Gly Phe Gly Pro Tyr Ile Ile Ala Asn Gln His Leu
        2035                2040                2045

Phe Arg Arg Asn Asn Gly Glu Leu Thr Ile Lys Thr Met His Gly Glu
        2050                2055                2060

Phe Lys Val Lys Asn Ser Thr Gln Leu Gln Met Lys Pro Val Glu Gly
2065                2070                2075                2080

Arg Asp Ile Ile Val Ile Lys Met Ala Lys Asp Phe Pro Pro Phe Pro
        2085                2090                2095

Gln Lys Leu Lys Phe Arg Gln Pro Thr Ile Lys Asp Arg Val Cys Met
        2100                2105                2110
```

-continued

```
Val Ser Thr Asn Phe Gln Gln Lys Ser Val Ser Ser Leu Val Ser Glu
        2115                2120                2125
Ser Ser His Ile Val His Lys Glu Asp Thr Ser Phe Trp Gln His Trp
    2130                2135                2140
Ile Thr Thr Lys Asp Gly Gln Cys Gly Ser Pro Leu Val Ser Ile Ile
2145                2150                2155                2160
Asp Gly Asn Ile Leu Gly Ile His Ser Leu Thr His Thr Thr Asn Gly
                2165                2170                2175
Ser Asn Tyr Phe Val Glu Phe Pro Glu Lys Phe Val Ala Thr Tyr Leu
            2180                2185                2190
Asp Ala Ala Asp Gly Trp Cys Lys Asn Trp Lys Phe Asn Ala Asp Lys
        2195                2200                2205
Ile Ser Trp Gly Ser Phe Thr Leu Val Glu Asp Ala Pro Glu Asp Asp
    2210                2215                2220
Phe Met Ala Lys Lys Thr Val Ala Ala Ile Met Asp Asp Leu Val Arg
2225                2230                2235                2240
Thr Gln Gly Glu Lys Arg Lys Trp Met Leu Glu Ala Ala His Thr Asn
                2245                2250                2255
Ile Gln Pro Val Ala His Leu Gln Ser Gln Leu Val Thr Lys His Ile
            2260                2265                2270
Val Lys Gly Arg Cys Lys Met Phe Ala Leu Tyr Leu Gln Glu Asn Ala
        2275                2280                2285
Asp Ala Arg Asp Phe Phe Lys Ser Phe Met Gly Ala Tyr Gly Pro Ser
    2290                2295                2300
His Leu Asn Lys Glu Ala Tyr Ile Lys Asp Ile Met Lys Tyr Ser Lys
2305                2310                2315                2320
Gln Ile Val Val Gly Ser Val Asp Cys Asp Thr Phe Glu Ser Ser Leu
                2325                2330                2335
Lys Val Leu Ser Arg Lys Met Lys Glu Trp Gly Phe Glu Asn Leu Glu
            2340                2345                2350
Tyr Val Thr Asp Glu Gln Thr Ile Lys Asn Ala Leu Asn Met Asp Ala
        2355                2360                2365
Ala Val Gly Ala Leu Tyr Ser Gly Lys Lys Gln Tyr Phe Glu Asp
    2370                2375                2380
Leu Ser Asp Asp Ala Val Ala Asn Leu Val Gln Lys Ser Cys Leu Arg
2385                2390                2395                2400
Leu Phe Lys Asn Lys Leu Gly Val Trp Asn Gly Ser Leu Lys Ala Glu
            2405                2410                2415
Leu Arg Pro Phe Glu Lys Leu Ile Glu Asn Lys Thr Arg Thr Phe Thr
        2420                2425                2430
Ala Ala Pro Ile Glu Thr Leu Leu Gly Gly Lys Val Cys Val Asp Asp
    2435                2440                2445
Phe Asn Asn His Phe Tyr Ser Lys His Ile Gln Cys Pro Trp Ser Val
2450                2455                2460
Gly Met Thr Lys Phe Tyr Gly Gly Trp Asn Glu Leu Leu Gly Lys Leu
2465                2470                2475                2480
Pro Asp Gly Trp Val Tyr Cys Asp Ala Asp Gly Ser Gln Phe Asp Ser
            2485                2490                2495
Ser Leu Ser Pro Tyr Leu Ile Asn Ala Val Leu Arg Leu Arg Leu Ser
        2500                2505                2510
Ser Met Glu Glu Trp Asp Val Gly Gln Lys Met Leu Gln Asn Leu Tyr
    2515                2520                2525
```

```
Thr Glu Ile Val Tyr Thr Pro Ile Ser Thr Pro Asp Gly Thr Ile Val
            2530                2535                2540

Lys Lys Phe Lys Gly Asn Asn Ser Gly Gln Pro Ser Thr Val Val Asp
2545                2550                2555                2560

Asn Thr Leu Met Val Val Leu Ala Met Tyr Tyr Ala Leu Ser Lys Leu
                2565                2570                2575

Gly Val Asp Ile Asn Ser Gln Glu Asp Val Cys Lys Phe Phe Ala Asn
            2580                2585                2590

Gly Asp Asp Leu Ile Ile Ala Ile Ser Pro Glu Leu Glu His Val Leu
            2595                2600                2605

Asp Gly Phe Gln Gln His Phe Ser Asp Leu Gly Leu Asn Tyr Asp Phe
    2610                2615                2620

Ser Ser Arg Thr Arg Asp Lys Lys Glu Leu Trp Phe Met Ser His Arg
2625                2630                2635                2640

Ala Leu Ser Lys Asp Gly Ile Leu Ile Pro Lys Leu Glu Pro Glu Arg
                2645                2650                2655

Ile Val Ser Ile Leu Glu Trp Asp Arg Ser Ala Glu Pro His His Arg
            2660                2665                2670

Leu Glu Ala Ile Cys Ala Ser Met Ile Glu Ala Trp Gly Tyr Thr Asp
            2675                2680                2685

Leu Leu Gln Asn Ile Arg Arg Phe Tyr Lys Trp Thr Ile Glu Gln Glu
    2690                2695                2700

Pro Tyr Arg Ser Leu Ala Glu Gln Gly Leu Ala Pro Tyr Leu Ser Glu
2705                2710                2715                2720

Val Ala Leu Arg Arg Leu Tyr Thr Ser Gln Ile Ala Thr Asp Asn Glu
                2725                2730                2735

Leu Thr Asp Tyr Tyr Lys Glu Ile Leu Ala Asn Asn Glu Phe Leu Arg
            2740                2745                2750

Glu Thr Val Arg Phe Gln Ser Asp Thr Val Asp Ala Gly Lys Asp Lys
            2755                2760                2765

Ala Arg Asp Gln Lys Leu Ala Asp Lys Pro Thr Leu Ala Ile Asp Arg
    2770                2775                2780

Thr Lys Asp Lys Asp Val Asn Thr Gly Thr Ser Gly Thr Phe Ser Ile
2785                2790                2795                2800

Pro Arg Leu Lys Lys Ala Ala Met Asn Met Lys Leu Pro Lys Val Gly
                2805                2810                2815

Gly Ser Ser Val Val Asn Leu Asp His Leu Leu Thr Tyr Lys Pro Ala
            2820                2825                2830

Gln Glu Phe Val Val Asn Thr Arg Ala Thr His Ser Gln Phe Lys Ala
            2835                2840                2845

Trp His Thr Asn Val Met Ala Glu Leu Glu Leu Asn Glu Glu Gln Met
    2850                2855                2860

Lys Ile Val Leu Asn Gly Phe Met Ile Trp Cys Ile Glu Asn Gly Thr
2865                2870                2875                2880

Ser Pro Asn Ile Ser Gly Val Trp Thr Met Met Asp Gly Asp Glu Gln
                2885                2890                2895

Val Glu Tyr Pro Ile Glu Pro Met Val Lys His Ala Asn Pro Ser Leu
            2900                2905                2910

Arg Gln Ile Met Lys His Phe Ser Asn Leu Ala Glu Ala Tyr Ile Arg
            2915                2920                2925

Met Arg Asn Ser Glu Gln Val Tyr Ile Pro Arg Tyr Gly Leu Gln Arg
    2930                2935                2940

Gly Leu Val Asp Arg Asn Leu Ala Pro Phe Ala Phe Asp Phe Phe Glu
```

```
                2945              2950              2955              2960
            Val Asn Gly Ala Thr Pro Val Arg Ala Arg Glu Ala His Ala Gln Met
                          2965              2970              2975

Lys Ala Ala Leu Arg Asn Ser Gln Gln Arg Met Phe Cys Leu Asp
                      2980              2985              2990

Gly Ser Val Ser Gly Gln Glu Glu Asn Thr Glu Arg His Thr Val Asp
                      2995              3000              3005

Asp Val Asn Ala Gln Met His His Leu Leu Gly Val Lys Gly Val
                  3010              3015              3020

<210> SEQ ID NO 25
<211> LENGTH: 381
<212> TYPE: PRT
<213> ORGANISM: Bacillus subtilis

<400> SEQUENCE: 25

Met Arg Gly Lys Lys Val Trp Ile Ser Leu Leu Phe Ala Leu Thr Leu
 1               5                   10                  15

Ile Phe Thr Met Ala Phe Ser Asn Met Ser Ala Gln Ala Ala Gly Lys
                20                  25                  30

Ser Ser Thr Glu Lys Lys Tyr Ile Val Gly Phe Lys Gln Thr Met Ser
            35                  40                  45

Ala Met Ser Ser Ala Lys Lys Lys Asp Val Ile Ser Glu Lys Gly Gly
        50                  55                  60

Lys Val Gln Lys Gln Phe Lys Tyr Val Asn Ala Ala Thr Ala Thr Leu
65                  70                  75                  80

Asp Glu Lys Ala Val Lys Glu Leu Lys Gln Asp Pro Ser Val Ala Tyr
                85                  90                  95

Val Glu Glu Asp His Ile Ala His Glu Tyr Ala Gln Ser Val Pro Tyr
            100                 105                 110

Gly Ile Ser Gln Ile Lys Ala Pro Ala Leu His Ser Gln Gly Tyr Thr
        115                 120                 125

Gly Ser Asn Val Lys Val Ala Val Ile Asp Ser Gly Ile Asp Ser Ser
    130                 135                 140

His Pro Asp Leu Asn Val Lys Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Thr Ile Gly Val Leu Gly Val Ala Pro
            180                 185                 190

Asn Ala Ser Leu Tyr Ala Val Lys Val Leu Asp Ser Thr Gly Ser Gly
        195                 200                 205

Gln Tyr Ser Trp Ile Ile Asn Gly Ile Glu Trp Ala Ile Ser Asn Asn
    210                 215                 220

Met Asp Val Ile Asn Met Ser Leu Gly Gly Pro Ser Gly Ser Thr Ala
225                 230                 235                 240

Leu Lys Thr Val Val Asp Lys Ala Val Ser Ser Gly Ile Val Val Ala
                245                 250                 255

Ala Ala Ala Gly Asn Glu Gly Ser Ser Gly Ser Thr Ser Thr Val Gly
            260                 265                 270

Tyr Pro Ala Lys Tyr Pro Ser Thr Ile Ala Val Gly Ala Val Asn Ser
        275                 280                 285

Ser Asn Gln Arg Ala Ser Phe Ser Ser Ala Gly Ser Glu Leu Asp Val
    290                 295                 300
```

```
Met Ala Pro Gly Val Ser Ile Gln Ser Thr Leu Pro Gly Gly Thr Tyr
305                 310                 315                 320

Gly Ala Tyr Asn Gly Thr Ser Met Ala Thr Pro His Val Ala Gly Ala
                325                 330                 335

Ala Ala Leu Ile Leu Ser Lys His Pro Thr Trp Thr Asn Ala Gln Val
            340                 345                 350

Arg Asp Arg Leu Glu Ser Thr Ala Thr Tyr Leu Gly Ser Ser Phe Tyr
        355                 360                 365

Tyr Gly Lys Gly Leu Ile Asn Val Gln Ala Ala Gln
370                 375                 380
```

<210> SEQ ID NO 26
<211> LENGTH: 277
<212> TYPE: PRT
<213> ORGANISM: Rattus norvegicus

<400> SEQUENCE: 26

```
Met Asp Asn Asn Glu Thr Ser Val Asp Ser Lys Ser Ile Asn Asn Phe
1               5                   10                  15

Glu Thr Lys Thr Ile His Gly Ser Lys Ser Met Asp Ser Gly Ile Tyr
            20                  25                  30

Leu Asp Ser Ser Tyr Lys Met Asp Tyr Pro Glu Met Gly Leu Cys Ile
        35                  40                  45

Ile Ile Asn Asn Lys Asn Phe His Lys Ser Thr Gly Met Ser Ala Arg
50                  55                  60

Asn Gly Thr Asp Val Asp Ala Ala Asn Leu Arg Glu Thr Phe Met Ala
65                  70                  75                  80

Leu Lys Tyr Glu Val Arg Asn Lys Asn Asp Leu Thr Arg Glu Glu Ile
                85                  90                  95

Met Glu Leu Met Asp Ser Val Ser Lys Glu Asp His Ser Lys Arg Ser
            100                 105                 110

Ser Phe Val Cys Val Ile Leu Ser His Gly Asp Glu Gly Val Ile Phe
        115                 120                 125

Gly Thr Asn Gly Pro Val Asp Leu Lys Lys Leu Thr Ser Phe Phe Arg
130                 135                 140

Gly Asp Tyr Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Thr Asp Asp Asp Met Ala Cys Gln Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Arg Asp Gly Ser Trp Phe Ile Gln Ser Leu Cys Ala Met Leu Lys
210                 215                 220

Leu Tyr Ala His Lys Leu Glu Phe Met His Ile Leu Thr Arg Val Asn
225                 230                 235                 240

Arg Lys Val Ala Thr Glu Phe Glu Ser Phe Ser Leu Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275
```

<210> SEQ ID NO 27

```
<211> LENGTH: 7
<212> TYPE: PRT
<213> ORGANISM: Artificial Sequence
<220> FEATURE:
<223> OTHER INFORMATION: Tobacco Etch Virus protease cleavage site
      consensus sequence
<220> FEATURE:
<221> NAME/KEY: VARIANT
<222> LOCATION: 2, 3, 5
<223> OTHER INFORMATION: Xaa can be any amino acid

<400> SEQUENCE: 27

Glu Xaa Xaa Tyr Xaa Gln Gly
 1               5

<210> SEQ ID NO 28
<211> LENGTH: 7
<212> TYPE: PRT
<213> ORGANISM: Artificial Sequence
<220> FEATURE:
<223> OTHER INFORMATION: Tobacco Etch Virus protease cleavage site
      consensus sequence
<220> FEATURE:
<221> NAME/KEY: VARIANT
<222> LOCATION: 2, 3, 5
<223> OTHER INFORMATION: Xaa can be any amino acid

<400> SEQUENCE: 28

Glu Xaa Xaa Tyr Xaa Gln Ser
 1               5

<210> SEQ ID NO 29
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 29

Glu Asn Leu Tyr Phe Gln Gly
 1               5

<210> SEQ ID NO 30
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 30

Glu Asn Leu Tyr Phe Gln Ser
 1               5

<210> SEQ ID NO 31
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 31

Glu Asn Ile Tyr Thr Gln Gly
 1               5

<210> SEQ ID NO 32
<211> LENGTH: 7
<212> TYPE: PRT
<213> ORGANISM: Artificial Sequence
<220> FEATURE:
```

<223> OTHER INFORMATION: Tobacco Etch Virus protease cleavage site

<400> SEQUENCE: 32

Glu Asn Ile Tyr Thr Gln Ser
1               5

<210> SEQ ID NO 33
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 33

Glu Asn Ile Tyr Leu Gln Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 34

Glu Asn Ile Tyr Leu Gln Ser
1               5

<210> SEQ ID NO 35
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 35

Glu Asn Val Tyr Phe Gln Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 36

Glu Asn Val Tyr Ser Gln Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 37

Glu Asn Val Tyr Ser Gln Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Tobacco Etch Virus protease cleavage site

```
<400> SEQUENCE: 38

Glu Asn Val Tyr Ser Gln Ser
1               5

<210> SEQ ID NO 39
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site consensus sequence
<220> FEATURE:
<221> NAME/KEY: VARIANT
<222> LOCATION: 1, 2
<223> OTHER INFORMATION: Xaa can be any amino acid

<400> SEQUENCE: 39

Xaa Xaa Val Arg Phe Gln Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site consensus sequence
<220> FEATURE:
<221> NAME/KEY: VARIANT
<222> LOCATION: 1, 2
<223> OTHER INFORMATION: Xaa can be any amino acid

<400> SEQUENCE: 40

Xaa Xaa Val Arg Phe Gln Ser
1               5

<210> SEQ ID NO 41
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 41

Glu Thr Val Arg Phe Gln Gly
1               5

<210> SEQ ID NO 42
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 42

Glu Thr Val Arg Phe Gln Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site
```

```
<400> SEQUENCE: 43

Asn Asn Val Arg Phe Gln Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 44

Asn Asn Val Arg Phe Gln Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Human Rhinovirus 3C protease cleavage site
      consensus sequence
<220> FEATURE:
<221> NAME/KEY: VARIANT
<222> LOCATION: 1
<223> OTHER INFORMATION: Xaa can be amino acid, with D or E preferred
<220> FEATURE:
<221> NAME/KEY: VARIANT
<222> LOCATION: 2
<223> OTHER INFORMATION: Xaa can be G, A, V, L, I, M, S or T

<400> SEQUENCE: 45

Xaa Xaa Leu Phe Gln Gly Pro
1               5

<210> SEQ ID NO 46
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 46

Glu Ala Leu Phe Gln Gly Pro
1               5

<210> SEQ ID NO 47
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 47

Glu Val Leu Phe Gln Gly Pro
1               5

<210> SEQ ID NO 48
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 48

Glu Leu Leu Phe Gln Gly Pro
1               5
```

```
<210> SEQ ID NO 49
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 49

Asp Ala Leu Phe Gln Gly Pro
1               5

<210> SEQ ID NO 50
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 50

Asp Val Leu Phe Gln Gly Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 51

Asp Leu Leu Phe Gln Gly Pro
1               5

<210> SEQ ID NO 52
<211> LENGTH: 6
<212> TYPE: PRT
<213> ORGANISM: Artificial Sequence
<220> FEATURE:
<223> OTHER INFORMATION: Subtilisin protease cleavage site consensus
      sequence
<220> FEATURE:
<221> NAME/KEY: VARIANT
<222> LOCATION: 1, 2, 3, 4
<223> OTHER INFORMATION: Xaa can be any amino acid

<400> SEQUENCE: 52

Xaa Xaa Xaa Xaa His Tyr
1               5

<210> SEQ ID NO 53
<211> LENGTH: 6
<212> TYPE: PRT
<213> ORGANISM: Artificial Sequence
<220> FEATURE:
<223> OTHER INFORMATION: Subtilisin protease cleavage site consensus
      sequence
<220> FEATURE:
<221> NAME/KEY: VARIANT
<222> LOCATION: 1, 2, 3, 4
<223> OTHER INFORMATION: Xaa can be any amino acid

<400> SEQUENCE: 53

Xaa Xaa Xaa Xaa His Tyr
1               5

<210> SEQ ID NO 54
<211> LENGTH: 2
```

```
<212> TYPE: PRT
<213> ORGANISM: Artificial Sequence
<220> FEATURE:
<223> OTHER INFORMATION: Subtilisin protease cleavage site

<400> SEQUENCE: 54

His Tyr
 1

<210> SEQ ID NO 55
<211> LENGTH: 2
<212> TYPE: PRT
<213> ORGANISM: Artificial Sequence
<220> FEATURE:
<223> OTHER INFORMATION: Subtilisin protease cleavage site

<400> SEQUENCE: 55

Tyr His
 1

<210> SEQ ID NO 56
<211> LENGTH: 6
<212> TYPE: PRT
<213> ORGANISM: Artificial Sequence
<220> FEATURE:
<223> OTHER INFORMATION: Subtilisin protease cleavage site

<400> SEQUENCE: 56

Pro Gly Ala Ala His Tyr
 1               5

<210> SEQ ID NO 57
<211> LENGTH: 5
<212> TYPE: PRT
<213> ORGANISM: Artificial Sequence
<220> FEATURE:
<223> OTHER INFORMATION: Caspase 3 protease cleavage site consensus
      sequence
<220> FEATURE:
<221> NAME/KEY: VARIANT
<222> LOCATION: 2
<223> OTHER INFORMATION: Xaa can be any amino acid with E preferred
<220> FEATURE:
<221> NAME/KEY: VARIANT
<222> LOCATION: 3
<223> OTHER INFORMATION: Xaa can be any amino acid
<220> FEATURE:
<221> NAME/KEY: VARIANT
<222> LOCATION: 5
<223> OTHER INFORMATION: Xaa can be any amino acid with G or S preferred

<400> SEQUENCE: 57

Asp Xaa Xaa Asp Xaa
 1               5

<210> SEQ ID NO 58
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 58

Asp Glu Val Asp Gly
 1               5

<210> SEQ ID NO 59
<211> LENGTH: 5
<212> TYPE: PRT
```

```
<213> ORGANISM: Artificial Sequence
<220> FEATURE:
<223> OTHER INFORMATION: Caspase 3 protease cleavage site

<400> SEQUENCE: 59

Asp Glu Val Asp Ser
1               5

<210> SEQ ID NO 60
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 60

Asp Glu Pro Asp Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 61

Asp Glu Pro Asp Ser
1               5

<210> SEQ ID NO 62
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 62

Asp Glu Leu Asp Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 63

Asp Glu Leu Asp Ser
1               5

<210> SEQ ID NO 64
<211> LENGTH: 5
<212> TYPE: PRT
<213> ORGANISM: Artificial Sequence
<220> FEATURE:
<223> OTHER INFORMATION: Enterokinase protease cleavage site consensus
      sequence

<400> SEQUENCE: 64

Asp Asp Asp Asp Lys
1               5

<210> SEQ ID NO 65
<211> LENGTH: 753
<212> TYPE: DNA
```

<213> ORGANISM: Artificial Sequence
<220> FEATURE:
<223> OTHER INFORMATION: Codon-optimized TEV open reading frame

<400> SEQUENCE: 65

```
atgggcgaat ctctgttcaa gggtccgcgt gattataacc cgatatcttc tactatttgt      60
catctgacta acgaaagcga cggccacacg acttctctgt acggtatcgg tttcggtccg     120
ttcatcatta ccaacaagca tctgttccgc cgtaacaacg gtaccctgct ggttcaatct     180
ctgcacggcg tcttcaaggt aaaaaatacc actacgctgc agcagcacct gattgacggc     240
cgtgacatga tcatcatccg catgccgaaa gattttccgc cgttcccgca aaaactgaag     300
tttcgtgaac cgcaacgcga agaacgtatt tgcctggtta ccaccaactt tcagaccaaa     360
agcatgtctt ctatggtttc cgataccctc tgcaccttcc caagctctga cggtattttc     420
tggaaacatt ggatccagac caaagatggt cagtgcggct ctccgctggt gtctacgcgt     480
gacggtttca tcgttggtat ccattctgct tctaacttca ctaacactaa caactacttt     540
acttccgttc cgaaaaactt catggagctg ctgactaacc aagaggccca gcagtgggtg     600
tccggttggc gcctgaacgc agattctgta ctgtggggtg gtcataaggt attcatgaac     660
aaaccggagg agccgttcca gccggtcaaa gaggcgaccc agctgatgaa cgaactggtt     720
tactctcagg gtcaccacca tcaccaccat taa                                  753
```

<210> SEQ ID NO 66
<211> LENGTH: 250
<212> TYPE: PRT
<213> ORGANISM: Artificial Sequence
<220> FEATURE:
<223> OTHER INFORMATION: TEV protease (S219N) with amino-terminus
    polyhistidine affinity tag

<400> SEQUENCE: 66

```
Met Gly Glu Ser Leu Phe Lys Gly Pro Arg Asp Tyr Asn Pro Ile Ser
  1               5                  10                  15

Ser Thr Ile Cys His Leu Thr Asn Glu Ser Asp Gly His Thr Thr Ser
             20                  25                  30

Leu Tyr Gly Ile Gly Phe Gly Pro Phe Ile Ile Thr Asn Lys His Leu
         35                  40                  45

Phe Arg Arg Asn Asn Gly Thr Leu Leu Val Gln Ser Leu His Gly Val
     50                  55                  60

Phe Lys Val Lys Asn Thr Thr Thr Leu Gln Gln His Leu Ile Asp Gly
 65                  70                  75                  80

Arg Asp Met Ile Ile Ile Arg Met Pro Lys Asp Phe Pro Pro Phe Pro
                 85                  90                  95

Gln Lys Leu Lys Phe Arg Glu Pro Gln Arg Glu Glu Arg Ile Cys Leu
            100                 105                 110

Val Thr Thr Asn Phe Gln Thr Lys Ser Met Ser Ser Met Val Ser Asp
        115                 120                 125

Thr Ser Cys Thr Phe Pro Ser Ser Asp Gly Ile Phe Trp Lys His Trp
    130                 135                 140

Ile Gln Thr Lys Asp Gly Gln Cys Gly Ser Pro Leu Val Ser Thr Arg
145                 150                 155                 160

Asp Gly Phe Ile Val Gly Ile His Ser Ala Ser Asn Phe Thr Asn Thr
                165                 170                 175

Asn Asn Tyr Phe Thr Ser Val Pro Lys Asn Phe Met Glu Leu Leu Thr
            180                 185                 190
```

```
Asn Gln Glu Ala Gln Gln Trp Val Ser Gly Trp Arg Leu Asn Ala Asp
            195                 200                 205

Ser Val Leu Trp Gly Gly His Lys Val Phe Met Asn Lys Pro Glu Glu
    210                 215                 220

Pro Phe Gln Pro Val Lys Glu Ala Thr Gln Leu Met Asn Glu Leu Val
225                 230                 235                 240

Tyr Ser Gln Gly His His His His His His
                245                 250
```

<210> SEQ ID NO 67
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 67

```
atgggtcacc accatcacca ccatggcgaa tctctgttca agggtccgcg tgattataac    60
ccgatatctt ctactatttg tcatctgact aacgaaagcg acggcacac gacttctctg    120
tacggtatcg gtttcggtcc gttcatcatt accaacaagc atctgttccg ccgtaacaac    180
ggtaccctgg tggttcaatc tctgcacggc gtcttcaagg taaaaaatac cactacgctg    240
cagcagcacc tgattgacgg ccgtgacatg atcatcatcc gcatgccgaa agattttccg    300
ccgttcccgc aaaaactgaa gtttcgtgaa ccgcaacgcg aagaacgtat ttgcctggtt    360
accaccaact tcagaccaa agcatgtct tctatggttt ccgatacctc ttgcaccttc    420
ccaagcggtg acggtatttt ctggaaacat tggatccaga ccaaagatgg tcagtgcggc    480
tctccgctgg tgtctacgcg tgacggttc atcgttggta ccattctgc ttctaacttc    540
actaacacta caactactt tacttccgtt ccgaaaaact tcatggagct gctgactaac    600
caagaggccc agcagtgggt gtccggttgg cgcctgaacg cagattctgt actgtggggt    660
ggtcataagg tattcatgaa caaaccggag gagccgttcc agccggtcaa agaggcgacc    720
cagctgatga cgaactggt ttactctcag taa                                  753
```

<210> SEQ ID NO 68
<211> LENGTH: 250
<212> TYPE: PRT
<213> ORGANISM: Artificial Sequence
<220> FEATURE:
<223> OTHER INFORMATION: TEV protease (L56V, S135G, S219N) with
      amino-terminus polyhistidine affinity tag

<400> SEQUENCE: 68

```
Met Gly His His His His His Gly Glu Ser Leu Phe Lys Gly Pro
  1               5                  10                  15

Arg Asp Tyr Asn Pro Ile Ser Ser Thr Ile Cys His Leu Thr Asn Glu
             20                  25                  30

Ser Asp Gly His Thr Thr Ser Leu Tyr Gly Ile Gly Phe Gly Pro Phe
         35                  40                  45

Ile Ile Thr Asn Lys His Leu Phe Arg Arg Asn Asn Gly Thr Leu Val
 50                  55                  60

Val Gln Ser Leu His Gly Val Phe Lys Val Lys Asn Thr Thr Thr Leu
 65                  70                  75                  80

Gln Gln His Leu Ile Asp Gly Arg Asp Met Ile Ile Ile Arg Met Pro
             85                  90                  95

Lys Asp Phe Pro Pro Phe Pro Gln Lys Leu Lys Phe Arg Glu Pro Gln
            100                 105                 110
```

```
Arg Glu Glu Arg Ile Cys Leu Val Thr Thr Asn Phe Gln Thr Lys Ser
            115                 120                 125
Met Ser Ser Met Val Ser Asp Thr Ser Cys Thr Phe Pro Ser Gly Asp
        130                 135                 140
Gly Ile Phe Trp Lys His Trp Ile Gln Thr Lys Asp Gly Gln Cys Gly
145                 150                 155                 160
Ser Pro Leu Val Ser Thr Arg Asp Gly Phe Ile Val Gly Ile His Ser
                165                 170                 175
Ala Ser Asn Phe Thr Asn Thr Asn Tyr Phe Thr Ser Val Pro Lys
            180                 185                 190
Asn Phe Met Glu Leu Leu Thr Asn Gln Glu Ala Gln Trp Val Ser
        195                 200                 205
Gly Trp Arg Leu Asn Ala Asp Ser Val Leu Trp Gly Gly His Lys Val
    210                 215                 220
Phe Met Asn Lys Pro Glu Glu Pro Phe Gln Pro Val Lys Glu Ala Thr
225                 230                 235                 240
Gln Leu Met Asn Glu Leu Val Tyr Ser Gln
                245                 250

<210> SEQ ID NO 69
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 69
atgggtcacc accatcacca ccatggcgaa tctctgttca agggtccgcg tgattataac      60
ccgatatctt cttctatttg tcatctgact aacgaaagcg acggccacac gacttctctg     120
tacggtatcg tttcggtcc gttcatcatt accaacaagc atctgttccg ccgtaacaac      180
ggtaccctgc tggttcaatc tctgcacggc gtcttcaagg taaagacac cactacgctg      240
cagcagcacc tggtcgacgg ccgtgacatg atcatcatcc gcatgccgaa agattttccg     300
ccgttcccgc aaaaactgaa gtttcgtgaa ccgcaacgcg aagaacgtat tgcctggtt      360
accaccaact ttcagaccaa agcatgtct tctatggttt ccgataccct tgcaccttc       420
ccaagctctg acggtatttt ctggaaacat tggatccaga ccaaagatgg tcagtgcggc     480
tctccgctgg tgtctacgcg tgacggtttc atcgttggta tccattctgc ttctaacttc     540
actaacacta caactactt tacttccgtt ccgaaaaact tcatggagct gctgactaac      600
caagaggccc agcagtgggt gtccggttgg cgcctgaacg cagattctgt actgtggggt     660
ggtcataagg tattcatgaa caaaccggag gagccgttcc agccggtcaa agaggcgacc     720
cagctgatga acgaactggt ttactctcag taa                                  753

<210> SEQ ID NO 70
<211> LENGTH: 250
<212> TYPE: PRT
<213> ORGANISM: Artificial Sequence
<220> FEATURE:
<223> OTHER INFORMATION: TEV protease (T17S, N68D, I77V, S219N) with
      amino-terminus polyhistidine affinity tag

<400> SEQUENCE: 70

Met Gly His His His His His His Gly Glu Ser Leu Phe Lys Gly Pro
1               5                   10                  15
Arg Asp Tyr Asn Pro Ile Ser Ser Ser Ile Cys His Leu Thr Asn Glu
```

|  | 20 |  |  |  | 25 |  |  |  | 30 |  |  |
|---|---|---|---|---|---|---|---|---|---|---|---|

Ser Asp Gly His Thr Thr Ser Leu Tyr Gly Ile Gly Phe Gly Pro Phe
    35       40       45

Ile Ile Thr Asn Lys His Leu Phe Arg Arg Asn Asn Gly Thr Leu Leu
50       55       60

Val Gln Ser Leu His Gly Val Phe Lys Val Lys Asp Thr Thr Thr Leu
65       70       75       80

Gln Gln His Leu Val Asp Gly Arg Asp Met Ile Ile Ile Arg Met Pro
      85       90       95

Lys Asp Phe Pro Pro Phe Pro Gln Lys Leu Lys Phe Arg Glu Pro Gln
    100       105       110

Arg Glu Glu Arg Ile Cys Leu Val Thr Thr Asn Phe Gln Thr Lys Ser
    115       120       125

Met Ser Ser Met Val Ser Asp Thr Ser Cys Thr Phe Pro Ser Ser Asp
    130       135       140

Gly Ile Phe Trp Lys His Trp Ile Gln Thr Lys Asp Gly Gln Cys Gly
145       150       155       160

Ser Pro Leu Val Ser Thr Arg Asp Gly Phe Ile Val Gly Ile His Ser
      165       170       175

Ala Ser Asn Phe Thr Asn Thr Asn Asn Tyr Phe Thr Ser Val Pro Lys
    180       185       190

Asn Phe Met Glu Leu Leu Thr Asn Gln Glu Ala Gln Gln Trp Val Ser
    195       200       205

Gly Trp Arg Leu Asn Ala Asp Ser Val Leu Trp Gly Gly His Lys Val
210       215       220

Phe Met Asn Lys Pro Glu Glu Pro Phe Gln Pro Val Lys Glu Ala Thr
225       230       235       240

Gln Leu Met Asn Glu Leu Val Tyr Ser Gln
    245       250

<210> SEQ ID NO 71
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 71

```
atgggtcacc accatcacca ccatggcgaa tctctgttca agggtccgcg tgattataac      60
ccgatatctt ctactatttg tcatctgact aacgaaagcg acggccacac gacttctctg     120
tacggtatcg gtttcggtcc gttcatcatt accgtgaagc atctgttccg ccgtaacaac     180
ggtaccctgg tggttcaatc tctgcacggc gtcttcaagg taaaaaatac cactacgctg     240
cagcagcacc tgattgacgg ccgtgacatg atcatcatcc gcatgccgaa agattttccg     300
ccgttcccgc aaaaactgaa gtttcgtgaa ccgcaacgcg aagaacgtat ttgcctggtt     360
accaccaact ttcagaccaa aagcatgtct tctatggttt ccgataccct ttgcaccttc     420
ccaagcggtg acggtatttt ctggaaacat tggatccaga ccaaagatgg tcagtgcggc     480
tctccgctgg tgtctacgcg tgacggtttc atcgttggta ccattctgc ttctaacttc     540 actaacacta caactactt tacttccgtt ccgaaaaact tcatggagct gctgactaac     600
caagaggccc agcagtgggt gtccggttgg cgcctgaacg cagattctgt actgtggggt     660
ggtcataagg tattcatgaa caaaccggag gagccgttcc agccggtcaa agaggcgacc     720
cagctgatga acgaactggt ttactctcag taa                                  753
```

<210> SEQ ID NO 72
<211> LENGTH: 250
<212> TYPE: PRT
<213> ORGANISM: Artificial Sequence
<220> FEATURE:
<223> OTHER INFORMATION: TEV protease (N44V, L56V, S135G, S219N) with amino-terminus polyhistidine affinity tag

<400> SEQUENCE: 72

Met Gly His His His His His Gly Glu Ser Leu Phe Lys Gly Pro
1               5                   10                  15

Arg Asp Tyr Asn Pro Ile Ser Ser Thr Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Val Lys His Leu Phe Arg Arg Asn Asn Gly Thr Leu Val
50                  55                  60

Val Gln Ser Leu His Gly Val Phe Lys Val Lys Asn Thr Thr Thr Leu
65                  70                  75                  80

Gln Gln His Leu Ile Asp Gly Arg Asp Met Ile Ile Ile Arg Met Pro
                85                  90                  95

Lys Asp Phe Pro Pro Phe Pro Gln Lys Leu Lys Phe Arg Glu Pro Gln
            100                 105                 110

Arg Glu Glu Arg Ile Cys Leu Val Thr Thr Asn Phe Gln Thr Lys Ser
        115                 120                 125

Met Ser Ser Met Val Ser Asp Thr Ser Cys Thr Phe Pro Ser Gly Asp
130                 135                 140

Gly Ile Phe Trp Lys His Trp Ile Gln Thr Lys Asp Gly Gln Cys Gly
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
            180                 185                 190

Asn Phe Met Glu Leu Leu Thr Asn Gln Glu Ala Gln Gln Trp Val Ser
        195                 200                 205

Gly Trp Arg Leu Asn Ala Asp Ser Val Leu Trp Gly Gly His Lys Val
210                 215                 220

Phe Met Asn Lys Pro Glu Glu Pro Phe Gln Pro Val Lys Glu Ala Thr
225                 230                 235                 240

Gln Leu Met Asn Glu Leu Val Tyr Ser Gln
                245                 250

<210> SEQ ID NO 73
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 73
atgggtcacc accatcacca ccatggcgaa tctctgttca gggtccgcg tgattataac      60 ccgatatctt ctactatttg tcatctgact aacgaaagcg acggccacac gacttctctg     120
tacggtatcg gtttcggtcc gttcatcatt accaacaagc atctgttccg ccgtaacaac     180
ggtaccctgg tggttcaatc tctgcacggg gtcttcaagg taaagacac cactacgctg     240 cagcagcacc tgattgacgg ccgtgacatg atcatcatcc gcatgccgaa agatttcccg     300

```
ccgttcccgc aaaaactgaa gtttcgtgaa ccgcaacgcg aagaacgtat ttgcctggtt      360
accaccaact ttcagaccaa aagcatgtct tctatggttt ccgatacctc ttgcaccttc      420
ccaagcggtg acggtatttt ctggaaacat tggatccaga ccaaagatgg tcagtgcggc      480
tctccgctgg tgtctacgcg tgacggtttc atcgttggta ccattctgc ttctaacttc       540 actaacacta caactactt tacttccgtt ccgaaaaact tcatggagct gctgactaac       600
caagaggccc agcagtgggt gtccggttgg cgcctgaacg cagattctgt actgtggggt      660
ggtcataagg tattcatgaa caaaccggag gagccgttcc agccggtcaa agaggcgacc      720
cagctgatga cgaactggt ttactctcag taa                                    753
```

<210> SEQ ID NO 74
<211> LENGTH: 250
<212> TYPE: PRT
<213> ORGANISM: Artificial Sequence
<220> FEATURE:
<223> OTHER INFORMATION: TEV protease (L56V, N68D, S135G, S219N) with amino-terminus polyhistidine affinity tag

<400> SEQUENCE: 74

```
Met Gly His His His His His Gly Glu Ser Leu Phe Lys Gly Pro
1               5                   10                  15

Arg Asp Tyr Asn Pro Ile Ser Ser Thr Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Asn Lys His Leu Phe Arg Arg Asn Asn Gly Thr Leu Val
50                  55                  60

Val Gln Ser Leu His Gly Val Phe Lys Val Lys Asp Thr Thr Thr Leu
65                  70                  75                  80

Gln Gln His Leu Ile Asp Gly Arg Asp Met Ile Ile Ile Arg Met Pro
                85                  90                  95

Lys Asp Phe Pro Pro Phe Pro Gln Lys Leu Lys Phe Arg Glu Pro Gln
            100                 105                 110

Arg Glu Glu Arg Ile Cys Leu Val Thr Thr Asn Phe Gln Thr Lys Ser
        115                 120                 125

Met Ser Ser Met Val Ser Asp Thr Ser Cys Thr Phe Pro Ser Gly Asp
130                 135                 140

Gly Ile Phe Trp Lys His Trp Ile Gln Thr Lys Asp Gly Gln Cys Gly
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
            180                 185                 190

Asn Phe Met Glu Leu Leu Thr Asn Gln Glu Ala Gln Gln Trp Val Ser
        195                 200                 205

Gly Trp Arg Leu Asn Ala Asp Ser Val Leu Trp Gly Gly His Lys Val
    210                 215                 220

Phe Met Asn Lys Pro Glu Glu Pro Phe Gln Pro Val Lys Glu Ala Thr
225                 230                 235                 240

Gln Leu Met Asn Glu Leu Val Tyr Ser Gln
                245                 250
```

<210> SEQ ID NO 75
<211> LENGTH: 753

```
<212> TYPE: DNA
<213> ORGANISM: Artificial Sequence
<220> FEATURE:
<223> OTHER INFORMATION: Codon-optimized TEV open reading frame

<400> SEQUENCE: 75
atgggtcacc accatcacca ccatggcgaa tctctgttca gggtccgcg tgattataac      60
ccgatatctt cttctatttg tcatctgact aacgaaagcg acggccacac gacttctctg    120
tacggtatcg gtttcggtcc gttcatcatt accaacaagc atctgttccg ccgtaacaac    180
ggtaccctgg tggttcaatc tctgcacggc gtcttcaagg taaaagacac cactacgctg    240
cagcagcacc tggtcgacgg ccgtgacatg atcatcatcc gcatgccgaa agattttccg    300
ccgttcccgc aaaaactgaa gtttcgtgaa ccgcaacgcg aagaacgtat tgcctggtt    360
accaccaact ttcagaccaa aagcatgtct tctatggttt ccgataccct cttgcacctc    420
ccaagctctg acggtatttt ctggaaacat tggatccaga ccaaagatgg tcagtgcggc    480
tctccgctgg tgtctacgcg tgacggtttc atcgttggta ccattctgc ttctaacttc     540
actaacacta caaactactt tacttccgtt ccgaaaaact tcatggagct gctgactaac    600
caagaggccc agcagtgggt gtccggttgg cgcctgaacg cagattctgt actgtggggt    660
ggtcataagg tattcatgaa caaaccggag gagccgttcc agccggtcaa agaggcgacc    720
cagctgatga cgaactggt ttactctcag taa                                   753

<210> SEQ ID NO 76
<211> LENGTH: 250
<212> TYPE: PRT
<213> ORGANISM: Artificial Sequence
<220> FEATURE:
<223> OTHER INFORMATION: TEV protease (T17S, L56V, N68D, I77V, S219N)
      with amino-terminus polyhistidine affinity tag

<400> SEQUENCE: 76

Met Gly His His His His His Gly Glu Ser Leu Phe Lys Gly Pro
 1               5                  10                  15

Arg Asp Tyr Asn Pro Ile Ser Ser Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Asn Lys His Leu Phe Arg Arg Asn Asn Gly Thr Leu Val
    50                  55                  60

Val Gln Ser Leu His Gly Val Phe Lys Val Lys Asp Thr Thr Leu
65                  70                  75                  80

Gln Gln His Leu Val Asp Gly Arg Asp Met Ile Ile Ile Arg Met Pro
                85                  90                  95

Lys Asp Phe Pro Pro Phe Pro Gln Lys Leu Lys Phe Arg Glu Pro Gln
            100                 105                 110

Arg Glu Glu Arg Ile Cys Leu Val Thr Thr Asn Phe Gln Thr Lys Ser
        115                 120                 125

Met Ser Ser Met Val Ser Asp Thr Ser Cys Thr Phe Pro Ser Ser Asp
    130                 135                 140

Gly Ile Phe Trp Lys His Trp Ile Gln Thr Lys Asp Gly Gln Cys Gly
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
            180                 185                 190
```

Asn Phe Met Glu Leu Leu Thr Asn Gln Glu Ala Gln Gln Trp Val Ser
            195                 200                 205

Gly Trp Arg Leu Asn Ala Asp Ser Val Leu Trp Gly Gly His Lys Val
    210                 215                 220

Phe Met Asn Lys Pro Glu Glu Pro Phe Gln Pro Val Lys Glu Ala Thr
225                 230                 235                 240

Gln Leu Met Asn Glu Leu Val Tyr Ser Gln
                245                 250

<210> SEQ ID NO 77
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 77
atgggtcacc accatcacca ccatggcgaa tctctgttca gggtccgcg tgattataac      60 ccgatatctt cttctatttg tcatctgact aacgaaagcg acggccacac gacttctctg    120
tacggtatcg gtttcggtcc gttcatcatt accaacaagc atctgttccg ccgtaacaac    180
ggtaccctgc tggttcaatc tctgcacggc gtcttcaagg taaagacac cactacgctg    240 cagcagcacc tggtcgacgg ccgtgacatg atcatcatcc gcatgccgaa agattttccg    300
ccgttcccgc aaaaactgaa gtttcgtgaa ccgcaacgcg aagaacgtat tgcctggtt    360 accaccaact ttcagaccaa agcatgtct tctatggttt ccgataccctc ttgcaccttc    420 ccaagcggtg acggtatttt ctggaaacat tggatccaga ccaaagatgg tcagtgcggc    480
tctccgctgg tgtctacgcg tgacggtttc atcgttggta ccattctgc ttctaacttc    540 actaacacta caactactt tacttccgtt ccgaaaaact tcatggagct gctgactaac    600
caagaggccc agcagtgggt gtccggttgg cgcctgaacg cagattctgt actgtggggt    660
ggtcataagg tattcatgaa caaaccggag gagccgttcc agccggtcaa agaggcgacc    720
cagctgatga acgaactggt ttactctcag taa                                  753

<210> SEQ ID NO 78
<211> LENGTH: 250
<212> TYPE: PRT
<213> ORGANISM: Artificial Sequence
<220> FEATURE:
<223> OTHER INFORMATION: TEV protease (T17S, N68D, I77V, S135G, S219N)
      with amino-terminus polyhistidine affinity tag

<400> SEQUENCE: 78

Met Gly His His His His His His Gly Glu Ser Leu Phe Lys Gly Pro
1               5                   10                  15

Arg Asp Tyr Asn Pro Ile Ser Ser Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Asn Lys His Leu Phe Arg Arg Asn Asn Gly Thr Leu Leu
    50                  55                  60

Val Gln Ser Leu His Gly Val Phe Lys Val Lys Asp Thr Thr Thr Leu
65                  70                  75                  80

Gln Gln His Leu Val Asp Gly Arg Asp Met Ile Ile Ile Arg Met Pro
                85                  90                  95

Lys Asp Phe Pro Pro Phe Pro Gln Lys Leu Lys Phe Arg Glu Pro Gln

```
            100                 105                 110
Arg Glu Glu Arg Ile Cys Leu Val Thr Thr Asn Phe Gln Thr Lys Ser
                115                 120                 125

Met Ser Ser Met Val Ser Asp Thr Ser Cys Thr Phe Pro Ser Gly Asp
    130                 135                 140

Gly Ile Phe Trp Lys His Trp Ile Gln Thr Lys Asp Gly Gln Cys Gly
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
    180                 185                 190

Asn Phe Met Glu Leu Leu Thr Asn Gln Glu Ala Gln Gln Trp Val Ser
                195                 200                 205

Gly Trp Arg Leu Asn Ala Asp Ser Val Leu Trp Gly Gly His Lys Val
    210                 215                 220

Phe Met Asn Lys Pro Glu Glu Pro Phe Gln Pro Val Lys Glu Ala Thr
225                 230                 235                 240

Gln Leu Met Asn Glu Leu Val Tyr Ser Gln
                245                 250

<210> SEQ ID NO 79
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 79
atgggcgaat ctctgttcaa gggtccgcgt gattataacc cgatatcttc ttctatttgt      60
catctgacta cgaaagcga cggccacacg acttctctgt acggtatcgg tttcggtccg     120
ttcatcatta ccgtgaagca tctgttccgc cgtaacaacg gtaccctggt ggttcaatct     180
ctgcacggcg tcttcaaggt aaaagacacc actacgctgc agcagcacct ggtcgacggc     240
cgtgacatga tcatcatccg catgccgaaa gattttccgc cgttcccgca aaaactgaag     300
tttcgtgaac cgcaacgcga agaacgtatt tgcctggtta ccaccaactt tcagaccaaa     360
agcatgtctt ctatggtttc cgataccctc tgcaccttcc caagcggtga cggtattttc     420
tggaaacatt ggatccagac caagatggt cagtgcggct ctccgctggt gtctacgcgt     480
gacggtttca tcgttggtat ccattctgct tctaacttca ctaacactaa caactacttt     540
acttccgttc cgaaaaactt catggagctg ctgactaacc aagaggccca gcagtgggtg     600
tccggttggc gcctgaacgc agattctgta ctgtggggtg gtcataaggt attcatgaac     660
aaaccggagg agccgttcca gccggtcaaa gaggcgaccc agctgatgaa cgaactggtt     720
tactctcagg gtcaccacca tcaccaccat taa                                  753

<210> SEQ ID NO 80
<211> LENGTH: 250
<212> TYPE: PRT
<213> ORGANISM: Artificial Sequence
<220> FEATURE:
<223> OTHER INFORMATION: TEV protease (T17S, N44V, L56V, N68D, I77V,
      S135G, S219N) with carboxyl-terminus polyhistidine
      affinity tag

<400> SEQUENCE: 80

Met Gly Glu Ser Leu Phe Lys Gly Pro Arg Asp Tyr Asn Pro Ile Ser
1               5                   10                  15
```

Ser Ser Ile Cys His Leu Thr Asn Glu Ser Asp Gly His Thr Thr Ser
            20                  25                  30

Leu Tyr Gly Ile Gly Phe Gly Pro Phe Ile Ile Thr Val Lys His Leu
        35                  40                  45

Phe Arg Arg Asn Asn Gly Thr Leu Val Val Gln Ser Leu His Gly Val
    50                  55                  60

Phe Lys Val Lys Asp Thr Thr Thr Leu Gln Gln His Leu Val Asp Gly
65                  70                  75                  80

Arg Asp Met Ile Ile Ile Arg Met Pro Lys Asp Phe Pro Pro Phe Pro
                85                  90                  95

Gln Lys Leu Lys Phe Arg Glu Pro Gln Arg Glu Arg Ile Cys Leu
            100                 105                 110

Val Thr Thr Asn Phe Gln Thr Lys Ser Met Ser Ser Met Val Ser Asp
            115                 120                 125

Thr Ser Cys Thr Phe Pro Ser Gly Asp Gly Ile Phe Trp Lys His Trp
    130                 135                 140

Ile Gln Thr Lys Asp Gly Gln Cys Gly Ser Pro Leu Val Ser Thr Arg
145                 150                 155                 160

Asp Gly Phe Ile Val Gly Ile His Ser Ala Ser Asn Phe Thr Asn Thr
                165                 170                 175

Asn Asn Tyr Phe Thr Ser Val Pro Lys Asn Phe Met Glu Leu Leu Thr
            180                 185                 190

Asn Gln Glu Ala Gln Gln Trp Val Ser Gly Trp Arg Leu Asn Ala Asp
        195                 200                 205

Ser Val Leu Trp Gly Gly His Lys Val Phe Met Asn Lys Pro Glu Glu
        210                 215                 220

Pro Phe Gln Pro Val Lys Glu Ala Thr Gln Leu Met Asn Glu Leu Val
225                 230                 235                 240

Tyr Ser Gln Gly His His His His His His
            245                 250

<210> SEQ ID NO 81
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 81
atgggtcacc accatcacca ccatggcgaa tctctgttca agggtccgcg tgattataac      60
ccgatatctt cttctatttg tcatctgact aacgaaagcg acggccacac gacttctctg     120
tacggtatcg gtttcggtcc gttcatcatt accgtgaagc atctgttccg ccgtaacaac     180
ggtaccctgg tggttcaatc tctgcacggc gtcttcaagg taaaagacac cactacgctg     240
cagcagcacc tggtcgacgg ccgtgacatg atcatcatcc gcatgccgaa agattttccg     300
ccgttcccgc aaaaactgaa gtttcgtgaa ccgcaacgcg aagaacgtat ttgcctggtt     360
accaccaact ttcagaccaa agcatgtctt ctatggtttt ccgataccct tgcaccttc      420 ccaagcggtg acggtatttt ctggaaacat tggatccaga ccaaagatgg tcagtgcggc     480
tctccgctgg tgtctacgcg tgacggtttc atcgttggta ccattctgc ttctaacttc      540 actaacacta acaactactt tacttccgtt ccgaaaaact tcatggagct gctgactaac     600
caagaggccc agcagtgggt gtccggttgg cgcctgaacg cagattctgt actgtggggt     660
ggtcataagg tattcatggt gaaaccggag gagccgttcc agccggtcaa agaggcgacc     720

-continued cagctgatga acgaactggt ttactctcag taa                                   753

<210> SEQ ID NO 82
<211> LENGTH: 250
<212> TYPE: PRT
<213> ORGANISM: Artificial Sequence
<220> FEATURE:
<223> OTHER INFORMATION: TEV protease (T17S, N44V, L56V, N68D, I77V,
    S135G, S219V) with amino-terminus polyhistidine affinity
    tag

<400> SEQUENCE: 82

Met Gly His His His His His Gly Glu Ser Leu Phe Lys Gly Pro
 1               5                  10                  15

Arg Asp Tyr Asn Pro Ile Ser Ser Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Val Lys His Leu Phe Arg Arg Asn Asn Gly Thr Leu Val
50                  55                  60

Val Gln Ser Leu His Gly Val Phe Lys Val Lys Asp Thr Thr Leu
65                  70                  75                  80

Gln Gln His Leu Val Asp Gly Arg Asp Met Ile Ile Arg Met Pro
            85                  90                  95

Lys Asp Phe Pro Pro Phe Pro Gln Lys Leu Lys Phe Arg Glu Pro Gln
            100                 105                 110

Arg Glu Glu Arg Ile Cys Leu Val Thr Thr Asn Phe Gln Thr Lys Ser
            115                 120                 125

Met Ser Ser Met Val Ser Asp Thr Ser Cys Thr Phe Pro Ser Gly Asp
    130                 135                 140

Gly Ile Phe Trp Lys His Trp Ile Gln Thr Lys Asp Gly Gln Cys Gly
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
            180                 185                 190

Asn Phe Met Glu Leu Leu Thr Asn Gln Glu Ala Gln Gln Trp Val Ser
            195                 200                 205

Gly Trp Arg Leu Asn Ala Asp Ser Val Leu Trp Gly Gly His Lys Val
        210                 215                 220

Phe Met Val Lys Pro Glu Glu Pro Phe Gln Pro Val Lys Glu Ala Thr
225                 230                 235                 240

Gln Leu Met Asn Glu Leu Val Tyr Ser Gln
            245                 250

<210> SEQ ID NO 83
<211> LENGTH: 753
<212> TYPE: DNA
<213> ORGANISM: Artificial Sequence
<220> FEATURE:
<223> OTHER INFORMATION: Codon-optimized TEV open reading frame

<400> SEQUENCE: 83
atgggtcacc accatcacca ccatggcgaa tctctgttca aggtccgcg tgattataac     60 ccgatatctt cttctatttg tcatctgact aacgaaagcg acggccacac gacttctctg    120
tacggtatcg gtttcggtcc gttcatcatt accgtgaagc atctgttccg ccgtaacaac    180

```
ggtaccctgg tggttcaatc tctgcacggc gtcttcaagg taaaagacac cactacgctg    240
cagcagcacc tggtcgacgg ccgtgacatg atcatcatcc gcatgccgaa agatttccg     300 ccgttcccgc aaaaactgaa gtttcgtgaa ccgcaacgcg aagaacgtat tgcctggtt    360 accaccaact ttcagaccaa aagcatgtct tctatggttt ccgataccte ttgcaccttc    420 ccaagcggtg acggtatttt ctggaaacat tggatccaga ccaaagatgg tcagtgcggc    480
tctccgctgg tgtctacgcg tgacggtttc atcgttggta ccattctgc ttctaacttc    540 actaacacta caactactt tacttccgtt ccgaaaaact tcatggagct gctgactaac    600
caagaggccc agcagtgggt gtccggttgg cgcctgaacg cagattctgt actgtggggt    660
ggtcataagg tattcatgaa caaaccggag gagccgttcc agccggtcaa agaggcgacc    720
cagctgatga acgaactggt ttactctcag taa                                 753
```

<210> SEQ ID NO 84
<211> LENGTH: 250
<212> TYPE: PRT
<213> ORGANISM: Artificial Sequence
<220> FEATURE:
<223> OTHER INFORMATION: TEV protease (T17S, N44V, L56V, N68D, I77V, S135G, S219N) with amino-terminus polyhistidine affinity tag

<400> SEQUENCE: 84

```
Met Gly His His His His His His Gly Glu Ser Leu Phe Lys Gly Pro
 1               5                  10                  15

Arg Asp Tyr Asn Pro Ile Ser Ser Ser Ile Cys His Leu Thr Asn Glu
            20                  25                  30

Ser Asp Gly His Thr Thr Ser Leu Tyr Gly Ile Gly Phe Gly Pro Phe
        35                  40                  45

Ile Ile Thr Val Lys His Leu Phe Arg Arg Asn Asn Gly Thr Leu Val
    50                  55                  60

Val Gln Ser Leu His Gly Val Phe Lys Val Lys Asp Thr Thr Thr Leu
65                  70                  75                  80

Gln Gln His Leu Val Asp Gly Arg Asp Met Ile Ile Ile Arg Met Pro
                85                  90                  95

Lys Asp Phe Pro Pro Phe Pro Gln Lys Leu Lys Phe Arg Glu Pro Gln
            100                 105                 110

Arg Glu Glu Arg Ile Cys Leu Val Thr Thr Asn Phe Gln Thr Lys Ser
        115                 120                 125

Met Ser Ser Met Val Ser Asp Thr Ser Cys Thr Phe Pro Ser Gly Asp
130                 135                 140

Gly Ile Phe Trp Lys His Trp Ile Gln Thr Lys Asp Gly Gln Cys Gly
145                 150                 155                 160

Ser Pro Leu Val Ser Thr Arg Asp Gly Phe Ile Val Gly Ile His Ser
                165                 170                 175

Ala Ser Asn Phe Thr Asn Thr Asn Asn Tyr Phe Thr Ser Val Pro Lys
            180                 185                 190

Asn Phe Met Glu Leu Leu Thr Asn Gln Glu Ala Gln Gln Trp Val Ser
        195                 200                 205

Gly Trp Arg Leu Asn Ala Asp Ser Val Leu Trp Gly Gly His Lys Val
    210                 215                 220

Phe Met Asn Lys Pro Glu Glu Pro Phe Gln Pro Val Lys Glu Ala Thr
225                 230                 235                 240

Gln Leu Met Asn Glu Leu Val Tyr Ser Gln
                245                 250
```

<210> SEQ ID NO 85
<211> LENGTH: 750
<212> TYPE: DNA
<213> ORGANISM: Artificial Sequence
<220> FEATURE:
<223> OTHER INFORMATION: Native TEV open reading frame

<400> SEQUENCE: 85

```
atgcatcacc atcaccacca tggagaaagc ttgtttaagg gaccacgtga ttacaacccg      60
atatcgagca ccatttgtca tttgacgaat gaatctgatg ggcacacaac atcgttgtat     120
ggtattggat ttggtccctt catcattaca aacaagcact gtttcgccg taataatgga     180
acactgttgg tccaatcact acatggtgta ttcaaggtca agaacaccac gactttgcaa     240
caacacctca ttgatgggag ggacatgata attattcgca tgcctaagga tttcccacca     300
tttcctcaaa agctgaaatt tagagagcca caaagggaag agcgcatctg tcttgtgaca     360
accaacttcc aaactaagag catgtctagc atggtgtcag acactagttg cacattccct     420
tcatctgatg gcatattctg gaagcattgg atccaaacca aggatgggca gtgtggcagt     480
ccattagtat caactagaga tgggttcatt gttggtatac actcagcatc gaatttcacc     540
aacacaaaca attatttcac aagcgtgccg aaaaacttca tggaattgtt gacaaatcag     600
gaggcgcagc agtgggttag tggttggcga ttaaatgctg actcagtatt gtggggggc      660
cataaagttt tcatgaacaa acctgaagag cctttcagc cagttaagga agcgactcaa      720
ctcatgaatg aattggtgta ctcgcaataa                                      750
```

<210> SEQ ID NO 86
<211> LENGTH: 249
<212> TYPE: PRT
<213> ORGANISM: Artificial Sequence
<220> FEATURE:
<223> OTHER INFORMATION: TEV protease (S219N) with amino-terminus polyhistidine affinity tag

<400> SEQUENCE: 86

```
Met His His His His His His Gly Glu Ser Leu Phe Lys Gly Pro Arg
1               5                   10                  15

Asp Tyr Asn Pro Ile Ser Ser Thr Ile Cys His Leu Thr Asn Glu Ser
            20                  25                  30

Asp Gly His Thr Thr Ser Leu Tyr Gly Ile Gly Phe Gly Pro Phe Ile
        35                  40                  45

Ile Thr Asn Lys His Leu Phe Arg Arg Asn Asn Gly Thr Leu Leu Val
    50                  55                  60

Gln Ser Leu His Gly Val Phe Lys Val Lys Asn Thr Thr Thr Leu Gln
65                  70                  75                  80

Gln His Leu Ile Asp Gly Arg Asp Met Ile Ile Ile Arg Met Pro Lys
                85                  90                  95

Asp Phe Pro Pro Phe Pro Gln Lys Leu Lys Phe Arg Glu Pro Gln Arg
            100                 105                 110

Glu Glu Arg Ile Cys Leu Val Thr Thr Asn Phe Gln Thr Lys Ser Met
        115                 120                 125

Ser Ser Met Val Ser Asp Thr Ser Cys Thr Phe Pro Ser Ser Asp Gly
    130                 135                 140

Ile Phe Trp Lys His Trp Ile Gln Thr Lys Asp Gly Gln Cys Gly Ser
145                 150                 155                 160

Pro Leu Val Ser Thr Arg Asp Gly Phe Ile Val Gly Ile His Ser Ala
```

```
                    165                 170                 175
Ser Asn Phe Thr Asn Thr Asn Asn Tyr Phe Thr Ser Val Pro Lys Asn
            180                 185                 190

Phe Met Glu Leu Leu Thr Asn Gln Glu Ala Gln Gln Trp Val Ser Gly
        195                 200                 205

Trp Arg Leu Asn Ala Asp Ser Val Leu Trp Gly Gly His Lys Val Phe
    210                 215                 220

Met Asn Lys Pro Glu Glu Pro Phe Gln Pro Val Lys Glu Ala Thr Gln
225                 230                 235                 240

Leu Met Asn Glu Leu Val Tyr Ser Gln
            245

<210> SEQ ID NO 87
<211> LENGTH: 3984
<212> TYPE: DNA
<213> ORGANISM: Artificial Sequence
<220> FEATURE:
<223> OTHER INFORMATION: Open reading frame encoding BoNT/A-TEV

<400> SEQUENCE: 87
atgccgttcg taaacaaaca gttcaactat aaagacccag tcaacggcgt ggacattgcc      60
tatatcaaaa tcccgaatgc gggtcaaatg cagcccgtga agcatttaaa atccataac     120 aaaatttggg tgatcccgga gcgcgatacg ttcacgaacc cggaagaagg agatttaaac    180
ccaccgcctg aggctaaaca ggtcccggtg tcttactatg atagcacata cctgagtacc    240
gacaatgaaa aggacaacta cctgaaaggt gttaccaaac tgttcgagcg catttattcg    300
acagatctcg gtcgcatgtt gctgacttct attgtgcgcg gcattccgtt ttggggtggt    360
agcaccatcg atacagaact caaagtgatt gacaccaact gcatcaatgt gattcagcct    420
gatgggagct accggtccga agagcttaac ctcgtaatca ttggcccgag cgcggatatt    480
atccaattcg aatgtaaatc ttttgggcat gaagtcctga atctgacgcg gaatggctat    540
ggatcgacgc agtatattcg ttttctcca gatttcacat ttggatttga agaaagcctc    600
gaagttgata cgaaccctct tttaggcgcg ggaaaattcg cgacggaccc agcggtgacc    660
ttggcacatg aacttattca tgccgggcat cgcttgtatg aatcgccat taacccgaac    720 cgtgttttca ggtgaatac gaacgcgtat acgagatgt cgggcttaga agtgtccttt    780
gaagaactgc gcacgtttgg cggtcatgat gcaaaattta tgatagtct gcaagaaaac    840 gaatttcggc tgtactatta cataaaattc aaagacattg catcaacctt aaacaaggcg    900
aaaagcattg tgggtaccac ggctagctta caatatatga aaaacgtttt caaagaaaaa    960
tacctcctta gcgaagacac ttccggcaaa ttctctgtcg ataaactgaa atttgataaa   1020
ctgtataaaa tgctcaccga gatctacaca gaggataact tgtcaaatt cttcaaggtc   1080 ttgaatcgga aaacctatct gaacttcgat aaagccgtct taagatcaa catcgtaccg   1140 aaagttaact acaccatcta tgatggcttt aatctgcgca atacgaatct ggcggcgaac   1200
tttaacggcc agaacaccga atcaacaac atgaacttta ctaaactgaa aaatttacc   1260 ggcttgtttg aattctataa gctcctgtgt gtccgcggta ttatcaccag caaaaccaaa   1320
tccttgggcg gtggtggcga aaacctgtac ttccagggcg tggcggtgg tgataagggc   1380 tataacaagg cctaaatga tttatgcatc aaggtgaaca actgggactt gttttctct   1440 ccatctgaag ataattttac taacgacttg aacaaggag aggaaattac ttccgatacc   1500
aacatcgaag cagcggaaga gaatattagc ctggatctta ttcaacaata ttacctgacc   1560
```

```
tttaattttg ataacgagcc tgagaacatt tccattgaga atctcagctc tgacatcatc    1620
ggccagctgg aactgatgcc gaatatcgaa cgctttccta atggaaagaa atatgaattg    1680
gacaaataca ccatgttcca ctatctccgc gcgcaggagt ttgagcacgg caagtctcgt    1740
attgctctga ccaattcggt aaacgaagcc cttttaaatc cttcgcgtgt gtacacctttt   1800 ttctcaagcg attatgttaa aaaagtgaac aaggcgaccg aagcggcgat gttttttggga   1860 tgggtggaac aactggtata tgactttacg gatgaaactt ctgaagtctc gaccaccgac    1920
aaaattgccg atattaccat tatcattccc tatattggcc ctgcactgaa cattggtaac    1980
atgctgtata aagatgattt tgtgggcgcc ctgatctttt caggcgctgt tatcctgctg    2040
gaatttatcc cggaaatcgc cattccagta ctcggtacct ttgcgctggt gtcctatatc    2100
gcaaacaaag ttttgactgt ccagacgatc gacaacgcgc tcagtaaacg taacgaaaaa    2160
tgggatgagg tgtataagta tattgttacc aactggctcg ctaaagtaaa cacccagatt    2220
gacctgattc gcaagaagat gaaagaagcg ctggaaaacc aagcagaagc gaccaaagct    2280
attatcaact atcaatataa ccagtacaca gaggaagaaa agaataacat caacttcaac    2340
atcgacgact tatcttcaaa gctgaatgaa tctattaaca aagcgatgat taatattaac    2400
aagttcttga accaatgtag tgtcagctat ctgatgaact cgatgatccc ttacggtgtg    2460
aaacgtctgg aagacttcga tgcaagcctt aaagatgccc ttctgaagta tatttacgat    2520
aatcgcggaa ctcttattgg ccaagtggat cgcttaaaag ataaagtcaa caacacgctg    2580
agtacagaca tcccttttca gctgtctaaa tatgtggaca atcagcgcct gctgtccacg    2640
tttacggaat acatcaaaaa catcatcaac actagtattc tgaacttgcg ttacgagagt    2700
aaccatctga ttgatctgag ccgttacgca tctaaaatca acatcggctc gaaggtgaac    2760
ttcgatccta tcgacaaaaa ccagattcaa ttgttcaact tagaatcgtc aaagattgaa    2820
gttatcttaa aaaatgcgat tgtatataat tcaatgtacg aaaatttctc tacgagctttt   2880 tggattcgta ttccgaaata tttcaacagt atctctttaa acaacgagta tactatcatc    2940
aattgtatgg agaataacag cgggtggaaa gtgagcctta actatggtga atcatctgg    3000 actctgcagg acactcaaga aattaaacaa cgcgtggtgt ttaaatactc acagatgatt    3060
aacatctcgg attatattaa tcgctggatt tttgtgacaa ttactaacaa ccggctgaac    3120
aacagcaaaa tttacattaa cggtcgcctg atcgatcaga aaccaatcag taatctcggt    3180
aacattcacg catcgaataa tatcatgttc aaactggatg gttgtcgcga cacgcaccgt    3240
tacatttgga tcaaatactt caatttattc gacaaagaac tcaacgaaaa ggagattaag    3300
gatctttatg acaatcagtc taattcgggt attctgaaag acttttgggg tgattacctt    3360
cagtacgata aaccgtatta tatgttaaac ttatatgatc cgaataaata cgttgacgtc    3420
aacaacgttg gcattcgtgg ctatatgtat ctgaaagggc cgcgtggcag cgtgatgacc    3480
actaacattt acttaaactc ctccctctat cgcggtacta aatttattat caagaaatat    3540
gcctctggca acaaggacaa tatcgtacgc aataacgatc gcgtctacat taacgtggtg    3600
gtgaagaata agaatatcg tctggcgacc aatgctagtc aggcgggcgt ggagaaaatt    3660
ctgtctgcac ttgaaatccc ggatgtgggt aatttatccc aggtggttgt gatgaaaagt    3720
aaaaatgacc aagggatcac caataaatgc aaaatgaatc tgcaagataa caacggcaac    3780
gacattggtt ttatcggctt ccaccaattc aataatatcg cgaaactggt ggcctcaaat    3840
tggtacaacc gtcagattga gcgcagctcc cgcactttag gctgtagctg ggagttcatt    3900
ccggtagatg acggttgggg agaacgccca ttgaaagtcg acaagcttgc ggccgcactc    3960
```
gagcaccacc accaccacca ctga                                              3984

<210> SEQ ID NO 88
<211> LENGTH: 1327
<212> TYPE: PRT
<213> ORGANISM: Artificial Sequence
<220> FEATURE:
<223> OTHER INFORMATION: BoNT/A-TEV

<400> SEQUENCE: 88

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350
```

```
Asn Phe Val Lys Phe Lys Val Leu Asn Arg Lys Thr Tyr Leu Asn
            355                 360                 365
Phe Asp Lys Ala Val Phe Lys Ile Asn Ile Val Pro Lys Val Asn Tyr
    370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Gly Gly Gly Gly Glu Asn
            435                 440                 445
Leu Tyr Phe Gln Gly Gly Gly Gly Asp Lys Gly Tyr Asn Lys Ala
    450                 455                 460
Leu Asn Asp Leu Cys Ile Lys Val Asn Asn Trp Asp Leu Phe Phe Ser
465                 470                 475                 480
Pro Ser Glu Asp Asn Phe Thr Asn Asp Leu Asn Lys Gly Glu Glu Ile
                485                 490                 495
Thr Ser Asp Thr Asn Ile Glu Ala Ala Glu Glu Asn Ile Ser Leu Asp
            500                 505                 510
Leu Ile Gln Gln Tyr Tyr Leu Thr Phe Asn Phe Asp Asn Glu Pro Glu
    515                 520                 525
Asn Ile Ser Ile Glu Asn Leu Ser Ser Asp Ile Ile Gly Gln Leu Glu
            530                 535                 540
Leu Met Pro Asn Ile Glu Arg Phe Pro Asn Gly Lys Lys Tyr Glu Leu
545                 550                 555                 560
Asp Lys Tyr Thr Met Phe His Tyr Leu Arg Ala Gln Glu Phe Glu His
                565                 570                 575
Gly Lys Ser Arg Ile Ala Leu Thr Asn Ser Val Asn Glu Ala Leu Leu
            580                 585                 590
Asn Pro Ser Arg Val Tyr Thr Phe Phe Ser Ser Asp Tyr Val Lys Lys
    595                 600                 605
Val Asn Lys Ala Thr Glu Ala Ala Met Phe Leu Gly Trp Val Glu Gln
610                 615                 620
Leu Val Tyr Asp Phe Thr Asp Glu Thr Ser Glu Val Ser Thr Thr Asp
625                 630                 635                 640
Lys Ile Ala Asp Ile Thr Ile Ile Pro Tyr Ile Gly Pro Ala Leu
                645                 650                 655
Asn Ile Gly Asn Met Leu Tyr Lys Asp Asp Phe Val Gly Ala Leu Ile
            660                 665                 670
Phe Ser Gly Ala Val Ile Leu Leu Glu Phe Ile Pro Glu Ile Ala Ile
    675                 680                 685
Pro Val Leu Gly Thr Phe Ala Leu Val Ser Tyr Ile Ala Asn Lys Val
690                 695                 700
Leu Thr Val Gln Thr Ile Asp Asn Ala Leu Ser Lys Arg Asn Glu Lys
705                 710                 715                 720
Trp Asp Glu Val Tyr Lys Tyr Ile Val Thr Asn Trp Leu Ala Lys Val
                725                 730                 735
Asn Thr Gln Ile Asp Leu Ile Arg Lys Lys Met Lys Glu Ala Leu Glu
            740                 745                 750
Asn Gln Ala Glu Ala Thr Lys Ala Ile Ile Asn Tyr Gln Tyr Asn Gln
    755                 760                 765
Tyr Thr Glu Glu Glu Lys Asn Asn Ile Asn Phe Asn Ile Asp Asp Leu
```

```
            770             775             780
Ser Ser Lys Leu Asn Glu Ser Ile Asn Lys Ala Met Ile Asn Ile Asn
785             790             795             800

Lys Phe Leu Asn Gln Cys Ser Val Ser Tyr Leu Met Asn Ser Met Ile
                805             810             815

Pro Tyr Gly Val Lys Arg Leu Glu Asp Phe Asp Ala Ser Leu Lys Asp
                820             825             830

Ala Leu Leu Lys Tyr Ile Tyr Asp Asn Arg Gly Thr Leu Ile Gly Gln
                835             840             845

Val Asp Arg Leu Lys Asp Lys Val Asn Thr Leu Ser Thr Asp Ile
850             855             860

Pro Phe Gln Leu Ser Lys Tyr Val Asp Asn Gln Arg Leu Leu Ser Thr
865             870             875             880

Phe Thr Glu Tyr Ile Lys Asn Ile Ile Asn Thr Ser Ile Leu Asn Leu
                885             890             895

Arg Tyr Glu Ser Asn His Leu Ile Asp Leu Ser Arg Tyr Ala Ser Lys
                900             905             910

Ile Asn Ile Gly Ser Lys Val Asn Phe Asp Pro Ile Asp Lys Asn Gln
                915             920             925

Ile Gln Leu Phe Asn Leu Glu Ser Ser Lys Ile Glu Val Ile Leu Lys
                930             935             940

Asn Ala Ile Val Tyr Asn Ser Met Tyr Glu Asn Phe Ser Thr Ser Phe
945             950             955             960

Trp Ile Arg Ile Pro Lys Tyr Phe Asn Ser Ile Ser Leu Asn Asn Glu
                965             970             975

Tyr Thr Ile Ile Asn Cys Met Glu Asn Asn Ser Gly Trp Lys Val Ser
                980             985             990

Leu Asn Tyr Gly Glu Ile Ile Trp Thr Leu Gln Asp Thr Gln Glu Ile
                995             1000            1005

Lys Gln Arg Val Val Phe Lys Tyr Ser Gln Met Ile Asn Ile Ser Asp
        1010            1015            1020

Tyr Ile Asn Arg Trp Ile Phe Val Thr Ile Thr Asn Asn Arg Leu Asn
1025            1030            1035            1040

Asn Ser Lys Ile Tyr Ile Asn Gly Arg Leu Ile Asp Gln Lys Pro Ile
                1045            1050            1055

Ser Asn Leu Gly Asn Ile His Ala Ser Asn Asn Ile Met Phe Lys Leu
                1060            1065            1070

Asp Gly Cys Arg Asp Thr His Arg Tyr Ile Trp Ile Lys Tyr Phe Asn
                1075            1080            1085

Leu Phe Asp Lys Glu Leu Asn Glu Lys Glu Ile Lys Asp Leu Tyr Asp
                1090            1095            1100

Asn Gln Ser Asn Ser Gly Ile Leu Lys Asp Phe Trp Gly Asp Tyr Leu
1105            1110            1115            1120

Gln Tyr Asp Lys Pro Tyr Tyr Met Leu Asn Leu Tyr Asp Pro Asn Lys
                1125            1130            1135

Tyr Val Asp Val Asn Asn Val Gly Ile Arg Gly Tyr Met Tyr Leu Lys
                1140            1145            1150

Gly Pro Arg Gly Ser Val Met Thr Thr Asn Ile Tyr Leu Asn Ser Ser
                1155            1160            1165

Leu Tyr Arg Gly Thr Lys Phe Ile Ile Lys Lys Tyr Ala Ser Gly Asn
                1170            1175            1180

Lys Asp Asn Ile Val Arg Asn Asn Asp Arg Val Tyr Ile Asn Val Val
1185            1190            1195            1200
```

```
Val Lys Asn Lys Glu Tyr Arg Leu Ala Thr Asn Ala Ser Gln Ala Gly
                1205                1210                1215

Val Glu Lys Ile Leu Ser Ala Leu Glu Ile Pro Asp Val Gly Asn Leu
            1220                1225                1230

Ser Gln Val Val Val Met Lys Ser Lys Asn Asp Gln Gly Ile Thr Asn
        1235                1240                1245

Lys Cys Lys Met Asn Leu Gln Asp Asn Asn Gly Asn Asp Ile Gly Phe
    1250                1255                1260

Ile Gly Phe His Gln Phe Asn Asn Ile Ala Lys Leu Val Ala Ser Asn
1265                1270                1275                1280

Trp Tyr Asn Arg Gln Ile Glu Arg Ser Ser Arg Thr Leu Gly Cys Ser
                1285                1290                1295

Trp Glu Phe Ile Pro Val Asp Asp Gly Trp Gly Glu Arg Pro Leu Lys
            1300                1305                1310

Val Asp Lys Leu Ala Ala Ala Leu Glu His His His His His His
        1315                1320                1325
```

<210> SEQ ID NO 89
<211> LENGTH: 1044
<212> TYPE: DNA
<213> ORGANISM: Artificial Sequence
<220> FEATURE:
<223> OTHER INFORMATION: Intervening sequence containing transcriptional and translational sites.

<400> SEQUENCE: 89

```
aagcttgtgg cctcaaattg gtacaaccgt cagattgagc gcagctcccg cactttaggc     60
tgtagctggg agttcattcc ggtagatgac ggttggggag aacgcccatt gcaccatcat    120
caccatcact gagcggccgc ataatgctta agtcgaacag attgatatgt agctataagt    180
aatcgtattg tacacggccg cataatcgaa attaatacga ctcactatag gggaattgtg    240
agcggataac aattccccat cttagtatat tagttaagta taagaaggag atataccatg    300
ggcgaatctc tgttcaaggg tccgcgtgat tataacccga tatcttcttc tatttgtcat    360
ctgactaacg aaagcgacgg ccacacgact tctctgtacg gtatcggttt cggtccgttc    420
atcattacca acaagcatct gttccgccgt aacaacggta ccctgctggt tcaatctctg    480
cacggcgtct tcaaggtaaa agacaccact acgctgcagc agcacctggt cgacggccgt    540
gacatgatca tcatccgcat gccgaaagat tttccgccgt tcccgcaaaa actgaagttt    600
cgtgaaccgc aacgcgaaga acgtatttgc ctggttacca ccaactttca gaccaaaagc    660
atgtcttcta tggtttccga tacctcttgc accttcccaa gcggtgacgg tattttctgg    720
aaacattgga ttcagaccaa agatggtcag tgcggctctc cgctggtgtc tacgcgtgac    780
ggtttcatcg ttggtatcca ttctgcttct aacttcacta acactaacaa ctactttact    840
tccgttccga aaaacttcat ggagctgctg actaaccaag aggcccagca gtgggtgtcc    900
ggttggcgcc tgaacgcaga ttctgtactg tggggtggtc ataaggtatt catgaacaaa    960
ccggaggagc cgttccagcc ggtcaaagag gcgacccagc tgatgaacga actggtttac   1020
tctcagtaag agctctgtct cgag                                          1044
```

<210> SEQ ID NO 90
<211> LENGTH: 4851
<212> TYPE: DNA
<213> ORGANISM: Artificial Sequence
<220> FEATURE:
<223> OTHER INFORMATION: BoNT/A-TEV and TEV protease variant 4 open reading frames with the intervening transcription and
translation elements.

<400> SEQUENCE: 90

```
atgccgttcg taaacaaaca gttcaactat aaagacccag tcaacggcgt ggacattgcc      60
tatatcaaaa tcccgaatgc gggtcaaatg cagcccgtga aagcatttaa aatccataac     120
aaaatttggg tgatcccgga gcgcgatacg ttcacgaacc cggaagaagg agatttaaac     180
ccaccgcctg aggctaaaca ggtcccggtg tcttactatg atagcacata cctgagtacc     240
gacaatgaaa aggacaacta cctgaaaggt gttaccaaac tgttcgagcg catttattcg     300
acagatctcg gtcgcatgtt gctgacttct attgtgcgcg gcattccgtt ttggggtggt     360
agcaccatcg atacagaact caaagtgatt gacaccaact gcatcaatgt gattcagcct     420
gatgggagct accggtccga agagcttaac ctcgtaatca ttggcccgag cgcggatatt     480
atccaattcg aatgtaaatc ttttgggcat gaagtcctga atctgacgcg aatggctat     540
ggatcgacgc agtatattcg ttttctcca gatttcacat ttggatttga agaaagcctc     600
gaagttgata cgaaccctct tttaggcgcg ggaaaattcg cgacggaccc agcggtgacc     660
ttggcacatg aacttattca tgccgggcat cgcttgtatg gaatcgccat taacccgaac     720
cgtgttttca aggtgaatac gaacgcgtat tacgagatgt cgggcttaga agtgtccttt     780
gaagaactgc gcacgtttgg cggtcatgat gcaaaattta ttgatagtct gcaagaaaac     840
gaatttcggc tgtactatta caataaattc aaagacattg catcaacctt aaacaaggcg     900
aaaagcattg tgggtaccac ggctagctta caatatatga aaaacgttt caagaaaaa     960
tacctcctta gcgaagacac ttccggcaaa ttctctgtcg ataaactgaa atttgataaa    1020
ctgtataaaa tgctcaccga gatctacaca gaggataact ttgtcaaatt cttcaaggtc    1080
ttgaatcgga aaacctatct gaacttcgat aaagccgtct ttaagatcaa catcgtaccg    1140
aaagttaact acaccatcta tgatggcttt aatctgcgca atacgaatct ggcggcgaac    1200
tttaacggcc agaacaccga aatcaacaac atgaacttta ctaaactgaa aaattttacc    1260
ggcttgtttg aattctataa gctcctgtgt gtccgcggta ttatcaccag caaaaccaaa    1320
tccttgggcg gtggtggcga aaacctgtac ttccagggcg gtggcggtgg tgataagggc    1380
tataacaagg ccttcaatga tttatgcatc aaggtgaaca actgggactt gttttctct    1440
ccatctgaag ataattttac taacgacttg aacaaaggag aggaaattac ttccgatacc    1500
aacatcgaag cagcggaaga gaatattagt ctagatctta ttcaacaata ttacctgacc    1560
tttaattttg ataacgagcc tgagaacatt tccattgaga atctcagctc tgacatcatc    1620
ggccagctgg aactgatgcc gaatatcgaa cgctttccta atggaaagaa atatgaattg    1680
gacaaataca ccatgttcca ctatctccgc gcgcaggagt ttgagcacgg caagtctcgt    1740
attgctctga ccaattcggt aaacgaagcc cttttaaatc cttcgcgtgt gtacaccttt    1800
ttctcaagcg attatgttaa aaaagtgaac aaggcgaccg aagcggcgat gtttttggga    1860
tgggtggaac aactggtata tgactttacg gatgaaactt ctgaagtctc gaccaccgac    1920
aaaattgccg atattaccat tatcattccc tatattggcc ctgcactgaa cattggtaac    1980
atgctgtata aagatgattt tgtgggcgcc ctgatctttt caggcgctgt tatcctgctg    2040
gaatttatcc cggaaatcgc cattccagta ctcggtacct ttgcgctggt gtcctatatc    2100
gcaaacaaag ttttgactgt ccagacgatc gacaacgcgc tcagtaaacg taacgaaaaa    2160
tgggatgagg tgtataagta tattgttacc aactggctcg ctaaagtaaa cacccagatt    2220
```

```
gacctgattc gcaagaagat gaaagaagcg ctggaaaacc aagcagaagc gaccaaagct    2280
attatcaact atcaatataa ccagtacaca gaggaagaaa agaataacat caacttcaac    2340
atcgacgact tatcttcaaa gctgaatgaa tctattaaca aagcgatgat taatattaac    2400
aagttcttga accaatgtag tgtcagctat ctgatgaact cgatgatccc ttacggtgtg    2460
aaacgtctgg aagacttcga tgcaagcctt aaagatgccc ttctgaagta tatttacgat    2520
aatcgcggaa ctcttattgg ccaagtggat cgcttaaaag ataaagtcaa caacacgctg    2580
agtacagaca tcccttttca gctgtctaaa tatgtggaca atcagcgcct gctgtccacg    2640
tttacggaat acatcaaaaa catcatcaac actagtattc tgaacttgcg ttacgagagt    2700
aaccatctga ttgatctgag ccgttacgca tctaaaatca acatcggatc caaggtgaac    2760
ttcgatccta tcgacaaaaa ccagattcaa ttgttcaact tagaatcgtc aaagattgaa    2820
gttatcttaa aaaatgcgat tgtatataat tcaatgtacg aaaatttctc tacgagcttt    2880
tggattcgta ttccgaaata tttcaacagt atctctttaa acaacgagta tactatcatc    2940
aattgtatgg agaataacag cgggtggaaa gtgagcctta actatggtga aatcatctgg    3000
actctgcagg acactcaaga aattaaacaa cgcgtggtgt ttaaatactc acagatgatt    3060
aacatctcgg attatattaa tcgctggatt tttgtgacaa ttactaacaa ccggctgaac    3120
aacagcaaaa tttacattaa cggtcgcctg atcgatcaga aaccaatcag taatctcggt    3180
aacattcacg catcgaataa tatcatgttc aaactggatg gttgtcgcga cacgcaccgt    3240
tacatttgga tcaaatactt caatttattc gacaaagaac tcaacgaaaa ggagattaag    3300
gatctttatg acaatcagtc taattcgggt attctgaaag acttttgggg tgattaccct    3360
cagtacgata aaccgtatta tatgttaaac ttatatgatc cgaataaata cgttgacgtc    3420
aacaacgttg gcattcgtgg ctatatgtat ctgaaagggc cgcgtggcag cgtgatgacc    3480
actaacattt acttaaactc ctccctctat cgcggtacta aatttattat caagaaatat    3540
gcctctggca acaaggacaa tatcgtacgc aataacgatc gcgtctacat taacgtggtg    3600
gtgaagaata aagaatatcg tctggcgacc aatgctagtc aggcgggcgt ggagaaaatt    3660
ctgtctgcac ttgaaatccc ggatgtgggt aatttatccc aggtggttgt gatgaaaagt    3720
aaaaatgacc aagggatcac caataaatgc aaaatgaatc tgcaagataa caacggcaac    3780
gacattggtt ttatcggctt ccaccaattc aataatatcg cgaagcttgt ggcctcaaat    3840
tggtacaacc gtcagattga gcgcagctcc cgcactttag gctgtagctg ggagttcatt    3900
ccggtagatg acggttgggg agaacgccca ttgcaccatc atcaccatca ctgagcggcc    3960
gcataatgct taagtcgaac agattgatat gtagctataa gtaatcgtat tgtacacggc    4020
cgcataatcg aaattaatac gactcactat aggggaattg tgagcggata acaattcccc    4080
atcttagtat attagttaag tataagaagg agatatacca tgggcgaatc tctgttcaag    4140
ggtccgcgtg attataaccc gatatcttct tctatttgtc atctgactaa cgaaagcgac    4200
ggccacacga cttctctgta cggtatcggt ttcggtccgt tcatcattac caacaagcat    4260
ctgttccgcc gtaacaacgg taccctgctg gttcaatctc tgcacggcgt cttcaaggta    4320
aaagacacca ctacgctgca gcagcacctg gtcgacggcc gtgacatgat catcatccgc    4380
atgccgaaag attttccgcc gttcccgcaa aaactgaagt tcgtgaacc gcaacgcgaa    4440
gaacgtattt gcctggttac caccaacttt cagaccaaaa gcatgtcttc tatggttttc    4500
gatacctctt gcaccttccc aagcggtgac ggtatttcct ggaaacattg gattcagacc    4560
aaagatggtc agtgcggctc tccgctggtg tctacgcgtg acggtttcat cgttggtatc    4620
```

```
cattctgctt ctaacttcac taacactaac aactacttta cttccgttcc gaaaaacttc    4680
atggagctgc tgactaacca agaggcccag cagtgggtgt ccggttggcg cctgaacgca    4740
gattctgtac tgtggggtgg tcataaggta ttcatgaaca aaccggagga gccgttccag    4800
ccggtcaaag aggcgaccca gctgatgaac gaactggttt actctcagta a             4851
```

<210> SEQ ID NO 91
<211> LENGTH: 732
<212> TYPE: DNA
<213> ORGANISM: Artificial Sequence
<220> FEATURE:
<223> OTHER INFORMATION: TEV variant 7

<400> SEQUENCE: 91

```
atgggcgaat ctctgttcaa gggtccgcgt gattataacc cgatatcttc ttctatttgt      60
catctgacta acgaaagcga cggccacacg acttctctgt acggtatcgg tttcggtccg     120
ttcatcatta ccaacaagca tctgttccgc cgtaacaacg gtaccctgct ggttcaatct     180
ctgcacggcg tcttcaaggt aaaagacacc actacgctgc agcagcacct ggtcgacggc     240
cgtgacatga tcatcatccg catgccgaaa gattttccgc cgttcccgca aaaactgaag     300
tttcgtgaac cgcaacgcga agaacgtatt tgcctggtta ccaccaactt tcagaccaaa     360
agcatgtctt ctatggtttc cgatacctct tgcaccttcc caagcggtga cggtattttc     420
tggaaacatt ggatccagac caaagatggt cagtgcggct ctccgctggt gtctacgcgt     480
gacggtttca tcgttggtat ccattctgct tctaacttca ctaacactaa caactacttt     540
acttccgttc cgaaaaactt catggagctg ctgactaacc aagaggccca gcagtgggtg     600
tccggttggc gcctgaacgc agattctgta ctgtggggtg gtcataaggt attcatgaac     660
aaaccggagg agccgttcca gccggtcaaa gaggcgaccc agctgatgaa cgaactggtt     720
tactctcagt aa                                                        732
```

<210> SEQ ID NO 92
<211> LENGTH: 415
<212> TYPE: DNA
<213> ORGANISM: Artificial Sequence
<220> FEATURE:
<223> OTHER INFORMATION: Intervening sequence containing transcriptional
      and translational sites and T7 termination site.

<400> SEQUENCE: 92

```
aagcttgtgg cctcaaattg gtacaaccgt cagattgagc gcagctcccg cactttaggc      60
tgtagctggg agttcattcc ggtagatgac ggttggggag aacgcccatt gcaccatcat     120
caccatcact gagcggccgc ataatgctta agtcgaacag attgatatgt agctataagt     180
aattgtatga ctgaacctag gctgctgcca ccgctgagca ataactagca taaccccttg     240
gggcctctaa acgggtcttg aggggttttt tgctgatcgt atactctcag gcatctatga     300
gttgtacacg tccgcataat cgaaattaat acgactcact atagggggaat tgtgagcgga     360 taacaattcc ccatcttagt atattagtta agtataagaa ggagatatac catgg          415
```

<210> SEQ ID NO 93
<211> LENGTH: 4965
<212> TYPE: DNA
<213> ORGANISM: Artificial Sequence
<220> FEATURE:
<223> OTHER INFORMATION: BoNT/A-TEV and TEV protease variant 4 open
      reading frames with the intervening transcription and
      translation elements and termination site.

<400> SEQUENCE: 93

```
atgccgttcg taaacaaaca gttcaactat aaagacccag tcaacggcgt ggacattgcc    60
tatatcaaaa tcccgaatgc gggtcaaatg cagcccgtga aagcatttaa aatccataac   120
aaaatttggg tgatcccgga gcgcgatacg ttcacgaacc cggaagaagg agatttaaac   180
ccaccgcctg aggctaaaca ggtcccggtg tcttactatg atagcacata cctgagtacc   240
gacaatgaaa aggacaacta cctgaaaggt gttaccaaac tgttcgagcg catttattcg   300
acagatctcg gtcgcatgtt gctgacttct attgtgcgcg gcattccgtt ttggggtggt   360
agcaccatcg atacagaact caaagtgatt gacaccaact gcatcaatgt gattcagcct   420
gatgggagct accggtccga agagcttaac ctcgtaatca ttggcccgag cgcggatatt   480
atccaattcg aatgtaaatc ttttgggcat gaagtcctga atctgacgcg gaatggctat   540
ggatcgacgc agtatattcg ttttctcca gatttcacat ttggatttga agaaagcctc   600
gaagttgata cgaaccctct tttaggcgcg ggaaaattcg cgacggaccc agcggtgacc   660
ttggcacatg aacttattca tgccgggcat cgcttgtatg gaatcgccat taacccgaac   720
cgtgttttca aggtgaatac gaacgcgtat tacgagatgt cgggcttaga agtgtccttt   780
gaagaactgc gcacgtttgg cggtcatgat gcaaaattta ttgatagtct gcaagaaaac   840
gaatttcggc tgtactatta aataaattc aaagacattg catcaacctt aaacaaggcg   900
aaaagcattg tgggtaccac ggctagctta caatatatga aaaacgtttt caagaaaaaa   960
tacctcctta gcgaagacac ttccggcaaa ttctctgtcg ataaactgaa atttgataaa  1020
ctgtataaaa tgctcaccga gatctacaca gaggataact ttgtcaaatt cttcaaggtc  1080
ttgaatcgga aaacctatct gaacttcgat aaagccgtct ttaagatcaa catcgtaccg  1140
aaagttaact acaccatcta tgatggcttt aatctgcgca atacgaatct ggcggcgaac  1200
tttaacggcc agaacaccga atcaacaac atgaacttta ctaaactgaa aaattttacc  1260
ggcttgtttg aattctataa gctcctgtgt gtccgcggta ttatcaccag caaaaccaaa  1320
tccttgggcg tggtggcga aaacctgtac ttccagggcg gtggcggtgg tgataagggc  1380
tataacaagg ccttcaatga tttatgcatc aaggtgaaca actgggactt gttttctct  1440
ccatctgaag ataattttac taacgacttg aacaaggag aggaaattac ttccgatacc  1500
aacatcgaag cagcggaaga gaatattagt ctagatctta ttcaacaata ttacctgacc  1560
tttaattttg ataacgagcc tgagaacatt tccattgaga atctcagctc tgacatcatc  1620
ggccagctga aactgatgcc gaatatcgaa cgctttccta atggaaagaa atatgaattg  1680
gacaaataca ccatgttcca ctatctccgc gcgcaggagt ttgagcacgg caagtctcgt  1740
attgctctga ccaattcggt aaacgaagcc cttttaaatc cttcgcgtgt gtacaccttt  1800
ttctcaagcg attatgttaa aaagtgaac aaggcgaccg aagcggcgat gttttggga  1860
tgggtggaac aactggtata tgactttacg gatgaaactt ctgaagtctc gaccaccgac  1920
aaaattgccg atattaccat tatcattccc tatattggcc ctgcactgaa cattggtaac  1980
atgctgtata agatgatttt tgtgggcgcc ctgatctttt caggcgctgt tatcctgctg  2040
gaatttatcc cggaaatcgc cattccagta ctcggtacct ttgcgctggt gtcctatatc  2100
gcaaacaaag ttttgactgt ccagacgatc gacaacgcgc tcagtaaacg taacgaaaaa  2160
tgggatgagg tgtataagta tattgttacc aactggctcg ctaaagtaaa cacccagatt  2220
gacctgattc gcaagaagat gaagaagcg ctggaaaacc aagcagaagc gaccaaagct  2280
```

```
attatcaact atcaatataa ccagtacaca gaggaagaaa agaataacat caacttcaac    2340
atcgacgact tatcttcaaa gctgaatgaa tctattaaca aagcgatgat taatattaac    2400
aagttcttga accaatgtag tgtcagctat ctgatgaact cgatgatccc ttacggtgtg    2460
aaacgtctgg aagacttcga tgcaagcctt aaagatgccc ttctgaagta tatttacgat    2520
aatcgcggaa ctcttattgg ccaagtggat cgcttaaaag ataaagtcaa caacacgctg    2580
agtacagaca tcccttttca gctgtctaaa tatgtggaca atcagcgcct gctgtccacg    2640
tttacggaat acatcaaaaa catcatcaac actagtattc tgaacttgcg ttacgagagt    2700
aaccatctga ttgatctgag ccgttacgca tctaaaatca acatcggatc caaggtgaac    2760
ttcgatccta tcgacaaaaa ccagattcaa ttgttcaact tagaatcgtc aaagattgaa    2820
gttatcttaa aaaatgcgat tgtatataat tcaatgtacg aaaatttctc tacgagcttt    2880
tggattcgta ttccgaaata tttcaacagt atctctttaa acaacgagta tactatcatc    2940
aattgtatgg agaataacag cgggtggaaa gtgagcctta actatggtga atcatctgg    3000 actctgcagg acactcaaga aattaaacaa cgcgtggtgt ttaaatactc acagatgatt    3060
aacatctcgg attatattaa tcgctggatt tttgtgacaa ttactaacaa ccggctgaac    3120
aacagcaaaa tttacattaa cggtcgcctg atcgatcaga aaccaatcag taatctcggt    3180
aacattcacg catcgaataa tatcatgttc aaactggatg ttgtcgcga cacgcaccgt    3240 tacatttgga tcaaatactt caatttattc gacaagaaac tcaacgaaaa ggagattaag    3300
gatctttatg acaatcagtc taattcgggt attctgaaag acttttgggg tgattacctt    3360
cagtacgata aaccgtatta tatgttaaac ttatatgatc cgaataaata cgttgacgtc    3420
aacaacgttg gcattcgtgg ctatatgtat ctgaaagggc cgcgtggcag cgtgatgacc    3480
actaacattt acttaaactc ctccctctat cgcggtacta aatttattat caagaaatat    3540
gcctctggca acaaggacaa tatcgtacgc aataacgatc gcgtctacat taacgtggtg    3600
gtgaagaata aagaatatcg tctggcgacc aatgctagtc aggcgggcgt ggagaaaatt    3660
ctgtctgcac ttgaaatccc ggatgtgggt aatttatccc aggtggttgt gatgaaaagt    3720
aaaaatgacc aagggatcac caataaatgc aaaatgaatc tgcaagataa caacggcaac    3780
gacattggtt ttatcggctt ccaccaattc aataatatcg cgaagcttgt ggcctcaaat    3840
tggtacaacc gtcagattga gcgcagctcc cgcactttag gctgtagctg ggagttcatt    3900
ccggtagatg acggttgggg agaacgccca ttgcaccatc atcaccatca ctgagcggcc    3960
gcataatgct taagtcgaac agattgatat gtagctataa gtaattgtat gactgaacct    4020
aggctgctgc caccgctgag caataactag cataacccct ggggcctct aaacgggtct    4080 tgaggggttt tttgctgatc gtatactctc aggcatctat gagttgtaca cgtccgcata    4140
atcgaaatta atacgactca ctatagggga attgtgagcg ataacaatt ccccatctta    4200 gtatattagt taagtataag aaggagatat accatgggcg aatctctgtt caagggtccg    4260
cgtgattata acccgatatc ttcttctatt tgtcatctga ctaacgaaag cgacggccac    4320
acgacttctc tgtacggtat cggtttcggt ccgttcatca ttaccaacaa gcatctgttc    4380
cgccgtaaca acgtaccct gctggttcaa tctctgcacg cgtcttcaa ggtaaaagac    4440 accactacgc tgcagcagca cctggtcgac ggccgtgaca tgatcatcat ccgcatgccg    4500
aaagattttc cgccgttccc gcaaaaactg aagtttcgtg aaccgcaacg cgaagaacgt    4560
atttgcctgg ttaccaccaa cttttcagacc aaaagcatgt cttctatggt ttccgatacc    4620
tcttgcacct tcccaagcgg tgacggtatt ttctggaaac attggattca gaccaaagat    4680
```

```
ggtcagtgcg gctctccgct ggtgtctacg cgtgacggtt tcatcgttgg tatccattct    4740
gcttctaact tcactaacac taacaactac tttacttccg ttccgaaaaa cttcatggag    4800
ctgctgacta accaagaggc ccagcagtgg gtgtccggtt ggcgcctgaa cgcagattct    4860
gtactgtggg gtggtcataa ggtattcatg aacaaaccgg aggagccgtt ccagccggtc    4920
aaagaggcga cccagctgat gaacgaactg gtttactctc agtaa                    4965
```

<210> SEQ ID NO 94
<211> LENGTH: 2697
<212> TYPE: DNA
<213> ORGANISM: Artificial Sequence
<220> FEATURE:
<223> OTHER INFORMATION: Open reading frame for NociLHN/A-TEV

<400> SEQUENCE: 94

```
atgccgttcg taaacaaaca gttcaactat aaagacccag tcaacggcgt ggacattgcc      60
tatatcaaaa tcccgaatgc gggtcaaatg cagcccgtga agcatttaa aatccataac     120 aaaatttggg tgatcccgga gcgcgatacg ttcacgaacc cggaagaagg agatttaaac     180
ccaccgcctg aggctaaaca ggtcccggtg tcttactatg atagcacata cctgagtacc     240
gacaatgaaa aggacaacta cctgaaaggt gttaccaaac tgttcgagcg catttattcg     300
acagatctcg gtcgcatgtt gctgacttct attgtgcgcg gcattccgtt ttggggtggt     360
agcaccatcg atacagaact caaagtgatt gacaccaact gcatcaatgt gattcagcct     420
gatgggagct accggtccga agagcttaac ctcgtaatca ttggcccgag cgcggatatt     480
atccaattcg aatgtaaatc ttttgggcat gaagtcctga atctgacgcg gaatggctat     540
ggatcgacgc agtatattcg ttttttctcca gatttcacat ttggatttga agaaagcctc     600
gaagttgata cgaaccctct tttaggcgcg ggaaaattcg cgacggaccc agcggtgacc     660
ttggcacatg aacttattca tgccgggcat cgcttgtatg gaatcgccat taacccgaac     720
cgtgttttca aggtgaatac gaacgcgtat tacgagatgt cgggcttaga agtgtccttt     780
gaagaactgc gcacgtttgg cggtcatgat gcaaaattta ttgatagtct gcaagaaaac     840
gaatttcggc tgtactatta caataaattc aaagacattg catcaacctt aaacaaggcg     900
aaaagcattg tgggtaccac ggctagctta caatatatga aaaacgtttt caaagaaaaa     960
tacctcctta gcgaagacac ttccggcaaa ttctctgtcg ataaactgaa atttgataaa    1020
ctgtataaaa tgctcaccga gatctacaca gaggataact tgtcaaatt cttcaaggtc    1080 ttgaatcgga aaacctatct gaacttcgat aaagccgtct ttaagatcaa catcgtaccg    1140
aaagttaact acaccatcta tgatggcttt aatctgcgca tacgaatct ggcggcgaac    1200 tttaacggcc agaacaccga atcaacaac atgaacttta ctaaactgaa aaattttacc    1260
ggcttgtttg aattctataa gctcctgtgt gtccgcggta ttatcaccag caaagaaaac    1320
ctgtacttcc agttcggtgg ttttaccggc gctcgtaaat ctgcacgtaa acgcaagaat    1380
caggctctgg ctggtggcgg tggctctggt ggtggcggta gcggcggtgg cggttctgcg    1440
ctcaatgatt tatgcatcaa ggtgaacaac tgggacttgt ttttctctcc atctgaagat    1500
aattttacta cgacttgaa caaaggagag gaaattactt ccgataccaa catcgaagca    1560
gcggaagaga atattagtct agatcttatt caacaatatt acctgacctt aatttttgat    1620
aacgagcctg agaacatttc cattgagaat ctcagctctg acatcatcgg ccagctggaa    1680
ctgatgccga atatcgaacg ctttcctaat ggaaagaaat atgaattgga caaatacacc    1740
```

```
atgttccact atctccgcgc gcaggagttt gagcacggca agtctcgtat tgctctgacc    1800
aattcggtaa acgaagccct tttaaatcct tcgcgtgtgt acaccttttt ctcaagcgat    1860
tatgttaaaa aagtgaacaa ggcgaccgaa gcggcgatgt ttttgggatg ggtggaacaa    1920
ctggtatatg actttacgga tgaaacttct gaagtctcga ccaccgacaa aattgccgat    1980
attaccatta tcattcccta tattggccct gcactgaaca ttggtaacat gctgtataaa    2040
gatgattttg tgggcgccct gatcttttca ggcgctgtta tcctgctgga atttatcccg    2100
gaaatcgcca ttccagtact cggtaccttt gcgctggtgt cctatatcgc aaacaaagtt    2160
ttgactgtcc agacgatcga caacgcgctc agtaaacgta acgaaaaatg ggatgaggtg    2220
tataagtata ttgttaccaa ctggctcgct aaagtaaaca cccagattga cctgattcgc    2280
aagaagatga agaagcgct  ggaaaaccaa gcagaagcga ccaaagctat tatcaactat    2340
caatataacc agtacacaga ggaagaaaag aataacatca acttcaacat cgacgactta    2400
tcttcaaagc tgaatgaatc tattaacaaa gcgatgatta atattaacaa gttcttgaac    2460
caatgtagtg tcagctatct gatgaactcg atgatcccct acggtgtgaa acgtctggaa    2520
gacttcgatg caagccttaa agatgcccct ctgaagtata tttacgataa tcgcggaact    2580
cttattggcc aagtggatcg cttaaaagat aaagtcaaca cacgctgag  tacagacatc    2640 cctttcagc tgtctaaata tgtggacaat cagcgccacc atcaccatca ccactaa      2697
```

<210> SEQ ID NO 95
<211> LENGTH: 898
<212> TYPE: PRT
<213> ORGANISM: Artificial Sequence
<220> FEATURE:
<223> OTHER INFORMATION: NociLHN/A-TEV

<400> SEQUENCE: 95

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
```

```
                195                 200                 205
Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
                370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Glu Asn Leu Tyr Phe Gln Phe Gly Gly Phe
                435                 440                 445

Thr Gly Ala Arg Lys Ser Ala Arg Lys Arg Lys Asn Gln Ala Leu Ala
                450                 455                 460

Gly Gly Gly Gly Ser Gly Gly Gly Ser Gly Gly Gly Ser Ala
465                 470                 475                 480

Leu Asn Asp Leu Cys Ile Lys Val Asn Asn Trp Asp Leu Phe Phe Ser
                485                 490                 495

Pro Ser Glu Asp Asn Phe Thr Asn Asp Leu Asn Lys Gly Glu Glu Ile
                500                 505                 510

Thr Ser Asp Thr Asn Ile Glu Ala Ala Glu Glu Asn Ile Ser Leu Asp
                515                 520                 525

Leu Ile Gln Gln Tyr Tyr Leu Thr Phe Asn Phe Asp Asn Glu Pro Glu
                530                 535                 540

Asn Ile Ser Ile Glu Asn Leu Ser Ser Asp Ile Ile Gly Gln Leu Glu
545                 550                 555                 560

Leu Met Pro Asn Ile Glu Arg Phe Pro Asn Gly Lys Lys Tyr Glu Leu
                565                 570                 575

Asp Lys Tyr Thr Met Phe His Tyr Leu Arg Ala Gln Glu Phe Glu His
                580                 585                 590

Gly Lys Ser Arg Ile Ala Leu Thr Asn Ser Val Asn Glu Ala Leu Leu
                595                 600                 605

Asn Pro Ser Arg Val Tyr Thr Phe Phe Ser Ser Asp Tyr Val Lys Lys
                610                 615                 620
```

```
Val Asn Lys Ala Thr Glu Ala Ala Met Phe Leu Gly Trp Val Glu Gln
625                 630                 635                 640

Leu Val Tyr Asp Phe Thr Asp Glu Thr Ser Glu Val Ser Thr Thr Asp
            645                 650                 655

Lys Ile Ala Asp Ile Thr Ile Ile Ile Pro Tyr Ile Gly Pro Ala Leu
        660                 665                 670

Asn Ile Gly Asn Met Leu Tyr Lys Asp Asp Phe Val Gly Ala Leu Ile
        675                 680                 685

Phe Ser Gly Ala Val Ile Leu Leu Glu Phe Ile Pro Glu Ile Ala Ile
690                 695                 700

Pro Val Leu Gly Thr Phe Ala Leu Val Ser Tyr Ile Ala Asn Lys Val
705                 710                 715                 720

Leu Thr Val Gln Thr Ile Asp Asn Ala Leu Ser Lys Arg Asn Glu Lys
                725                 730                 735

Trp Asp Glu Val Tyr Lys Tyr Ile Val Thr Asn Trp Leu Ala Lys Val
                740                 745                 750

Asn Thr Gln Ile Asp Leu Ile Arg Lys Lys Met Lys Glu Ala Leu Glu
            755                 760                 765

Asn Gln Ala Glu Ala Thr Lys Ala Ile Ile Asn Tyr Gln Tyr Asn Gln
770                 775                 780

Tyr Thr Glu Glu Glu Lys Asn Asn Ile Asn Phe Asn Ile Asp Asp Leu
785                 790                 795                 800

Ser Ser Lys Leu Asn Glu Ser Ile Asn Lys Ala Met Ile Asn Ile Asn
                805                 810                 815

Lys Phe Leu Asn Gln Cys Ser Val Ser Tyr Leu Met Asn Ser Met Ile
                820                 825                 830

Pro Tyr Gly Val Lys Arg Leu Glu Asp Phe Asp Ala Ser Leu Lys Asp
            835                 840                 845

Ala Leu Leu Lys Tyr Ile Tyr Asp Asn Arg Gly Thr Leu Ile Gly Gln
850                 855                 860

Val Asp Arg Leu Lys Asp Lys Val Asn Asn Thr Leu Ser Thr Asp Ile
865                 870                 875                 880

Pro Phe Gln Leu Ser Lys Tyr Val Asp Asn Gln Arg His His His His
                885                 890                 895

His His

<210> SEQ ID NO 96
<211> LENGTH: 2709
<212> TYPE: DNA
<213> ORGANISM: Artificial Sequence
<220> FEATURE:
<223> OTHER INFORMATION: Open reading frame for DynLHN/A-TEV

<400> SEQUENCE: 96
atgccgttcg taaacaaaca gttcaactat aaagacccag tcaacggcgt ggacattgcc    60
tatatcaaaa tcccgaatgc gggtcaaatg cagcccgtga agcatttaa atccataac    120 aaaatttggg tgatcccgga gcgcgatacg ttcacgaacc cggaagaagg agatttaaac    180
ccaccgcctg aggctaaaca ggtcccggtg tcttactatg atagcacata cctgagtacc    240
gacaatgaaa aggacaacta cctgaaaggt gttaccaaac tgttcgagcg catttattcg    300
acagatctcg gtcgcatgtt gctgacttct attgtgcgcg gcattccgtt ttggggtggt    360
agcaccatcg atacagaact caaagtgatt gacaccaact gcatcaatgt gattcagcct    420
gatgggagct accggtccga agagcttaac ctcgtaatca ttggcccgag cgcggatatt    480
```

```
atccaattcg aatgtaaatc ttttgggcat gaagtcctga atctgacgcg gaatggctat    540
ggatcgacgc agtatattcg tttttctcca gatttcacat ttggatttga agaaagcctc    600
gaagttgata cgaaccctct tttaggcgcg ggaaaattcg cgacggaccc agcggtgacc    660
ttggcacatg aacttattca tgccgggcat cgcttgtatg gaatcgccat taacccgaac    720
cgtgttttca aggtgaatac gaacgcgtat tacgagatgt cgggcttaga agtgtccttt    780
gaagaactgc gcacgtttgg cggtcatgat gcaaaattta ttgatagtct gcaagaaaac    840
gaatttcggc tgtactatta caataaattc aaagacattg catcaacctt aaacaaggcg    900
aaaagcattg tgggtaccac ggctagctta caatatatga aaaacgtttt caagaaaaa    960 tacctcctta gcgaagacac ttccggcaaa ttctctgtcg ataaactgaa atttgataaa   1020
ctgtataaaa tgctcaccga gatctacaca gaggataact ttgtcaaatt cttcaaggtc   1080
ttgaatcgga aaacctatct gaacttcgat aaagccgtct ttaagatcaa catcgtaccg   1140
aaagttaact acaccatcta tgatggcttt aatctgcgca atacgaatct ggcggcgaac   1200
tttaacggcc agaacaccga atcaacaac atgaactta ctaaactgaa aaattttacc   1260
ggcttgtttg aattctataa gctcctgtgt gtccgtggta ttatcaccag caaagaaaac   1320
ctgtacttcc agtatggcgg tttcctgcgt cgcattcgtc ctaagcttaa atgggataac   1380
caggctcttg ctggtggtgg tggctctggt ggtggcggta gcggcggtgg tggttctgca   1440
ctcaatgatt tatgtatcaa ggtgaacaac tgggacttgt ttttctctcc atctgaagat   1500
aattttacta cgacttgaa caaaggagag gaaattactt ccgataccaa catcgaagca   1560
gcggaagaga atattagtct agatcttatt caacaatatt acctgaccctt taattttgat   1620 aacgagcctg agaacatttc cattgagaat ctcagctctg acatcatcgg ccagctggaa   1680
ctgatgccga atatcgaacg ctttcctaat ggaaagaaat atgaattgga caaatacacc   1740
atgttccact atctccgcgc gcaggagttt gagcacggca gtctcgtat tgctctgacc   1800 aattcggtaa acgaagccct tttaaatcct tcgcgtgtgt acaccttttt ctcaagcgat   1860
tatgttaaaa aagtgaacaa ggcgaccgaa gcggcgatgt ttttgggatg ggtggaacaa   1920
ctggtatatg actttacgga tgaaacttct gaagtctcga ccaccgacaa aattgccgat   1980
attaccatta tcattcccta tattggccct gcactgaaca ttggtaacat gctgtataaa   2040
gatgattttg tgggcgccct gatcttttca ggcgctgtta tcctgctgga atttatcccg   2100
gaaatcgcca ttccagtact cggtacccttt gcgctggtgt cctatatcgc aaacaaagtt   2160
ttgactgtcc agacgatcga caacgcgctc agtaaacgta acgaaaaatg ggatgaggtg   2220
tataagtata ttgttaccaa ctggctcgct aaagtaaaca cccagattga cctgattcgc   2280
aagaagatga agaagcgct ggaaaaccaa gcagaagcga ccaaagctat tatcaactat   2340
caatataacc agtacacaga ggaagaaaag aataacatca acttcaacat cgacgactta   2400
tcttcaaagc tgaatgaatc tattaacaaa gcgatgatta atattaacaa gttcttgaac   2460
caatgtagtg tcagctatct gatgaactcg atgatcccctt acggtgtgaa acgtctggaa   2520
gacttcgatg caagccttaa agatgccctt ctgaagtata tttacgataa tcgcggaact   2580
cttattggcc aagtggatcg cttaaaagat aaagtcaaca cacgctgag tacagacatc   2640 ccttttcagc tgtctaaata tgtggacaat cagcgcctgc tgtccacgca ccatcaccat   2700
caccactaa                                                           2709
```

<210> SEQ ID NO 97

<211> LENGTH: 902
<212> TYPE: PRT
<213> ORGANISM: Artificial Sequence
<220> FEATURE:
<223> OTHER INFORMATION: DynLHN/A-TEV

<400> SEQUENCE: 97

```
Met Pro Phe Val Asn Lys Gln Phe Asn Tyr Lys Asp Pro Val Asn Gly
1               5                   10                  15
Val Asp Ile Ala Tyr Ile Lys Ile Pro Asn Ala Gly Gln Met Gln Pro
            20                  25                  30
Val Lys Ala Phe Lys Ile His Asn Lys Ile Trp Val Ile Pro Glu Arg
        35                  40                  45
Asp Thr Phe Thr Asn Pro Glu Glu Gly Asp Leu Asn Pro Pro Pro Glu
    50                  55                  60
Ala Lys Gln Val Pro Val Ser Tyr Tyr Asp Ser Thr Tyr Leu Ser Thr
65                  70                  75                  80
Asp Asn Glu Lys Asp Asn Tyr Leu Lys Gly Val Thr Lys Leu Phe Glu
                85                  90                  95
Arg Ile Tyr Ser Thr Asp Leu Gly Arg Met Leu Leu Thr Ser Ile Val
            100                 105                 110
Arg Gly Ile Pro Phe Trp Gly Gly Ser Thr Ile Asp Thr Glu Leu Lys
        115                 120                 125
Val Ile Asp Thr Asn Cys Ile Asn Val Ile Gln Pro Asp Gly Ser Tyr
    130                 135                 140
Arg Ser Glu Glu Leu Asn Leu Val Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
    210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
    370                 375                 380
```

```
Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Glu Asn Leu Tyr Phe Gln Tyr Gly Gly Phe
            435                 440                 445

Leu Arg Arg Ile Arg Pro Lys Leu Lys Trp Asp Asn Gln Ala Leu Ala
450                 455                 460

Gly Gly Gly Gly Ser Gly Gly Gly Ser Gly Gly Gly Gly Ser Ala
465                 470                 475                 480

Leu Asn Asp Leu Cys Ile Lys Val Asn Asn Trp Asp Leu Phe Phe Ser
            485                 490                 495

Pro Ser Glu Asp Asn Phe Thr Asn Asp Leu Asn Lys Gly Glu Glu Ile
            500                 505                 510

Thr Ser Asp Thr Asn Ile Glu Ala Ala Glu Glu Asn Ile Ser Leu Asp
            515                 520                 525

Leu Ile Gln Gln Tyr Tyr Leu Thr Phe Asn Phe Asp Asn Glu Pro Glu
530                 535                 540

Asn Ile Ser Ile Glu Asn Leu Ser Ser Asp Ile Ile Gly Gln Leu Glu
545                 550                 555                 560

Leu Met Pro Asn Ile Glu Arg Phe Pro Asn Gly Lys Lys Tyr Glu Leu
            565                 570                 575

Asp Lys Tyr Thr Met Phe His Tyr Leu Arg Ala Gln Glu Phe Glu His
            580                 585                 590

Gly Lys Ser Arg Ile Ala Leu Thr Asn Ser Val Asn Glu Ala Leu Leu
            595                 600                 605

Asn Pro Ser Arg Val Tyr Thr Phe Phe Ser Ser Asp Tyr Val Lys Lys
            610                 615                 620

Val Asn Lys Ala Thr Glu Ala Ala Met Phe Leu Gly Trp Val Glu Gln
625                 630                 635                 640

Leu Val Tyr Asp Phe Thr Asp Glu Thr Ser Glu Val Ser Thr Thr Asp
            645                 650                 655

Lys Ile Ala Asp Ile Thr Ile Ile Pro Tyr Ile Gly Pro Ala Leu
            660                 665                 670

Asn Ile Gly Asn Met Leu Tyr Lys Asp Asp Phe Val Gly Ala Leu Ile
            675                 680                 685

Phe Ser Gly Ala Val Ile Leu Leu Glu Phe Ile Pro Glu Ile Ala Ile
            690                 695                 700

Pro Val Leu Gly Thr Phe Ala Leu Val Ser Tyr Ile Ala Asn Lys Val
705                 710                 715                 720

Leu Thr Val Gln Thr Ile Asp Asn Ala Leu Ser Lys Arg Asn Glu Lys
            725                 730                 735

Trp Asp Glu Val Tyr Lys Tyr Ile Val Thr Asn Trp Leu Ala Lys Val
            740                 745                 750

Asn Thr Gln Ile Asp Leu Ile Arg Lys Lys Met Lys Glu Ala Leu Glu
            755                 760                 765

Asn Gln Ala Glu Ala Thr Lys Ala Ile Ile Asn Tyr Gln Tyr Asn Gln
            770                 775                 780

Tyr Thr Glu Glu Glu Lys Asn Asn Ile Asn Phe Asn Ile Asp Asp Leu
785                 790                 795                 800
```

-continued

Ser Ser Lys Leu Asn Glu Ser Ile Asn Lys Ala Met Ile Asn Ile Asn
            805                 810                 815

Lys Phe Leu Asn Gln Cys Ser Val Ser Tyr Leu Met Asn Ser Met Ile
        820                 825                 830

Pro Tyr Gly Val Lys Arg Leu Glu Asp Phe Asp Ala Ser Leu Lys Asp
            835                 840                 845

Ala Leu Leu Lys Tyr Ile Tyr Asp Asn Arg Gly Thr Leu Ile Gly Gln
    850                 855                 860

Val Asp Arg Leu Lys Asp Lys Val Asn Asn Thr Leu Ser Thr Asp Ile
865                 870                 875                 880

Pro Phe Gln Leu Ser Lys Tyr Val Asp Asn Gln Arg Leu Leu Ser Thr
                885                 890                 895

His His His His His His
            900

<210> SEQ ID NO 98
<211> LENGTH: 320
<212> TYPE: DNA
<213> ORGANISM: Artificial Sequence
<220> FEATURE:
<223> OTHER INFORMATION: DNA fragment encoding a di-chain loop region
      comprising an integrated TEV protease cleavage
      site-Galanin binding domain

<400> SEQUENCE: 98
gaattctaca agctgctgtg cgtggacggc atcattacct ccaaaactaa atctgaaaac      60
ctgtacttcc agggctggac tttgaactct gctggttatc tcctgggccc acatgcggtt    120
gctcttgctg gtggcggtgg ctctggcggt ggcggtagcg gcggtggcgg ttctgcacta    180
gtgcttcagt gtatcaaggt taacaactgg gatttattct tcagcccgag tgaagacaac    240
ttcaccaacg acctgaacaa aggtgaagaa atcacctcag atactaacat cgaagcagcc    300
gaagaaaaca tcagtctaga                                                 320

<210> SEQ ID NO 99
<211> LENGTH: 106
<212> TYPE: PRT
<213> ORGANISM: Artificial Sequence
<220> FEATURE:
<223> OTHER INFORMATION: Di-chain loop region comprising an integrated
      TEV protease cleavage site-Galanin binding domain

<400> SEQUENCE: 99

Glu Phe Tyr Lys Leu Leu Cys Val Asp Gly Ile Ile Thr Ser Lys Thr
1               5                   10                  15

Lys Ser Glu Asn Leu Tyr Phe Gln Gly Trp Thr Leu Asn Ser Ala Gly
            20                  25                  30

Tyr Leu Leu Gly Pro His Ala Val Ala Leu Ala Gly Gly Gly Gly Ser
        35                  40                  45

Gly Gly Gly Gly Ser Gly Gly Gly Ser Ala Leu Val Leu Gln Cys
    50                  55                  60

Ile Lys Val Asn Asn Trp Asp Leu Phe Phe Ser Pro Ser Glu Asp Asn
65                  70                  75                  80

Phe Thr Asn Asp Leu Asn Lys Gly Glu Glu Ile Thr Ser Asp Thr Asn
                85                  90                  95

Ile Glu Ala Ala Glu Glu Asn Ile Ser Leu
            100                 105

<210> SEQ ID NO 100

<211> LENGTH: 2703
<212> TYPE: DNA
<213> ORGANISM: Artificial Sequence
<220> FEATURE:
<223> OTHER INFORMATION: Open reading frame for GalLHN/A-TEV

<400> SEQUENCE: 100

| | |
|---|---:|
| atgccgttcg taaacaaaca gttcaactat aaagacccag tcaacggcgt ggacattgcc | 60 |
| tatatcaaaa tcccgaatgc gggtcaaatg cagcccgtga agcatttaa atccataac | 120 |
| aaaatttggg tgatcccgga gcgcgatacg ttcacgaacc cggaagaagg agatttaaac | 180 |
| ccaccgcctg aggctaaaca ggtcccggtg tcttactatg atagcacata cctgagtacc | 240 |
| gacaatgaaa aggacaacta cctgaaaggt gttaccaaac tgttcgagcg catttattcg | 300 |
| acagatctcg gtcgcatgtt gctgacttct attgtgcgcg gcattccgtt ttggggtggt | 360 |
| agcaccatcg atacagaact caaagtgatt gacaccaact gcatcaatgt gattcagcct | 420 |
| gatgggagct accggtccga agagcttaac ctcgtaatca ttggcccgag cgcggatatt | 480 |
| atccaattcg aatgtaaatc ttttgggcat gaagtcctga tctgacgcg aatggctat | 540 |
| ggatcgacgc agtatattcg ttttctcca gatttcacat ttggatttga agaaagcctc | 600 |
| gaagttgata cgaaccctct tttaggcgcg gaaaattcg cgacggaccc agcggtgacc | 660 |
| ttggcacatg aacttattca tgccgggcat cgcttgtatg gaatcgccat taacccgaac | 720 |
| cgtgtttttca aggtgaatac gaacgcgtat acgagatgt cgggcttaga agtgtccttt | 780 |
| gaagaactgc gcacgtttgg cggtcatgat gcaaaattta ttgatagtct gcaagaaaac | 840 |
| gaatttcggc tgtactatta caataaattc aagacattg catcaacctt aaacaaggcg | 900 |
| aaaagcattg tgggtaccac ggctagctta caatatatga aaaacgtttt caagaaaaa | 960 |
| tacctcctta gcgaagacac ttccggcaaa ttctctgtcg ataaactgaa atttgataaa | 1020 |
| ctgtataaaa tgctcaccga gatctacaca gaggataact ttgtcaaatt cttcaaggtc | 1080 |
| ttgaatcgga aaacctatct gaacttcgat aaagccgtct ttaagatcaa catcgtaccg | 1140 |
| aaagttaact acaccatcta tgatggcttt aatctgcgca atacgaatct ggcggcgaac | 1200 |
| tttaacggcc agaacaccga atcaacaac atgaactttta ctaaactgaa aaatttacc | 1260 |
| ggcttgtttg aattctacaa gctgctgtgc gtggacggca tcattacctc caaaactaaa | 1320 |
| tctgaaaacc tgtacttcca gggctggact ttgaactctg ctggttatct cctgggccca | 1380 |
| catgcggttg ctcttgctgg tggcggtggc tctggcggtg gcggtagcgg cggtggcggt | 1440 |
| tctgcactag tgcttcagtg tatcaaggtt aacaactggg atttattctt cagcccgagt | 1500 |
| gaagacaact tcaccaacga cctgaacaaa ggtgaagaaa tcacctcaga tactaacatc | 1560 |
| gaagcagccg aagaaacat cagtctagat cttattcaac aatattacct gaccttaat | 1620 |
| tttgataacg agcctgagaa catttccatt gagaatctca gctctgacat catcggccag | 1680 |
| ctggaactga tgccgaatat cgaacgcttt cctaatggaa agaaatatga attggacaaa | 1740 |
| tacaccatgt tccactatct ccgcgcgcag gagtttgagc acggcaagtc tcgtattgct | 1800 |
| ctgaccaatt cggtaaacga agcccttta aatccttcgc gtgtgtacac cttttctca | 1860 |
| agcgattatg ttaaaaaagt gaacaaggcg accgaagcgg cgatgttttt gggatgggtg | 1920 |
| gaacaactgg tatatgactt tacggatgaa acttctgaag tctcgaccac cgacaaaatt | 1980 |
| gccgatatta ccattatcat tcctatatt ggccctgcac tgaacattgg taacatgctg | 2040 |
| tataaagatg atttttgtggg cgccctgatc ttttcaggcg ctgttatcct gctggaattt | 2100 |
| atcccggaaa tcgccattcc agtactcggt accttttgcgc tggtgtccta tcgcaaac | 2160 |

```
aaagttttga ctgtccagac gatcgacaac gcgctcagta aacgtaacga aaaatgggat   2220
gaggtgtata agtatattgt taccaactgg ctcgctaaag taaacaccca gattgacctg   2280
attcgcaaga agatgaaaga agcgctggaa aaccaagcag aagcgaccaa agctattatc   2340
aactatcaat ataaccagta cacagaggaa gaaaagaata acatcaactt caacatcgac   2400
gacttatctt caaagctgaa tgaatctatt aacaaagcga tgattaatat taacaagttc   2460
ttgaaccaat gtagtgtcag ctatctgatg aactcgatga tcccttacgg tgtgaaacgt   2520
ctggaagact tcgatgcaag ccttaaagat gcccttctga agtatattta cgataatcgc   2580
ggaactctta ttggccaagt ggatcgctta aaagataaag tcaacaacac gctgagtaca   2640
gacatccctt ttcagctgtc taaatatgtg gacaatcagc gccaccatca ccatcaccac   2700
taa                                                                2703
```

<210> SEQ ID NO 101
<211> LENGTH: 900
<212> TYPE: PRT
<213> ORGANISM: Artificial Sequence
<220> FEATURE:
<223> OTHER INFORMATION: GalLHN/A-TEV

<400> SEQUENCE: 101

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Glu Asn Leu Tyr Phe Gln Gly
            435                 440                 445

Trp Thr Leu Asn Ser Ala Gly Tyr Leu Leu Gly Pro His Ala Val Ala
450                 455                 460

Leu Ala Gly Gly Gly Gly Ser Gly Gly Gly Gly Ser Gly Gly Gly Gly
465                 470                 475                 480

Ser Ala Leu Val Leu Gln Cys Ile Lys Val Asn Asn Trp Asp Leu Phe
            485                 490                 495

Phe Ser Pro Ser Glu Asp Asn Phe Thr Asn Asp Leu Asn Lys Gly Glu
            500                 505                 510

Glu Ile Thr Ser Asp Thr Asn Ile Glu Ala Ala Glu Glu Asn Ile Ser
            515                 520                 525

Leu Asp Leu Ile Gln Gln Tyr Tyr Leu Thr Phe Asn Phe Asp Asn Glu
530                 535                 540

Pro Glu Asn Ile Ser Ile Glu Asn Leu Ser Ser Asp Ile Ile Gly Gln
545                 550                 555                 560

Leu Glu Leu Met Pro Asn Ile Glu Arg Phe Pro Asn Gly Lys Lys Tyr
            565                 570                 575

Glu Leu Asp Lys Tyr Thr Met Phe His Tyr Leu Arg Ala Gln Glu Phe
            580                 585                 590

Glu His Gly Lys Ser Arg Ile Ala Leu Thr Asn Ser Val Asn Glu Ala
            595                 600                 605

Leu Leu Asn Pro Ser Arg Val Tyr Thr Phe Phe Ser Ser Asp Tyr Val
            610                 615                 620

Lys Lys Val Asn Lys Ala Thr Glu Ala Ala Met Phe Leu Gly Trp Val
625                 630                 635                 640

Glu Gln Leu Val Tyr Asp Phe Thr Asp Glu Thr Ser Glu Val Ser Thr
            645                 650                 655

Thr Asp Lys Ile Ala Asp Ile Thr Ile Ile Pro Tyr Ile Gly Pro
            660                 665                 670

Ala Leu Asn Ile Gly Asn Met Leu Tyr Lys Asp Asp Phe Val Gly Ala
```

```
              675                 680                 685
Leu Ile Phe Ser Gly Ala Val Ile Leu Glu Phe Ile Pro Glu Ile
    690                 695                 700
Ala Ile Pro Val Leu Gly Thr Phe Ala Leu Val Ser Tyr Ile Ala Asn
705                 710                 715                 720
Lys Val Leu Thr Val Gln Thr Ile Asp Asn Ala Leu Ser Lys Arg Asn
                725                 730                 735
Glu Lys Trp Asp Glu Val Tyr Lys Tyr Ile Val Thr Asn Trp Leu Ala
            740                 745                 750
Lys Val Asn Thr Gln Ile Asp Leu Ile Arg Lys Lys Met Lys Glu Ala
                755                 760                 765
Leu Glu Asn Gln Ala Glu Ala Thr Lys Ala Ile Ile Asn Tyr Gln Tyr
    770                 775                 780
Asn Gln Tyr Thr Glu Glu Glu Lys Asn Asn Ile Asn Phe Asn Ile Asp
785                 790                 795                 800
Asp Leu Ser Ser Lys Leu Asn Glu Ser Ile Asn Lys Ala Met Ile Asn
                805                 810                 815
Ile Asn Lys Phe Leu Asn Gln Cys Ser Val Ser Tyr Leu Met Asn Ser
            820                 825                 830
Met Ile Pro Tyr Gly Val Lys Arg Leu Glu Asp Phe Asp Ala Ser Leu
                835                 840                 845
Lys Asp Ala Leu Leu Lys Tyr Ile Tyr Asp Asn Arg Gly Thr Leu Ile
850                 855                 860
Gly Gln Val Asp Arg Leu Lys Asp Lys Val Asn Asn Thr Leu Ser Thr
865                 870                 875                 880
Asp Ile Pro Phe Gln Leu Ser Lys Tyr Val Asp Asn Gln Arg His His
                885                 890                 895
His His His His
        900

<210> SEQ ID NO 102
<211> LENGTH: 314
<212> TYPE: DNA
<213> ORGANISM: Artificial Sequence
<220> FEATURE:
<223> OTHER INFORMATION: DNA fragment encoding a di-chain loop region
      comprising an integrated TEV protease cleavage
      site-Nociceptin binding domain

<400> SEQUENCE: 102
gaattctata agctcctgtg tgtccgcggt attatcacca gcaaagaaaa cctgtacttc      60
cagttcggtg gttttaccgg cgctcgtaaa tctgcacgta aacgcaagaa tcaggctctg     120
gctggtggcg gtggctctgg tggtggcggt agcggcggtg gcggttctgc gctcaatgat     180
ttatgcatca aggtgaacaa ctgggacttg ttttctctc catctgaaga taatttact       240 aacgacttga acaaaggaga ggaaattact tccgatacca catcgaagc agcggaagag      300 aatattagtc taga                                                       314

<210> SEQ ID NO 103
<211> LENGTH: 104
<212> TYPE: PRT
<213> ORGANISM: Artificial Sequence
<220> FEATURE:
<223> OTHER INFORMATION: Di-chain loop region comprising an integrated
      TEV protease cleavage site-Nociceptin binding domain

<400> SEQUENCE: 103
```

```
Glu Phe Tyr Lys Leu Leu Cys Val Arg Gly Ile Ile Thr Ser Lys Glu
1               5                   10                  15

Asn Leu Tyr Phe Gln Phe Gly Gly Phe Thr Gly Ala Arg Lys Ser Ala
            20                  25                  30

Arg Lys Arg Lys Asn Gln Ala Leu Ala Gly Gly Gly Ser Gly Gly
        35                  40                  45

Gly Gly Ser Gly Gly Gly Ser Ala Leu Asn Asp Leu Cys Ile Lys
    50                  55                  60

Val Asn Asn Trp Asp Leu Phe Phe Ser Pro Ser Glu Asp Asn Phe Thr
65                  70                  75                  80

Asn Asp Leu Asn Lys Gly Glu Glu Ile Thr Ser Asp Thr Asn Ile Glu
                85                  90                  95

Ala Ala Glu Glu Asn Ile Ser Leu
            100
```

<210> SEQ ID NO 104
<211> LENGTH: 314
<212> TYPE: DNA
<213> ORGANISM: Artificial Sequence
<220> FEATURE:
<223> OTHER INFORMATION: DNA fragment encoding a di-chain loop region
      comprising an integrated TEV protease cleavage
      site-Dynorphin binding domain

<400> SEQUENCE: 104

```
gaattctata agctcctgtg tgtccgtggt attatcacca gcaaagaaaa cctgtacttc      60
cagtatggcg gtttcctgcg tcgcattcgt cctaagctta atgggataa

<211> LENGTH: 750
<212> TYPE: DNA
<213> ORGANISM: Artificial Sequence
<220> FEATURE:
<223> OTHER INFORMATION: Open reading frame encoding TEV protease variant 7

<400> SEQUENCE: 106

```
ccatggatgg gtggcgaatc tctgttcaag ggtccgcgtg attataaccc gatatcttct      60
actatttgtc atctgactaa cgaaagcgac ggccacacga cttctctgta cggtatcggt     120
ttcggtccgt tcatcattac caacaagcat ctgttccgcc gtaacaacgg taccctgctg     180
gttcaatctc tgcacggcgt cttcaaggta aagacacca ctacgctgca gcagcacctg      240
gtcgacggcc gtgacatgat catcatccgc atgccgaaag attttccgcc gttcccgcaa     300
aaactgaagt tcgtgaacc gcaacgcgaa gaacgtattt gcctggttac caccaacttt      360
cagaccaaaa gcatgtcttc tatggttttcc gatacctctt gcaccttccc aagcggtgac    420
ggtatttctc tggaaacattg gatccagacc aaagatggtc agtgcggctc tccgctggtg    480
tctacgcgtg acggtttcat cgttggtatc cattctgctt ctaacttcac taacactaac    540
aactacttta cttccgttcc gaaaaacttc atggagctgc tgactaacca agaggcccag     600
cagtgggtgt ccggttggcg cctgaacgca gattctgtac tgtggggtgg tcataaggta     660
ttcatgaaca aaccggagga gccgttccag ccggtcaaag aggcgaccca gctgatgaac    720
gaactggttt actctcagta atgaaagctt                                      750
```

<210> SEQ ID NO 107
<211> LENGTH: 3791
<212> TYPE: DNA
<213> ORGANISM: Artificial Sequence
<220> FEATURE:
<223> OTHER INFORMATION: ORF encoding p10-TEV variant 7 and polH-DynLHn/A-TEV

<400> SEQUENCE: 107

```
agatcttatg cggccgcact cgagtcatta gtggtgatgg tgatggtggg ttgacagaag       60
tctctgatta tcaacatact tcgacagttg aacgggatg tctgttgaca gagtgttgtt      120
taccttatct ttcagacggt caacttggcc aatgagcgtt ccctgttat cgtagatgta      180
cttaagaagg gcgtctttca gcgaggcgtc gaagtcctcc agtctcttta ccacatatgg     240
gatcattgag ttcatcaagt atgatacact gcattggttg aggaacttgt taatgtttat     300
cattgccttg tttatgctct cgttgagttt actagagagg tcgtcaatgt tgaagttgat     360
gttgttcttt tcctcctcgg tgtactggtt gtactgatag ttaatgatgg cctttgtcgc    420
ttcagcctgg ttctccagcg cctccttcat ctttttcctg atgaggtcga tttgggtgtt     480
gaccttagcg agccagttag tcacgatgta tttgtacact tcatcccact tctcgtttct     540
ttttgacaga gcattatcga ttgttttggac agtgaggacc ttgttagcaa tgtagctgac   600
caaagcgaag gtaccaagaa caggaatagc gatctctggg atgaactcca acaaaatcac    660
tgctcccgag aaaatcaacg caccgacgaa gtcgtccttg tacagcatat gccgatgtt    720
aagagcaggt ccaatgtagg gtatgatgat agtgatgtct gcgatcttgt ccgtagtcga    780
aacttcacta gtctcgtcgg tgaaatcgta aaccaactgt tcaacccaac ccagaaacat    840
cgctgcttcg gttgcttat tcaccttctt aacgtaatcc gaactgaaga aggtgtagac    900
acgagaagga ttgagaagag cctcgttgac cgagttagtc agggcgattc tactttttcc   960
gtgctcaaac tcttgagctc tgaggtagtg gaacatcgtg tatttgtcca attcgtactt  1020
```

-continued

```
cttgccgtta gggaatctct cgatattggg catgagttcc agctgtccga tgatgtcgct    1080
gctcagattt tcgatagaaa tgttttccgg ctcgttatcg aaattgaacg tgagatagta    1140
ctgctgaatc aggtctagac taatattctc ttccgctgct tcgatgttgg tatcggaagt    1200
aatttcctct cctttgttca agtcgttagt aaaattatct tcagatggag agaaaaacaa    1260
gtcccagttg ttcaccttga tacataaatc attgagtgca gaaccaccac cgccgctacc    1320
gccaccacca gagccaccac caccagcaag agcctggtta tcccatttaa gcttaggacg    1380
aatgcgacgc aggaaaccgc catactggaa gtacaggttt tctttgctgg tgataatacc    1440
acggacacac aggagcttat agaattcaaa caggccggtg aaattcttga ctttgtgaa     1500 gttcatgtta ttgatctcgg tattctgacc attgaagtta gccgccaaat tggtgttcct    1560
aaggttaaag ccatcataga tggtgtagtt cacctttggc acgatattga tcttaaacac    1620
agctttgtcg aagttaagat aagtcttgcg gttcaatacc ttgaagaact taacaaagtt    1680
gtcctcggta tagatctctg taagcatttt gtacagcttg tcaaacttga gtttgtccac    1740
ggaaaacttt ccggaggtgt cctcggaaag caagtacttt tccttaaaga cgttcttcat    1800
atactgaagg ctagccgtgg tgccgactat acttttagcc ttattcagcg tactggcaat    1860
atctttgaat ttgttgtagt aatacagtct gaactcattc tcttgcaagg agtcgatgaa    1920
cttagcatcg tgtccaccga aggtacgaag ttcttcgaag gagacttcca gaccggacat    1980
ctcatagtat gcgttggtgt tcaccttgaa aacgcggttt ggattgatgg caattccgta    2040
cagtctatgg cctgcgtgaa tcagctcgtg agccaaggtc accgcgggat ctgtggcgaa    2100
cttgccagcg cccaacaacg gattagtgtc aacctccaat gactcttcga agccgaaagt    2160
gaaatcgggg gaaaacctga tgtattgagt agaaccataa ccgtttctgg tcaggttcag    2220
cacctcatgg ccgaaggact tacattcaaa ctgaatgatg tcggcagagg gaccgatgat    2280
caccaagttg agttcctctg aacggtagga gccgtcaggt tggatcacgt tgatacagtt    2340
tgtatcgatc actttcagct ctgtatctat ggttgatccg ccccaaaagg ggattccacg    2400
gacgatggaa gtgagcagca tgcgaccgag gtcagtggaa tagatacgct cgaaaagttt    2460
ggtcactccc ttgaggtaat tgtctttctc gttatctgtc gacaagtacg tggagtcata    2520
gtaggacacc ggcacctgct tggcctctgg tggcggattc aaatctcctt cttcggggtt    2580
agtgaaggtg tctctttcgg gaatgaccca tatcttgtta tgaatcttga aggccttaac    2640
aggctgcatt tgaccggcat tcggaatctt gatatacgca atatcgactc cgttgacagg    2700
gtccttatag ttgaattgct tgttgacaaa tcccatggga ttatatttat aggttttttt    2760
attacaaaac tgttacgaaa acagtaaaat acttatttat ttgcgagatg gttatcattt    2820
taattatctc catgatccaa taacctagaa taaaggccga cctttaattc aacccaacac    2880
aatatattat agttaaataa gaattattat caaatcattt gtatattaat taaaatacta    2940
tactgtaaat tacattttat ttacaatcac agatccatat gggcgagtca ttgttcaagg    3000
gaccgagaga ttacaacccc atctcgtcgt caatctgcca cttgacaaac gaatccgacg    3060
gtcacactac ttctctgtac ggtatcggct tcggaccttt catcatcacc aacaagcatt    3120
tgtttaggag aaacaacggt acactccttg tccagtccct gcacggcgta ttcaaagtca    3180
aagataccac gactctgcaa cagcatctgg tcgacggaag ggacatgata atcattcgca    3240
ttcctaaaga cttcccaccc ttccctcaaa agctcaagtt tcgtgagccc cagcgtgagg    3300
agaggatttg tcttgtcacg actaacttcc agaccaaatc tatgtctagc atggtcagcg    3360
```

-continued

```
atacctcgtg cacttttcca agcggcgatg gaatcttttg gaagcactgg attcagacaa    3420
aggacggcca atgcggttct cctctcgtaa gtacgcgcga cggattcatc gtgggtattc    3480
actccgcttc caacttcacc aacaccaaca actatttcac tagcgtgcca aagaatttca    3540
tggaattgct caccaaccag gaggcccaac aatgggttag tggttggcgt cttaatgcgg    3600
actcagtgct gtggggaggc cataaagttt tcatgaataa gccggaggaa ccttttcaac    3660
ccgtgaagga agcaacacag ctcatgaatg agctggttta ctcacagtga taactcgagc    3720
aatctgatac tagtaataaa agatgtttat tttcattaga tgtgtgtgtt ggtttttgt     3780
ctatagcatg c                                                         3791
```

METHODS OF INTRACELLULAR CONVERSION OF SINGLE-CHAIN PROTEINS INTO THEIR DI-CHAIN FORM

This application is a divisional of U.S. patent application Ser. No. 14/038,328, filed Sep. 26, 2013, now U.S. Pat. No. 9,340,813, which is a continuation and claims priority pursuant to 35 U.S.C. § 120 to U.S. patent application Ser. No. 13/575,222, filed Jul. 25, 2012, now U. S. Pat. No. 8,546,108, which is a national stage application under 35 U.S.C. § 371 of PCT patent application PCT/US2011/022272, filed on Jan. 24, 2011, which claims the benefit of U.S. Provisional Patent Application 61/286,963 filed Jan. 25, 2010, each of which is hereby incorporated by reference in its entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Beaufour Ipsen, Porton Down, England), NEURONOX® (Medy-Tox, Inc., Ochang-myeon, South Korea) BTX-A (Lanzhou Institute Biological Products, China) and XEOMIN® (Merz Pharmaceuticals, GmbH, Frankfurt, Germany); and BoNT/B preparations, such as, e.g., MYOBLOC™/NEUROBLOC™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

The therapeutic utility of Clostridial toxins has been expanded beyond their current myorelaxant applications to treat sensory nerve-based ailments, such as, e.g., various kinds of chronic pain, neurogenic inflammation and urogenital disorders, as well as non-neuronal-based disorders, such as, e.g., pancreatitis. One approach that is currently being exploited to expand Clostridial toxin-based therapies involves modifying a Clostridial toxin so that the modified toxin has an altered cell targeting capability for a non-Clostridial toxin target cell. This re-targeted capability is achieved by replacing a naturally-occurring targeting domain of a Clostridial toxin with a targeting domain showing a selective binding activity for a non-Clostridial toxin receptor present in a non-Clostridial toxin target cell. Such modifications to a targeting domain result in a modified toxin that is able to selectively bind to a non-Clostridial toxin receptor (target receptor) present on a non-Clostridial toxin target cell (re-targeted). A re-targeted Clostridial toxin with a targeting activity for a non-Clostridial toxin target cell can bind to a receptor present on the non-Clostridial toxin target cell, translocate into the cytoplasm, and exert its proteolytic effect on the SNARE complex of the non-Clostridial toxin target cell.

Non-limiting examples of re-targeted Clostridial toxins with a targeting activity for a non-Clostridial toxin target cell are described in, e.g., Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Stephan Donovan, Clostridial Toxin Derivatives and Methods For Treating Pain, U.S. Pat. No. 6,500,436; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; J. Oliver Dolly et al., Activatable Recombinant Neurotoxins, U.S. Pat. No. 7,419,676; Lance E. Steward et al., Multivalent Clostridial Toxin Derivatives and Methods of Their Use, U.S. Pat. No. 7,514,088; Keith A. Foster et al., Inhibition of Secretion from Non-neural Cells, U.S. Patent Publication 2003/0180289; and Keith A. Foster et al., Re-targeted Toxin Conjugates, International Patent Publication WO 2005/023309. The ability to re-target the therapeutic effects associated with Clostridial toxins has greatly extended the number of medicinal applications able to use a Clostridial toxin therapy. As a non-limiting example, modified Clostridial toxins retargeted to sensory neurons are useful in treating various kinds of chronic pain, such as, e.g., hyperalgesia and allodynia, neuropathic pain and inflammatory pain, see, e.g., Foster, supra, (1999); and Donovan, supra, (2002); and Stephan Donovan, Method For Treating Neurogenic Inflammation Pain with Botulinum Toxin and Substance P Components, U.S. Pat. No. 7,022,329. As another non-limiting example, modified Clostridial toxins retargeted to pancreatic cells are useful in treating pancreatitis, see, e.g., Steward, supra, (2005).

Clostridial toxins, whether naturally occurring or modified, are processed into a di-chain form in order to achieve full activity. Naturally-occurring Clostridial toxins are each translated as a single-chain polypeptide of approximately 150 kDa that is subsequently cleaved by proteolytic scission within a disulfide loop by a naturally-occurring protease (FIG. 1). This cleavage occurs within the discrete di-chain loop region created between two cysteine residues that form a disulfide bridge. This post-translational processing yields a di-chain molecule comprising an approximately 50 kDa light chain (LC), comprising the enzymatic domain, and an approximately 100 kDa heavy chain (HC), comprising the translocation and cell binding domains, the LC and HC being held together by the single disulfide bond and non-covalent interactions (FIG. 1). Recombinantly-produced Clostridial toxins generally substitute the naturally-occurring di-chain loop protease cleavage site with an exogenous protease cleavage site (FIG. 2). See e.g., Dolly, J. O. et al., Activatable Clostridial Toxins, U.S. Pat. No. 7,419,676, which is hereby incorporated by reference. Although re-targeted Clostridial toxins vary in their overall molecular weight because of the size of the targeting moiety, the activation process and its reliance on exogenous cleavage sites is essentially the same as that for recombinantly-produced Clostridial toxins. See e.g., Steward, L. E. et al., Activatable Clostridial Toxins, U.S. Patent Publication 2009/0005313; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Steward, L. E. et al., Modified Clostridial Toxins with Enhanced Translocation Capabilities and Altered Targeting Activity for Clostridial Toxin Target Cells, U.S. Patent Publication 2008/0241881, each of which is hereby incorporated by reference.

To date, the conversion of the single-chain form of a recombinantly produced Clostridial toxin or modified Clostridial toxin into its di-chain form required an in vitro activation process. First, the bacterial cells used to recombinantly produce these toxins lack the naturally-occurring protease present in the Clostridial strains that produce the native toxins. Second, there has been no great need for bacterial cells to produce activated toxins recombinantly because of safety concerns raised in handling activated toxins. See e.g., Dolly, U.S. Pat. No. 7,419,676, supra, (2008). However, if these concerns could be overcome, the production of recombinantly produced activated toxins would streamline the manufacturing process of recombinantly produced Clostridial toxins or modified Clostridial toxins. For example, currently the manufacture of recombinantly produced Clostridial toxins or modified Clostridial toxins involves the following purification steps: 1) immobilized metal affinity chromatography, 2) buffer exchange dialysis, 3) protease cleavage reaction, 4), ion exchange chromatography and 5) addition of PEG and flash freezing for storage at −80° C. The use of a bacterial cell that can proteolytically cleave the recombinant Clostridial toxin intracellularly while it is still expressing the toxin can reduce the number of purification steps to the following: 1) immobilized metal affinity chromatography, 2) buffer exchange dialysis, 3) ion exchange chromatography, and 4) addition of PEG and flash freezing for storage at −80° C.

The present specification discloses a method of converting a single-chain protein comprising a di-chain loop region into its di-chain form that does not rely on an in vitro process for converting the single-chain form of the toxin into its di-chain form. This is accomplished by the use of cells that express both the protein and the protease necessary to convert it to active di-chain.

Thus, aspects of the present specification provide, a dual expression construct that includes an open reading frame encoding a single-chain protein comprising a di-chain loop region comprising an exogenous protease cleavage site and an open reading frame encoding a protease that can proteolytically cleave the exogenous protease cleavage site located in the di-chain loop region. In further aspects, the single-chain protein comprising a di-chain loop region comprising an exogenous protease cleavage site can be, e.g., a Clostridial toxin comprising a di-chain loop region comprising an exogenous protease cleavage site, a modified Clostridial toxin comprising a di-chain loop region comprising an exogenous protease cleavage site, or a single-chain protein comprising a Clostridial toxin enzymatic domain, a Clostridial toxin translocation domain, a non-Clostridial toxin binding domain, and a di-chain loop region comprising an exogenous protease cleavage site. Polynucleotides, as well as the Clostridial toxins comprising a di-chain loop region comprising an exogenous protease cleavage site that they encode, are described in, e.g., Dolly, J. O. et al., Activatable Clostridial Toxins, U.S. Pat. No. 7,132,259; Dolly, J. O. et al., Activatable Clostridial Toxins, U.S. Pat. No. 7,419,676, each of which is hereby incorporated by reference in its entirety. Polynucleotides, as well as the proteins comprising a Clostridial toxin enzymatic domain, a Clostridial toxin translocation domain, a non-Clostridial toxin binding domain, and a di-chain loop region comprising an exogenous protease cleavage site that they encode, are described in, e.g., Steward, L. E. et al., Multivalent Clostridial Toxins, U.S. Patent Publication 2009/0048431; Steward, L. E. et al., Activatable Clostridial Toxins, U.S. Patent Publication 2009/0069238; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Steward, L. E. et al., Modified Clostridial Toxins with Enhanced Translocation Capabilities and Altered Targeting Activity for Clostridial Toxin Target Cells, U.S. Patent Publication 2008/0241881; Foster, K. A. et al., Fusion Proteins, U.S. Patent Publication 2009/0035822; Foster, K. A. et al., Non-Cytotoxic Protein Conjugates, U.S. Patent Publication 2009/0162341; Steward, L. E. et al., Activatable Clostridial Toxins, U.S. Patent Publication 2008/0032931; Foster, K. A. et al., Non-Cytotoxic Protein Conjugates, U.S. Patent Publication 2008/0187960; Steward, L. E. et al., Degradable Clostridial Toxins, U.S. Patent Publication 2008/0213830; Steward, L. E. et al., Modified Clostridial Toxins With Enhanced Translocation Capabilities and Altered Targeting Activity For Clostridial Toxin Target Cells, U.S. Patent Publication 2008/0241881; Dolly, J. O. et al., Activatable Clostridial Toxins, U.S. Pat. No. 7,419,676; and a companion patent application Ghanshani, et al., Modified Clostridial Toxins Comprising an Integrated Protease Cleavage Site-Binding Domain, U.S. Provisional Application No. 61/286,954, each of which is hereby incorporated by reference in its entirety.

Other aspects of the present specification provide a cell comprising a dual expression construct that includes an open reading frame encoding a single-chain protein comprising a di-chain loop region comprising an exogenous protease cleavage site and an open reading frame encoding a protease that can proteolytically cleave the exogenous protease cleavage site located in the di-chain loop region. In further aspects, the single-chain protein comprising a di-chain loop region comprising an exogenous protease cleavage site can be, e.g., a Clostridial toxin comprising a di-chain loop region comprising an exogenous protease cleavage site, a modified Clostridial toxin comprising a di-chain loop region comprising an exogenous protease cleavage site, or a single-chain protein comprising a Clostridial toxin enzymatic domain, a Clostridial toxin translocation domain, a non-Clostridial toxin binding domain, and a di-chain loop region comprising an exogenous protease cleavage site as disclosed in the present specification.

Yet other aspects of the present specification provide an intracellular method of converting a single-chain protein into its di-chain form, the method comprising the steps of a) growing a cell comprising a dual expression construct at a first temperature for a certain period of time in order to achieve maximal cell density, the dual expression construct comprising: i) an open reading frame encoding a single-chain protein comprising a di-chain loop region comprising an exogenous protease cleavage site; and ii) an open reading frame encoding a protease; wherein the protease can cleave the exogenous protease cleavage site located within the di-chain loop; b) growing the cell at a second temperature for a certain period of time in order to achieve maximal induction of protein expression from the open reading frame encoding the single-chain protein, wherein growth at step (b) induces expression of the single-chain protein and the protease from the dual expression construct; and wherein the produced protease cleaves the single-chain protein at the exogenous protease cleavage site located within the di-chain loop region, thereby converting the single-chain protein into its di-chain form.

Still other aspects of the present specification provide an intracellular method of converting a single-chain Clostridial toxin into its di-chain form, the method comprising the steps of: a) growing a cell comprising a dual expression construct at 37° C. for about 2 to about 3.5 hours, the dual expression construct comprising; i) an open reading frame encoding a single-chain Clostridial toxin, the single-chain Clostridial toxin comprising an enzymatic domain, a translocation domain, a binding domain, and a di-chain loop region comprising an exogenous protease cleavage site; and ii) an open reading frame encoding a protease; wherein the protease can cleave the exogenous protease cleavage site located within the di-chain loop; b) growing the cell at 22° C. for about 16 to about 18 hours, wherein growth at step (b) induces expression of the single-chain Clostridial toxin and the protease from the dual expression construct; and wherein the produced protease cleaves the single-chain Clostridial toxin at the exogenous protease cleavage site located within the di-chain loop region, thereby converting the single-chain Clostridial toxin into its di-chain form.

Further aspects of the present specification provide an intracellular method of converting a single-chain protein into its di-chain form, the method comprising the steps of a) growing a cell comprising a dual expression construct at 37° C. for about 2 to about 8 hours, the dual expression construct comprising; i) an open reading frame encoding a single-chain protein, the single-chain protein comprising an enzymatic domain, a translocation domain, and an integrated TEV protease cleavage site-opioid binding domain; and ii) an open reading frame encoding a TEV protease; b) growing the cell at about 12 to about 16° C. for about 16 to about 18 hours, wherein growth at step (b) induces expression of the single-chain protein and the TEV protease from the dual expression construct; and wherein the produced TEV protease cleaves the single-chain protein at the TEV protease cleavage site located within the integrated TEV cleavage site opioid binding domain, thereby converting the single-chain protein into its di-chain form.

Further aspects of the present specification provide an intracellular method of converting a single-chain protein into its di-chain form, the method comprising the steps of a) growing a cell comprising a dual expression construct at 37° C. for about 2 to about 8 hours, the dual expression construct comprising; i) an open reading frame encoding a single-chain protein, the single-chain protein comprising an enzymatic domain, a translocation domain, and an integrated TEV protease cleavage site-opioid binding domain; and ii) an open reading frame encoding a TEV protease; b) growing the cell at about 20 to about 24° C. for about 16 to about 18 hours, wherein growth at step (b) induces expression of the single-chain protein and the TEV protease from the dual expression construct; and wherein the produced TEV protease cleaves the single-chain protein at the TEV protease cleavage site located within the integrated TEV cleavage site opioid binding domain, thereby converting the single-chain protein into its di-chain form.

Yet further aspects of the present specification provide an intracellular method of converting a single-chain protein into its di-chain form, the method comprising the steps of a) growing a cell comprising a dual expression construct at 37° C. for about 2 to about 8 hours, the dual expression construct comprising; i) an open reading frame encoding a single-chain protein, the single-chain protein comprising an enzymatic domain, a translocation domain, a non-Clostridial toxin binding domain and a di-chain loop region comprising a TEV protease cleavage site; and ii) an open reading frame encoding a TEV protease; b) growing the cell at about 12 to about 16° C. for about 16 to about 18 hours, wherein growth at step (b) induces expression of the single-chain protein and the TEV protease from the dual expression construct; and wherein the produced TEV protease cleaves the single-chain protein at the TEV protease cleavage site located within the di-chain loop region, thereby converting the single-chain protein into its di-chain form.

Yet further aspects of the present specification provide an intracellular method of converting a single-chain protein into its di-chain form, the method comprising the steps of a) growing a cell comprising a dual expression construct at 37° C. for about 2 to about 8 hours, the dual expression construct comprising; i) an open reading frame encoding a single-chain protein, the single-chain protein comprising an enzymatic domain, a translocation domain, a non-Clostridial toxin binding domain and a di-chain loop region comprising a TEV protease cleavage site; and ii) an open reading frame encoding a TEV protease; b) growing the cell at about 20 to about 24° C. for about 16 to about 18 hours, wherein growth at step (b) induces expression of the single-chain protein and the TEV protease from the dual expression construct; and wherein the produced TEV protease cleaves the single-chain protein at the TEV protease cleavage site located within the di-chain loop region, thereby converting the single-chain protein into its di-chain form.

Other aspects of the present specification provide, an expression construct comprising an open reading frame encoding a single-chain protein comprising a di-chain loop region comprising an exogenous protease cleavage site. In further aspects, the single-chain protein comprising a di-chain loop region comprising an exogenous protease cleavage site can be, e.g., a Clostridial toxin comprising a di-chain loop region comprising an exogenous protease cleavage site, a modified Clostridial toxin comprising a di-chain loop region comprising an exogenous protease cleavage site, or a single-chain protein comprising a Clostridial toxin enzymatic domain, a Clostridial toxin translocation domain, a non-Clostridial toxin binding domain, and a di-chain loop region comprising an exogenous protease cleavage site as disclosed in the present specification.

Other aspects of the present specification provide, an expression construct comprising an open reading frame encoding a protease that can proteolytically cleave the exogenous protease cleavage site located in the di-chain loop region of a single-chain protein comprising a di-chain loop region comprising an exogenous protease cleavage site.

Other aspects of the present specification provide a cell comprising an expression construct comprising an open reading frame encoding a single-chain protein comprising a di-chain loop region comprising an exogenous protease cleavage site and another expression construct comprising an open reading frame encoding a protease that can proteolytically cleave the exogenous protease cleavage site located in the di-chain loop region of a single-chain protein comprising a di-chain loop region comprising an exogenous protease cleavage site. In further aspects, the single-chain protein comprising a di-chain loop region comprising an exogenous protease cleavage site can be, e.g., a Clostridial toxin comprising a di-chain loop region comprising an exogenous protease cleavage site, a modified Clostridial toxin comprising a di-chain loop region comprising an exogenous protease cleavage site, or a single-chain protein comprising a Clostridial toxin enzymatic domain, a Clostridial toxin translocation domain, a non-Clostridial toxin binding domain, and a di-chain loop region comprising an exogenous protease cleavage site as disclosed in the present specification.

Yet other aspects of the present specification provide an intracellular method of converting a single-chain protein into its di-chain form, the method comprising the steps of a) growing a cell comprising i) an expression construct comprising an open reading frame encoding a single-chain protein comprising a di-chain loop region comprising an exogenous protease cleavage site and ii) another expression construct comprising an open reading frame encoding a protease that can proteolytically cleave the exogenous protease cleavage site located in the di-chain loop region of a single-chain protein comprising a di-chain loop region comprising an exogenous protease cleavage site; b) growing the cell at a second temperature for a certain period of time in order to achieve maximal induction of protein expression from the open reading frame encoding the single-chain protein, wherein growth at step (b) induces expression of the single-chain protein and the protease from the expression constructs; and wherein the produced protease cleaves the single-chain protein at the exogenous protease cleavage site located within the di-chain loop region, thereby converting the single-chain protein into its di-chain form.

Still other aspects of the present specification provide an intracellular method of converting a single-chain Clostridial toxin into its di-chain form, the method comprising the steps of: a) growing at 37° C. for about 2 to about 3.5 hours a cell, the cell comprising i) an expression construct comprising an open reading frame encoding a single-chain Clostridial toxin comprising an enzymatic domain, a translocation domain, a binding domain, and a di-chain loop region comprising an exogenous protease cleavage site and ii) another expression construct comprising an open reading frame encoding a protease that can proteolytically cleave the exogenous protease cleavage site located in the di-chain loop region of a single-chain protein comprising a di-chain loop region comprising an exogenous protease cleavage site; b) growing the cell at 22° C. for about 16 to about 18 hours, wherein growth at step (b) induces expression of the single-chain Clostridial toxin and the protease from the expression constructs; and wherein the produced protease cleaves the single-chain Clostridial toxin at the exogenous protease cleavage site located within the di-chain loop region, thereby converting the single-chain Clostridial toxin into its di-chain form.

Further aspects of the present specification provide an intracellular method of converting a single-chain protein into its di-chain form, the method comprising the steps of a) growing at 37° C. for about 2 to about 8 hours a cell, the cell comprising i) an expression construct comprising an open reading frame encoding a single-chain protein comprising an enzymatic domain, a translocation domain, and an integrated TEV protease cleavage site-opioid binding domain and ii) another expression construct comprising an open reading frame encoding TEV protease; b) growing the cell at about 12 to about 16° C. for about 16 to about 18 hours, wherein growth at step (b) induces expression of the single-chain protein and the TEV protease from the expression constructs; and wherein the produced TEV protease cleaves the single-chain protein at the TEV protease cleavage site located within the integrated TEV cleavage site opioid binding domain, thereby converting the single-chain protein into its di-chain form.

Further aspects of the present specification provide an intracellular method of converting a single-chain protein into its di-chain form, the method comprising the steps of a) growing at 37° C. for about 2 to about 8 hours a cell, the cell comprising i) an expression construct comprising an open reading frame encoding a single-chain protein comprising an enzymatic domain, a translocation domain, and an integrated TEV protease cleavage site-opioid binding domain and ii) another expression construct comprising an open reading frame encoding TEV protease; b) growing the cell at about 20 to about 24° C. for about 16 to about 18 hours, wherein growth at step (b) induces expression of the single-chain protein and the TEV protease from the expression constructs; and wherein the produced TEV protease cleaves the single-chain protein at the TEV protease cleavage site located within the integrated TEV cleavage site opioid binding domain, thereby converting the single-chain protein into its di-chain form.

Yet further aspects of the present specification provide an intracellular method of converting a single-chain protein into its di-chain form, the method comprising the steps of a) growing at 37° C. for about 2 to about 8 hours a cell, the cell comprising i) an expression construct comprising an open reading frame encoding a single-chain protein comprising an enzymatic domain, a translocation domain, a non-Clostridial toxin binding domain and a di-chain loop region comprising a TEV protease cleavage site and ii) another expression construct comprising an open reading frame encoding TEV protease; b) growing the cell at about 12 to about 16° C. for about 16 to about 18 hours, wherein growth at step (b) induces expression of the single-chain protein and the TEV protease from the expression constructs; and wherein the produced TEV protease cleaves the single-chain protein at the TEV protease cleavage site located within the integrated TEV cleavage site opioid binding domain, thereby converting the single-chain protein into its di-chain form.

Yet further aspects of the present specification provide an intracellular method of converting a single-chain protein into its di-chain form, the method comprising the steps of a) growing at 37° C. for about 2 to about 8 hours a cell, the cell comprising i) an expression construct comprising an open reading frame encoding a single-chain protein comprising an enzymatic domain, a translocation domain, a non-Clostridial toxin binding domain and a di-chain loop region comprising a TEV protease cleavage site and ii) another expression construct comprising an open reading frame encoding TEV protease; b) growing the cell at about 20 to about 24° C. for about 16 to about 18 hours, wherein growth at step (b) induces expression of the single-chain protein and the TEV protease from the expression constructs; and wherein the produced TEV protease cleaves the single-chain protein at the TEV protease cleavage site located within the integrated TEV cleavage site opioid binding domain, thereby converting the single-chain protein into its di-chain form.

BRIEF DESCRIPTION OF THE DRAWINGS

Figure 2B:
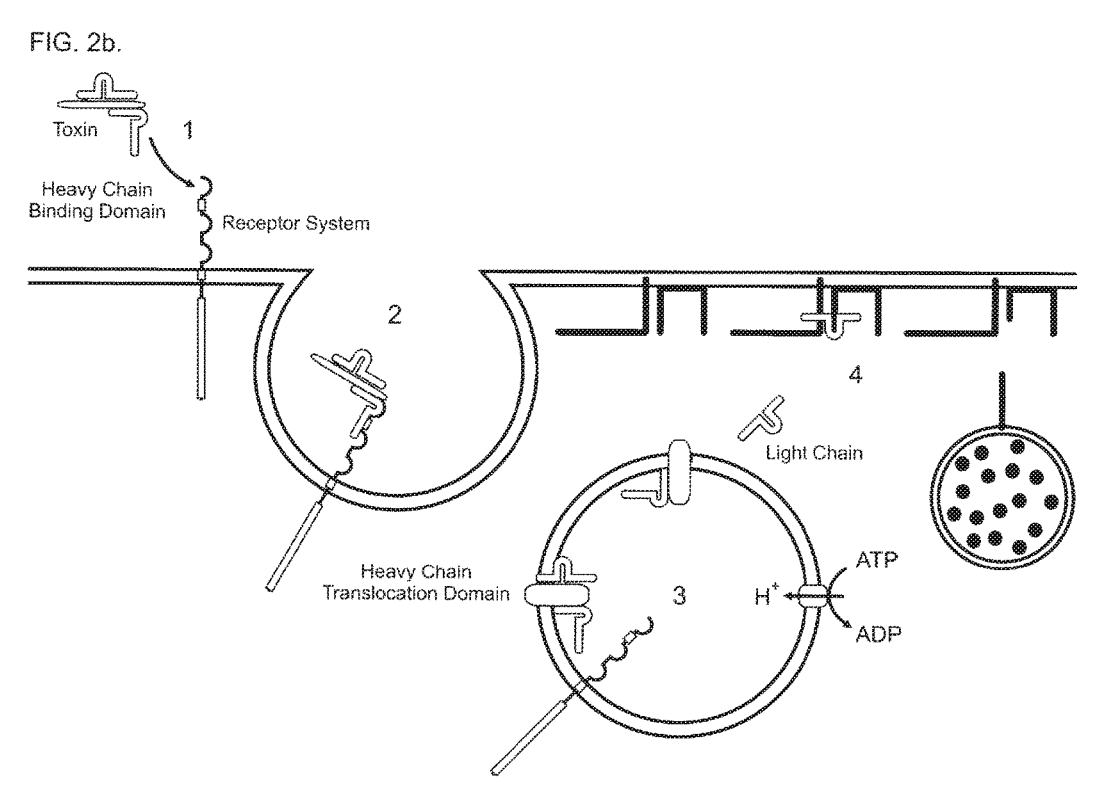

FIGS. 2a and 2b show a schematic of the current paradigm of neurotransmitter release and Clostridial toxin intoxication in a central and peripheral neuron. FIG. 2a shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 2b shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the $H_N$ domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

Figure 1:
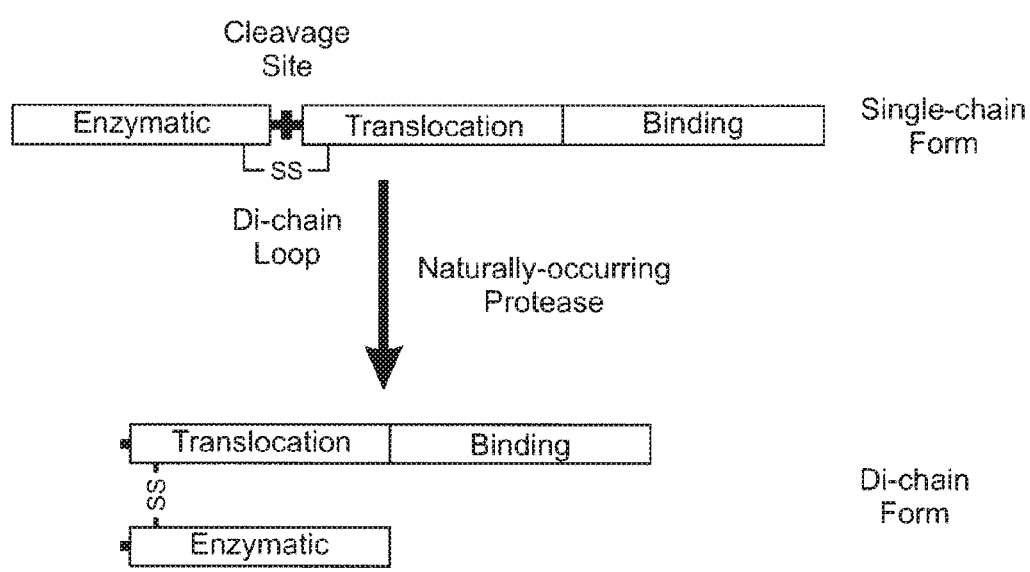
FIG. 1 shows the domain organization of naturally-occurring Clostridial toxins. The single chain form depicts the amino to carboxyl linear organization comprising an enzymatic domain, a translocation domain, and a $H_C$ binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single chain form of the toxin into the di-chain form.

Clostridia toxins produced by *Clostridium botulinum*, *Clostridium tetani*, *Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other Clostridia species, *C. baratii* and *C. butyricum*, produce toxins, BaNT and BuNT, which are similar to BoNT/F and BoNT/E, respectively.

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain ($H_N$) contained within the amino-terminal half of the HC that facilitates release of the LC from intracellular vesicles into the cytoplasm of the target cell; and 3) a binding domain ($H_C$) found within the carboxyl-terminal half of the HC that determines the binding activity and binding specificity of the toxin to the receptor complex located at the surface of the target cell. The $H_C$ domain comprises two distinct structural features of roughly equal size that indicate function and are designated the $H_{CN}$ and $H_{CC}$ subdomains. Table 1 gives approximate boundary regions for each domain found in exemplary Clostridial toxins.

TABLE 1

Clostridial Toxin Reference Sequences and Regions

| Toxin | SEQ ID NO: LC | | $H_N$ | $H_c$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |

TABLE 1-continued

Clostridial Toxin Reference Sequences and Regions

| Toxin | SEQ ID NO: LC | | $H_N$ | $H_c$ |
|---|---|---|---|---|
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |
| BaNT | 9 | M1-K431 | N432-I857 | I858-E1268 |
| BuNT | 10 | M1-R422 | K423-I847 | K848-K1251 |

The binding, translocation, and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (FIG. 3). The process is initiated when the $H_c$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation of the di-chain form of the toxin. Once activated, light chain endopeptidase of the toxin is released from the intracellular vesicle into the cytosol where it appears to specifically target one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure,Function and Therapeutic Utility*, 27(11) Trends Biochem. Sci.

552-558 (2002); Giovanna Lalli et al., *The Journey of Tetanus and Botulinum Neurotoxins in Neurons,* 11(9) Trends Microbiol. 431-437, (2003).

In an aspect of the invention, a modified Clostridial toxin comprises, in part, a single-chain modified Clostridial toxin and a di-chain modified Clostridial toxin. As discussed above, a Clostridial toxin, whether naturally-occurring or non-naturally-occurring, are initially synthesized as a single-chain polypeptide. This single-chain form is subsequently cleaved at a protease cleavage site located within a discrete di-chain loop region created between two cysteine residues that form a disulfide bridge by a protease. This post-translational processing yields a di-chain molecule comprising a light chain (LC) and a heavy chain. As used herein, the term "di-chain loop region" refers to loop region of a naturally-occurring or non-naturally-occurring Clostridial toxin formed by a disulfide bridge located between the LC domain and the HC domain. As used herein, the term "single-chain modified Clostridial toxin" refers to any modified Clostridial toxin disclosed in the present specification that is in its single-chain form, i.e., the toxin has not been cleaved at the protease cleavage site located within the di-chain loop region by its cognate protease. As used herein, the term "di-chain modified Clostridial toxin" refers to any modified Clostridial toxin disclosed in the present specification that is in its di-chain form, i.e., the toxin has been cleaved at the protease cleavage site located within the di-chain loop region by its cognate protease.

Aspects of the present invention provide, in part, polynucleotide molecules. As used herein, the term "polynucleotide molecule" is synonymous with "nucleic acid molecule" and means a polymeric form of nucleotides, such as, e.g., ribonucleotides and deoxyribonucleotides, of any length. Useful polynucleotide molecules, include, without limitation, naturally-occurring and non-naturally-occurring DNA molecules and naturally-occurring and non-naturally-occurring RNA molecules. Non-limiting examples of naturally-occurring and non-naturally-occurring DNA molecules include single-stranded DNA molecules, double-stranded DNA molecules, genomic DNA molecules, cDNA molecules, vector constructs, such as, e.g., plasmid constructs, phagemid constructs, bacteriophage constructs, retroviral constructs and artificial chromosome constructs. Non-limiting examples of naturally-occurring and non-naturally-occurring RNA molecules include single-stranded RNA, double stranded RNA and mRNA.

Well-established molecular biology techniques that may be necessary to make a polynucleotide molecule encoding a modified Clostridial toxin disclosed in the present specification include, but not limited to, procedures involving polymerase chain reaction (PCR) amplification, restriction enzyme reactions, agarose gel electrophoresis, nucleic acid ligation, bacterial transformation, nucleic acid purification, nucleic acid sequencing and recombination-based techniques are routine and well within the scope of one skilled in the art and from the teaching herein. Non-limiting examples of specific protocols necessary to make a polynucleotide molecule encoding a modified Clostridial toxin are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). Additionally, a variety of commercially available products useful for making a polynucleotide molecule encoding a modified Clostridial toxin are widely available. These protocols are routine procedures well within the scope of one skilled in the art and from the teaching herein.

The methods disclosed in the present specification include, in part, an open reading frame. As used herein, the term "open reading frame" is synonymous with "ORF" and means any polynucleotide molecule that encodes a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a polynucleotide molecule that specifies a particular amino acid during protein synthesis; also called a triplet or codon-triplet.

The methods disclosed in the present specification include, in part, an expression construct. An expression construct comprises a polynucleotide molecule including an open reading frame disclosed in the present specification operably-linked to an expression vector useful for expressing the polynucleotide molecule in a cell or cell-free extract. A wide variety of expression vectors can be employed for expressing a polynucleotide molecule disclosed in the present specification, including, without limitation, a viral expression vector; a prokaryotic expression vector; eukaryotic expression vectors, such as, e.g., a yeast expression vector, an insect expression vector and a mammalian expression vector; and a cell-free (in vitro) expression vector. It is further understood that expression vectors useful to practice aspects of these methods may include those which express the polynucleotide molecule under control of a constitutive, tissue-specific, cell-specific or inducible promoter element, enhancer element or both. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

The expression constructs disclosed in the present specification can comprise an open reading frame encoding a protein including a di-chain loop region comprising an exogenous protease cleavage site, wherein cleavage of the exogenous protease cleavage site converts the single-chain protein into its di-chain form. In aspects of this embodiment, a viral expression vector is operably-linked to a polynucleotide molecule encoding a protein comprising an exogenous protease cleavage site located within the di-chain loop; a prokaryotic expression vector is operably-linked to a polynucleotide molecule encoding a protein comprising an exogenous protease cleavage site located within the di-chain loop; a yeast expression vector is operably-linked to a polynucleotide molecule encoding a protein comprising an exogenous protease cleavage site located within the di-chain loop; an insect expression vector is operably-linked to a polynucleotide molecule encoding a protein comprising an exogenous protease cleavage site located within the di-chain loop; and a mammalian expression vector is operably-linked to a polynucleotide molecule encoding a protein comprising an exogenous protease cleavage site located within the di-chain loop. In other aspects of this embodiment, an expression construct—suitable for expressing a polynucleotide molecule disclosed in the present specification can be expressed using a cell-free extract. In an aspect of this embodiment, a cell-free expression vector is operably linked to a polynucleotide molecule encoding a protein comprising an exogenous protease cleavage site located within the di-chain loop.

In an embodiment, an expression construct disclosed in the present specification can comprise an open reading frame encoding a Clostridial toxin comprising a di-chain loop region comprising an exogenous protease cleavage site. In aspects of this embodiment, an expression construct disclosed in the present specification can comprise an open reading frame encoding a Clostridial toxin comprising a Clostridial toxin enzymatic domain, a Clostridial toxin translocation domain, a Clostridial toxin binding domain, and a di-chain loop region comprising an exogenous protease cleavage site. In aspects of this embodiment, the single-chain Clostridial toxin comprises a linear amino-to-carboxyl order of 1) the Clostridial enzymatic domain, the di-chain loop region comprising an exogenous protease cleavage site, the Clostridial translocation domain and the Clostridial binding domain; 2) the Clostridial enzymatic domain, the di-chain loop region comprising an exogenous protease cleavage site, the Clostridial binding domain and the Clostridial translocation domain; 3) the Clostridial binding domain, the Clostridial toxin translocation domain, the di-chain loop region comprising an exogenous protease cleavage site and the Clostridial toxin enzymatic domain; 4) the Clostridial binding domain, the Clostridial toxin enzymatic domain, the di-chain loop region comprising an exogenous protease cleavage site and the Clostridial toxin translocation domain; 5) the Clostridial toxin translocation domain, the di-chain loop region comprising an exogenous protease cleavage site, the Clostridial toxin enzymatic domain and the Clostridial binding domain; or 6) the Clostridial toxin translocation domain, the di-chain loop region comprising an exogenous protease cleavage site, the Clostridial binding domain and the Clostridial toxin enzymatic domain.

In other aspects of this embodiment, an expression construct comprises an open reading frame encoding 1) a BoNT/A toxin enzymatic domain, a BoNT/A translocation domain, a BoNT/A binding domain, and a di-chain loop region comprising an exogenous protease cleavage site; 2) a BoNT/B enzymatic domain, a BoNT/B translocation domain, a BoNT/B binding domain, and a di-chain loop region comprising an exogenous protease cleavage site; 3) a BoNT/C1 enzymatic domain, a BoNT/C1 translocation domain, a BoNT/C1 binding domain, and a di-chain loop region comprising an exogenous protease cleavage site; 4) a BoNT/D enzymatic domain, a BoNT/D translocation domain, a BoNT/D binding domain, and a di-chain loop region comprising an exogenous protease cleavage site; 5) a BoNT/E enzymatic domain, a BoNT/E translocation domain, a BoNT/E binding domain, and a di-chain loop region comprising an exogenous protease cleavage site; 6) a BoNT/F enzymatic domain, a BoNT/F translocation domain, a BoNT/F binding domain, and a di-chain loop region comprising an exogenous protease cleavage site; 7) a BoNT/G enzymatic domain, a BoNT/G translocation domain, a BoNT/G binding domain, and a di-chain loop region comprising an exogenous protease cleavage site; 8) a TeNT enzymatic domain, a TeNT translocation domain, a TeNT binding domain, and a di-chain loop region comprising an exogenous protease cleavage site; 9) a BaNT enzymatic domain, a BaNT translocation domain, a BaNT binding domain, and a di-chain loop region comprising an exogenous protease cleavage site; 10) a BuNT enzymatic domain, a BuNT translocation domain, a BuNT binding domain, and a di-chain loop region comprising an exogenous protease cleavage site.

In further other aspects of this embodiment, an expression construct comprises an open reading frame encoding 1) a BoNT/A toxin enzymatic domain, a BoNT/A translocation domain, a BoNT/A binding domain, and a di-chain loop region comprising a TEV protease cleavage site; 2) a BoNT/B enzymatic domain, a BoNT/B translocation domain, a BoNT/B binding domain, and a di-chain loop region comprising a TEV protease cleavage site; 3) a BoNT/C1 enzymatic domain, a BoNT/C1 translocation domain, a BoNT/C1 binding domain, and a di-chain loop region comprising a TEV protease cleavage site; 4) a BoNT/D enzymatic domain, a BoNT/D translocation domain, a BoNT/D binding domain, and a di-chain loop region comprising a TEV protease cleavage site; 5) a BoNT/E enzymatic domain, a BoNT/E translocation domain, a BoNT/E binding domain, and a di-chain loop region comprising a TEV protease cleavage site; 6) a BoNT/F enzymatic domain, a BoNT/F translocation domain, a BoNT/F binding domain, and a di-chain loop region comprising a TEV protease cleavage site; 7) a BoNT/G enzymatic domain, a BoNT/G translocation domain, a BoNT/G binding domain, and a di-chain loop region comprising a TEV protease cleavage site; 8) a TeNT enzymatic domain, a TeNT translocation domain, a TeNT binding domain, and a di-chain loop region comprising a TEV protease cleavage site; 9) a BaNT enzymatic domain, a BaNT translocation domain, a BaNT binding domain, and a di-chain loop region comprising a TEV protease cleavage site; 10) a BuNT enzymatic domain, a BuNT translocation domain, a BuNT binding domain, and a di-chain loop region comprising a TEV protease cleavage site.

Examples of such Clostridial toxins comprising a di-chain loop region comprising an exogenous protease cleavage sit are described in, e.g., J. Oliver Dolly, et al., Activatable Recombinant Neurotoxins, U.S. Pat. No. 7,132,529; J. Oliver Dolly, et al., Activatable Recombinant Neurotoxins, U.S. Pat. No. 7,419,676; Lance Steward, et al., Leucine-Based Motifs and Clostridial Neurotoxins, U.S. Pat. No. 6,903,187; Lance Steward, et al., Leucine-Based Motifs and Clostridial Neurotoxins, U.S. Pat. No. 7,393,925; Wei-Jen Lin, et al., Neurotoxins with Enhanced Target Specificity, U.S. Pat. No. 7,273,722; Lance Steward, et al., Modified Botulinum Neurotoxins, U.S. Pat. No. 7,491,799; Lance E. Steward, et al., Optimized Expression of Active Botulinum Toxin Type E, U.S. Patent Publication 2008/0138893; Ester Fernandez-Salas, et al., Optimized Expression of Active Botulinum Toxin Type A, U.S. Patent Publication 2008/0057575; each of which is hereby incorporated by reference in its entirety.

In another embodiment, an expression construct disclosed in the present specification can comprise an open reading frame encoding a protein comprising a Clostridial toxin enzymatic domain, a Clostridial toxin translocation domain, a non-Clostridial toxin binding domain, and a di-chain loop region comprising an exogenous protease cleavage site. In aspects of this embodiment, the single-chain protein comprises a linear amino-to-carboxyl order of 1) the Clostridial enzymatic domain, the di-chain loop region comprising an exogenous protease cleavage site, the Clostridial translocation domain and the non-Clostridial binding domain; 2) the Clostridial enzymatic domain, the di-chain loop region comprising an exogenous protease cleavage site, the non-Clostridial binding domain and the Clostridial translocation domain; 3) the non-Clostridial binding domain, the Clostridial toxin translocation domain, the di-chain loop region comprising an exogenous protease cleavage site and the Clostridial toxin enzymatic domain; 4) the non-Clostridial binding domain, the Clostridial toxin enzymatic domain, the di-chain loop region comprising an exogenous protease cleavage site and the Clostridial toxin translocation domain; 5) the Clostridial toxin translocation domain, the di-chain loop region comprising an exogenous protease cleavage site, the Clostridial toxin enzymatic domain and the non-Clostridial binding domain; or 6) the Clostridial toxin translocation domain, the di-chain loop region comprising an exogenous protease cleavage site, the non-Clostridial binding domain and the Clostridial toxin enzymatic domain.

In other aspects of this embodiment, an expression construct comprises an open reading frame encoding a Clostridial toxin enzymatic domain, a Clostridial toxin translocation domain, an opioid binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, an enkephalin binding domain, and a di-chain loop region comprising an exogenous protease cleavage site; 2) a Clostridial toxin enzymatic domain, a Clostridial toxin translocation domain, a bovine adrenomedullary-22 (BAM22) peptide binding domain, and a di-chain loop region comprising an exogenous protease cleavage site; 3) a Clostridial toxin enzymatic domain, a Clostridial toxin translocation domain, an endomorphin binding domain, and a di-chain loop region comprising an exogenous protease cleavage site; 4) a Clostridial toxin enzymatic domain, a Clostridial toxin translocation domain, an endorphin binding domain, and a di-chain loop region comprising an exogenous protease cleavage site; 5) a Clostridial toxin enzymatic domain, a Clostridial toxin translocation domain, a dynorphin binding domain, and a di-chain loop region comprising an exogenous protease cleavage site; 6) a Clostridial toxin enzymatic domain, a Clostridial toxin translocation domain, a nociceptin binding domain, and a di-chain loop region comprising an exogenous protease cleavage site; 7) a Clostridial toxin enzymatic domain, a Clostridial toxin translocation domain, a hemorphin binding domain, and a di-chain loop region comprising an exogenous protease cleavage site; or 8) a Clostridial toxin enzymatic domain, a Clostridial toxin translocation domain, a rimorphin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a melanocortin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, an melanocyte stimulating hormone binding domain, and a di-chain loop region comprising an exogenous protease cleavage site; 2) a Clostridial toxin enzymatic domain, a Clostridial toxin translocation domain, an adrenocorticotropin binding domain, and a di-chain loop region comprising an exogenous protease cleavage site; or 3) a Clostridial toxin enzymatic domain, a Clostridial toxin translocation domain, a lipotropin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a galanin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a galanin binding domain, and a di-chain loop region comprising an exogenous protease cleavage site; or 2) a Clostridial toxin enzymatic domain, a Clostridial toxin translocation domain, a galanin message-associated peptide (GMAP) binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a granin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a chromogranin A binding domain, and a di-chain loop region comprising an exogenous protease cleavage site; 2) a Clostridial toxin enzymatic domain, a Clostridial toxin translocation domain, a chromogranin B binding domain, and a di-chain loop region comprising an exogenous protease cleavage site; or 3) a Clostridial toxin enzymatic domain, a Clostridial toxin translocation domain, a chromogranin C binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a tachykinin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a Substance P binding domain, and a di-chain loop region comprising an exogenous protease cleavage site; 2) a Clostridial toxin enzymatic domain, a Clostridial toxin translocation domain, a neuropeptide K binding domain, and a di-chain loop region comprising an exogenous protease cleavage site; 3) a Clostridial toxin enzymatic domain, a Clostridial toxin translocation domain, a neuropeptide gamma binding domain, and a di-chain loop region comprising an exogenous protease cleavage site; 4) a Clostridial toxin enzymatic domain, a Clostridial toxin translocation domain, a neurokinin A binding domain, and a di-chain loop region comprising an exogenous protease cleavage site; 5) a Clostridial toxin enzymatic domain, a Clostridial toxin translocation domain, a hemokinin binding domain, and a di-chain loop region comprising an exogenous protease cleavage site; or 6) a Clostridial toxin enzymatic domain, a Clostridial toxin translocation domain, a endokinin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Neuropeptide Y related peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a neuropeptide Y (NPY) binding domain, and a di-chain loop region comprising an exogenous protease cleavage site; 2) a Clostridial toxin enzymatic domain, a Clostridial toxin translocation domain, a Peptide YY (PYY) binding domain, and a di-chain loop region comprising an exogenous protease cleavage site; 3) a Clostridial toxin enzymatic domain, a Clostridial toxin translocation domain, a Pancreatic peptide (PP) binding domain, and a di-chain loop region comprising an exogenous protease cleavage site; or 4) a Clostridial toxin enzymatic domain, a Clostridial toxin translocation domain, a Pancreatic icosapeptide (PIP) binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a neurohormone peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a corticotropin-releasing hormone (CCRH) binding domain, and a di-chain loop region comprising an exogenous protease cleavage site; 2) a Clostridial toxin enzymatic domain, a Clostridial toxin translocation domain, a parathyroid hormone (PTH) binding domain, and a di-chain loop region comprising an exogenous protease cleavage site; 3) a Clostridial toxin enzymatic domain, a Clostridial toxin translocation domain, a thyrotropin-releasing hormone (TRH) binding domain, and a di-chain loop region comprising an exogenous protease cleavage site; or 4) a Clostridial toxin enzymatic domain, a Clostridial toxin translocation domain, a somatostatin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a cytokine peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a ciliary neurotrophic factor (CNTF) binding domain, and a di-chain loop region comprising an exogenous protease cleavage site; 2) a Clostridial toxin enzymatic domain, a Clostridial toxin translocation domain, a glycophorin-A (GPA) binding domain, and a di-chain loop region comprising an exogenous protease cleavage site; 3) a Clostridial toxin enzymatic domain, a Clostridial toxin translocation domain, a leukemia inhibitory factor (LIF) binding domain, and a di-chain loop region comprising an exogenous protease cleavage site; 4) a Clostridial toxin enzymatic domain, a Clostridial toxin translocation domain, an interleukin (IL) binding domain, and a di-chain loop region comprising an exogenous protease cleavage site; 5) a Clostridial toxin enzymatic domain, a Clostridial toxin translocation domain, an oncostatin M binding domain, and a di-chain loop region comprising an exogenous protease cleavage site; 6) a Clostridial toxin enzymatic domain, a Clostridial toxin translocation domain, a cardiotrophin-1 (CT-1) binding domain, and a di-chain loop region comprising an exogenous protease cleavage site; 7) a Clostridial toxin enzymatic domain, a Clostridial toxin translocation domain, a cardiotrophin-like cytokine (CLC) binding domain, and a di-chain loop region comprising an exogenous protease cleavage site; 8) a Clostridial toxin enzymatic domain, a Clostridial toxin translocation domain, a neuroleukin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a kinin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a bradykinin binding domain, and a di-chain loop region comprising an exogenous protease cleavage site; 2) a Clostridial toxin enzymatic domain, a Clostridial toxin translocation domain, a kallidin binding domain, and a di-chain loop region comprising an exogenous protease cleavage site; 3) a Clostridial toxin enzymatic domain, a Clostridial toxin translocation domain, a desArg9 bradykinin binding domain, and a di-chain loop region comprising an exogenous protease cleavage site; or 4) a Clostridial toxin enzymatic domain, a Clostridial toxin translocation domain, a desArg10 bradykinin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Fibroblast growth factor (FGF) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a FGF-1 binding domain, and a di-chain loop region comprising an exogenous protease cleavage site; 2) a Clostridial toxin enzymatic domain, a Clostridial toxin translocation domain, a FGF-2 binding domain, and a di-chain loop region comprising an exogenous protease cleavage site; 3) a Clostridial toxin enzymatic domain, a Clostridial toxin translocation domain, a FGF-4 binding domain, and a di-chain loop region comprising an exogenous protease cleavage site; 4) a Clostridial toxin enzymatic domain, a Clostridial toxin translocation domain, a FGF-8 binding domain, and a di-chain loop region comprising an exogenous protease cleavage site; 5) a Clostridial toxin enzymatic domain, a Clostridial toxin translocation domain, a FGF-9 binding domain, and a di-chain loop region comprising an exogenous protease cleavage site; 6) a Clostridial toxin enzymatic domain, a Clostridial toxin translocation domain, a FGF-17 binding domain, and a di-chain loop region comprising an exogenous protease cleavage site; or 4) a Clostridial toxin enzymatic domain, a Clostridial toxin translocation domain, a FGF-18 binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a neurotrophin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a nerve growth factor (NGF) binding domain, and a di-chain loop region comprising an exogenous protease cleavage site; 2) a Clostridial toxin enzymatic domain, a Clostridial toxin translocation domain, a brain derived neurotrophic factor (BDNF) binding domain, and a di-chain loop region comprising an exogenous protease cleavage site; 3) a Clostridial toxin enzymatic domain, a Clostridial toxin translocation domain, a neurotrophin-3 (NT-3) binding domain, and a di-chain loop region comprising an exogenous protease cleavage site; 4) a Clostridial toxin enzymatic domain, a Clostridial toxin translocation domain, a neurotrophin-4/5 (NT-4/5) binding domain, and a di-chain loop region comprising an exogenous protease cleavage site; or 5) a Clostridial toxin enzymatic domain, a Clostridial toxin translocation domain, a head activator peptide (HA) binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a tumor necrosis factor (TNF) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Glial derived growth factor (GDNF) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a neurturin binding domain, and a di-chain loop region comprising an exogenous protease cleavage site; 2) a Clostridial toxin enzymatic domain, a Clostridial toxin translocation domain, a persephin binding domain, and a di-chain loop region comprising an exogenous protease cleavage site; or 3) a Clostridial toxin enzymatic domain, a Clostridial toxin translocation domain, an artemin binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Transformation growth factor β (TGFβ) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a TGFβ1 binding domain, and a di-chain loop region comprising an exogenous protease cleavage site; 2) a Clostridial toxin enzymatic domain, a Clostridial toxin translocation domain, a TGFβ2 binding domain, and a di-chain loop region comprising an exogenous protease cleavage site; 3) a Clostridial toxin enzymatic domain, a Clostridial toxin translocation domain, a TGFβ3 binding domain, and a di-chain loop region comprising an exogenous protease cleavage site; or 4) a Clostridial toxin enzymatic domain, a Clostridial toxin translocation domain, a TGFβ4 binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Bone morphogenetic protein β (BMP) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a BMP2 binding domain, and a di-chain loop region comprising an exogenous protease cleavage site; 2) a Clostridial toxin enzymatic domain, a Clostridial toxin translocation domain, a BMP3 binding domain, and a di-chain loop region comprising an exogenous protease cleavage site; 3) a Clostridial toxin enzymatic domain, a Clostridial toxin translocation domain, a BMP4 binding domain, and a di-chain loop region comprising an exogenous protease cleavage site; 4) a Clostridial toxin enzymatic domain, a Clostridial toxin translocation domain, a BMP5 binding domain, and a di-chain loop region comprising an exogenous protease cleavage site; 5) a Clostridial toxin enzymatic domain, a Clostridial toxin translocation domain, a BMP6 binding domain, and a di-chain loop region comprising an exogenous protease cleavage site; 6) a Clostridial toxin enzymatic domain, a Clostridial toxin translocation domain, a BMP7 binding domain, and a di-chain loop region comprising an exogenous protease cleavage site; 7) a Clostridial toxin enzymatic domain, a Clostridial toxin translocation domain, a BMP8 binding domain, and a di-chain loop region comprising an exogenous protease cleavage site; or 8) a Clostridial toxin enzymatic domain, a Clostridial toxin translocation domain, a BMP10 binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Growth differentiation factor β (GDF) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a GDF1 binding domain, and a di-chain loop region comprising an exogenous protease cleavage site; 2) a Clostridial toxin enzymatic domain, a Clostridial toxin translocation domain, a GDF2 binding domain, and a di-chain loop region comprising an exogenous protease cleavage site; 3) a Clostridial toxin enzymatic domain, a Clostridial toxin translocation domain, a GDF3 binding domain, and a di-chain loop region comprising an exogenous protease cleavage site; 4) a Clostridial toxin enzymatic domain, a Clostridial toxin translocation domain, a GDF5 binding domain, and a di-chain loop region comprising an exogenous protease cleavage site; 5) a Clostridial toxin enzymatic domain, a Clostridial toxin translocation domain, a GDF6 binding domain, and a di-chain loop region comprising an exogenous protease cleavage site; 6) a Clostridial toxin enzymatic domain, a Clostridial toxin translocation domain, a GDF7 binding domain, and a di-chain loop region comprising an exogenous protease cleavage site; 7) a Clostridial toxin enzymatic domain, a Clostridial toxin translocation domain, a GDF8 binding domain, and a di-chain loop region comprising an exogenous protease cleavage site; 8) a Clostridial toxin enzymatic domain, a Clostridial toxin translocation domain, a GDF10 binding domain, and a di-chain loop region comprising an exogenous protease cleavage site; 9) a Clostridial toxin enzymatic domain, a Clostridial toxin translocation domain, a GDF11 binding domain, and a di-chain loop region comprising an exogenous protease cleavage site; or 10) a Clostridial toxin enzymatic domain, a Clostridial toxin translocation domain, a GDF15 binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, an activin peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, an activin A binding domain, and a di-chain loop region comprising an exogenous protease cleavage site; 2) a Clostridial toxin enzymatic domain, a Clostridial toxin translocation domain, an activin B binding domain, and a di-chain loop region comprising an exogenous protease cleavage site; 3) a Clostridial toxin enzymatic domain, a Clostridial toxin translocation domain, an activin C binding domain, and a di-chain loop region comprising an exogenous protease cleavage site; 4) a Clostridial toxin enzymatic domain, a Clostridial toxin translocation domain, an activin E binding domain, and a di-chain loop region comprising an exogenous protease cleavage site; or 5) a Clostridial toxin enzymatic domain, a Clostridial toxin translocation domain, an inhibin A binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Vascular endothelial growth factor (VEGF) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, an insulin growth factor (IGF) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, an IGF-1 binding domain, and a di-chain loop region comprising an exogenous protease cleavage site; or 2) a Clostridial toxin enzymatic domain, a Clostridial toxin translocation domain, an IGF-2 binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, an Epidermal growth factor (EGF) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Glucagon like hormone peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a secretin binding domain, and a di-chain loop region comprising an exogenous protease cleavage site; or 2) a Clostridial toxin enzymatic domain, a Clostridial toxin translocation domain, a glucagon-like peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Pituitary adenylate cyclase activating peptide (PACAP) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Growth hormone-releasing hormone (GHRH) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Growth hormone-releasing hormone (GHRH) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Vasoactive intestinal peptide (VIP) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a VIP1 binding domain, and a di-chain loop region comprising an exogenous protease cleavage site; or 2) a Clostridial toxin enzymatic domain, a Clostridial toxin translocation domain, a VIP2 binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Gastric inhibitory polypeptide (GIP) peptide binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a Calcitonin-related peptides visceral gut peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a gastrin binding domain, and a di-chain loop region comprising an exogenous protease cleavage site; 2) a Clostridial toxin enzymatic domain, a Clostridial toxin translocation domain, a gastrin-releasing peptide binding domain, and a di-chain loop region comprising an exogenous protease cleavage site; or 3) a Clostridial toxin enzymatic domain, a Clostridial toxin translocation domain, a cholecystokinin (CCK) binding domain, and a di-chain loop region comprising an exogenous protease cleavage site.

In other aspects of this embodiment, an expression construct comprises an open reading frame encoding a Clostridial toxin enzymatic domain, a Clostridial toxin translocation domain, a protease activated receptor (PAR) peptide binding domain, and a di-chain loop region comprising an exogenous protease cleavage site. In further aspects of this embodiment, an expression construct comprises an open reading frame encoding 1) a Clostridial toxin enzymatic domain, a Clostridial toxin translocation domain, a PAR1 binding domain, and a di-chain loop region comprising an exogenous protease cleavage site; 2) a Clostridial toxin enzymatic domain, a Clostridial toxin translocation domain, a PAR2 binding domain, and a di-chain loop region comprising an exogenous protease cleavage site; 3) a Clostridial toxin enzymatic domain, a Clostridial toxin translocation domain, a PAR3 binding domain, and a di-chain loop region comprising an exogenous protease cleavage site; or 4) a Clostridial toxin enzymatic domain, a Clostridial toxin translocation domain, a PAR3 binding domain, and a di-chain loop region comprising an exogenous protease cleavage site.

Examples, of such proteins comprising a di-chain loop region comprising an exogenous protease cleavage site are described in, e.g., J. Oliver Dolly, et al., Activatable Recombinant Neurotoxins, U.S. Pat. No. 7,132,529; J. Oliver Dolly, et al., Activatable Recombinant Neurotoxins, U.S. Pat. No. 7,419,676; Lance E. Steward et al., Multivalent Clostridial Toxin Derivatives and Methods of Their Use, U.S. Pat. No. 7,514,088; Keith A. Foster et al., Re-targeted Toxin Conjugates, International Patent Publication WO 2005/023309; Lance E. Steward, et al., Activatable Recombinant Neurotoxins, U.S. Patent Publication 2008/0032930; Lance E. Steward, et al., Activatable Recombinant Neurotoxins, U.S. Patent Publication 2008/0032931; Lance E. Steward, et al., Activatable Recombinant Neurotoxins, U.S. Patent Publication 2008/0161226; Lance E. Steward, et al., Activatable Recombinant Neurotoxins, U.S. Patent Publication 2008/0221012; Lance E. Steward, et al., Activatable Recombinant Neurotoxins, U.S. Patent Publication 2009/0004224; Lance E. Steward, et al., Activatable Recombinant Neurotoxins, U.S. Patent Publication 2009/0005313; Lance E. Steward, et al., Activatable Recombinant Neurotoxins, U.S. Patent Publication 2009/0018081; Lance E. Steward, et al., Activatable Recombinant Neurotoxins, U.S. Patent Publication 2009/0069238; and Lance E. Steward et al., Multivalent Clostridial Toxin Derivatives and Methods of Their Use, U.S. Patent Publication 2009/0048431, each of which is hereby incorporated by reference in its entirety.

In another embodiment, an expression construct comprises an open reading frame encoding a protein comprising a Clostridial toxin enzymatic domain, a Clostridial toxin translocation domain, and an integrated protease cleavage site-binding domain. In aspects of this embodiment, the single-chain protein comprises a linear amino-to-carboxyl order of 1) an integrated protease cleavage site-binding domain, a Clostridial toxin translocation domain and a Clostridial toxin enzymatic domain; 2) an integrated protease cleavage site-binding domain, a Clostridial toxin enzymatic domain, and a Clostridial toxin translocation domain; 3) a Clostridial toxin enzymatic domain, an integrated protease cleavage site-binding domain, and a Clostridial toxin translocation domain; 4) a Clostridial toxin translocation domain, an integrated protease cleavage site-binding domain, and a Clostridial toxin enzymatic domain; 5) a Clostridial toxin translocation domain, a Clostridial toxin enzymatic domain, and an integrated protease cleavage site-binding domain; and 6) a Clostridial toxin enzymatic domain, a Clostridial toxin translocation domain, and an integrated protease cleavage site-binding domain.

In other aspects of this embodiment, an expression construct comprises an open reading frame encoding a Clostridial toxin enzymatic domain, a Clostridial toxin translocation domain, an integrated TEV protease cleavage site-opioid binding domain. In further aspects of this embodiment, an expression construct comprises an open reading frame encoding 1) a Clostridial toxin enzymatic domain, a Clostridial toxin translocation domain, an integrated TEV protease cleavage site-enkephalin binding domain; 2) a Clostridial toxin enzymatic domain, a Clostridial toxin translocation domain, an integrated TEV protease cleavage site-bovine adrenomedullary-22 (BAM22) binding domain; 3) a Clostridial toxin enzymatic domain, a Clostridial toxin translocation domain, an integrated TEV protease cleavage site-endomorphin binding domain; 4) a Clostridial toxin enzymatic domain, a Clostridial toxin translocation domain, an integrated TEV protease cleavage site-endorphin binding domain; 5) a Clostridial toxin enzymatic domain, a Clostridial toxin translocation domain, an integrated TEV protease cleavage site-dynorphin binding domain; 6) a Clostridial toxin enzymatic domain, a Clostridial toxin translocation domain, an integrated TEV protease cleavage site-nociceptin binding domain; 7) a Clostridial toxin enzymatic domain, a Clostridial toxin translocation domain, an integrated TEV protease cleavage site-hemorphin binding domain; or 8) a Clostridial toxin enzymatic domain, a Clostridial toxin translocation domain, an integrated TEV protease cleavage site-rimorphin binding domain.

Examples, of such proteins comprising integrated protease cleavage site-binding domain are described in, e.g., companion patent application Sanjiv Ghanshani, et al., Modified Clostridial Toxins Comprising an Integrated Protease Cleavage Site-Binding Domain, which is hereby incorporated by reference in its entirety.

The expression constructs disclosed in the present specification can comprise an open reading frame encoding a protease. In aspects of this embodiment, a viral expression vector is operably-linked to a polynucleotide molecule encoding a protease; a prokaryotic expression vector is operably-linked to a polynucleotide molecule encoding a protease; a yeast expression vector is operably-linked to a polynucleotide molecule encoding a protease; an insect expression vector is operably-linked to a polynucleotide molecule encoding a protease; and a mammalian expression vector is operably-linked to a polynucleotide molecule encoding a protease. In other aspects of this embodiment, an expression construct is suitable for expressing a polynucleotide molecule disclosed in the present specification can be expressed using a cell-free extract. In an aspect of this embodiment, a cell-free extract expression vector is operably linked to a polynucleotide molecule encoding a protease.

In aspect of this embodiment, an expression construct comprising an open reading frame encodes an enterokinase, a human rhinovirus 3C protease, a human enterovirus 3C protease, a tobacco etch virus (TEV) protease, a Tobacco Vein Mottling Virus (TVMV) protease, a subtilisin protease, or a Caspase 3 protease. Examples of Enterokinase proteases and the polynucleotide molecules that encode them are described in, e.g., Edward R. LaVallie, Cloning of Enterokinase and Method of Use, U.S. Pat. No. 5,665,566; Edward R. LaVallie, Cloning of Enterokinase and Method of Use, U.S. Pat. No. 6,746,859, each of which is hereby incorporated by reference in its entirety. Examples of subtilisin proteases and the polynucleotide molecules that encode them are described in, e.g., Donn N. Rubingh, et al., Subtilisin Protease Variants having Amino Acid Deletions and Substitutions in Defined Epitope Regions, U.S. Pat. No. 6,586,224, which is hereby incorporated by reference in its entirety.

In another aspect of this embodiment, an enterokinase is SEQ ID NO: 11. In another aspect of this embodiment, an enterokinase comprises amino acids 239-1035 of SEQ ID NO: 11. In yet another aspect of this embodiment, an enterokinase is a naturally occurring enterokinase variant, such as, e.g., an enterokinase isoform. In still another aspect of this embodiment, an enterokinase is a non-naturally occurring enterokinase variant, such as, e.g., a conservative enterokinase variant, a non-conservative enterokinase variant, an enterokinase chimeric, an active enterokinase fragment, or any combination thereof. In another aspect of this embodiment, an Enterokinase is one disclosed in U.S. Pat. No. 5,665,566 or U.S. Pat. No. 6,746,859. In another aspect of this embodiment, an enterokinase, a naturally occurring enterokinase variant, or a non-naturally occurring enterokinase variant is obtained from a species of mammal such as, e.g., a human, a cow, or a rodent.

In other aspects of this embodiment, an enterokinase comprises a polypeptide having an amino acid identity of, e.g., at least 70%, at least 75%, at least 80%, at least 85%, at least 90% or at least 95% to SEQ ID NO: 11; or at most 70%, at most 75%, at most 80%, at most 85%, at most 90% or at most 95% to SEQ ID NO: 11. In yet other aspects of this embodiment, an enterokinase comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 11; or at most 1, 2, 3, 4, 5, 6, 7, 8, 9, 10, 20, 30, 40, 50, or 100 non-contiguous amino acid deletions, additions, and/or substitutions relative to SEQ ID NO: 11. In still other aspects of this embodiment, an enterokinase comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 11; or at most 1, 2, 3, 4, 5, 6, 7, 8, 9, 10, 20, 30, 40, 50, or 100 contiguous amino acid deletions, additions, and/or substitutions relative to SEQ ID NO: 11.

In another aspect of this embodiment, a human rhinovirus 3C protease is SEQ ID NO: 12. In yet another aspect of this embodiment, a human rhinovirus 3C protease is a naturally occurring human rhinovirus 3C protease variant, such as, e.g., a human rhinovirus 3C protease isoform. In still another aspect of this embodiment, a human rhinovirus 3C protease is a non-naturally occurring human rhinovirus 3C protease variant, such as, e.g., a conservative human rhinovirus 3C protease variant, a non-conservative human rhinovirus 3C protease variant, a human rhinovirus 3C protease chimeric, an active human rhinovirus 3C protease fragment, or any combination thereof. In another aspect of this embodiment, a human rhinovirus 3C protease, a naturally occurring human rhinovirus 3C protease variant, or a non-naturally occurring human rhinovirus 3C protease variant is obtained from a species of Rhinovirus.

In other aspects of this embodiment, a human rhinovirus 3C protease comprises a polypeptide having an amino acid identity of, e.g., at least 70%, at least 75%, at least 80%, at least 85%, at least 90% or at least 95% to SEQ ID NO: 12; or at most 70%, at most 75%, at most 80%, at most 85%, at most 90% or at most 95% to SEQ ID NO: 12. In yet other aspects of this embodiment, a human rhinovirus 3C protease comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 12; or at most 1, 2, 3, 4, 5, 6, 7, 8, 9, 10, 20, 30, 40, 50, or 100 non-contiguous amino acid deletions, additions, and/or substitutions relative to SEQ ID NO: 12. In still other aspects of this embodiment, a human rhinovirus 3C protease comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 12; or at most 1, 2, 3, 4, 5, 6, 7, 8, 9, 10, 20, 30, 40, 50, or 100 contiguous amino acid deletions, additions, and/or substitutions relative to SEQ ID NO: 12.

In another aspect of this embodiment, a human enterovirus 3C protease is SEQ ID NO: 13. In yet another aspect of this embodiment, a human enterovirus 3C protease is a naturally occurring human enterovirus 3C protease variant, such as, e.g., a human enterovirus 3C protease isoform. In still another aspect of this embodiment, a human enterovirus 3C protease is a non-naturally occurring human enterovirus 3C protease variant, such as, e.g., a conservative human enterovirus 3C protease variant, a non-conservative human enterovirus 3C protease variant, a human enterovirus 3C protease chimeric, an active human enterovirus 3C protease fragment, or any combination thereof. In another aspect of this embodiment, a human enterovirus 3C protease, a naturally occurring human enterovirus 3C protease variant, or a non-naturally occurring human enterovirus 3C protease variant is obtained from a species of Enterovirus.

In other aspects of this embodiment, a human enterovirus 3C protease comprises a polypeptide having an amino acid identity of, e.g., at least 70%, at least 75%, at least 80%, at least 85%, at least 90% or at least 95% to SEQ ID NO: 13; or at most 70%, at most 75%, at most 80%, at most 85%, at most 90% or at most 95% to SEQ ID NO: 13. In yet other aspects of this embodiment, a human enterovirus 3C protease comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 13; or at most 1, 2, 3, 4, 5, 6, 7, 8, 9, 10, 20, 30, 40, 50, or 100 non-contiguous amino acid deletions, additions, and/or substitutions relative to SEQ ID NO: 13. In still other aspects of this embodiment, a human enterovirus 3C protease comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 13; or at most 1, 2, 3, 4, 5, 6, 7, 8, 9, 10, 20, 30, 40, 50, or 100 contiguous amino acid deletions, additions, and/or substitutions relative to SEQ ID NO: 13.

In another aspect of this embodiment, a TEV protease is SEQ ID NO: 14. In another aspect of this embodiment, a TEV protease comprises amino acids 2038-2270 of SEQ IS NO: 14. In another aspect of this embodiment, a TEV protease comprises SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23. In yet another aspect of this embodiment, a TEV protease is a naturally occurring TEV protease variant, such as, e.g., a TEV protease isoform. In still another aspect of this embodiment, a TEV protease is a non-naturally occurring TEV protease variant, such as, e.g., a conservative TEV protease variant, a non-conservative TEV protease variant, a TEV protease chimeric, an active TEV protease fragment, or any combination thereof. In another aspect of this embodiment, a TEV protease, a naturally occurring TEV protease variant, or a non-naturally occurring TEV protease variant is obtained from a species of Potyvirus.

In other aspects of this embodiment, a TEV protease comprises a polypeptide having an amino acid identity of, e.g., at least 70%, at least 75%, at least 80%, at least 85%, at least 90% or at least 95% to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23; or at most 70%, at most 75%, at most 80%, at most 85%, at most 90% or at most 95% to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23. In yet other aspects of this embodiment, a TEV protease comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23; or at most 1, 2, 3, 4, 5, 6, 7, 8, 9, 10, 20, 30, 40, 50, or 100 non-contiguous amino acid deletions, additions, and/or substitutions relative to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23. In still other aspects of this embodiment, a TEV protease comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23; or at most 1, 2, 3, 4, 5, 6, 7, 8, 9, 10, 20, 30, 40, 50, or 100 contiguous amino acid deletions, additions, and/or substitutions relative to SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23.

In another aspect of this embodiment, a TVMV protease is SEQ ID NO: 24. In another aspect of this embodiment, a TEV protease comprises amino acids 2002-2236 of SEQ IS NO: 24. In yet another aspect of this embodiment, a TVMV protease is a naturally occurring TVMV protease variant, such as, e.g., a TVMV protease isoform. In still another aspect of this embodiment, a TVMV protease is a non-naturally occurring TVMV protease variant, such as, e.g., a conservative TVMV protease variant, a non-conservative TVMV protease variant, a TVMV protease chimeric, an active TVMV protease fragment, or any combination thereof. In another aspect of this embodiment, a TVMV protease, a naturally occurring TVMV protease variant, or a non-naturally occurring TVMV protease variant is obtained from a species of Potyvirus.

In other aspects of this embodiment, a TVMV protease comprises a polypeptide having an amino acid identity of, e.g., at least 70%, at least 75%, at least 80%, at least 85%, at least 90% or at least 95% to SEQ ID NO: 24 or amino acids 2002-2236 of SEQ IS NO: 24; or at most 70%, at most 75%, at most 80%, at most 85%, at most 90% or at most 95% to SEQ ID NO: 24 or amino acids 2002-2236 of SEQ IS NO: 24. In yet other aspects of this embodiment, a TVMV protease comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 24 or amino acids 2002-2236 of SEQ IS NO: 24; or at most 1, 2, 3, 4, 5, 6, 7, 8, 9, 10, 20, 30, 40, 50, or 100 non-contiguous amino acid deletions, additions, and/or substitutions relative to SEQ ID NO: 24 or amino acids 2002-2236 of SEQ IS NO: 24. In still other aspects of this embodiment, a TVMV protease comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 24 or amino acids 2002-2236 of SEQ IS NO: 24; or at most 1, 2, 3, 4, 5, 6, 7, 8, 9, 10, 20, 30, 40, 50, or 100 contiguous amino acid deletions, additions, and/or substitutions relative to SEQ ID NO: 24 or amino acids 2002-2236 of SEQ IS NO: 24.

In another aspect of this embodiment, a subtilisin protease is SEQ ID NO: 25. In another aspect of this embodiment, a subtilisin protease comprises amino acids 107-365 of SEQ IS NO: 25. In yet another aspect of this embodiment, a subtilisin protease is a naturally occurring subtilisin protease variant, such as, e.g., a subtilisin protease isoform. In still another aspect of this embodiment, a subtilisin protease is a non-naturally occurring subtilisin protease variant, such as, e.g., a conservative subtilisin protease variant, a non-conservative subtilisin protease variant, a subtilisin protease chimeric, an active subtilisin protease fragment, or any combination thereof. In another aspect of this embodiment, a subtilisin protease, a naturally occurring subtilisin protease variant, or a non-naturally occurring subtilisin protease variant is obtained from a species of Bacillus.

In other aspects of this embodiment, a subtilisin protease comprises a polypeptide having an amino acid identity of, e.g., at least 70%, at least 75%, at least 80%, at least 85%, at least 90% or at least 95% to SEQ ID NO: 25 or amino acids 107-365 of SEQ IS NO: 25; or at most 70%, at most 75%, at most 80%, at most 85%, at most 90% or at most 95% to SEQ ID NO: 25 or amino acids 107-365 of SEQ IS NO: 25. In yet other aspects of this embodiment, a subtilisin protease comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 25 or amino acids 107-365 of SEQ IS NO: 25; or at most 1, 2, 3, 4, 5, 6, 7, 8, 9, 10, 20, 30, 40, 50, or 100 non-contiguous amino acid deletions, additions, and/or substitutions relative to SEQ ID NO: 25 or amino acids 107-365 of SEQ IS NO: 25. In still other aspects of this embodiment, a subtilisin protease comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 25 or amino acids 107-365 of SEQ IS NO: 25; or at most 1, 2, 3, 4, 5, 6, 7, 8, 9, 10, 20, 30, 40, 50, or 100 contiguous amino acid deletions, additions, and/or substitutions relative to SEQ ID NO: 25 or amino acids 107-365 of SEQ IS NO: 25.

In another aspect of this embodiment, a Caspase 3 protease is SEQ ID NO: 26. In yet another aspect of this embodiment, a Caspase 3 protease is a naturally occurring Caspase 3 protease variant, such as, e.g., a Caspase 3 protease isoform. In still another aspect of this embodiment, a Caspase 3 protease is a non-naturally occurring Caspase 3 protease variant, such as, e.g., a conservative Caspase 3 protease variant, a non-conservative Caspase 3 protease variant, a Caspase 3 protease chimeric, an active Caspase 3 protease fragment, or any combination thereof. In another aspect of this embodiment, a Caspase 3 protease, a naturally occurring Caspase 3 protease variant, or a non-naturally occurring Caspase 3 protease variant is obtained from a species of mammal such as, e.g., a human, a cow, or a rodent.

In other aspects of this embodiment, a Caspase 3 protease comprises a polypeptide having an amino acid identity of, e.g., at least 70%, at least 75%, at least 80%, at least 85%, at least 90% or at least 95% to SEQ ID NO: 26; or at most 70%, at most 75%, at most 80%, at most 85%, at most 90% or at most 95% to SEQ ID NO: 26. In yet other aspects of this embodiment, a Caspase 3 protease comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to SEQ ID NO: 26; or at most 1, 2, 3, 4, 5, 6, 7, 8, 9, 10, 20, 30, 40, 50, or 100 non-contiguous amino acid deletions, additions, and/or substitutions relative to SEQ ID NO: 26. In still other aspects of this embodiment, a Caspase 3 protease comprises a polypeptide having, e.g., at least 1, 2, 3, 4, 5, 6, 7, 8, 9, 10, 20, 30, 40, 50, or 100 contiguous amino acid deletions, additions, and/or substitutions relative to SEQ ID NO: 26; or at most 1, 2, 3, 4, 5, 6, 7, 8, 9, 10, 20, 30, 40, 50, or 100 contiguous amino acid deletions, additions, and/or substitutions relative to SEQ ID NO: 26.

The methods disclosed in the present specification include, in part, a dual expression construct. A dual expression construct comprises two polynucleotide molecules, each including an open reading frame disclosed in the present specification operably-linked to an expression vector useful for expressing both polynucleotide molecules in a cell or cell-free extract. A wide variety of dual expression vectors can be employed for expressing a polynucleotide molecule disclosed in the present specification, including, without limitation, a viral dual expression vector; a prokaryotic dual expression vector; an eukaryotic dual expression vector, such as, e.g., a yeast dual expression vector, an insect dual expression vector and a mammalian dual expression vector; and a cell-free extract dual expression vector. It is further understood that dual expression vectors useful to practice aspects of these methods may include those which express the polynucleotide molecules under the control of a constitutive, tissue-specific, cell-specific or inducible promoter element, enhancer element or both. Non-limiting examples of dual expression vectors, along with well-established reagents and conditions for making and using an expression construct from such expression vectors are readily available from commercial vendors that include, without limitation, EMD Biosciences-Novagen, Madison, Wis. The selection, making and use of an appropriate dual expression vector are routine procedures well within the scope of one skilled in the art and from the teachings herein.

The dual expression constructs disclosed in the present specification can comprise an open reading frame encoding a protein including a di-chain loop region comprising an exogenous protease cleavage site and another open reading frame encoding a protease that can cleave the exogenous protease cleavage site located within the di-chain loop, thereby converting the single-chain protein into its di-chain form.

Thus, in an embodiment, a dual expression construct comprises an open reading frame encoding a protein comprising a di-chain loop region comprising an exogenous protease cleavage site as disclosed in the present specification and another open reading frame encoding a protease that can cleave the exogenous protease cleavage site located within the di-chain loop as disclosed in the present specification.

In an aspect of this embodiment, a dual expression construct can comprise one open reading frame encoding a Clostridial toxin including a di-chain loop region comprising a TEV protease cleavage site and another open reading frame encoding a TEV protease. In another aspect of this embodiment, a dual expression construct can comprise one open reading frame encoding a Clostridial toxin including a Clostridial toxin enzymatic domain, a Clostridial toxin translocation domain, a Clostridial toxin binding domain, and a di-chain loop region comprising a TEV protease cleavage site and another open reading frame encoding a TEV protease. In yet another aspect of this embodiment, a dual expression construct can comprise one open reading frame encoding a Clostridial toxin including a Clostridial toxin enzymatic domain, a Clostridial toxin translocation domain, a Clostridial toxin binding domain, a di-chain loop region, and a TEV protease cleavage site, wherein the TEV protease cleavage site is located within the di-chain loop region and another open reading frame encoding a TEV protease.

In an aspect of this embodiment, a dual expression construct comprises an open reading frame encoding a protein comprising a Clostridial toxin enzymatic domain, a Clostridial toxin translocation domain, a non-Clostridial toxin binding domain, and a di-chain loop region comprising an exogenous protease cleavage site and another open reading frame encoding a protease that can cleave the exogenous protease cleavage site located within the di-chain loop region. In another aspect of this embodiment, a dual expression construct can comprise one open reading frame encoding a protein comprising a Clostridial toxin enzymatic domain, a Clostridial toxin translocation domain, a non-Clostridial toxin binding domain, and a di-chain loop region comprising a TEV protease cleavage site and another open reading frame encoding a TEV protease. In yet another aspect of this embodiment, a dual expression construct can comprise one open reading frame encoding a protein comprising a Clostridial toxin enzymatic domain, a Clostridial toxin translocation domain, a non-Clostridial toxin binding domain, a di-chain loop region, and a TEV protease cleavage site, wherein the TEV protease cleavage site is located within the di-chain loop region and another open reading frame encoding a TEV protease.

In an aspect of this embodiment, a dual expression construct comprises an open reading frame encoding a protein comprising a Clostridial toxin enzymatic domain, a Clostridial toxin translocation domain, and an integrated protease cleavage site-binding domain. In another aspect of this embodiment, a dual expression construct can comprise one open reading frame encoding a protein comprising a Clostridial toxin enzymatic domain, a Clostridial toxin translocation domain, an integrated TEV protease cleavage site-binding domain and another open reading frame encoding a TEV protease. In yet another aspect of this embodiment, a dual expression construct can comprise one open reading frame encoding a protein comprising a Clostridial toxin enzymatic domain, a Clostridial toxin translocation domain, and an integrated TEV protease cleavage site-binding domain, wherein the TEV protease cleavage site is located within the di-chain loop region and another open reading frame encoding a TEV protease.

The location of one of the open reading frames contained within the dual expression construct can be in any order relative to the location of the other open reading frame, with the proviso that transcription from both open reading frames can still occur. When a dual expression construct is made, transcriptional initiation from the first promoter region typically transcribes both open reading frames, whereas, transcriptional initiation from the second promoter region typically transcribes only one of the open reading frames. Thus, depending on the location of the open reading frame relative to the first and second promoter regions, twice as many transcripts can be made from one of the open reading frames.

Thus, in one embodiment, the open reading frame encoding a protease is under the control of the first promoter region whereas the open reading frame encoding a protein comprising a di-chain loop region comprising an exogenous protease cleavage site is under the control of both the first promoter and second promoter regions. In an aspect of this embodiment, the open reading frame encoding a TEV protease is under the control of the first promoter region whereas the open reading frame encoding a Clostridial toxin comprising a TEV protease cleavage site located within the di-chain loop region is under the control of both the first promoter and second promoter regions. In another aspect of this embodiment, the open reading frame encoding a TEV protease is under the control of the first promoter region whereas the open reading frame encoding a protein comprising a Clostridial toxin enzymatic domain, a Clostridial toxin translocation domain, a non-Clostridial toxin binding domain, and a di-chain loop region comprising a TEV protease cleavage site is under the control of both the first promoter and second promoter regions. In yet another aspect of this embodiment, the open reading frame encoding a TEV protease is under the control of the first promoter region whereas the open reading frame encoding a protein comprising a Clostridial toxin enzymatic domain, a Clostridial toxin translocation domain, and an integrated TEV protease cleavage site-binding domain is under the control of both the first promoter and second promoter regions.

In another embodiment, the open reading frame encoding a protein comprising a di-chain loop region comprising an exogenous protease cleavage site is under the control of the first promoter region whereas the open reading frame encoding a protease is under the control of both the first promoter and second promoter regions. In an aspect of this embodiment, the open reading frame encoding a Clostridial toxin comprising a di-chain loop region comprising a TEV protease cleavage site is under the control of the first promoter region whereas the open reading frame encoding a TEV protease is under the control of both the first promoter and second promoter regions. In another aspect of this embodiment, the open reading frame encoding a protein comprising a Clostridial toxin enzymatic domain, a Clostridial toxin translocation domain, a non-Clostridial toxin binding domain, and a di-chain loop region comprising a TEV protease cleavage site is under the control of the first promoter region whereas the open reading frame encoding a TEV protease is under the control of both the first promoter and second promoter regions. In yet another aspect of this embodiment, the open reading frame encoding a protein comprising a Clostridial toxin enzymatic domain, a Clostridial toxin translocation domain, and an integrated TEV protease cleavage site-binding domain is under the control of the first promoter region whereas the open reading frame encoding a TEV protease is under the control of both the first promoter and second promoter regions.

The 5'-3' orientation of one of the open reading frames contained within the dual expression construct can be in any direction relative to the 5'-3' orientation of the other open reading frame, with the proviso that transcription from both open reading frames can still occur. In one embodiment, the 5'-3' orientation of one of the open reading frames is in the same direction as the 5'-3' orientation of the other open reading frame. In another embodiment, the 5'-3' orientation of one of the open reading frames is in the opposite direction as the 5'-3' orientation of the other open reading frame. In an aspect of this embodiment, the 5'-3' orientation of one of the open reading frames is convergent relative to the 5'-3' orientation of the other open reading frame. In another aspect of this embodiment, the 5'-3' orientation of one of the open reading frames is divergent relative to the 5'-3' orientation of the other open reading frame.

The methods disclosed in the present specification include, in part, a protein comprising a di-chain loop region comprising an exogenous protease cleavage site. As used herein, the term "di-chain loop region" means the amino acid sequence of a Clostridial toxin containing a protease cleavage site used to convert the single-chain form of a Clostridial toxin into the di-chain form. Non-limiting examples of a Clostridial toxin di-chain loop region, include, a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; a di-chain loop region of TeNT comprising amino acids 439-467 of SEQ ID NO: 8; a di-chain loop region of BaNT comprising amino acids 421-435 of SEQ ID NO: 9; and a di-chain loop region of BuNT comprising amino acids 412-426 of SEQ ID NO: 10 (Table 2).

TABLE 2

Di-chain Loop Region of Clostridial Toxins

| Toxin | Light Chain Region | Di-chain Loop Region Containing the Naturally-occurring Protease Cleavage Site | Heavy Chain Region |
|---|---|---|---|
| BoNT/A | NMNFTKLKNFTGLFEFYKLL | CVRGIITSKTKSLDKGYNK*----ALNDLC | IKVNNWDL |
| BoNT/B | KQAYEEISKEHLAVYKIQM | CKSVK*------------------APGIC | IDVDNEDL |
| BoNT/C1 | PALRKVNPENMLYLFTKF | CHKAIDGRSLYNK*------------TLDC | RELLVKNTDL |
| BoNT/D | PALQKLSSESVVDLFTKV | CLRLTKNSR*--------------DDSTC | IKVKNNRL |
| BoNT/E | PRIITPITGRGLVKKIIRF | CKNIVSVKGIR*--------------KSIC | IEINNGEL |
| BoNT/F | PKIIDSIPDKGLVEKIVKF | CKSVIPRKGTK*------------APPRLC | IRVNNSEL |
| BoNT/G | KEAYEEISLEHLVIYRIAM | CKPVMYKNTGK*--------------SEQC | IIVNNEDL |
| TeNT | TNAFRNVDGSGLVSKLIGL | CKKIIPPTNIRENLYNRTA*SLTDLGGELC | IKIKNEDL |

TABLE 2-continued

Di-chain Loop Region of Clostridial Toxins

| Toxin | Light Chain Region | Di-chain Loop Region Containing the Naturally-occurring Protease Cleavage Site | Heavy Chain Region |
|---|---|---|---|
| BaNT | SRIVGPIPDNGLVERFVGL | CKS-IVSKKGTK*-------------NSLC | IKVNNRDL |
| BuNT | PRIITPITGRGLVKKIIRF | CKN-IVSVKGIR*-------------KSIC | IEINNGEL |

The amino acid sequence displayed are as follows:
BoNT/A, residues 410-462 of SEQ ID No: 1; BONT/A, residues 410-462 of SEQ ID No. 1; BoNT/B, residues 418-454 of SEQ ID No: 2; BoNT/C1, residues 419-463 of SEQ ID No: 3; BoNT/D, residues 419-458 of SEQ ID No: 4; BoNT/E, residues 393-434 of SEQ ID No: 5; BoNT/F, residues 410-453 of SEQ ID No: 6; BoNT/G, residues 419-458 of SEQ ID No: 7; TeNT, residues 422-475 of SEQ ID No: 8; BaNT, residues 402-443 of SEQ ID No: 9; and BuNT, residues 393-434 of SEQ ID No: 10. An asterisks (*) indicates the peptide bond that is cleaved by a Clostridial toxin protease.

As mentioned above, Clostridial toxins are translated as a single-chain polypeptide of approximately 150 kDa that is subsequently cleaved by proteolytic scission within a disulfide loop by a naturally-occurring protease. This post-translational processing yields a di-chain molecule comprising an approximately 50 kDa light chain (LC) and an approximately 100 kDa heavy chain (HC) held together by a single disulphide bond and noncovalent interactions. While the identity of the protease is currently unknown, the di-chain loop protease cleavage site for many Clostridial toxins has been determined. In BoNTs, cleavage at K448-A449 converts the single polypeptide form of BoNT/A into the di-chain form; cleavage at K441-A442 converts the single polypeptide form of BoNT/B into the di-chain form; cleavage at K449-T450 converts the single polypeptide form of BoNT/C1 into the di-chain form; cleavage at R445-D446 converts the single polypeptide form of BoNT/D into the di-chain form; cleavage at R422-K423 converts the single polypeptide form of BoNT/E into the di-chain form; cleavage at K439-A440 converts the single polypeptide form of BoNT/F into the di-chain form; and cleavage at K446-S447 converts the single polypeptide form of BoNT/G into the di-chain form. Proteolytic cleavage of the single polypeptide form of TeNT at A457-5458 results in the di-chain form. Proteolytic cleavage of the single polypeptide form of BaNT at K431-N432results in the di-chain form. Proteolytic cleavage of the single polypeptide form of BuNT at R422-K423 results in the di-chain form. Such a di-chain loop protease cleavage site is operably-linked in-frame to a modified Clostridial toxin as a fusion protein. However, it should also be noted that additional cleavage sites within the di-chain loop also appear to be cleaved resulting in the generation of a small peptide fragment being lost. As a non-limiting example, cleavage of a BoNT/A single-chain polypeptide ultimately results in the loss of a ten amino acid fragment within the di-chain loop.

It is envisioned that any molecule that comprises a di-chain loop region can be modified to include an exogenous protease cleavage site useful for the disclosed methods. Examples of molecules that can have the di-chain loop modified to include an exogenous protease cleavage site useful for the disclosed methods include, e.g., Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; Stephan Donovan, Clostridial Toxin Derivatives and Methods For Treating Pain, U.S. Pat. No. 7,244,437; Stephan Donovan, Clostridial Toxin Derivatives and Methods For Treating Pain, U.S. Pat. No. 7,413,742; Stephan Donovan, Clostridial Toxin Derivatives and Methods For Treating Pain, U.S. Pat. No. 7,425,338; each of which is hereby incorporated by reference in its entirety.

A di-chain loop region is modified by the addition of an exogenous protease cleavage site. As used herein, the term "exogenous protease cleavage site" is synonymous with a "non-naturally occurring protease cleavage site" or "non-native protease cleavage site" and refers to a protease cleavage site that is not normally present in a di-chain loop region from a naturally occurring Clostridial toxin. It is envisioned that any and all exogenous protease cleavage sites that can be used to convert the single-chain polypeptide form of a Clostridial toxin into the di-chain form are useful to practice aspects of the present invention. Non-limiting examples of exogenous protease cleavage sites include, e.g., an enterokinase protease cleavage site, a human rhinovirus 3C protease cleavage site, a human enterovirus 3C protease cleavage site, a tobacco etch virus (TEV) protease cleavage site, a Tobacco Vein Mottling Virus (TVMV) protease cleavage site, a subtilisin protease cleavage site, or a Caspase 3 protease cleavage site.

It is envisioned that an exogenous protease cleavage site of any and all lengths can be useful in aspects of the present invention with the proviso that the exogenous protease cleavage site is capable of being cleaved by its respective protease. Thus, in aspects of this embodiment, an exogenous protease cleavage site can have a length of, e.g., at least 6, 7, 8, 9, 10, 15, 20, 25, 30, 40, 50, or 60 amino acids; or at most 6, 7, 8, 9, 10, 15, 20, 25, 30, 40, 50, or 60 amino acids.

In an embodiment, a di-chain loop region comprises an exogenous protease cleavage site. In aspects of this embodiment, a di-chain loop region is modified to comprise, e.g., an enterokinase protease cleavage site, a Tobacco Etch Virus protease cleavage site, a Tobacco Vein Mottling Virus protease cleavage site, a human rhinovirus 3C protease cleavage site, a human enterovirus 3C protease cleavage site, a subtilisin cleavage site, and a Caspase 3 cleavage site. In other aspects of this embodiment, an exogenous protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In other aspects of this embodiment, an exogenous protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

In an aspect of this embodiment, a di-chain loop region comprises a Tobacco Etch Virus protease cleavage site having the consensus sequence E-P5-P4-Y-P2-Q*-G (SEQ ID NO: 27) or E-P5-P4-Y-P2-Q*-S(SEQ ID NO: 28), where P2, P4 and P5 can be any amino acid. In other aspects of the embodiment, a di-chain loop region comprises a Tobacco Etch Virus protease cleavage site comprising SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37 or SEQ ID NO: 38. In still other aspects of this embodiment, a Tobacco Etch Virus protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In other aspects of this embodiment, a Tobacco Etch Virus protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

In another aspect of this embodiment, a di-chain loop region comprises a Tobacco Vein Mottling Virus protease cleavage site having the consensus sequence P6-P5-V-R-F-Q*-G (SEQ ID NO: 39) or P6-P5-V-R-F-Q*-S(SEQ ID NO: 40), where P5 and P6 can be any amino acid. In other aspects of the embodiment, a di-chain loop region comprises a Tobacco Vein Mottling Virus protease cleavage site comprising SEQ ID NO: 41, SEQ ID NO: 42, SEQ ID NO: 43, or SEQ ID NO: 44. In still other aspects of this embodiment, a Tobacco Vein Mottling Virus protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In other aspects of this embodiment, a Tobacco Vein Mottling Virus protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

In yet another aspect of this embodiment, a di-chain loop region comprises a human rhinovirus 3C protease cleavage site having the consensus sequence P5-P4-L-F-Q*-G-P (SEQ ID NO: 45), where P4 is G, A, V, L, I, M, S or T and P5 can any amino acid, with D or E preferred. In other aspects of the embodiment, a di-chain loop region comprises a human rhinovirus 3C protease cleavage site comprising SEQ ID NO: 46, SEQ ID NO: 47, SEQ ID NO: 48, SEQ ID NO: 49, SEQ ID NO: 50 or SEQ ID NO: 51. In still other aspects of this embodiment, a human rhinovirus 3C protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In other aspects of this embodiment, a human rhinovirus 3C protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

In still another aspect of this embodiment, a di-chain loop region comprises a subtilisin protease cleavage site having the consensus sequence P6-P5-P4-P3-H*-Y (SEQ ID NO: 52) or P6-P5-P4-P3-Y-H* (SEQ ID NO: 53), where P3, P4 and P5 and P6 can be any amino acid. In other aspects of the embodiment, a di-chain loop region comprises a subtilisin protease cleavage site comprising SEQ ID NO: 54, SEQ ID NO: 55, or SEQ ID NO: 56. In still other aspects of this embodiment, a subtilisin protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In other aspects of this embodiment, a subtilisin protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

In a further aspect of this embodiment, a di-chain loop region comprises a Caspase 3 protease cleavage site having the consensus sequence D-P3-P2-D*P1' (SEQ ID NO: 57), where P3 can be any amino acid, with E preferred, P2 can be any amino acid and P1' can any amino acid, with G or S preferred. In other aspects of the embodiment, a di-chain loop region comprises a Caspase 3 protease cleavage site comprising SEQ ID NO: 58, SEQ ID NO: 59, SEQ ID NO: 60, SEQ ID NO: 61, SEQ ID NO: 62, or SEQ ID NO: 63. In still other aspects of this embodiment, a Caspase 3 protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In other aspects of this embodiment, a Caspase 3 protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

In yet another aspect of this embodiment, a di-chain loop region comprises an enterokinase protease cleavage site having the consensus sequence DDDDK (SEQ ID NO: 64). In other aspects of this embodiment, an enterokinase protease cleavage site is located within the di-chain loop of, e.g., a BoNT/A, a BoNT/B, a BoNT/C1, a BoNT/D, a BoNT/E, a BoNT/F, a BoNT/G, a TeNT, a BaNT, or a BuNT. In yet other aspects of this embodiment, an enterokinase protease cleavage site is located within the di-chain loop of a protein disclosed in, e.g., U.S. Pat. No. 5,989,545; U.S. Pat. No. 6,461,617; U.S. Pat. No. 6,632,440; U.S. Pat. No. 6,843,998; U.S. Pat. No. 7,244,437; U.S. Pat. No. 7,413,742; and U.S. Pat. No. 7,425,338.

A di-chain loop region is modified to replace a naturally-occurring di-chain loop protease cleavage site for an exogenous protease cleavage site. In this modification, the naturally-occurring di-chain loop protease cleavage site is made inoperable and thus can not be cleaved by its protease. Only the exogenous protease cleavage site can be cleaved by its corresponding exogenous protease. In this type of modification, the exogenous protease site is operably-linked in-frame to a modified Clostridial toxin as a fusion protein and the site can be cleaved by its respective exogenous protease. Replacement of an endogenous di-chain loop protease cleavage site with an exogenous protease cleavage site can be a substitution of the sites where the exogenous site is engineered at the position approximating the cleavage site location of the endogenous site. Replacement of an endogenous di-chain loop protease cleavage site with an exogenous protease cleavage site can be the addition of an exogenous site where the exogenous site is engineered at a position different from the cleavage site location of the endogenous site, the endogenous site being engineered to be inoperable.

A naturally-occurring protease cleavage site contained within the di-chain loop region can be made inoperable by altering at least the two amino acids flanking the peptide bond cleaved by the naturally-occurring di-chain loop protease. More extensive alterations can be made, with the proviso that the two cysteine residues of the di-chain loop region remain intact and the region can still form a disulfide bridge. Non-limiting examples of an amino acid alteration include deletion of an amino acid or replacement of the original amino acid with a different amino acid. Thus, in one embodiment, a naturally-occurring protease cleavage site contained within the di-chain loop region is made inoperable by altering the two amino acids flanking the peptide bond cleaved by a naturally-occurring protease. In other aspects of this embodiment, a naturally-occurring protease cleavage site contained within the di-chain loop region is made inoperable by altering, e.g., at least three amino acids including the two amino acids flanking the peptide bond cleaved by a naturally-occurring protease; at least four amino acids including the two amino acids flanking the peptide bond cleaved by a naturally-occurring protease; at least five amino acids including the two amino acids flanking the peptide bond cleaved by a naturally-occurring protease; at least six amino acids including the two amino acids flanking the peptide bond cleaved by a naturally-occurring protease; at least seven amino acids including the two amino acids flanking the peptide bond cleaved by a naturally-occurring protease; at least eight amino acids including the two amino acids flanking the peptide bond cleaved by a naturally-occurring protease; at least nine amino acids including the two amino acids flanking the peptide bond cleaved by a naturally-occurring protease; at least ten amino acids including the two amino acids flanking the peptide bond cleaved by a naturally-occurring protease; at least 15 amino acids including the two amino acids flanking the peptide bond cleaved by a naturally-occurring protease; or at least 20 amino acids including the two amino acids flanking the peptide bond cleaved by a naturally-occurring protease.

In still other aspects of this embodiment, a naturally-occurring di-chain protease cleavage site contained within the di-chain loop region is made inoperable by altering, e.g., at most three amino acids including the two amino acids flanking the peptide bond cleaved by a naturally-occurring protease; at most four amino acids including the two amino acids flanking the peptide bond cleaved by a naturally-occurring protease; at most five amino acids including the two amino acids flanking the peptide bond cleaved by a naturally-occurring protease; at most six amino acids including the two amino acids flanking the peptide bond cleaved by a naturally-occurring protease; at most seven amino acids including the two amino acids flanking the peptide bond cleaved by a naturally-occurring protease; at most eight amino acids including the two amino acids flanking the peptide bond cleaved by a naturally-occurring protease; at most nine amino acids including the two amino acids flanking the peptide bond cleaved by a naturally-occurring protease; at most ten amino acids including the two amino acids flanking the peptide bond cleaved by a naturally-occurring protease; at most 15 amino acids including the two amino acids flanking the peptide bond cleaved by a naturally-occurring protease; or at most 20 amino acids including the two amino acids flanking the peptide bond cleaved by a naturally-occurring protease.

The methods disclosed in the present specification include, in part, a cell. It is envisioned that any and all cells can be used. Thus, aspects of this embodiment include, without limitation, prokaryotic cells including, without limitation, strains of aerobic, microaerophilic, capnophilic, facultative, anaerobic, gram-negative and gram-positive bacterial cells such as those derived from, e.g., *Escherichia coli*, *Bacillus subtilis*, *Bacillus licheniformis*, *Bacteroides fragilis*, Clostridia *perfringens*, Clostridia *difficile*, *Caulobacter crescentus*, *Lactococcus lactis*, *Methylobacterium extorquens*, *Neisseria meningirulls*, *Neisseria meningitidis*, *Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae, GENERAL TECHNIQUES OF CELL CULTURE (Cambridge University Press, 1997); CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, $4^{th}$ ed. 2000); ANIMAL CELL CULTURE: A PRACTICAL APPROACH (John R. W. Masters ed., Oxford University Press, $3^{rd}$ ed. 2000); MOLECULAR CLONING A LABORATORY MANUAL, supra, (2001); BASIC CELL CULTURE: A PRACTICAL APPROACH (John M. Davis, Oxford Press, $2^{nd}$ ed. 2002); and CURRENT PROTOCOLS IN MOLECULAR BIOLOGY, supra, (2004). These protocols are routine procedures within the scope of one skilled in the art and from the teaching herein.

The methods disclosed in the present specification include, in part, introducing into a cell an expression construct or dual expression construct as disclosed in the present specification. An expression construct or dual expression construct introduced into a cell can be transiently or stably maintained by that cell. Stably-maintained expression constructs or dual expression constructs may be extra-chromosomal and replicate autonomously, or they may be integrated into the chromosomal material of the cell and replicate non-autonomously. It is envisioned that any and all methods for introducing an expression construct or a dual expression construct disclosed in the present specification into a cell can be used. Methods useful for introducing an expression construct or a dual expression construct into a cell include, without limitation, chemical-mediated transfection such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated transfection, such as, e.g., biolistic particle delivery, microinjection, protoplast fusion and electroporation; and viral-mediated transfection, such as, e.g., retroviral-mediated transfection, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001). One skilled in the art understands that selection of a specific method to introduce an expression construct or a dual expression construct into a cell will depend, in part, on whether the cell will transiently contain the expression construct or dual expression construct, or whether the cell will stably contain the expression construct or dual expression construct. These protocols are routine procedures within the scope of one skilled in the art and from the teaching herein.

In an aspect of this embodiment, a chemical-mediated method, termed transfection, is used to introduce an expression construct or a dual expression construct disclosed in the present specification into a cell. In chemical-mediated methods of transfection the chemical reagent forms a complex with the expression construct or dual expression construct that facilitates its uptake into the cells. Such chemical reagents include, without limitation, calcium phosphate-mediated, see, e.g., Martin Jordan & Florian Wurm, *Transfection of adherent and suspended cells by calcium phosphate*, 33(2) Methods 136-143 (2004); diethyl-aminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., *Polyethylenimine strategies for plasmid delivery to brain-derived cells*, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physically-mediated method is used to introduce an expression construct or a dual expression construct disclosed in the present specification into a cell. Physical techniques include, without limitation, electroporation, biolistic and microinjection. Biolistics and microinjection techniques perforate the cell wall in order to introduce the expression construct or dual expression construct into the cell, see, e.g., Jeike E. Biewenga et al., *Plasmid-mediated gene transfer in neurons using the biolistics technique*, 71(1) J. Neurosci. Methods. 67-75 (1997); and John O'Brien & Sarah C. R. Lummis, *Biolistic and diolistic transfection: using the gene gun to deliver DNA and lipophilic dyes into mammalian cells*, 33(2) Methods 121-125 (2004). Electroporation, also termed electropermeabilization, uses brief, high-voltage, electrical pulses to create transient pores in the membrane through which the polynucleotide molecules enter and can be used effectively for stable and transient transfections of all cell types, see, e.g., M. Golzio et al., *In vitro and in vivo electric field-mediated permeabilization, gene transfer, and expression*, 33(2) Methods 126-135 (2004); and Oliver Gresch et al., *New non-viral method for gene transfer into primary cells*, 33(2) Methods 151-163 (2004).

In another aspect of this embodiment, a viral-mediated method, termed transduction, is used to introduce an expression construct or a dual expression construct disclosed in the present specification into a cell. In viral-mediated methods of transient transduction, the process by which viral particles infect and replicate in a host cell has been manipulated in order to use this mechanism to introduce the expression construct or dual expression construct into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, *Lentiviral and MLV based retroviral vectors for ex vivo and in vivo gene transfer*, 33(2) Methods 164-172 (2004); and Maurizio Federico, *From lentiviruses to lentivirus vectors*, 229 Methods Mol. Biol. 3-15 (2003); E. M. Poeschla, *Non-primate lentiviral vectors*, 5(5) Curr. Opin. Mol. Ther. 529-540 (2003); Karim Benihoud et al, *Adenovirus vectors for gene delivery*, 10(5) Curr. Opin. Biotechnol. 440-447 (1999); H. Bueler, *Adeno-associated viral vectors for gene transfer and gene therapy*, 380(6) Biol. Chem. 613-622 (1999); Chooi M. Lai et al., *Adenovirus and adeno-associated virus vectors*, 21(12) DNA Cell Biol. 895-913 (2002); Edward A. Burton et al., *Gene delivery using herpes simplex virus vectors*, 21(12) DNA Cell Biol. 915-936 (2002); Paola Grandi et al., *Targeting HSV amplicon vectors*, 33(2) Methods 179-186 (2004); Ilya Frolov et al., *Alphavirus-based expression vectors: strategies and applications*, 93(21) Proc. Natl. Acad. Sci. U.S.A. 11371-11377 (1996); Markus U. Ehrengruber, *Alphaviral gene transfer in neurobiology*, 59(1) Brain Res. Bull. 13-22 (2002); Thomas A. Kost & J. Patrick Condreay, *Recombinant baculoviruses as mammalian cell gene-delivery vectors*, 20(4) Trends Biotechnol. 173-180 (2002); and A. Huser & C. Hofmann, *Baculovirus vectors: novel mammalian cell gene-delivery vehicles and their applications*, 3(1) Am. J. Pharmacogenomics 53-63 (2003).

Adenoviruses, which are non-enveloped, double-stranded DNA viruses, are often selected for mammalian cell transduction because adenoviruses handle relatively large polynucleotide molecules of about 36 kb, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71(1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the nucleic acid molecule is carried by an episome in the cell nucleus, rather than being integrated into the host cell chromosome. Adenoviral vector systems and specific protocols for how to use such vectors are disclosed in, e.g., VIRAPOWER™ Adenoviral Expression System (Invitrogen, Inc., Carlsbad, Calif.) and VIRAPOWER™ Adenoviral Expression System Instruction Manual 25-0543 version A, Invitrogen, Inc., (Jul. 15, 2002); and ADEASY™ Adenoviral Vector System (Stratagene, Inc., La Jolla, Calif.) and ADEASY™ Adenoviral Vector System Instruction Manual 064004f, Stratagene, Inc.

Introduction of an expression construct or dual expression construct disclosed in the present specification into a cell can also be achieved using single-stranded RNA retroviruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., *Transient production of retroviral-and lentiviral-based vectors for the transduction of Mammalian cells*, 285 Methods Mol. Biol. 141-148 (2004); Armin Blesch, *Lentiviral and MLV based retroviral vectors for ex vivo and in vivo gene transfer*, 33(2) Methods 164-172 (2004); Félix Recillas-Targa, *Gene transfer and expression in mammalian cell lines and transgenic animals*, 267 Methods Mol. Biol. 417-433 (2004); and Roland Wolkowicz et al., *Lentiviral vectors for the delivery of DNA into mammalian cells*, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persistent expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., *In vivo gene delivery and stable transduction of nondividing cells by a lentiviral vector*, 272(5259) Science 263-267 (1996). The Oncoretroviruses-derived vector systems, such as, e.g., Moloney murine leukemia virus (MoMLV), are widely used and infect many different nondividing cells. Lentiviruses can also infect many different cell types, including dividing and non-dividing cells and possess complex envelope proteins, which allows for highly specific cellular targeting.

Retroviral vectors and specific protocols for how to use such vectors are disclosed in, e.g., Manfred Gossen & Hermann Bujard, Tight control of gene expression in eukaryotic cells by tetracycline-responsive promoters, U.S. Pat. No. 5,464,758, Hermann Bujard & Manfred Gossen, Methods for regulating gene expression, U.S. Pat. No. 5,814,618, David S. Hogness, Polynucleotides encoding insect steroid hormone receptor polypeptides and cells transformed with same, U.S. Pat. No. 5,514,578, and David S. Hogness, Polynucleotide encoding insect ecdysone receptor, U.S. Pat. No. 6,245,531; Elisabetta Vegeto et al., Progesterone receptor having C. terminal hormone binding domain truncations, U.S. Pat. No. 5,364,791, Elisabetta Vegeto et al., Mutated steroid hormone receptors, methods for their use and molecular switch for gene therapy, U.S. Pat. No. 5,874,534, and Elisabetta Vegeto et al., Mutated steroid hormone receptors, methods for their use and molecular switch for gene therapy, U.S. Pat. No. 5,935,934. Furthermore, such viral delivery systems can be prepared by standard methods and are commercially available, see, e.g., BD™ Tet-Off and Tet-On Gene Expression Systems (BD Biosciences-Clontech, Palo Alto, Calif.) and BD™ Tet-Off and Tet-On Gene Expression Systems User Manual, PT3001-1, BD Biosciences Clontech, (Mar. 14, 2003), GENESWITCH™ System (Invitrogen, Inc., Carlsbad, Calif.) and GENESWITCH™ System A Mifepristone-Regulated Expression System for Mammalian Cells version D, 25-0313, Invitrogen, Inc., (Nov. 4, 2002); VIRAPOWER™ Lentiviral Expression System (Invitrogen, Inc., Carlsbad, Calif.) and VIRAPOWER™ Lentiviral Expression System Instruction Manual 25-0501 version E, Invitrogen, Inc., (Dec. 8, 2003); and COMPLETE CONTROL® Retroviral Inducible Mammalian Expression System (Stratagene, La Jolla, Calif.) and COMPLETE CONTROL® Retroviral Inducible Mammalian Expression System Instruction Manual, 064005e.

The methods disclosed in the present specification include, in part, expressing an expression construct or dual expression construct disclosed in the present specification. It is envisioned that any of a variety of expression systems may be useful for expressing an expression construct or a dual expression construct disclosed in the present specification, including, without limitation, cell-based systems, and cell-free expression systems. Cell-based systems include, without limitation, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts and generally are equivalent to the method disclosed herein. Expression of an expression construct or dual expression construct using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins*, 80(9) CURRENT SCIENCE 1121-1128, (2001). These protocols are routine procedures well within the scope of one skilled in the art and from the teaching herein.

A variety of cell-based expression procedures are useful for expressing an expression construct or a dual expression construct disclosed in the present specification. Examples included, without limitation, viral expression systems, prokaryotic expression systems, yeast expression systems, baculoviral expression systems, insect expression systems and mammalian expression systems. Viral expression systems include, without limitation, the VI RAPOWER™ Lentiviral (Invitrogen, Inc., Carlsbad, Calif.), the Adenoviral Expression Systems (Invitrogen, Inc., Carlsbad, Calif.), the ADEASY™ XL Adenoviral Vector System (Stratagene, La Jolla, Calif.) and the VIRAPORT® Retroviral Gene Expression System (Stratagene, La Jolla, Calif.). Non-limiting examples of prokaryotic expression systems include the CHAMPION™ pET Expression System (EMD Biosciences-Novagen, Madison, Wis.), the TRIEX™ Bacterial Expression System (EMD Biosciences-Novagen, Madison, Wis.), the QIAEXPRESS® Expression System (QIAGEN, Inc.), and the AFFINITY® Protein Expression and Purification System (Stratagene, La Jolla, Calif.). Yeast expression systems include, without limitation, the EASYSELECT™ *Pichia* Expression Kit (Invitrogen, Inc., Carlsbad, Calif.), the YES-ECHO™ Expression Vector Kits (Invitrogen, Inc., Carlsbad, Calif.) and the SPECTRA™ *S. pombe* Expression System (Invitrogen, Inc., Carlsbad, Calif.). Non-limiting examples of baculoviral expression systems include the BACULODIRECT™ (Invitrogen, Inc., Carlsbad, Calif.), the BAC-TO-BAC® (Invitrogen, Inc., Carlsbad, Calif.), and the BD BACULOGOLD™ (BD Biosciences-Pharmingen, San Diego, Calif.). Insect expression systems include, without limitation, the *Drosophila* Expression System (DES®) (Invitrogen, Inc., Carlsbad, Calif.), INSECT-SELECT™ System (Invitrogen, Inc., Carlsbad, Calif.) and INSECTDIRECT™ System (EMD Biosciences-Novagen, Madison, Ws.). Non-limiting examples of mammalian expression systems include the T-REXT™ (Tetracycline-Regulated Expression) System (Invitrogen, Inc., Carlsbad, Calif.), the FLP-IN™ T-REX™ System (Invitrogen, Inc., Carlsbad, Calif.), the pcDNA™ system (Invitrogen, Inc., Carlsbad, Calif.), the pSecTag2 system (Invitrogen, Inc., Carlsbad, Calif.), the EXCHANGER® System, INTERPLAY™ Mammalian TAP System (Stratagene, La Jolla, Calif.), COMPLETE CONTROL® Inducible Mammalian Expression System (Stratagene, La Jolla, Calif.) and LAC-SWITCH® II Inducible Mammalian Expression System (Stratagene, La Jolla, Calif.).

Another procedure of expressing an expression construct or a dual expression construct disclosed in the present specification employs a cell-free expression system such as, without limitation, prokaryotic extracts and eukaryotic extracts. Non-limiting examples of prokaryotic cell extracts include the RTS 100 *E. coli* HY Kit (Roche Applied Science, Indianapolis, Ind.), the ACTIVEPRO™ In Vitro Translation Kit (Ambion, Inc., Austin, Tex.), the ECOPRO™ System (EMD Biosciences-Novagen, Madison, Wis.) and the Expressway™ Plus Expression System (Invitrogen, Inc., Carlsbad, Calif.). Eukaryotic cell extract include, without limitation, the RTS 100 Wheat Germ CECF Kit (Roche Applied Science, Indianapolis, Ind.), the TNT® Coupled Wheat Germ Extract Systems (Promega Corp., Madison, Wis.), the Wheat Germ IVT™ Kit (Ambion, Inc., Austin, Tex.), the Retic Lysate IVT™ Kit (Ambion, Inc., Austin, Tex.), the PROTEINSCRIPT® II System (Ambion, Inc., Austin, Tex.) and the TNT® Coupled Reticulocyte Lysate Systems (Promega Corp., Madison, Wis.).

The methods disclosed in the present specification include, in part, growing a cell at a first temperature for a certain period of time and then growing the cell at a second temperature for a certain period of time. The first and second temperatures and the periods of time the cells are grown at the first and second temperatures are determined based on the desired amount of protein to be expressed by the cell, and the desired cleavage efficiency at the exogenous protease cleavage site located within the di-chain loop region to convert the single-chain protein into its di-chain form.

In one embodiment, a cell is grown at a first temperature for a certain period of time in order to achieve maximum cell density. In aspects of this embodiment, a cell is grown at about 37° C. for about 0.5 hours, about 1.0 hour, about 1.5 hours, about 2.0 hours, about 3.0 hours, about 3.5 hours, about 4.0 hours, about 5.0 hours, about 6.0 hours, about 7.0 hours, about 8.0 hours, about 9.0 hours or about 10 hours. In other aspects of this embodiment, a cell is grown at about 42° C. for about 0.5 hours, about 1.0 hour, about 1.5 hours, about 2.0 hours, about 3.0 hours, about 3.5 hours, about 4.0 hours, about 5.0 hours. In aspects of this embodiment, a cell is grown at about 30° C. for about 0.5 hours, about 1.0 hour, about 1.5 hours, about 2.0 hours, about 3.0 hours, about 3.5 hours, about 4.0 hours, or about 5.0 hours. In yet other aspects, of this embodiment, a cell is grown at about 12° C. for about 2 hours to about 8 hours, at about 16° C. for about 2 hours to about 8 hours, at about 20° C. for about 2 hours to about 8 hours, or at about 24° C. for about 2 hours to about 8 hours. In still other aspects, of this embodiment, a cell is grown at about 12° C. to about 16° C. for about 2 hours to about 8 hours, or at about 20° C. to about 24° C. for about 2 hours to about 8 hours.

In another embodiment, a cell is grown at a second temperature for a certain period of time in order to achieve maximum induction of protein expression. In aspects of this embodiment, a cell is grown at about 37° C. for about 1.5 hours, about 2.5 hours, about 3.5 hours, about 4.5 hours, about 5.5 hours, about 6.5 hours, about 7.5 hours, about 8.5 hours, about 9.5 hours, about 10.5 hours, about 11.5 hours, about 12.5 hours, about 13.5 hours, about 14.5 hours, about 15.5 hours, about 16.5 hours, or about 24.5 hours. In other aspects of this embodiment, a cell is grown at about 30° C. for about 1.5 hours, about 2.5 hours, about 3.5 hours, about 4.5 hours, about 5.5 hours, about 6.5 hours, about 7.5 hours, about 8.5 hours, about 9.5 hours, about 10.5 hours, about 11.5 hours, about 12.5 hours, about 13.5 hours, about 14.5 hours, about 15.5 hours, about 16.5 hours, or about 24.5 hours. In yet other aspects of this embodiment, a cell is grown at about 25° C. for about 1.5 hours, about 2.5 hours, about 3.5 hours, about 4.5 hours, about 5.5 hours, about 6.5 hours, about 7.5 hours, about 8.5 hours, about 9.5 hours, about 10.5 hours, about 11.5 hours, about 12.5 hours, about 13.5 hours, about 14.5 hours, about 15.5 hours, about 16.5 hours, or about 24.5 hours. In still other aspects of this embodiment, a cell is grown at about 22° C. for about 1.5 hours, about 2.5 hours, about 3.5 hours, about 4.5 hours, about 5.5 hours, about 6.5 hours, about 7.5 hours, about 8.5 hours, about 9.5 hours, about 10.5 hours, about 11.5 hours, about 12.5 hours, about 13.5 hours, about 14.5 hours, about 15.5 hours, about 16.5 hours, or about 24.5 hours. In further aspects of this embodiment, a cell is grown at about 16° C. for about 1.5 hours, about 2.5 hours, about 3.5 hours, about 4.5 hours, about 5.5 hours, about 6.5 hours, about 7.5 hours, about 8.5 hours, about 9.5 hours, about 10.5 hours, about 11.5 hours, about 12.5 hours, about 13.5 hours, about 14.5 hours, about 15.5 hours, about 16.5 hours, or about 24.5 hours. In yet further aspects of this embodiment, a cell is grown at about 12° C. for about 1.5 hours, about 2.5 hours, about 3.5 hours, about 4.5 hours, about 5.5 hours, about 6.5 hours, about 7.5 hours, about 8.5 hours, about 9.5 hours, about 10.5 hours, about 11.5 hours, about 12.5 hours, about 13.5 hours, about 14.5 hours, about 15.5 hours, about 16.5 hours, or about 24.5 hours.

Aspects of the present invention can also be described as follows:

1. An intracellular method of converting a single-chain protein into its di-chain form, the method comprising the steps of:
    a) growing a cell comprising a dual expression construct at a first temperature for a certain period of time in order to achieve maximal cell density, the dual expression construct comprising;
        i) an open reading frame encoding a single-chain protein comprising a di-chain loop region comprising an exogenous protease cleavage site; and
        ii) an open reading frame encoding a protease; wherein the protease can cleave the exogenous protease cleavage site located within the di-chain loop;
    b) growing the cell at a second temperature for a certain period of time in order to achieve maximal induction of protein expression from the open reading frame encoding the single-chain protein, wherein growth at step (b) induces expression of the single-chain protein and the protease from the dual expression construct; and
wherein the produced protease cleaves the single-chain protein at the exogenous protease cleavage site located within the di-chain loop region, thereby converting the single-chain protein into its di-chain form.

2. An intracellular method of converting a single-chain Clostridial toxin into its di-chain form, the method comprising the steps of:
    a) growing a cell comprising a dual expression construct at 37° C. for about 3.5 hours, the dual expression construct comprising;
        i) an open reading frame encoding a single-chain Clostridial toxin, the single-chain Clostridial toxin comprising an enzymatic domain, a translocation domain, a binding domain, and a di-chain loop region comprising an exogenous protease cleavage site; and ii) an open reading frame encoding a protease; wherein the protease can cleave the exogenous protease cleavage site located within the di-chain loop;

b) growing the cell at 22° C. for about 16 to about 18 hours, wherein growth at step (b) induces expression of the single-chain Clostridial toxin and the protease from the dual expression construct; and wherein the produced protease cleaves the single-chain Clostridial toxin at the exogenous protease cleavage site located within the di-chain loop region, thereby converting the single-chain Clostridial toxin into its di-chain form.

3. The intracellular method according to 2, wherein the single-chain Clostridial toxin comprises a linear amino-to-carboxyl single polypeptide order of 1) the Clostridial toxin enzymatic domain, the di-chain loop region comprising an exogenous protease cleavage site, the Clostridial toxin translocation domain and the Clostridial toxin binding domain; 2) the Clostridial toxin enzymatic domain, the di-chain loop region comprising an exogenous protease cleavage site, the Clostridial toxin binding domain and the Clostridial toxin translocation domain; 3) the Clostridial toxin binding domain, the Clostridial toxin translocation domain, the di-chain loop region comprising an exogenous protease cleavage site and the Clostridial toxin enzymatic domain; 4) the Clostridial toxin binding domain, the Clostridial toxin enzymatic domain, the di-chain loop region comprising an exogenous protease cleavage site and the Clostridial toxin translocation domain; 5) the Clostridial toxin translocation domain, the di-chain loop region comprising an exogenous protease cleavage site, the Clostridial toxin enzymatic domain and the Clostridial toxin binding domain; or 6) the Clostridial toxin translocation domain, the di-chain loop region comprising an exogenous protease cleavage site, the Clostridial binding domain and the Clostridial toxin enzymatic domain.

4. The intracellular method according to 2, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

5. The intracellular method according to 2, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

6. The intracellular method according to 2, wherein the Clostridial toxin binding domain is a BoNT/A binding domain, a BoNT/B binding domain, a BoNT/C1 binding domain, a BoNT/D binding domain, a BoNT/E binding domain, a BoNT/F binding domain, a BoNT/G binding domain, a TeNT binding domain, a BaNT binding domain, or a BuNT binding domain.

7. The intracellular method according to 2, wherein the exogenous protease cleavage site is an enterokinase protease cleavage site, a human rhinovirus 3C protease cleavage site, a human enterovirus 3C protease cleavage site, a tobacco etch virus (TEV) protease cleavage site, a Tobacco Vein Mottling Virus (TVMV) protease cleavage site, a subtilisin protease cleavage site, or a Caspase 3 protease cleavage site.

8. The intracellular method according to 2, wherein the protease is an enterokinase protease, a human rhinovirus 3C protease, a human enterovirus 3C protease, a tobacco etch virus (TEV) protease, a Tobacco Vein Mottling Virus (TVMV) protease, a subtilisin protease, or a Caspase 3 protease.

9. An intracellular method of converting a single-chain protein into its di-chain form, the method comprising the steps of:

a) growing a cell comprising a dual expression construct at 37° C. for about 8 hours, the dual expression construct comprising;

i) an open reading frame encoding a single-chain protein, the single-chain protein comprising an enzymatic domain, a translocation domain, an integrated TEV protease cleavage site-opioid binding domain; and ii) an open reading frame encoding a TEV protease;

b) growing the cell at about 12 to about 16° C. for about 16 to about 18 hours, wherein growth at step (b) induces expression of the single-chain protein and the TEV protease from the dual expression construct; and wherein the produced TEV protease cleaves the single-chain protein at the TEV protease cleavage site located within the integrated TEV cleavage site opioid binding domain, thereby converting the single-chain protein into its di-chain form.

10. The intracellular method according to 9, wherein the protein comprises a linear amino-to-carboxyl single polypeptide order of 1) the Clostridial toxin enzymatic domain, the Clostridial toxin translocation domain, and the integrated TEV protease cleavage site-opioid binding domain, 2) the Clostridial toxin enzymatic domain, the integrated TEV protease cleavage site-opioid binding domain, and the Clostridial toxin translocation domain, 3) the integrated TEV protease cleavage site-opioid binding domain, the Clostridial toxin translocation domain, and the Clostridial toxin enzymatic domain, 4) the integrated TEV protease cleavage site-opioid binding domain, the Clostridial toxin enzymatic domain, and the Clostridial toxin translocation domain, 5) the Clostridial toxin translocation domain, the integrated TEV protease cleavage site-opioid binding domain, and the Clostridial toxin enzymatic domain, or 6) the Clostridial toxin translocation domain, the Clostridial toxin enzymatic domain, and the integrated TEV protease cleavage site-opioid binding domain.

11. The intracellular method according to 9, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

12. The intracellular method according to 9, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

13. The intracellular method according to 9, wherein the integrated TEV protease cleavage site-opiod binding domain is an integrated TEV protease cleavage site-nociceptin binding domain, an integrated TEV protease cleavage site-dynorphin binding domain, an integrated TEV protease cleavage site-enkephalin binding domain, an integrated TEV protease cleavage site-BAM22 binding domain, an integrated TEV protease cleavage site-endomorphin binding domain, an integrated TEV protease cleavage site-endorphin binding domain, an integrated TEV protease cleavage site-hemorphin binding domain, or an integrated TEV protease cleavage site-rimorphin binding domain.

14. An intracellular method of converting a single-chain protein into its di-chain form, the method comprising the steps of:
 a) growing a cell comprising a dual expression construct at 37° C. for about 8 hours, the dual expression construct comprising;
  i) an open reading frame encoding a single-chain protein, the single-chain protein comprising an enzymatic domain, a translocation domain, a non-Clostridial toxin binding domain and a di-chain loop region comprising a TEV protease cleavage site; and
  ii) an open reading frame encoding a TEV protease;
 b) growing the cell at about 12 to about 16° C. for about 16 to about 18 hours, wherein growth at step (b) induces expression of the single-chain protein and the TEV protease from the dual expression construct; and
 wherein the produced TEV protease cleaves the single-chain protein at the TEV protease cleavage site located within the di-chain loop region, thereby converting the single-chain protein into its di-chain form.

15. The intracellular method according to 14, wherein the single-chain Clostridial toxin comprises a linear amino-to-carboxyl single polypeptide order of 1) the Clostridial toxin enzymatic domain, the di-chain loop region comprising a TEV protease cleavage site, the Clostridial toxin translocation domain and the non-Clostridial toxin binding domain; 2) the Clostridial toxin enzymatic domain, the di-chain loop region comprising a TEV protease cleavage site, the non-Clostridial toxin binding domain and the Clostridial toxin translocation domain; 3) the non-Clostridial toxin binding domain, the Clostridial toxin translocation domain, the di-chain loop region comprising a TEV protease cleavage site and the Clostridial toxin enzymatic domain; 4) the non-Clostridial toxin binding domain, the Clostridial toxin enzymatic domain, the di-chain loop region comprising a TEV protease cleavage site and the Clostridial toxin translocation domain; 5) the Clostridial toxin translocation domain, the di-chain loop region comprising a TEV protease cleavage site, the Clostridial toxin enzymatic domain and the non-Clostridial toxin binding domain; or 6) the Clostridial toxin translocation domain, the di-chain loop region comprising an exogenous protease cleavage site, the non-Clostridial binding domain and the Clostridial toxin enzymatic domain.

16. The intracellular method according to 14, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

17. The intracellular method according to 14, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

18. The intracellular method according to 14, wherein the non-Clostridial toxin binding domain is an opioid peptide binding domain, a melanocortin peptide binding domain, a galanin peptide binding domain, a granin peptide binding domain, a tachykinin peptide binding domain, a neuropeptide Y related peptide binding domain, a neurohormone peptide binding domain, a cytokine peptide binding domain, a kinin peptide binding domain, a fibroblast growth factor peptide binding domain, a neurotrophin peptide binding domain, a tumor necrosis factor peptide binding domain, a glial derived neurotrophic factor peptide binding domain, a transformation growth factor 6 peptide binding domain, a bone morphogenetic protein peptide binding domain, a growth and differentiation factor peptide binding domain, an activin peptide binding domain, a vascular endothelial growth factor peptide binding domain, an insulin growth factor peptide binding domain, an epidermal growth factor peptide binding domain, a glucagon like hormone peptide binding domain, a pituitary adenylate cyclase activating peptide binding domain, a growth hormone-releasing hormone peptide binding domain, a vasoactive intestinal peptide binding domain, a gastric inhibitory polypeptide peptide binding domain, a calcitonin-related peptides visceral gut peptide binding domain, or a protease activated receptor peptide binding domain.

EXAMPLES

Example 1

TEV Protease Variants

The following example illustrates how to make and use TEV protease variants that have increased stability and/or solubility.

A. Construction of pET29/TEV Expression Constructs.

In order to produce a TEV protease recombinantly, an open reading frame encoding the desired TEV protease was synthesized using standard procedures (BlueHeron Biotechnology, Bothell, Wash.).

Complementary oligonucleotides of 20 to 50 bases in length, spanning the entire open reading frame, were synthesized using standard phosphoramidite synthesis. These oligonucleotides were hybridized into double stranded duplexes that were sequentially ligated together to assemble the full-length polynucleotide molecule. This polynucleotide molecule was cloned using standard molecular biology methods into a pUCBHB1 carrier vector at the SmaI site to generate pUCBHB1/TEV plasmids. The synthesized polynucleotide molecule was verified by sequencing using BIG DYE TERMINATOR™ Chemistry 3.1 (Applied Biosystems, Foster City, Calif.) and an ABI 3100 sequencer (Applied Biosystems, Foster City, Calif.).

The open reading frame encoding the TEV variants were codon-optimized for *E. coli* expression and all encode an approximately 250 amino acid proteolytic fragment of approximately 27.5 kDa, corresponding to residues 2038-2279 of the full-length TEV polyprotein fused to either an N- or C-terminal poly-histidine affinity purification tag. Recombinant expression of wild-type TEV protease results in a protein that has a propensity to cleave itself at Serine 219 to generate a truncated protease with greatly diminished proteolytic activity. Thus, to largely eliminate autoproteolysis and subsequent generation of this truncated product, TEV variants were synthesized where Serine 219 was changed to either Asparagine (S219N) or Valine (S219V). In addition, it is well documented that although recombinant wild-type TEV protease is expressed at very high levels in *E. coli*, it is almost entirely insoluble (Kapust et al., 2001). Thus, to improve solubility of the expressed TEV, several amino acid variants were made and tested to determine whether the changes resulted in increased protein solubility. The TEV variants synthesized are shown in Table 3. Variant 1 represented a codon-optimized TEV construct engineered with a C-terminal His-tag and the S219N mutation. Variant 11 was a construct with native DNA sequence of TEV protease engineered with an N-terminal tag and the S219N mutation.

TABLE 3

TEV Protease Variants

| Variant | Autoproteolysis Elimination Change | Solubility Enhancing Changes | Affinity Tag | DNA SEQ ID NO: | Protein SEQ ID NO: |
|---|---|---|---|---|---|
| 1 | S219N | — | C-term | 65 | 66 |
| 2 | S219N | L56V, S135G | N-term | 67 | 68 |
| 3 | S219N | T17S, N68D, I77V | N-term | 69 | 70 |
| 4 | S219N | N44V, L56V, S135G | N-term | 71 | 72 |
| 5 | S219N | L56V, N68D, S135G | N-term | 73 | 74 |
| 6 | S219N | T17S, L56V, N68D, I77V | N-term | 75 | 76 |
| 7 | S219N | T17S, N68D, I77V, S135G | N-term | 77 | 78 |
| 8 | S219N | T17S, N44V, L56V, N68D, I77V, S135G | C-term | 79 | 80 |
| 9 | S219V | T17S, N44V, L56V, N68D, I77V, S135G | N-term | 81 | 82 |
| 10 | S219N | T17S, N44V, L56V, N68D, I77V, S135G | N-term | 83 | 84 |
| 11 | S219N | — | N-term | 85 | 86 |

To construct pET29/TEV variant expression constructs, a pUCBHB1/TEV construct was digested with restriction endonucleases that 1) excise the insert comprising the open reading frame encoding the TEV; and 2) enable this insert to be operably-linked to a pET29 vector (EMD Biosciences-Novagen, Madison, Wis.). Using a T4 DNA ligase procedure this insert was directionally ligated into a pET29 vector digested with the same restriction endonucleases in the multiple cloning site. The ligation mixture was transformed into electro-competent *E. coli* BL21(DE3) Acella cells (Edge BioSystems, Gaithersburg, Md.) by electroporation, plated on 1.5% Luria-Bertani agar plates (pH 7.0) containing 50 μg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by restriction endonuclease digest mapping and sequencing both DNA strands to confirm the presence and integrity of the TEV gene insert. This cloning strategy yielded a pET29 expression construct comprising the polynucleotide molecule encoding TEV variants operably-linked to either a carboxyl terminal or amino-terminal polyhistidine affinity purification peptide.

B. Analysis of TEV Expression Under Different Induction Conditions.

To determine the best growth and protein induction conditions to use, pET29/TEV variants 9 and 10 (Table 3) were grown and induced in an IPTG induced media and an auto-inducing media. In addition, the length of induction was examined.

To induce expression with IPTG, cells harboring the TEV expression construct were first grown overnight to produce a starter culture. Fresh LB media was inoculated at 1:1000 with the overnight culture and allowed to grow, with shaking, at 37° C. until $OD_{600}$ reached 0.7, at which time IPTG was added to a final concentration of 0.6 mM. Cells were harvested 4 hrs. following induction and total cell lysates evaluated to detect target expression.

To express constructs under auto-induction conditions, 3.0 mL of PA-0.5G media containing 50 μg/mL kanamycin was inoculated with a single colony of BL21(DE3) cells harboring the appropriate expression construct and grown at 37° C. with shaking overnight. 1.0 μL of this starter culture was used to inoculate 1.0 mL of ZYP-5052 auto-induction media containing 50 μg/mL kanamycin. Cells were grown at 37° C. with shaking and aliquots removed at 5, 8, 12, 20, and 28 hours.

To determine total TEV protease expression, 40 μL of the induced cell culture from each time-point was mixed with an equal volume of 2×Laemmli Sample Buffer and incubated at 95° C. for 10 minutes. 2 μL of 1 unit/μL Benzonase in 1 M $MgSO_4$ was added to this mixture and incubated at 95° C. for 5 minutes. A 15 μL aliquot was loaded and separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. The gel was washed and fixed in Fix Solution comprising 10% methanol, 7% acetic acid for 30 minutes. After fixing, the Fix Solution was removed and the gel incubated with SYPRO Ruby Protein Gel Stain at room temperature for 3 hours. The gel was then destained in Destain Solution comprising 10% methanol, 7% acetic acid at room temperature for 3 hours. The image was visualized with a Typhoon 9410 Variable Mode Imager and Imager Analysis software (GE Healthcare, Amersham Biosciences, Piscataway, N.J.).

To determine soluble TEV protease expression, 1.0 mL of the induced cell culture was lysed by adding 100 μL of a Cell Lysis Solution comprising 1×FASTBREAK™ Cell Lysis reagent (Promega Corp., Madison, Wis.), 500 mM NaCl, 250 units/mL benzonase nuclease (EMD Biosciences-Novagen, Madison, Wis.), and 1×Protease Inhibitor Cocktail III (EMD Biosciences-Calbiochem, Gibbstown, N.J.) and incubated at room temperature for 25 minutes with constant vortexing. The lysate was centrifuged at 4300 rpm for 15 minutes to pellet debris. 800 μL of the supernatant was transferred to a clean tube, to which 30 μL of Magne-His magnetic beads were added and the mixture incubated for 5 minutes with constant rotation. After incubation, the magnetic beads were sequestered on a magnetic stand, the solution was removed, and the beads washed three times with 150 μL wash buffer comprising 500 mM NaCl. The protein was eluted with 80 μL of elution buffer, an equal volume of 2×Laemmli Sample Buffer was added, and the mixture incubated at 95° C. for 10 minutes. A 15 μL aliquot was loaded and separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions.

Results of the induction experiments indicated that auto-induction conditions resulted in 5-10-fold more expressed TEV protease relative to IPTG-induction. Comparison of total and soluble TEV protease expression in the auto-induction media revealed that although longer induction times resulted in more total protein, the amount of recoverable soluble TEV protease decreased. In fact, about 8 hours of expression at 37° C. yielded the largest amount of soluble protein. Lastly, although both the TEV S219N and TEV S219V variants exhibited significantly less autoproteolysis, the TEV S219V variant showed more truncated product at prolonged induction times suggesting that the TEV S219V variant was more prone to autoproteolysis.

Once the growth and induction conditions were optimized using pET29/TEV variants 9 and 10, expression of all eleven pET29/TEV variants was examined in parallel under these conditions. The results indicated that the order of increasing yield of soluble TEV protease, from greatest to least of the five highest expressers, was from pET29/TEV variants 5, 10, 7, 3, and 6. In comparison, the TEV variant 11 was expressed at the lowest level of all.

C. Large-scale Expression and Purification.

To rigorously compare TEV protease expression levels from the top five pET29/TEV variants, along with variant 11 as a control, under large-scale conditions, 3.0 mL of PA-0.5G media containing 50 µg/mL Kanamycin was inoculated with a single colony of BL21(DE3) cells harboring the appropriate expression construct and grown at 37° C. with shaking overnight. 250 µL of this starter culture was used to inoculate 250 mL of ZYP-5052 containing 50 µg/mL kanamycin and grown at 37° C. with shaking for 8 hours. The cells were pelleted by centrifugation.

To lyse cells, the cell pellet was resuspended in a 5.0 mL/gram cell pellet of Lysis Solution comprising BUGBUSTER™ Protein Extraction Reagent (EMD Biosciences-Novagen, Madison, Wis.), 1× protease Inhibitor Cocktail Set III (EMD Biosciences-Calbiochem, Gibbstown, N.J.), 25 units/mL Benzonase nuclease, and 1 Kunit/mL rLysozyme (EMD Biosciences-Novagen, Madison, Wis.). The cell suspension was incubated at room temperature on a platform rocker for 20 minutes, followed by incubation on ice for 15 minutes. The suspension was centrifuged at 4° C. for 30 minutes at 30,350 rcf to pellet debris and the supernatant was transferred to a clean tube. To prepare the insoluble cell extract pellet for SDS-PAGE analysis, the pellet was resuspended to the original volume with 1×BUGBUSTER™ Protein Extraction Reagent.

To purify a TEV protease variant by IMAC purification, the clarified lysate was mixed with TALON™ SuperFlow Metal Affinity Cobalt Resin equilibrated with IMAC Wash Solution comprising 25 mM Sodium phosphate, pH 7.0, 500 mM NaCl, 10% glycerol and 35 mM imidazole. The lysate-resin mixture was incubated on a platform rocker at 4° C. for 1 hour and then transferred to a 20 mL disposable column support attached to a vacuum manifold. The column was washed twice with five column volumes of IMAC Wash Solution. The TEV protease was eluted from the resin with two column volumes of IMAC Elution Solution, comprising 25 mM sodium phosphate, pH 7.8, 500 mM NaCl, 10% glycerol and 500 mM imidazole, and collected in 1.0 mL fractions. Each fraction containing protein was identified by mixing 10 µL aliquot with 200 µL of QUICKSTART™ Bradford Dye reagent. Peak elution fractions were pooled and dialyzed for secondary ion exchange chromatography purification.

To dialyze an IMAC-purified TEV protease variant, the pooled sample comprising the peak elution fraction was dialyzed in a FASTDIALYZER® fitted with 25 kD MWCO membrane at 4° C. in 1 L of a Desalting Buffer with constant stirring overnight. For cation exchange chromatography, the desalting buffer (Buffer A) comprised 50 mM Tris-HCl, pH 8.0.

To purify a TEV protease variant by cation exchange chromatography, the desalted protein solution was loaded onto a 1 mL UNO-S1 cation exchange column, pre-equilibrated with Buffer A, at a flow rate of 0.5 mL/min. Bound protein was eluted by NaCl gradient with Buffer B comprising 25 mM sodium phosphate, pH 7.0, 1 M NaCl at a flow rate of 1.0 mL/min as follows: 5% Buffer B for 3 mL, 20% Buffer B for 10 mL, 20% to 100% Buffer B over 10 mL. Elution of proteins from the column was detected with a UV-Visible detector at 214 nm, 260 nm, and 280 nm, and all peak fractions were pooled and protein concentration determined. Aliquots were flash frozen in liquid nitrogen and stored at −80° C. TEV variant 7 had the highest yield of soluble protease (ca. 35 mg/L) followed by variant 3 (ca. 24 mg/L) and variant 10 (ca. 23 mg/L). The remaining two variants, 5 and 6, had yields of 18 and 8 mg/L, respectively. Yield of the TEV variant 11 was ca. 0.6 mg/L. As such, all of the top five TEV variants containing a solubility enhancing amino acid change resulted in at least a 10-fold increase in soluble TEV protease purified relative to the TEV variant 11 that only comprised the autoproteolysis eliminating amino acid change (S219N). When comparing the rank order of yield of TEV protease from small- and large-scale expression studies, variant 5 exhibited the highest yield in small-scale expressions (Example 1C). However, it was variant 7 that had the highest yield in large-scale expressions. Repeat comparison of yields from large-scale batches consistently revealed variant 7 to be the highest expressing variant. As a result, variant 7 represented the lead TEV protease construct and was used for all subsequent studies described here.

To determine total TEV protease expression, 40 µL of the induced cell culture from each time-point was mixed with an equal volume of 2×Laemmli Sample Buffer and incubated at 95° C. for 10 minutes. 2 µL of 1 unit/µL Benzonase in 1 M MgSO$_4$ was added to this mixture and incubated at 95° C. for 5 minutes. A 15 µL aliquot was loaded and separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. The gel was washed and fixed in Fix Solution comprising 10% methanol, 7% acetic acid for 30 minutes. After fixing, the Fix Solution was removed and the gel incubated with SYPRO Ruby Protein Gel Stain at room temperature for 3 hours. The gel was then destained in Destain Solution comprising 10% methanol, 7% acetic acid at room temperature for 3 hours. The image was visualized with a Typhoon 9410 Variable Mode Imager and Imager Analysis software (GE Healthcare, Amersham Biosciences, Piscataway, N.J.).

TABLE 4

TEV Protease Activity Assay

| TEV Protease | TEV Substrate Cleavage (%) | | |
|---|---|---|---|
| | 30 minute | 60 minute | 120 minute |
| AcTEV | 73.9 | 91.6 | 97.2 |
| TEV variant 3 | 96.5 | 97.7 | 98.1 |
| TEV variant 5 | 95.6 | 97.8 | 95.6 |

TABLE 4-continued

TEV Protease Activity Assay

| TEV Protease | TEV Substrate Cleavage (%) | | |
|---|---|---|---|
| | 30 minute | 60 minute | 120 minute |
| TEV variant 6 | 90.8 | 96.8 | 97.2 |
| TEV variant 7 | 96.6 | 97.8 | 97.7 |
| TEV variant 10 | 74.2 | 93.3 | 96.1 |

Example 2

Intracellular Activation of a Clostridial Toxin with a TEV Protease Cleavage Site Using Two Different Expression Constructs The following example illustrates a procedure useful for expressing in a cell a Clostridial toxin comprising a di-chain loop region comprising an exogenous protease cleavage site as disclosed in the present specification.

A. Construction of pET29/BoNT/A-TEV Expression Construct.

In order to produce a BoNT/A comprising a TEV protease cleavage site located within the di-chain loop region, an open reading frame (SEQ ID NO: 87) encoding the desired BoNT/A-TEV (SEQ ID NO: 88) was synthesized using standard procedures (BlueHeron Biotechnology, Bothell, Wash.). Complementary oligonucleotides of 20 to 50 bases in length, spanning the entire open reading frame of BoNT/A-TEV were synthesized using standard phosphoramidite synthesis. These oligonucleotides were hybridized into double stranded duplexes that were sequentially ligated together to assemble the full-length polynucleotide molecule. This polynucleotide molecule was cloned using standard molecular biology methods into a pUCBHB1 carrier vector at the SmaI site to generate the pUCBHB1/BoNT/A-TEV constructs. The synthesized polynucleotide molecule was verified by sequencing using BIG DYE TERMINATOR™ Chemistry 3.1 (Applied Biosystems, Foster City, Calif.) and an ABI 3100 sequencer (Applied Biosystems, Foster City, Calif.).

To generate the pET29/BoNT/A-TEV expression construct, pUCBHB1/BoNT/A-TEV was digested with restriction endonucleases that 1) excise the insert comprising the open reading frame encoding BoNT/A-TEV; and 2) enable this insert to be operably-linked to a pET29 vector (EMD Biosciences-Novagen, Madison, Wis.). This insert was subcloned using a T4 DNA ligase procedure into a pET29 vector digested with the analogous restriction endonucleases to yield the appropriate pET29/BoNT/A-TEV expression construct. The ligation mixture was transformed into electro-competent *E. coli* BL21(DE3) Acella cells (Edge BioSystems, Gaithersburg, Md.) by electroporation, plated on 1.5% Luria-Bertani agar plates (pH 7.0) containing 50 µg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded a pET29 expression construct comprising the polynucleotide molecule encoding BoNT/A-TEV operably-linked to a carboxyl-terminal polyhistidine affinity purification peptide.

B. Construction of pET22/TEV Expression Constructs.

To generate a pET22/TEV variant expression construct, a pET29/TEV variant 7 expression construct was digested with restriction endonucleases that 1) excise the insert comprising the open reading frame (SEQ ID NO: 77) encoding the TEV protease (SEQ ID NO: 78); and 2) enable this insert to be operably-linked to a pET22 vector (EMD Biosciences-Novagen, Madison, Wis.). This insert was subcloned using a T4 DNA ligase procedure into a pET22 vector digested with the analogous restriction endonucleases to yield the appropriate pET22/TEV expression construct. The ligation mixture was transformed into electro-competent *E. coli* BL21(DE3) Acella cells (Edge BioSystems, Gaithersburg, Md.) by electroporation, plated on 1.5% Luria-Bertani agar plates (pH 7.0) containing 50 µg/mL of ampicillin, and placed in a 37° C. incubator for overnight growth. Bacteria containing expression constructs were identified as ampicillin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded a pET22 expression construct comprising the polynucleotide molecule encoding TEV variant 7 operably-linked to an amino-terminal polyhistidine affinity purification peptide.

C. Construction of Cells Comprising pET29/BoNT/A-TEV and pET22/TEV Expression Constructs.

To make a cell comprising pET29/BoNT/A-TEV and pET22/TEV expression constructs, a pET29/BoNT/A-TEV expression construct was transformed into electro-competent *E. coli* BL21(DE3) cells harboring pET22/TEV variant 7 expression construct using electroporation, plated on 1.5% Luria-Bertani agar plates (pH 7.0) containing 50 µg/mL of ampicillin and 50 µg/mL of kanamycin, and placed in a 37° C. incubator for overnight growth. Bacteria containing both expression constructs were identified as ampicillin-kanamycin resistant colonies. Candidate constructs were isolated using an alkaline lysis plasmid mini-preparation procedure and analyzed by restriction endonuclease digest mapping to determine the presence of both constructs. This cloning strategy yielded cells comprising pET29/BoNT/A-TEV and pET22/TEV expression constructs.

D. In Situ Activation of BoNT/A-TEV.

To produce di-chain forms of BoNT/A-TEV under auto-induction conditions, 3.0 mL of PA-0.5G media containing 50 µg/mL kanamycin and 50 µg/mL ampicillin was inoculated with a single colony of BL21(DE3) cells harboring pET29/BoNT/A-TEV and pET22/TEV expression constructs and grown at 37° C. with shaking overnight. About 1.0 µL of this starter culture was used to inoculate a 1.0 mL of ZYP-5052 containing 50 µg/mL kanamycin and 50 µg/mL ampicillin and grown at 37° C. with shaking for 3.5 hours and then at 22° C. with shaking for 18.5 hours. As a control, BL21(DE3) cells harboring pET29/BoNT/A-TEV alone were grown and induced as described above, except only 50 µg/mL kanamycin was used as a selective agent.

Following growth and induction, the cells were lysed and IMAC purified essentially as described in Example 1B. The IMAC purified samples were analyzed by SDS-PAGE and the gels stained essentially as described in Example 1B.

The results indicate that when pET29/BoNT/A-TEV is expressed alone, an approximately 150 kDa band corresponding to the single-chain for of BoNT/A-TEV was detected under both reducing and non-reducing conditions. In contrast, when BoNT/A-TEV was co-expressed with TEV protease, two bands were observed under reducing conditions, one of approximately 50 kDa and the other of approximately 100 kDa. Moreover, when the same samples were run under non-reducing conditions, the approximately 50 kDa and approximately 100 kDa bands disappeared and a new band of approximately 150 kDa was observed. Taken together, these observations indicate that the approximately 50 kDa and approximately 100 kDa bands seen under reducing conditions correspond to the light and heavy chains of the BoNT/A-TEV, and that the presence of these two bands was indicative of di-chain formation of BoNT/A-TEV. Thus, co-expression of BoNT/A-TEV and TEV protease in these cells results in cleavage of BoNT/A-TEV at the TEV protease cleavage site located within the di-chain loop and the subsequent formation of the di-chain form of BoNT/A-TEV.

To confirm these results, a large scale expression of BL21(DE3) cells harboring pET29/BoNT/A-TEV and pET22/TEV expression constructs was done. 3.0 mL of PA-0.5G media containing 50 µg/mL kanamycin and 50 µg/mL ampicillin was inoculated with a single colony of BL21(DE3) cells comprising pET29/BoNT/A-TEV and pET22/TEV expression constructs and grown at 37° C. with shaking overnight. About 250 µL of this starter culture was used to inoculate 250 mL of ZYP-5052 containing 50 µg/mL kanamycin and 50 µg/mL ampicillin and grown at 37° C. with shaking for 3.5 hours and then at 22° C. with shaking for 18.5 hours. The cells were pelleted by centrifugation. The cells were lysed and IMAC purified as described in Example 1C.

To dialyze the IMAC-purified BoNT/A-TEV for secondary ion exchange chromatography, the pooled sample comprising the peak elution fractions were dialyzed in a FAST-DIALYZER® fitted with 25 kD MWCO membrane at 4° C. in 1 L of a Desalting Buffer with constant stirring overnight. For anion exchange chromatography, the desalting buffer (Buffer A) comprised 50 mM Tris-HCl, pH 8.0.

To purify BoNT/A-TEV by anion exchange chromatography, the desalted protein solution was loaded onto a 1 mL UNO-Q1 anion exchange column, pre-equilibrated with Buffer A, at a flow rate of 0.5 mL/min. Bound protein was eluted by NaCl gradient with Buffer B comprising 50 mM Tris-HCl, pH 8.0, 1 M NaCl at a flow rate of 0.5 mL/min as follows: 3% Buffer B for 3 mL, 7% Buffer B for 10 mL, 7% to 100% Buffer B over 10 mL. Elution of proteins from the column was detected with a UV-Visible detector at 214 nm, 260 nm, and 280 nm, and all peak fractions were pooled and protein concentration determined. Aliquots were flash frozen in liquid nitrogen and stored at −80° C. Purified BoNT/A-TEV protein was analyzed by SDS-PAGE, and the gels stained essentially as described in Example 1B. The results confirm the initial small scale experiments and indicate that the single-chain BoNT/A-TEV is converted to its di-chain form with near 100% efficiency.

To assess the activity of the BoNT/A-TEV di-chains, these toxins were evaluated in a cell-based assay and animal-based assay.

To test the activity of BoNT/A-TEV di-chains using a cell-based assay, an immuno-based BoNT/A activity assay using multiplex ECL sandwich ELISA was performed essentially as described in patent application Fernandez-Salas, et al., Immuno-Based BoNT/A Activity Assays, Attorney Docket No. 18383 (BOT), which is hereby incorporated by reference in its entirety.

To obtain a BoNT/A-TEV treated cell lysate for analysis, approximately 50,000 cells from a stock culture of a SiMa cell line were seeded into a poly-D-lysine 96-well plate containing a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES and 25 µg/mL of GTb1. These cells were incubated in a 37° C. incubator under 5% carbon dioxide until the cells differentiated, as assessed by standard and routine morphological criteria, such as growth arrest and neurite extension (approximately 3 days). The media was aspirated from each well and replaced with fresh media containing either 0 (untreated sample), 0.01 nM, 0.04 nM, 0.12 nM, 0.37 nM, 1.11 nM, 3.33 nM and 10.0 nM of a BoNT/A-TEV. After a 24 hr treatment, the cells were washed, incubated for an additional two days without toxin. To harvest the cells, the medium was aspirated, washed with 1×PBS, and lysed by adding 30 µl of Lysis Buffer comprising 50 mM HEPES, 150 mM NaCl, 1.5 mM $MgCl_2$, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cell debris and the supernatant was transferred to a capture antibody coated 96-well plate to perform the detection step.

To prepare the α-SNAP-25 capture antibody solution, the α-SNAP-25 monoclonal antibody contained in the ascites from hybridoma cell line 2E2A6 was purified using a standard Protein A purification protocol To prepare the α-SNAP-25 detection antibody solution, α-SNAP-25 rabbit polyclonal antibody S9684 (Sigma, St. Louis, Mo.) was conjugated to Ruthenium(II)-tris-bipyridine (4-methylsulfonate) NHS ester labeling reagent (Meso Scale Discovery, Gaithersburg, Md.) according to the manufacturer's instructions (Meso Scale Discovery, Gaithersburg, Md.). To prepare the solid phase support comprising the capture antibody that was specific for a SNAP-25 cleaved product, approximately 5 µL of α-SNAP-25 monoclonal antibody 2E2A6 solution (20 µg/mL in 1×PBS) was added to each well of a 96-well MSD High Bind plate and the solution was allowed to air dry in a biological safety cabinet for 2-3 hours in order to liquid evaporate the solution. The capture antibody-bound wells were then blocked and used directly to detect BoNT/A activity.

To detect the presence of a cleaved SNAP-25 product by ECL sandwich ELISA analysis, the Blocking Buffer from stored plates was aspirated, 25 µL of a lysate from cells treated with BoNT/A was added to each well and the plates were incubated at 4° C. for 2 hrs. Plate wells were washed three times by aspirating the cell lysate and rinsing each well three times with 200 µL 1×PBS, 0.1% TWEEN-20® (polyoxyethylene (20) sorbitan monolaurate). After washing, 25 µl of 5 µg/mL α-SNAP-25 detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature for 1 hour with shaking. After α-SNAP-25 detection antibody incubation, the wells were washed three times with 200 µL 1×PBS, 0.1% TWEEN-20® (polyoxyethylene (20) sorbitan monolaurate). The raw data obtained from the ECL imager was then transferred to SigmaPlot v. 9.0 and a 4-parameter logistics fit was used to define the dose-response curves. There were no constraints used for the 4-parameter logistic function when plotting the data. Graphical reports were generated using the following analysis: $R2$ (correlation coefficient), a (Max for data set), b (hillslope), and X0±SE ($EC_{50}$ value±standard error). The results from two independent runs indicate that the activity of both di-chains was nearly identical and within 2-fold of the native di-chain.

To test the activity of BoNT/A-TEV di-chains using an animal-based assay, an in vivo Digit Abduction Score (DAS) assay was performed. CD-1 Fe mice were weighed and placed into subsets of 10 animals for each discrete DAS assay. Mice were included into a particular subset based on the following criteria: 1) good health; 2) robust baseline DAS response of 0; 3) inclusion in a median weight range of X±2 g established for the selected subset and 4) weight greater than 17.0 g.

Each mouse was injected with 5 µL of one of seven different doses of BoNT/A-TEV (0.01 nM, 0.04 nM, 0.12 nM, 0.37 nM, 1.11 nM, 3.33 nM and 10.0 nM) with a 30-gauge needle in the gastrocnemius muscle of the right hind limb. As a control, the gastrocnemius muscle of the left hind limb was injected with 5 µL of a solution not containing any BoNT/A-TEV. Mice were observed for the DAS response consecutively for the first 4 days. The DAS was read by lifting each mouse by the tail and precisely observing the injected hind limbs. The abduction or no abduction of the hind digits reveals the effect of paralysis due to the test toxin injected in the muscle. The digit abduction of the injected hind limb was compared with that of the non-injected hind limb and scored accordingly. DAS data was analyzed by calculating the $ED_{50}$ dose based on peak mean DAS score and AUC (area under the curve) in terms of u/Kg and/or ng/Kg. This was accomplished as follows: 1) the mean peak DAS score for each dose was calculated in each study; 2) any dose that elicited more than five deaths in any study was eliminated from consideration; 3) the highest dose used in a given individual study was the lowest dose which elicited anaverage peak of 4.0; 4) the lowest dose used in a given individual study was the highest dose which elicited an average peak of 0; 5) curves were constructed for each individual study of average peak DAS vs. log(dose); 6) an AUC value was calculated for each group of 10 mice of the multiple groups in some studies; 7) curves were constructed for each individual study of average AUC vs. log(dose); 8) an x, y replicate response curve was constructed for each set of multiple identical studies; for each test toxin; 9) dose-response data were analyzed by non-linear regression (non-weighted) using a three-parameter logistic equation (Sigma Plot v 8.0; SPSS Science, Chicago, Ill.) using the following equation:

$$y = a/(1+(x/x0)^b)$$

where y is the response, a is the asymptotic $y_{max}$, b is the slope, x is the dose, and 0 is the $ED_{50}$ dose, for peak $ED_{50}$ determinations, $y_{max}$ was set to 4 (maximum DAS reading on scale). Mean (peak and/or AUC) $ED_{50}$ values were computed for each eight-dose study performed.

The results from two independent runs indicate that the level of activity of both di-chains was nearly identical and within 2-fold of the native di-chain. Taken together, the cell-based assay and DAS assay data indicate that the process of intracellular activation yields di-chain rBoNT/A which was not only structurally comparable to the in-vitro nicked material but also functionally indistinguishable.

Example 3

Intracellular Activation of a Clostridial Toxin with a TEV Protease Cleavage Site Using Two Different Expression Constructs Under Control of Independent Promoters The following example illustrates a procedure useful for expressing in a cell a Clostridial toxin comprising a di-chain loop region comprising an exogenous protease cleavage site as disclosed in the present specification. In this case, the formation of the di-chain form of the toxin is regulated by TEV protease under control of an independent promoter.

A. Construction of pBAD/TEV Expression Construct.

In order to produce a TEV protease recombinantly, the expression of which was under control of an arabinose promoter ($P_{BAD}$), the open reading frame encoding the TEV protease variant 7 (Table 3 [130]), minus an N-terminal His tag, was cloned into the expression vector pBAD/Myc-HisA to construct pBAD/TEV. To construct pBAD/TEV, an open reading frame encoding the TEV protease variant 7 (SEQ ID NO: 106), minus an N-terminal poly-histidine tag, was synthesized using standard procedures (BlueHeron Biotechnology, Carlsbad, Calif.). The synthetic fragment was also flanked by restriction sites to enable this insert to be operably-linked to a pBAD/Myc-HisA vector (Life Technologies, Madison, Wis.). Using a T4 DNA ligase procedure this insert was directionally ligated into a pBAD/Myc-HisA vector digested with the same restriction endonucleases in the multiple cloning site. The ligation mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 µg/mL of ampicillin, and placed in a 37° C. incubator for overnight growth. Bacteria containing expression constructs were identified as ampicillin resistant colonies. Candidate constructs were isolated using an alkaline lysis plasmid mini-preparation procedure and analyzed by restriction endonuclease digest mapping and sequencing both DNA strands to confirm the presence and integrity of the TEV gene insert. This cloning strategy yielded a pBAD/TEV expression construct comprising the polynucleotide molecule encoding TEV variant 7 free of a polyhistidine affinity purification peptide.

B. Construction of Cells Comprising pET29/BoNT/A-TEV and pBAD/TEV Expression Constructs.

To make a cell comprising pET29/BoNT/A-TEV and pET22/TEV expression constructs, a pET29/BoNT/A-TEV expression construct was transformed into electro-competent E. coli BL21(DE3) cells harboring pET22/TEV variant 7 expression construct using electroporation, plated on 1.5% Luria-Bertani agar plates (pH 7.0) containing 50 µg/mL of ampicillin and 50 µg/mL of kanamycin, and placed in a 37° C. incubator for overnight growth. Bacteria containing both expression constructs were identified as ampicillin-kanamycin resistant colonies. Candidate constructs were isolated using an alkaline lysis plasmid mini-preparation procedure and analyzed by restriction endonuclease digest mapping to determine the presence of both constructs. This cloning strategy yielded cells comprising pET29/BoNT/A-TEV and pET22/TEV expression constructs.

C. In Situ Activation of BoNT/A-TEV.

To produce di-chain forms of BoNT/A-TEV under autoinduction conditions, 3.0 mL of PA-0.5G media containing 50 µg/mL kanamycin and 50 µg/mL ampicillin was inoculated with a single colony of BL21(DE3) cells harboring pET29/BoNT/A-TEV and pBAD/TEV expression constructs and grown at 37° C. with shaking overnight. 250 µL of this starter culture was used to inoculate 250 mL of ZYP-5052 containing 50 µg/mL kanamycin and 100 µg/mL ampicillin and grown at 37° C. with shaking for 8 hours and then at 22° C. with shaking for 14 hours. At this point, TEV expression was induced with 0.2% L-arabinose and the culture was grown for an additional 4 hours at 22° C. As a control, BL21(DE3) cells harboring pET29/BoNT/A-TEV alone were grown and induced as described above, except only 50 µg/mL kanamycin was used as a selective agent.

Following growth and induction, the cells were lysed and IMAC purified essentially as described in Example 1C. To dialyze the IMAC-purified BoNT/A-TEV for secondary ion exchange chromatography, the pooled sample comprising the peak elution fractions were dialyzed in a FASTDIA-LYZER® fitted with 25 kD MWCO membrane at 4° C. in 1 L of a Desalting Buffer with constant stirring overnight. For anion exchange chromatography, the desalting buffer (Buffer A) comprised 50 mM Tris-HCl, pH 8.0.

To purify BoNT/A-TEV by anion exchange chromatography, the desalted protein solution was loaded onto a 1 mL UNO-Q1 anion exchange column, pre-equilibrated with Buffer A, at a flow rate of 0.5 mL/min. Bound protein was eluted by NaCl gradient with Buffer B comprising 50 mM Tris-HCl, pH 8.0, 1 M NaCl at a flow rate of 0.5 mL/min as follows: 3% Buffer B for 3 mL, 7% Buffer B for 10 mL, 7% to 100% Buffer B over 10 mL. Elution of proteins from the column was detected with a UV-Visible detector at 214 nm, 260 nm, and 280 nm, and all peak fractions were pooled and protein concentration determined.

Purified BoNT/A-TEV protein was analyzed by SDS-PAGE, and the gels stained essentially as described in Example 1B. The results indicate that when pET29/BoNT/A-TEV is expressed alone, an approximately 150 kDa band corresponding to the single-chain for of BoNT/A-TEV was detected under both reducing and non-reducing conditions. In contrast, when BoNT/A-TEV was co-expressed with TEV protease under control of the $P_{BAD}$ promoter and induced with arabinose, two bands were observed under reducing conditions, one of approximately 50 kDa and the other of approximately 100 kDa. Moreover, when the same samples were run under non-reducing conditions, the approximately 50 kDa and approximately 100 kDa bands disappeared and a new band of approximately 150 kDa was observed. Taken together, these observations indicate that the approximately 50 kDa and approximately 100 kDa bands seen under reducing conditions correspond to the light and heavy chains of the BoNT/A-TEV, and that the presence of these two bands was indicative of di-chain formation of BoNT/A-TEV. Thus, co-expression of BoNT/A-TEV and TEV protease in these cells results in cleavage of BoNT/A-TEV at the TEV protease cleavage site located within the di-chain loop and the subsequent formation of the di-chain form of BoNT/A-TEV. The results indicate that between 90-95% of the single-chain BoNT/A-TEV is converted to its di-chain form.

Example 4

Intracellular Activation of a Clostridial Toxin with a TEV Protease Cleavage Site Using a Dual Expression Construct The following example illustrates methods useful for purifying and quantifying a Clostridial toxin comprising an exogenous protease cleavage site as disclosed in the present specification.

A. Construction of pET29/BoNT/A-TEV/2xTEV Dual Expression Construct.

To construct pET29/BoNT/A-TEV/2xTEV dual expression construct, a synthetic fragment (SEQ ID NO: 89) encoding the last 37 amino acids of BoNT/A-TEV as well as transcription (T7 promoter, lac operator site) and translation (RBS) elements necessary for E. coli expression and the entire coding region of TEV variant 7 was synthesized using standard procedures (BlueHeron Biotechnology, Bothell, Wash.). Complementary oligonucleotides of 20 to 50 bases in length, were synthesized using standard phosphoramidite synthesis. These oligonucleotides were hybridized into double stranded duplexes that were sequentially ligated together to assemble the full-length polynucleotide molecule. This polynucleotide molecule was cloned using standard molecular biology methods into a pUCBHB1 carrier vector at the SmaI site to generate the pUCBHB1/BoNT/A-TEV_C-term/T7Prom/TEV plasmid. The synthesized polynucleotide molecule was verified by sequencing using BIG DYE TERMINATOR™ Chemistry 3.1 (Applied Biosystems, Foster City, Calif.) and an ABI 3100 sequencer (Applied Biosystems, Foster City, Calif.

To generate the pET29/BoNT/A-TEV/2xTEV expression construct, pUCBHB1/BoNT/A-TEV_C-term/T7Prom/TEV was digested with restriction endonucleases that 1) excise the insert comprising the C-terminus of BoNT/A-TEV, transcription and translation motifs necessary for E. coli expression of a second open reading frame, and the entire coding region of TEV variant 7; and 2) enable this insert to be operably-linked behind the BoNT/A gene in pET29/BoNT/A-TEV vector from Example 1A. This insert was subcloned using a T4 DNA ligase procedure into the pET29/BoNT/A-TEV vector digested with the analogous restriction endonucleases to yield the appropriate pET29/BoNT/A-TEV/2xTEV dual expression construct comprising the BoNT/A-TEV and TEV protease variant 7 open reading frames with the intervening transcription and translation elements of SEQ ID NO: 89. The ligation mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 µg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded a pET29 dual expression construct comprising the polynucleotide molecule encoding a BoNT/A-TEV variant operably-linked to a carboxyl terminal polyhistidine affinity purification tag and a TEV protease. The open reading frame organization was such that transcription initiation from the first T7 promoter yields an mRNA with the open reading frame encoding BoNT/A-TEV and the open reading frame encoding TEV protease. In addition, transcription initiation from the second T7 promoter yields mRNA with the open reading frame encoding only TEV protease. Thus, there would be twice as many transcripts encoding TEV protease compared to BoNT/A-TEV.

B. In Situ Activation of BoNT/A-TEV from pET29/BoNT/A-TEV/2xTEV.

To produce di-chain forms of BoNT/A-TEV under auto-induction conditions, 3.0 mL of PA-0.5G media containing 50 µg/mL Kanamycin was inoculated with a single colony of BL21(DE3) cells comprising pET29/BoNT/A-TEV/TEV dual expression construct and grown at 37° C. with shaking overnight. About 250 µL of this starter culture was used to inoculate 250 mL of ZYP-5052 containing 50 µg/mL kanamycin and grown at 37° C. with shaking for 3.5 hours and then at 22° C. with shaking for 18.5 hours. The cells were pelleted by centrifugation. The cells were lysed, IMAC purified, desalted, purified by anion exchange chromatography, analyzed by SDS-PAGE, and the gels stained essentially as described in Example 2D. As a control, BL21(DE3) cells harboring pET29/BoNT/A-TEV alone were grown and induced as described above, except only 50 μg/mL kanamycin was used as a selective agent.

The results indicate that when expressed alone, an approximately 150 kDa band corresponding to the single-chain for of BoNT/A-TEV was detected under both reducing and non-reducing conditions. In contrast, when BoNT/A-TEV was co-expressed with TEV protease, two bands were observed under reducing conditions, one of approximately 50 kDa and the other of approximately 100 kDa. Moreover, when the same samples were run under non-reducing conditions, the approximately 50 kDa and approximately 100 kDa bands disappeared and a new band of approximately 150 kDa was observed. Taken together, these observations indicate that the approximately 50 kDa and approximately 100 kDa bands seen under reducing conditions correspond to the light and heavy chains of the BoNT/A-TEV, and that the presence of these two bands was indicative of di-chain formation of BoNT/A-TEV. The results also indicated that the single-chain BoNT/A-TEV was converted to its di-chain form with greater than 95% efficiency. Thus, co-expression of BoNT/A-TEV and TEV protease from a dual expression construct in these cells results in cleavage of BoNT/A-TEV at the TEV protease cleavage site located within the di-chain loop and the subsequent formation of the di-chain form of BoNT/A-TEV.

C. Construction of pRSFduet/TEV/2xBoNT/A-TEV Dual Expression Constructs.

To determine if reversing the organization of the open reading frames encoding BoNT/A-TEV and the TEV protease would affect yield and cleavage efficiency of BoNT/A-TEV, a dual expression construct was made where transcription initiation from the first T7 promoter yields an mRNA with the open reading frames encoding TEV and BoNT/A-TEV and transcription initiation from the second T7 promoter yields mRNA with the open reading frame encoding only BoNT/A-TEV. Thus, there would be twice as many mRNA's encoding BoNT/A-TEV compared to TEV protease.

To construct pRSFduet/TEV/2xBoNT/A-TEV dual expression construct, two sequential cloning reactions were performed. First, the open reading frame (SEQ ID NO: 91) encoding TEV variant 7 (SEQ ID NO: 22) was amplified by PCR from the pET29/TEV variant 7 expression construct. The 5'-end of the open reading frame encoding the polyhistidine affinity tag was excluded from the amplification to encode a tag-less protease. Following amplification, the PCR product was digested at the unique restriction sites, incorporated at the ends of the PCR product by means of the PCR primers, and cloned into the corresponding sites in MCSI (multiple cloning site) of the dual expression plasmid pRSFduet-1 (EMD Biosciences-Novagen, Madison, Wis.) using a T4 DNA ligase procedure. This intermediate construct was designated pRSduet/TEV. Next, a pET29/BoNT-A/TEV expression construct was digested with restriction endonucleases that 1) excise the insert comprising the open reading frame (SEQ ID NO: 87) encoding the BoNT/A-TEV (SEQ ID NO: 88); and 2) enable this insert to be operably-linked to the MCS2 in pRSFduet/TEV. The BoNT/A-TEV insert was subcloned into the MCS2 of the pRSFduet vector using a T4 DNA ligase procedure to yield the appropriate pRSFduet/TEV/2xBoNT/A-TEV dual expression construct. This cloning strategy yielded a pRSFduet dual expression construct where transcription from the first T7 promoter would produce mRNA's encoding TEV and BoNT/A-TEV and transcription from the second T7 promoter would produce mRNA's encoding only BoNT/A-TEV.

This cloning strategy will yield a pRSFduet dual expression construct where the first T7 promoter will transcribe the open reading frame encoding BoNT/A-TEV and the second T7 promoter will transcribe the open reading encoding TEV protease.

D. Construction of pET29/BoNT/A-TEV/TEV Dual Expression Construct.

To determine BoNT/A-TEV yields and efficiency of conversion to di-chain from a transcription unit configuration where BoNT/A-TEV and TEV could only be produced from their own independent mRNA's, pET29/BoNT/A-TEV/TEV was constructed. To generate the pET29/BoNT/A-TEV/TEV dual expression construct, a short synthetic DNA fragment was used to incorporate a T7 terminator site (SEQ ID NO: 92) in the intervening sequence between the open reading frames of BoNT/A-TEV and TEV in the dual expression construct pET29/BoNT/A-TEV/2xTEV (Example 3A above). Using a T4 DNA ligase procedure, this was essentially accomplished by swapping the intervening region in pET29/BoNT/A-TEV/2xTEV which lacked a T7 terminator site with a synthetic DNA fragment harboring the intervening transcription and translation elements along with a T7 termination site of SEQ ID NO: 93. The resulting dual expression construct, designated pET29/BoNT/A-TEV/TEV, comprises the polynucleotide molecule encoding a BoNT/A-TEV variant operably-linked to a carboxyl terminal polyhistidine affinity tag and TEV protease, transcribed from the first and second T7 promoters, respectively.

E. In Situ Activation of BoNT/A-TEV.

The growth and induction of di-chain forms of BoNT/A-TEV under auto-induction conditions was done essentially as described in Example 2D, except the BL21(DE3) cells comprising a pET29/BoNT/A-TEV/2xTEV dual expression construct, a pRSF/TEV/2xBoNT/A-TEV dual expression construct, or a pET29/BoNT/A-TEV/TEV dual expression construct were used and single colonies from each of these cell lines were used to inoculate four 1.0 mL cultures in parallel. After growth and induction, the four 1.0 mL replicates were pooled together for processing. The cells were lysed and IMAC purified, and analyzed by SDS-PAGE, and the gels stained essentially as described in Example 1B. As a control, BL21(DE3) cells harboring pET29/BoNT/A-TEV alone were grown and induced as described above, except only 50 μg/mL kanamycin was used as a selective agent. The results indicate that BoNT/A-TEV was expressed at very comparable levels from cells containing any one of the three dual expression constructs; however, the extent of conversion to di-chain varied. Single-chain BoNT/A-TEV was converted to its di-chain form with ca. 96% efficiency when the proteins were expressed from pET29/BoNT/A-TEV/2xTEV, with ca. 81% efficiency when the proteins were expressed from pET29/BoNT/A-TEV/TEV, and with greater than 99% efficiency when the proteins were expressed from pRSFduet/TEV/2xBoNT/A-TEV.

Example 5

Intracellular Activation of a Protein Comprising an Integrated TEV Protease Cleavage Site-opioid Binding Domain Using a Dual Expression Construct The following example illustrates methods useful for purifying and quantifying any of the proteins comprising a di-chain loop comprising an exogenous protease cleavage site disclosed in the present specification.

A. Construction of pRSFduet/TEV/2xNociLHN/A-TEV Dual Expression Construct.

To construct pRSFduet/TEV/2xNociLHN/A-TEV dual expression construct, a pET29/NociLHN/A-TEV expression construct was digested with restriction endonucleases that 1) excise the insert comprising the open reading frame (SEQ ID NO: 94) encoding the NociLHN/A-TEV (SEQ ID NO: 95); and 2) enable this insert to be operably-linked to the MCS2 of pRSFduet/TEV, a pRSFduet-1 vector harboring TEV variant 7 in MCSI (Described in Example 3C). The NociLHN/A-TEV insert was subcloned into the MCS2 of the pRSFduet/TEV construct using a T4 DNA ligase procedure to yield the appropriate pRSFduet/TEV/2xNociLHN/A-TEV dual expression construct. The ligation mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 µg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded a pRSFduet dual expression construct where transcription from the first T7 promoter would produce mRNA's encoding TEV and NociLHN/A-TEV and transcription from the second T7 promoter would produce mRNA's encoding only NociLHN/A-TEV.

B. In Situ Activation of NociLHN/A-TEV.

To produce di-chain forms of NociLHN/A-TEV under auto-induction conditions, 3.0 mL of PA-0.5G media containing 50 µg/mL kanamycin was inoculated with a single colony of BL21(DE3) cells comprising pRSFduet/TEV/2xNociLHN/A-TEV dual expression construct and grown at 37° C. with shaking overnight. 250 µL of this starter culture was used to inoculate 250 mL of ZYP-5052 containing 50 µg/mL kanamycin and grown at 37° C. with shaking for 8 hours and then at 16° C. with shaking for 18 hours. The cells were pelleted by centrifugation. The cells were lysed, IMAC purified, desalted, purified by anion exchange chromatography, analyzed by SDS-PAGE, and the gels stained essentially as described in Example 2D. As a control, BL21 (DE3) cells harboring NociLHN/A-TEV alone were grown and induced as described above.

The results indicate that when expressed alone, an approximately 102 kDa band corresponding to the single-chain of NociLHN/A-TEV was detected under both reducing and non-reducing conditions. In contrast, when NociLHN/A-TEV was co-expressed with TEV protease, two bands were observed under reducing conditions, one of approximately 50.8 kDa and the other of approximately 51.3 kDa. Moreover, when the same samples were run under non-reducing conditions, the approximately 50.8 kDa and approximately 51.3 kDa bands disappeared and a new band of approximately 102 kDa was observed.

Taken together, these observations indicate that the approximately 50.8 kDa and approximately 51.3 kDa bands seen under reducing conditions respectively correspond to the Clostridial toxin enzymatic domain and the Clostridial toxin translocation domain with the nociceptin targeting moiety attached to its amino terminus. The presence of these two bands was indicative of di-chain formation of NociLHN/A-TEVand that the single-chain NociLHN/A-TEV was converted to its di-chain form with greater than 95% efficiency. Thus, co-expression of NociLHN/A-TEV and TEV protease from a dual expression construct in these cells results in cleavage of NociLHN/A-TEV at the TEV protease cleavage site located within the integrated TEV protease cleavage site-opioid binding domain and the subsequent formation of the di-chain form of NociLHN/A-TEV.

C. Construction of pRSFduet/TEV/2xDynLHN/A-TEV Dual Expression Construct.

pRSFduet/TEV/2xDynLHN/A-TEV dual expression construct was generated almost exactly as pRSFduet/TEV/2xNociLHN/A-TEV. A pET29/DynLHN/A-TEV expression construct was digested with restriction endonucleases that 1) excise the insert comprising the open reading frame (SEQ ID NO: 96) encoding the DynLHN/A-TEV (SEQ ID NO: 97); and 2) enable this insert to be operably-linked to the MCS2 of pRSFduet/TEV (Described in Example 3C). The DynLHN/A-TEV insert was subcloned into the MCS2 of the pRSFduet/TEV construct using a T4 DNA ligase procedure to yield the appropriate pRSFduet/TEV/2xDynLHN/A-TEV dual expression construct. The ligation mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 µg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded a pRSFduet dual expression construct where transcription from the first T7 promoter would produce mRNA's encoding TEV and DynLHN/A-TEV and transcription from the second T7 promoter would produce mRNA's encoding only DynLHN/A-TEV.

D. In Situ Activation of DynLHN/A-TEV.

To produce di-chain forms of NociLHN/A-TEV under auto-induction conditions, 3.0 mL of PA-0.5G media containing 50 µg/mL kanamycin was inoculated with a single colony of BL21(DE3) cells comprising pRSFduet/TEV/2xDynLHN/A-TEV dual expression construct and grown at 37° C. with shaking overnight. 250 µL of this starter culture was used to inoculate 250 mL of ZYP-5052 containing 50 µg/mL kanamycin and grown at 37° C. with shaking for 8 hours and then at 16° C. with shaking for 18 hours. The cells were pelleted by centrifugation. The cells were lysed, IMAC purified, desalted, purified by anion exchange chromatography, analyzed by SDS-PAGE, and the gels stained essentially as described in Example 2D. As a control, BL21(DE3) cells harboring DynLHN/A-TEV alone were grown and induced as described above.

The results indicate that when expressed alone, an approximately 102 kDa band corresponding to the single-chain for of DynLHN/A-TEV was detected under both reducing and non-reducing conditions. In contrast, when DynLHN/A-TEV was co-expressed with TEV protease, two bands were observed under reducing conditions, one of approximately 50.8 kDa and the other of approximately 52 kDa. Moreover, when the same samples were run under non-reducing conditions, the approximately 50.8 kDa and approximately 52 kDa bands disappeared and a new band of approximately 102 kDa was observed. Taken together, these observations indicate that the approximately 50.8 kDa band corresponds to the Clostridial toxin enzymatic domain and an approximately 52 kDa band corresponds to the Clostridial toxin translocation domain with the dynorphin targeting moiety attached to its amino terminus. The presence of these two bands was indicative of di-chain formation of DynLHN/A-TEV and also that the single-chain DynLHN/A-TEV was converted to its di-chain form with greater than 95% efficiency. Thus, co-expression of DynLHN/A-TEV and TEV protease from a dual expression construct in these cells results in cleavage of DynLHN/A-TEV at the TEV protease cleavage site located within the integrated TEV protease cleavage site-opioid binding domain and the subsequent formation of the di-chain form of DynLHN/A-TEV.

Example 6

Intracellular Activation of a Protein Comprising an Integrated TEV Protease Cleavage Site-galanin Binding Domain Using Two Different Expression Constructs The following example illustrates methods useful for purifying and quantifying any of the proteins comprising a di-chain loop comprising an integrated TEV protease cleavage site-opioid binding domain disclosed in the present specification where the target protein and the protease are expressed from separate plasmids and under control of different promoters.

A. Construction of pET29/GalLHN/A-TEV Expression Construct.

To construct the pET29/GalLHN/A-TEV expression construct, a pET29/DynLHN/A-TEV expression construct was first digested with restriction endonucleases to excise a DNA segment encoding the di-chain loop comprising an integrated TEV protease cleavage site-dynorphin binding domain. The resulting pET29/LHN/A framework fragment was ligated with a synthetic DNA fragment bracketed with the compatible restriction sites (SEQ ID NO: 98), comprising the di-chain loop comprising an integrated TEV protease cleavage site-galanin binding domain (SEQ ID NO: 99). The ligation mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 µg/mL of kanamycin, and placed in a 37° C. incubator for overnight growth. Bacteria containing expression constructs were identified as kanamycin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded the pET29/GalLHN/A-TEV expression construct comprising the open reading frame (SEQ ID NO: 100) encoding the GalLHN/A-TEV (SEQ ID NO: 101) in which expression of GalLHN/A-TEV is under control of the T7 promoter.

B. Construction of pColdIV/TEV Expression Construct.

To generate an expression construct in which TEV is under control of the cold-shock promoter (csp), the open reading frame (SEQ ID NO: 91) encoding TEV variant 7 (SEQ ID NO: 22) was amplified by PCR from the pET29/TEV variant 7 expression construct. The 5'-end of the open reading frame encoding the poly-histidine affinity tag was excluded from the amplification to encode a tag-less protease. Following amplification, the PCR product was digested at the unique restriction sites, incorporated at the ends of the PCR product by means of the PCR primers, and cloned into the corresponding sites in the multiple cloning site of the expression plasmid pColdIV (Clontech Laboratories, Inc. Madison, Wis.) using a T4 DNA ligase procedure. The ligation mixture was transformed into electro-competent E. coli BL21(DE3) Acella cells (Edge BioSystems, Gaithersburg, Md.) by electroporation, plated on 1.5% Luria-Bertani agar plates (pH 7.0) containing 50 µg/mL of ampicillin, and placed in a 37° C. incubator for overnight growth. Bacteria containing expression constructs were identified as ampicillin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded the pColdIV/TEV expression construct comprising the polynucleotide molecule encoding TEV variant 7 under control of the cold-shock promoter.

C. Construction of Cells Comprising pET29/GalLHN/A-TEV and pColdIV/TEV Expression Constructs.

To make a cell comprising pET29/GalLHN/A-TEV and pColdIV/TEV expression constructs, the pET29/GalLHN/A-TEV expression construct was transformed into electro-competent E. coli BL21(DE3) cells harboring pColdIV/TEV using electroporation, plated on 1.5% Luria-Bertani agar plates (pH 7.0) containing 100 µg/mL of ampicillin and 50 µg/mL of kanamycin, and placed in a 37° C. incubator for overnight growth. Bacteria containing both expression constructs were identified as ampicillin-kanamycin resistant colonies. Candidate constructs were isolated using an alkaline lysis plasmid mini-preparation procedure and analyzed by restriction endonuclease digest mapping to determine the presence of both constructs. This cloning strategy yielded cells comprising pET29/GalLHN/A-TEV and pColdIV/TEV expression constructs.

D. In Situ Activation of pET29/GalLHN/A.

To produce di-chain forms of GalLHN/A-TEV under auto-induction conditions, 3.0 mL of PA-0.5G media containing 50 µg/mL kanamycin and 100 µg/mL ampicillin was inoculated with a single colony of BL21(DE3) cells harboring pET29/GalLHN/A-TEV and pColdIV/TEV expression constructs and grown at 37° C. with shaking overnight. About 250 µL of this starter culture was used to inoculate 250 mL of ZYP-5052 containing 50 µg/mL kanamycin and 100 µg/mL ampicillin and grown at 37° C. with shaking for 8 hours and then at 15° C. with shaking for 18 hours. The cells were lysed and IMAC purified using Magne-His resin.

To purify di-chain GalLHN/A-TEV by Magne-His purification, induced cells from 250 mL expression cultures were resuspended in 16 mL of cold (4-6° C.) IMAC Wash Buffer consisting of 100 mM HEPES, pH 7.5, 10% v/v glycerol, 10 mM imidazole, 1 M NaCl. The cell suspension was transferred to a sealed-atmosphere treatment chamber (#101-021-006, Branson Ultrasonics Corporation) and sonicated by 15 pulses (10 sec, 30% amplitude, 0.5-inch disrupter horn) with 1 minute in between pulses (Sonifier® Digital 450, Branson Ultrasonics Corporation). During sonication the sealed-atmosphere treatment chamber was cooled by passing chilled water from a circulating water bath (3.5° C.) through the outer jacket of the chamber. Sonicated material was transferred from the treatment chamber to a clean Oakridge tube and centrifuged at 30,500 RCF for 30 min (SL-50T Rotor, Sorvall; FIBERLite® F21S-8X50 Rotor, Piramoon Technologies Inc.) at 4° C. to remove insoluble cellular debris. The clarified lysate was aspirated by syringe and passed first through a 0.8 µm and then a 0.45 µm syringe filter (Sartorius) in series into a clean 50 mL conical tube. Magne-His™ Protein Purification Resin (Promega Corp., Madison, Wis.) was vortexed to a uniform suspension and 4 mL of the suspension transferred to the clarified lysate. The tube was sealed and inverted several times to mix the particles well. The mixture was incubated for 30 min with gentle rocking to bind the target protein at 16° C. The tube was transferred to a MagneSil Magnetic Separation Unit (Promega Corp., Madison, Wis.) and ~2 min were allowed for capture of the resin particles. The supernatant solution was removed and the tube removed from the separation unit. The resin was then resuspended in 10 mL IMAC Wash Buffer, captured on the magnetic separation unit, and the wash buffer removed. The wash step was repeated two more times. To elute the target protein, the resin was resuspended in 5 mL of the Magne-His™ Elution Buffer (100 mM HEPES, pH 7.5, 500 mM Imidazole) incubated at room temperature for 2 min, the resin captured on the magnetic separation unit and the supernatant solution transferred to a new tube. The elution step was repeated once.

To dialyze the IMAC-purified GalLHN/A-TEV for secondary ion exchange chromatography, the pooled elution fractions were dialyzed in a FASTDIALYZER® fitted with 25 kD MWCO membrane at 4° C. in 1 L of a Desalting Buffer (Buffer A: 50 mM Tris-HCl, pH 8.0) with constant stirring overnight.

To purify di-chain GalLHN/A-TEV by anion exchange chromatography, the desalted protein solution was loaded onto a 1 mL UNO-Q1 anion exchange column, pre-equilibrated with Buffer A, at a flow rate of 1 mL/min. Bound protein was eluted by NaCl gradient with Buffer B comprising 50 mM Tris-HCl, pH 8.0, 1 M NaCl at a flow rate of 1 mL/min as follows: 7% Buffer B for 3 mL, 15% Buffer B for 7 mL, 10% to 50% Buffer B over 10 mL. Elution of proteins from the column was detected with a UV-Visible detector at 214 nm, 260 nm, and 280 nm, and all peak fractions were pooled and protein concentration determined. Aliquots were flash frozen in liquid nitrogen and stored at −80° C. Purified BoNT/A-TEV protein was analyzed by SDS-PAGE, and the gels stained essentially as described in Example 1B.

The results indicate that when GalLHN/A-TEV was co-expressed with TEV protease, two nearly superimposing bands were observed under reducing conditions, one of approximately 51.1 kDa and another of approximately 52.1 kDa. Moreover, when the same samples were run under non-reducing conditions, the two approximately 51.1 kDa and 52.1 kDa bands disappeared and a new band of approximately 103 kDa was observed. Taken together, these observations indicate that the approximately 51.1 kDa band corresponds to the Clostridial toxin enzymatic domain and the approximately 52.1 kDa band corresponds to the Clostridial toxin translocation domain with the galanin targeting moiety attached to its amino terminus. The presence of these two bands was indicative of di-chain formation of GalLHN/A-TEV and also that the single-chain GalLHN/A-TEV was converted to its di-chain form with approximately 90% efficiency. Thus, co-expression of GalLHN/A-TEV and TEV protease in these cells from independent plasmids results in cleavage of GalLHN/A-TEV at the TEV protease cleavage site located within the integrated TEV protease cleavage site-galanin binding domain and the subsequent formation of the di-chain form of GalLHN/A-TEV.

Example 7: Prophetic

Intracellular Activation of a Protein Comprising an Integrated TEV Protease Cleavage Site-galanin Binding Domain Using a Dual Expression Construct The following example illustrates methods useful for purifying and quantifying any of the proteins comprising a di-chain loop comprising an integrated TEV protease cleavage site-opioid binding domain disclosed in the present specification where the target protein and the protease are expressed from a dual expression plasmid.

A. Construction of pRSFduet/TEV/2xGalLHN/A-TEV Dual Expression Construct.

To construct pRSFduet/TEV/2xGalLHN/A-TEV dual expression construct similar to pRSFduet/TEV/2xNociLHN/A-TEV and pRSFduet/TEV/2xDynLHN/A-TEV constructed before (See Example 4), a pET29/GalLHN/A-TEV expression construct will be digested with restriction endonucleases to 1) excise the insert comprising the open reading frame (SEQ ID NO: 100) encoding the GalLHN/A-TEV (SEQ ID NO: 101); and 2) enable this insert to be operably-linked to the MCS2 of pRSFduet/TEV, a pRSFduet-1 vector harboring TEV variant 7 in MCSI (Described in Example 3C). The GalLHN/A-TEV insert will be subcloned into the MCS2 of the pRSFduet/TEV construct using a T4 DNA ligase procedure to yield the pRSFduet/TEV/2xGalLHN/A-TEV dual expression construct. The ligation mixture will be transformed into electro-competent *E. coli* BL21(DE3) Acella cells (Edge BioSystems, Gaithersburg, Md.) by electroporation, plated on 1.5% Luria-Bertani agar plates (pH 7.0) containing 50 μg/mL of kanamycin, and placed in a 37° C. incubator for overnight growth. Bacteria containing expression constructs will be identified as kanamycin resistant colonies and candidate constructs confirmed by restriction endonuclease digest mapping and sequencing both DNA strands to confirm the presence and integrity of the insert. This cloning strategy will yield a pRSFduet dual expression construct where transcription from the first T7 promoter will produce mRNA's encoding TEV and GalLHN/A-TEV and transcription from the second T7 promoter will produce mRNA's encoding only GalLHN/A-TEV.

B. In Situ Activation of GalLHN/A-TEV.

To produce di-chain forms of GalLHN/A-TEV under auto-induction conditions, 3.0 mL of PA-0.5G media containing 50 μg/mL kanamycin will be inoculated with a single colony of BL21(DE3) cells comprising pRSFduet/TEV/2xGalLHN/A-TEV dual expression construct and grown at 37° C. with shaking overnight. 250 μL of this starter culture will be used to inoculate 250 mL of ZYP-5052 containing 50 μg/mL kanamycin and grown at 37° C. with shaking for 8 hours and then at 16° C. with shaking for 18 hours. The cells will be pelleted by centrifugation, lysed, IMAC purified, desalted, and purified by anion exchange chromatography as described in Example 5D. Purified target protein will be analyzed by SDS-PAGE under both reducing and non-reducing conditions, and the gels stained essentially as described in Example 1B to assess expression levels and the extent to which GalLHN/A-TEV produced from the pRSFduet/TEV/2xGalLHN/A-TEV dual expression construct is converted to its di-chain form.

Example 8

Intracellular Activation of a Protein Comprising an Integrated TEV Protease Cleavage Site-dynorphin Binding Domain Using a Dual Expression Construct in BEVS The following example illustrates methods useful for purifying and quantifying any of the proteins comprising a di-chain loop comprising an integrated TEV protease cleavage site-opioid binding domain disclosed in the present specification where the target protein and the protease are co-expressed in a dual expression construct and under control of two independent promoters in the baculovirus expression vector system (BEVS).

A. Construction of pBAC-6/TEV/DynLHN/A-TEV Dual Expression Construct.

To construct the pBAC-6/TEV/DynLHN/A-TEV dual expression construct, a synthetic fragment (SEQ ID NO: 107) encoding recombinant TEV variant 7 downstream of the p10 promoter sequence and DynLHN/A-TEV downstream of the polH promoter sequence in the opposite orientation was synthesized using standard procedures (BlueHeron Biotechnology, Bothell, Wash.). Complementary oligonucleotides of 20 to 50 bases in length were synthesized using standard phosphoramidite synthesis. These oligonucleotides were hybridized into double stranded duplexes that were sequentially ligated together to assemble the full-length polynucleotide molecule. This polynucleotide molecule was cloned using standard molecular biology methods into a pUCBHB1 carrier vector at the Smal site to generate the pUCBHB1/p10-TEV/polH-DynLHN/A-TEV plasmid. The synthesized polynucleotide molecule was verified by sequencing using BIG DYE TERMINATOR™ Chemistry 3.1 (Applied Biosystems, Foster City, Calif.) and an ABI 3100 sequencer (Applied Biosystems, Foster City, Calif.

To generate the pBAC-6/TEV/DynLHN/A-TEV dual expression construct, pUCBHB1/p10-TEV/polH-DynLHN/A-TEV was digested with restriction endonucleases that 1) excise the insert comprising the entire coding region of TEV variant 7 under control of the p10 promoter and DynLHN/A-TEV in the opposite direction under control of the polH promoter; and 2) enable this insert to be operably-linked to a pBAC-6 transfer vector (EMD Biosciences-Novagen, Madison, Wis.). This insert was subcloned using a T4 DNA ligase procedure into the pBAC-6 transfer vector digested with the analogous restriction endonucleases to yield the engineered pBAC-6 dual expression construct comprising TEV protease variant 7 open reading frame downstream of the p10 promoter and a second open reading frame of DynLHN/A-TEV downstream of the polH promoter. The ligation mixture was transformed into electro-competent *E. coli* BL21(DE3) Acella cells (Edge BioSystems, Gaithersburg, Md.) by electroporation, plated on 1.5% Luria-Bertani agar plates (pH 7.0) containing 100 μg/mL of ampicillin, and placed in a 37° C. incubator for overnight growth. Bacteria containing expression construct were identified as ampicillin resistant colonies. Candidate constructs were isolated using an alkaline lysis plasmid mini-preparation procedure and analyzed by restriction endonuclease digest mapping and sequencing both DNA strands to confirm the presence and integrity of the insert. This cloning strategy yielded a pBAC-6 dual expression construct comprising the polynucleotide molecule encoding a DynLH/A-TEV operably-linked to a carboxyl terminal polyhistidine affinity purification tag and TEV protease.

B. Generation of High Titer TEV/DynLHN/A-TEV Recombinant Baculovirus Stock.

Before di-chain forms of DynLHN/A-TEV could be produced, high titre recombinant baculovirus stock comprising TEV/DynLHN/A-TEV were generated. Approximately $2\times10^6$ Sf9 insect cells were seeded in 35 mm dishes in a 2 mL volume of insect cell culture medium ESF921. A transfection solution was prepared by mixing Solution A (comprising 2 μg of pBAC-6/TEV/DynLHN/A-TEV, 0.5 μg of linearized flashBAC baculovirus DNA (Oxford Expression Technologies, Oxford, UK), and 100 μL of Transfection Medium) with solution B (comprising 6 μL of TRANSIT®-2020 transfection reagent and 100 μL of Transfection Medium) and incubating at room temperature for 30 minutes. An additional 800 μL of Transfection Medium was next added to the Solution A/B mixture, mixed gently, and added dropwise onto the cells. Cells were incubated at 28° C. for 5 hours, at the end which 3 mL of ESF 921 was added to bring the final volume up to 4 mL in each well. The incubation was continued at 28° C. for 4-5 days for the production of P0 recombinant virus. To generate higher titer P1 recombinant baculovirus seed stocks, virus isolated from P0 supernatant was titered using bacu/oQUANT (Oxford Expression Technologies, Oxford, UK) and further amplified in shake flasks. About 100-200 mL of Sf9 cells at a density of $2\times10^6$cells/mL were infected with PO virus an MOl (multiplicity of infection)<1 pfu/cell and incubated with shaking for 4-5 days. Following quantification, the high titer P1 stock was used to infect Tni cells for high-level protein expression.

C. In Situ Activation of DynLHN/A-TEV.

To produce di-chain forms of DynHN/A-TEV, 50 mL Tni cells at a concentration of $1\times10^6$/mL were infected at an MOI of 5 with recombinant P1 virus stock comprising TEV/DynLHN/A-TEV and harvested 3 days post-infection (pi). The cells were lysed and IMAC purified using Magne-His resin.

To purify di-chain DynLHN/A-TEV by Magne-His purification, the cell pellet was resuspended in 20 mL of PBS w/o $Ca^{2+}$ or $Mg^{2+}$ in the presence of 100 μL Insect PopCulture Reagent and 20 μL (10 U) Benzonase Nuclease, mixed gently and incubated for 15 minutes at room temperature. After clarifying the cell lysate by centrifugation at 16,000 rpm for 15 minutes at 4° C., the supernatant was mixed with 4 mL of uniformly suspended Magne-His™ Protein Purification Resin (Promega Corp., Madison, Wis.). The mixture was incubated for 20 min at room temperature with gentle rocking to bind the target protein. The tube was transferred to a MagneSil magnetic separation unit for about 2 min to allow capture of the resin particles. After removing the supernatant, the tube was removed from the separation unit and the resin resuspended in 10 mL of IMAC wash buffer. Again, the resin was captured on the magnetic separation unit and the wash buffer removed. The wash step was repeated two more times. To elute the target protein, the resin was resuspended in 2.5 mL of the Magne-His™ Elution Buffer (100 mM HEPES, pH 7.5, 500 mM Imidazole), incubated at room temperature for 2 min, the resin captured on the magnetic separation unit, and the supernatant solution transferred to a new tube. The elution step was repeated again to maximize target recovery from the magnetic resin.

To dialyze the IMAC-purified DynLHN/A-TEV for secondary ion exchange chromatography, the pooled elution fractions were dialyzed in a FASTDIALYZER® fitted with 25 kD MWCO membrane at 4° C. in 1 L of a Desalting Buffer (Buffer A: 50 mM Tris-HCl, pH 8.0) with constant stirring overnight.

To purify di-chain DynLHN/A-TEV by anion exchange chromatography, the desalted protein solution was loaded onto a 1 mL UNO-Q1 anion exchange column, pre-equilibrated with Buffer A, at a flow rate of 1 mL/min. Bound protein was eluted by NaCl gradient with Buffer B comprising 50 mM Tris-HCl, pH 8.0, 1 M NaCl at a flow rate of 1 mL/min as follows: 7% Buffer B for 3 mL, 15% Buffer B for 7 mL, 10% to 50% Buffer B over 10 mL. Elution of proteins from the column was detected with a UV-Visible detector at 214 nm, 260 nm, and 280 nm, and all peak fractions were pooled and protein concentration determined.

Aliquots were stored at −20° C. Purified DynLHN/A-TEV protein was analyzed by SDS-PAGE, and the gels stained essentially as described in Example 1B.

The results indicate that when DynLHN/A-TEV was co-expressed with TEV protease in insect cells and purified to near homogeneity, two nearly superimposing bands were observed under reducing conditions, one of approximately 51 kDa and another of approximately 52 kDa. Moreover, when the same samples were run under non-reducing conditions, the two approximately 50 kDa and 52 kDa bands disappeared and a new band of approximately 102 kDa was observed. Taken together, these observations indicate that the approximately 51 kDa band corresponds to the Clostridial toxin enzymatic domain and the approximately 52 kDa band corresponds to the Clostridial toxin translocation domain with the dynorphin targeting moiety attached to its amino terminus. The presence of these two bands was indicative of di-chain formation of DynLHN/A-TEV and also that the single-chain DynLHN/A-TEV was converted to its di-chain form with 80-90% efficiency. Thus, co-expression of DynLHN/A-TEV and TEV protease in insect cells infected with TEV/DynLHN/A-TEV recombinant baculovirus generated from pBAC-6/TEV/DynLHN/A-TEV dual expression construct results in cleavage of DynLHN/A-TEV at the TEV protease cleavage site located within the integrated TEV protease cleavage site-dynorphin binding domain and the subsequent formation of the di-chain form of DynLHN/A-TEV.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

---

What is claimed:

1. A dual expression construct comprising: i) an open reading frame encoding a single-chain Clostridial toxin, the single-chain Clostridial toxin comprising an enzymatic domain, a translocation domain, a binding domain, and a di-chain loop region comprising a TEV protease cleavage site; and ii) an open reading frame encoding a TEV protease.

2. A dual expression construct comprising: i) an open reading frame encoding a single-chain protein, the single-chain protein comprising an enzymatic domain, a translocation domain, an integrated TEV protease cleavage site-opioid binding domain; and
ii) an open reading frame encoding a TEV protease.

3. A dual expression construct comprising: i) an open reading frame encoding a single-chain protein, the single-chain protein comprising an enzymatic domain, a translocation domain, a non-Clostridial toxin binding domain and a di-chain loop region comprising a TEV protease cleavage site; and ii) an open reading frame encoding a TEV protease.

4. The dual expression of claim 1, wherein the open reading frame comprises SEQ ID NO: 87.

5. The dual expression of claim 1, wherein the single-chain Clostridial toxin comprises SEQ ID NO: 88.

* * * * *